US007572913B2

United States Patent

(12) United States Patent
McKerracher et al.

(10) Patent No.: US 7,572,913 B2
(45) Date of Patent: Aug. 11, 2009

(54) 4-SUBSTITUTED PIPERIDINE DERIVATIVES

(75) Inventors: Lisa McKerracher, Iles-des-Soeurs (CA); Eryk Thouin, Montréal (CA); William Lubell, Montréal (CA); Robert Snow, West Chester, PA (US); Karine Gingras, Montréal (CA)

(73) Assignee: Bioaxone Therapeutique Inc. (CA)

( * ) Notice: Subject to any disclaimer, the term of this patent is extended or adjusted under 35 U.S.C. 154(b) by 394 days.

(21) Appl. No.: 11/065,696

(22) Filed: Feb. 24, 2005

(65) Prior Publication Data

US 2005/0272751 A1 Dec. 8, 2005

Related U.S. Application Data

(60) Provisional application No. 60/546,936, filed on Feb. 24, 2004.

(51) Int. Cl.
*C07D 217/22* (2006.01)
*C07D 215/38* (2006.01)
*A61K 31/47* (2006.01)

(52) U.S. Cl. ....................... 546/141; 546/169; 514/309; 514/312

(58) Field of Classification Search ................. 546/169, 546/143; 514/309, 314
See application file for complete search history.

(56) References Cited

U.S. PATENT DOCUMENTS

| | | | | |
|---|---|---|---|---|
| 3,539,573 | A * | 11/1970 | Hunziker et al. | 540/551 |
| 4,584,303 | A | 4/1986 | Huang et al. | |
| 4,849,521 | A | 7/1989 | Kudzma et al. | |
| 4,857,301 | A | 8/1989 | Czarniecki et al. | |
| 4,866,077 | A | 9/1989 | Bogeso et al. | |
| 4,933,353 | A | 6/1990 | Jensen et al. | |
| 4,997,834 | A | 3/1991 | Muro et al. | |
| 5,478,838 | A | 12/1995 | Arita et al. | |
| 5,496,846 | A * | 3/1996 | Wilson et al. | 514/449 |
| 5,741,792 | A | 4/1998 | Kimball et al. | |
| 5,906,819 | A | 5/1999 | Kaibuchi et al. | |
| 6,020,352 | A | 2/2000 | Kapin et al. | |
| 6,140,333 | A | 10/2000 | Tsuchiya et al. | |
| 6,169,097 | B1 | 1/2001 | Janssens et al. | |
| 6,218,410 | B1 | 4/2001 | Uehata et al. | |
| 6,297,228 | B1 * | 10/2001 | Clark | 514/177 |
| 6,545,022 | B1 | 4/2003 | Bryans et al. | |
| 7,199,147 | B2 * | 4/2007 | Imazaki et al. | 514/394 |

FOREIGN PATENT DOCUMENTS

| | | |
|---|---|---|
| CA | 2304981 | 5/1999 |
| CA | 2342251 | 3/2000 |
| CA | 2325842 | 5/2002 |
| CA | 2443108 | 10/2002 |
| WO | WO 03/042174 | 5/2003 |

OTHER PUBLICATIONS

U.S. Appl. No. 10/022,301, filed Aug. 29, 2002, McKerracher et al.
U.S. Appl. No. 09/903,738, filed Mar. 28, 2002, Steffan et al.
Ishizaki et al.; "The small GTP-binding protein Rho binds to . . . "; EMBO; 1996; pp. 1885-1893; vol. 15; issue 8.
Sayas et al.; "Glycogen Synthase Kinase-3 . . . "; J. Neuroscience; Aug. 15, 2002; pp. 6863-6875; vol. 2, issue 16.
Weggen et al.; "A subset of NSAIDs lower . . . "; Nature; Nov. 8, 2001; pp. 212-216; vol. 414.
Ishizaki et al.; "Pharmacological Properties of Y-27632 . . . "; Molecular Pharmacology; Jan. 12, 2000; pp. 976-983; vol. 57.
Leemhuis et al.; "The Protein Kinase A Inhibitor H89 . . . "; J. Pharmacol. Exp. Ther.; Nov. 8, 2001; pp. 1000-1007; vol. 300; issue 3.
Ishizaki et al.; "p160ROCK, a Rho-associated coiled-coil forming protein kinase . . . "; FEBBS Letters; Jan. 16, 1997; pp. 118-124; vol. 404; issue 2.
Wibberley et al.; "Expression and functional role of Rho-kinase in rat urinary bladder smooth muscle"; British J. Pharmacology; 2003; pp. 757-766; vol. 138.

(Continued)

*Primary Examiner*—Rita J Desai
*Assistant Examiner*—John Mabry
(74) *Attorney, Agent, or Firm*—K&L Gates LLP

(57) ABSTRACT

Substituted piperidine compounds represented by the structure I are provided,

I

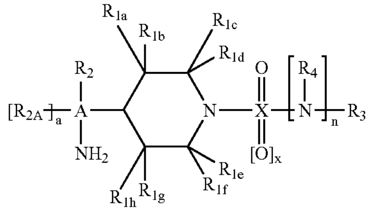

wherein each of $R_{1a}$, $R_{1b}$, $R_{1c}$, $R_{1d}$, $R_{1e}$, $R_{1f}$, $R_{1g}$, $R_{1h}$, $R_2$, $R_{2A}$, $R_3$, $R_4$, A, X, a, x and n is as defined in the specification. Substituted piperidine compounds of structure I may permeate or penetrate across a nerve cell membrane into the interior of a nerve cell, may inhibit intracellular Rho kinase enzyme found in nerve cells in mammals, and may find utility in repair of damaged nerves in the central and peripheral nervous system of such mammals. These compounds may induce the regeneration or growth of neurites in mammalian nerve cells and may thereby induce regeneration of damaged or diseased nerve tissue. These compounds also find additional utility as antagonists of the enzyme Rho kinase in treatment of disease states in which Rho kinase is implicated. Pharmaceutical compositions containing these substituted piperidine compounds may be useful to promote neurite growth and in the treatment of diseases in which Rho kinase inhibition is indicated.

19 Claims, 12 Drawing Sheets

OTHER PUBLICATIONS

Jick et al.; "Statins and the risk of dementia"; Lancet; Nov. 11, 2000; pp. 1627-1631; vol. 356.

Kato et al.; "Statin blocks Rho/Rho-kinase signalling . . . "; Biochimica et Biophysica Acta; May 31, 2004; pp. 267-272; vol. 1689.

DelPeso; "Rho proteins induce metastatic properties in vitro"; Oncogene; Aug. 13, 1997; pp. 3047-3057; vol. 15.

Alexopoulos et al.; "Design and Synthesis of Novel Biologically Active Thrombin Receptor . . . "; J. Med. Chem.; 2004; pp. 3338-3352; vol. 47.

Lee et al.; "Neurodegenerative Tauopathies"; Annu. Rev. Neurosci.; 2001; pp. 1121-1159; vol. 24.

McGeer et al.; "Anti-inflammatory drugs and Alzheimer disease"; Lancet; 1990; p. 1037; vol. 335.

McKerracher et al.; "Identification of Myelin-Associated Glycoprotein . . . "; Neuron; Oct. 1994; pp. 805-811; vol. 13.

Zhou et al.; "Nonsteroidal Anti-Inflammatory Drugs . . . "; Science; Nov. 14, 2003; pp. 1215-1217; vol. 302.

Nakagawa et al.; "ROCK-I and ROCK-II, two isoforms of Rho-associated coiled-coil forming protein serine/threonine kinase in mice"; FEBBS Letters; 1996; pp. 189-193; vol. 392.

Registry No. 289476-26-2 CAPLUS; Jun. 26, 2003.

Registry No. 289476-24-0 CAPLUS; Jun. 26, 2003.

* cited by examiner

4-SUBSTITUTED PIPERIDINE DERIVATIVES

REFERENCE TO RELATED APPLICATIONS

This application claims the benefit of U.S. Ser. No. 60/546,936, filed Feb. 24, 2004, the contents of which are incorporated by reference.

FIELD OF THE INVENTION

The present invention relates to substituted piperidine molecules or compounds which are inhibitors of Rho kinase, and in particular to substituted piperidine compounds which may be membrane permeable and that may promote neurite growth, and to pharmaceutical compositions comprising these compounds. The present invention also relates to the use of these compositions and compounds to repair damage to nerve cells and to components of nerve structures in the central nervous system and in the peripheral nervous system, to prevent ischemic cell death, and to treat various disease states wherein the treatment comprises inactivation or inhibition of Rho kinase.

BACKGROUND OF THE INVENTION

The central nervous system (CNS) is composed of the brain contained in the cranium, and the medulla spinalis or spinal cord in the vertebral canal. The brain contains 12 cranial nerves. The spinal nerves spring from the medulla spinalis, and are transmitted through the intervertebral foramina. The spinal cord, which originates immediately below the brain stem, extends to the first lumbar vertebra, designated L1. Beyond L1 the spinal cord becomes the cauda equina. The spinal cord is comprised of 31 pairs of nerves comprising 8 pairs of cervical spinal nerves, 12 pairs of thoracic spinal nerves, 5 pairs of lumbar spinal nerves, 5 pairs of sacral spinal nerves, and 1 pair of coccygeal spinal nerves. The first cervical nerve (called the suboccipital nerve) emerges from the vertebral canal between the occipital bone and the atlas; the eighth issues between the seventh cervical and first thoracic vertebra. Each nerve is attached to the medulla spinalis by two roots, an anterior or ventral, and a posterior or dorsal, the latter being characterized by the presence of a ganglion, the spinal ganglion. Each spinal nerve is formed from a ventral or anterior root comprising axons from motor neurons and a dorsal or posterior root comprising nerve fibers from sensory neurons. The anterior root (radix anterior; ventral root) emerges from the anterior surface of the medulla spinalis as a number of rootlets or filaments (fila radicularia), which coalesce to form two bundles near the intervertebral foramen. The posterior root (radix posterior; dorsal root) is larger than the anterior due to the greater size and number of its rootlets which are attached along the posterolateral furrow of the medulla spinalis and unite to form two bundles which join the spinal ganglion. The posterior root of the first cervical nerve is smaller than the anterior. The spinal ganglia (ganglion spinale) are collections of nerve cells on the posterior roots of the spinal nerves. Each ganglion is oval in shape, reddish in color, and its size is in proportion to that of the nerve root on which it is situated. It is bifid medially where it is joined by the two bundles of the posterior nerve root. The ganglia are usually but not always found in the intervertebral foramina, immediately outside the points where the nerve roots perforate the dura mater. The ganglia of the first and second cervical nerves lie on the vertebral arches of the atlas and axis respectively, the ganglia of the sacral nerves are inside the vertebral canal, while the ganglion on the posterior root of the coccygeal nerve lies within the sheath of dura mater. When a dorsal root and a ventral root unite, they form a spinal nerve providing both motor and sensory utility. Spinal nerves split into two main branches, the dorsal ramus which innervates the skin of the back and deep back muscles, and the ventral ramus which innervates everything else from the neck inferiorly and also forms nerve plexuses which are a network of converging and/or diverging nerve fibers. The ganglia are comprised of unipolar nerve cells, and from these the fibers of the posterior root originate. Two other forms of cells are also present, i.e., the cells of Dogiel, whose axons ramify close to the cell (type II, of Golgi), and which are distributed entirely within the ganglion; and multipolar cells similar to those found in the sympathetic ganglia. The ganglia of the first cervical nerve may be absent, while small aberrant ganglia consisting of groups of nerve cells are sometimes found on the posterior roots between the spinal ganglia and the medulla spinalis. Each nerve root has a covering comprising pia mater, and is loosely invested by the arachnoid, the latter being prolonged as far as the points where the roots pierce the dura mater. The two roots pierce the dura mater separately, each receiving a sheath from this membrane; where the roots join to form the spinal nerve this sheath is continuous with the epineurium of the nerve.

The largest nerve roots and the largest spinal nerves are those of the lower lumbar and upper sacral nerves, and are attached to the cervical and lumbar swellings of the medulla spinalis.

These nerves are distributed to the upper and lower limbs. Their individual filaments are the most numerous of all the spinal nerves. The roots of the coccygeal nerve are the smallest. Immediately beyond the spinal ganglion, the anterior and posterior nerve roots unite to form the spinal nerve which emerges through the intervertebral foramen. Each spinal nerve receives a branch (gray ramus communicans) from the adjacent ganglion of the sympathetic trunk, while the thoracic and the first and second lumbar nerves each contribute a branch (white ramus communicans) to the adjoining sympathetic ganglion. The second, third, and fourth sacral nerves also supply white rami. These are not connected with the ganglia of the sympathetic trunk, but run directly into the pelvic plexuses of the sympathetic nerve system. A typical spinal nerve contains fibers belonging to two systems, i.e., the somatic nerve system, and the sympathetic or splanchnic nerve system, together with nerve fibers connecting these systems with each other.

The somatic fibers are efferent and afferent. The efferent fibers originate in the cells of the anterior column of the medulla spinalis, and run outward through the anterior nerve roots to the spinal nerve. They convey impulses to the voluntary muscles, and are continuous from their origin to their peripheral distribution. The afferent fibers convey impressions inward, for example from the skin, and originate in the unipolar nerve cells of the spinal ganglia. The single processes of these cells divide into peripheral and central fibers, and the latter enter the medulla spinalis through the posterior nerve roots.

The sympathetic fibers are also efferent and afferent. The efferent fibers, preganglionic fibers, originate in the lateral column of the medulla spinalis, and are conveyed through the anterior nerve root and the white ramus communicans to the corresponding ganglion of the sympathetic trunk where they may end by forming synapses around its cells, or may run through the ganglion to end in another of the ganglia of the sympathetic trunk, or in a more distally placed ganglion in one of the sympathetic plexuses. They end by forming synapses around other nerve cells. From the cells of the ganglia of the sympathetic trunk other fibers, postganglionic fibers, take origin; some of these run through the gray rami communicantes to join the spinal nerves, along which they are carried to the blood vessels of the trunk and limbs, while others pass to the viscera, either directly or after interruption in one of the distal ganglia. The afferent fibers are derived partly from the unipolar cells and partly from the multipolar cells of the spinal ganglia. Their peripheral processes are carried through the white rami communicantes, and after passing through one or more sympathetic ganglia without interruption end in the tissues of the viscera. The central processes of the unipolar cells enter the medulla spinalis through the posterior nerve root and form synapses around either somatic or sympathetic efferent neurons to complete reflex arcs. The dendrites of the multipolar nerve cells form synapses around the cells of type II (cells of Dogiel) in the spinal ganglia. By this path an original impulse is transferred from the sympathetic to the somatic system, through which it is conveyed to the sensorium.

After emerging from the intervertebral foramen, each spinal nerve gives off a small meningeal branch which reenters the vertebral canal through the intervertebral foramen and supplies the vertebra and their ligaments as well as the blood vessels of the medulla spinalis and its membranes. The spinal nerve then splits into a posterior or dorsal, and an anterior or ventral division, each receiving fibers from both nerve roots.

The spinal cord provides a means of motor and sensory communication between the brain and the nerves of the peripheral nervous system (PNS) which includes the somatic nervous system (SNS) and the autonomic nervous system (ANS). The somatic nervous system is voluntary, includes the nerves serving the musculoskeletal system and the skin, and reacts to outside stimuli affecting the body. The autonomic nervous system is involuntary, and controls and maintains homeostasis or normal function. The autonomic nervous system is comprised of the sympathetic nervous system associated with the flight or fight response, and the parasympathetic nervous system responsible for maintaining regular life functions such as heartbeat and breathing during normal activity. Nerve roots pass out of the spinal canal through the intervertebral foramen and distribute to the body anteriorly for motor activity or posteriorly for sensory activity. The anterior nerve divisions supply the front of the spine including the limbs while the posterior nerve divisions are distributed to the muscles behind the spine.

Cerebrospinal fluid is secreted from the choroids plexus in the brain and is present in the brain ventricles, in the spinal canal, and in the spinal cord. The fluid circulates among these tissues and cushions the tissues in the CNS from the effects of traumatic injury. The CNS in a normal adult contains about 150 milliliters of cerebrospinal fluid.

The brain and spinal cord are covered and protected by meninges membranes comprising strong connective dura mater tissue, or dura, as a gray outer layer of the spinal cord and nerve roots; arachnoid mater, thinner than the dura mater; and pia mater, the innermost layer covering the nerves as a delicate and highly vascular membrane providing blood to the neural structures.

The dura membrane that covers the spine and nerve roots in the neck is surrounded by the epidural space. Nerves pass through the epidural space to the neck, shoulder and arms. Inflammation of these nerve roots may cause pain in these regions due to irritation from a damaged disc or from contract with the bony structure of the spine.

Injury to the nerves in the central nervous system such as nerves in the spinal cord can result in functional impairment which can take the form of permanent loss of sensation and paraplegia. Most of the deficits associated with spinal cord injury such as traumatic spinal cord injury, crush injury, or lesion in the spinal nerves result from cell death and the loss of axons in the spinal neuronal population that are damaged in the central nervous system (CNS) which is comprised of nerves in the spinal cord and brain. Axons do not otherwise regrow across a lesion site in a damaged nerve in the CNS. Neurodegenerative diseases of the CNS are also associated with cell death and axonal loss. Representative diseases of the CNS include those that can result in impairment include stroke, human immunodeficiency virus (HIV) dementia, prion diseases, Parkinson's disease, Alzheimer's disease, multiple sclerosis, traumatic brain injury, and glaucoma. The ability to stimulate growth of axons from the injured, damaged, diseased or otherwise affected neuronal population would improve recovery of lost neurological functions, and protection from cell death can limit the extent of damage in the CNS. For example, following a white matter stroke, axons are damaged and lost, even though the neuronal cell bodies are alive, and stroke in gray matter kills many neurons and non-neuronal (glial) cells.

Effective neuroprotective and neuroregenerative agents are desirable to potentially limit damage and to induce repair to the CNS. Compounds which promote axon growth in nerve cells of the CNS are especially desirable for treatment of damaged, injured, and/or diseased nerves in the CNS. Compounds which promote axon growth in nerve cells of the peripheral nervous system (the PNS) are also especially desirable for treatment of damaged, injured, and/or diseased nerves in the PNS.

Traumatic injury of the spinal cord can result in permanent functional impairment. Axon regeneration in nerve cells of the CNS does not occur at the site of injury or lesion site in the mammalian CNS because growth inhibitory proteins present in anatomical structures immediately proximal to nerves as substrate-bound proteins block axon growth. Anatomical structures such as myelin sheaths immediately proximal to nerves are referred to as inhibitory substrates. While compounds such as trophic factors can enhance neuronal differentiation and stimulate axon growth in tissue culture, most factors and compounds that enhance growth and differentiation cannot promote axon regenerative growth on inhibitory substrates.

A compound which stimulates axon growth in tissue cell culture and induces axon growth on growth inhibitory substrates is potentially useful for therapeutic use in axon regeneration when applied to cells residing in the CNS, such as directly to the site of a lesion in the CNS. Trophic and differentiation factors that stimulate growth on permissive substrates, that is, in the absence of inhibitory proteins or in the absence of inhibitory substrates, in tissue culture include neurotrophins such as nerve growth factor (NGF) and brain-derived growth factor (BDNF). Neither NGF nor BDNF promotes neurite growth or axon regeneration in nerve cells on inhibitory substrates, and neither is effective in promoting axon regeneration in nerve cells in the CNS in vivo.

Cell death can occur by two major mechanisms, necrosis and apoptosis. While necrotic cell death results in cell lysis and release of cell contents, cellular apoptosis is programmed cell death that results in the relatively tidy packaging of cells which die with the prevention of release of cellular contents. Apoptosis is characterized morphologically by cell shrinkage, nuclear pyknosis, chromatin condensation, and blebbing of the plasma membrane. Traumatic injury and ischemia can lead to apoptosis of both neurons and non-neuronal cells, and this cell death is responsible for functional deficits after injury or ischemia. A cascade of molecular and biochemical events is associated with apoptosis including activation of an endogenous endonuclease that cleaves DNA into oligonucleosomes detectable as a ladder of DNA fragments in agarose gels. Apoptotic endonucleases not only affect cellular DNA by producing the classical DNA ladder but also generate free 3'-OH groups at the deoxyribose ends of these DNA fragments. A technique called Tunel labeling labels DNA fragments as a means to detect apoptotic cells.

Rho kinase, an enzyme that resides in the interior of cells such as nerve cells, is a target for treatment of cancer, metastasis, and hypertension. Rho kinase inhibitors may be useful to treat eye diseases such as glaucoma, as well as to inhibit cancer cell migration and metastasis.

Rho kinase antagonists may be useful in treatment of hypertension, asthma, and vascular disease such as thrombosis.

The superfamily of small GTP-binding proteins or small G-proteins can be divided according to the similarity of amino acid sequences into 5 groups of Ras, Rho (short for Ras homologue), Rab, Arf and others. The small GTP-binding proteins have a molecular weight of 20,000-30,000 Daltons, specifically bind GDP and GTP, and exhibit GTPase activity by hydrolyzing bound GTP. Rho is specifically ADP ribosylated and inactivated by C3, a botulinum toxin.

Protein kinases are proteins that phosphorylate and control the activity of other proteins by transferring a phosphate from ATP (adenosine triphosphate) to an amino acid, e.g. serine, threonine, or tyrosine, on another (target) protein. Target proteins regulated by phosphorylation include enzymes that transduce signals in a cellular environment and enzymes that turn certain genes on or off and can thereby regulate progression of many different diseases.

Rho kinase regulates cell cytoskeleton organization, cell adhesion and cell motility, and a cell's cycle. Rho kinase is a serine/threonine kinase, and is a Rho binding protein or an effector of Rho which is a GTPase, which catalyzes the reaction: GTP (Guanosine 5'-triphosphate)+H2O (water) to GDP (Guanosine 5'-diphosphate)+phosphate ion, and is linked to a cell membrane in its active state. Inhibition of Rho kinase by a compound of this invention can have potential therapeutic applications in a mammal, such as reduction of tumor metastasis in cancer, relaxation of vascular tension in cardiovascular disease, and reduction of ocular pressure in glaucoma, among other applications. Two different Rho kinase inhibitors, Fasudil™ and Radicut™, are in use in humans for treatment of stroke. Rho kinase is called ROK (Rho-associated kinase) and ROCK (Rho associated Rho kinase), ROKa, or ROCKI. Isoforms of ROCK exist: ROCKII (has 64% sequence identity with ROCKI, and ROKβ is 90% identical. The protein has three important domains: a Rho-binding domain (RB), a C-terminal PH (Pleckstrin homology) domain, and a catalytic domain.

ROCKI and ROCKII are each activated by Rho. An important distinction between ROCKI and ROCKII comprises their respective in vivo tissue distributions in a mammal (e.g., see Nakagawa et al., FEBS Lett. 1996 Aug. 26; 392(2):189-93). Analysis of relevant mRNA concentration levels has shown that ROCKI has widespread tissue distribution, but that there is relatively little ROCKI in brain and in skeletal muscle. Expression of ROCKII is high in brain, heart and lung, but is relatively low in liver, stomach, spleen, kidney and testis. Western blots used to study protein concentration levels show ROCKII concentration levels to be low in liver and kidney (Wibberley et al. 2003, British J. Pharmacology 138:757-766), whereas ROCKII is highly expressed in brain as compared to ROCKI (Leemhuis et al. 2002, J Pharmacol Exp Ther. 300:1000). Therefore, for therapeutic and diagnostic use in the CNS of a mammal, an inhibitor that is specific for inhibition of ROCKII would be desirable.

In this regard, known Rho kinase inhibitor Y27632 [(R)-(+)-trans-4-(1-aminoethyl)-N-(4-pyridyl)cyclohexane-carboxamide as a dihydrochloride salt] inactivates (inhibits) both ROCKI and ROCKII (Ishizaki et al. 2000, Molecular Pharmacology 57:976).

In addition, a Rho kinase inhibitor that is in clinical use for treatment of stroke, Radicut™ (edaravone; 3-methyl-1-phenyl-2-pyrazoline-5-one; 5-methyl-2-phenyl-2,4-dihydro-3H-pyrazol-3-one), is known to have kidney toxicity. An estimated 180,000 patients have taken the drug Radicut™ since it was approved for use in 2001 in Japan. Ninety-three were later struck down with kidney failure and 40 died. A Rho kinase inhibitor specific for ROCKII may not be expected to show this adverse effect profile in part because of the low abundance of ROCKII in liver and kidney (Wibberley et al. 2003, British J. Pharmacology 138:757-766).

Nearly all protein kinase inhibitors that have been developed are ATP-competitive, and for this reason the "drug concentration required for 50% inhibition" ($IC_{50}$) of a protein kinase depends on the concentration of ATP used in the assays. A drug concentration required to suppress phosphorylation of a target substrate in a cell can be higher than the drug concentration required for inhibition of a protein kinase in vitro.

A compound known to inhibit the activity of Rho kinases is (R)-trans-4-(ethan-1'-amino)-N-(4"-pyridyl)cyclohexane carboxamide dihydrochloride known as Y-27632, which is available from Sigma Chemical Company and from Calbiochem in powder form and which can be dissolved in DMSO (dimethyl sulfoxide, Sigma) and which can be useful as a reference Rho kinase inhibiting compound.

Rho kinase regulates axon growth and regeneration in nerve cells, cell motility and metastasis, smooth muscle contraction, and apoptosis, and is a target for therapeutic treatment in many disease applications, including repair in the central nervous system. Rho kinase is activated by Rho and Rho kinase inhibitors block Rho signaling. Mutations of Rho family regulatory proteins have been found in clinical oncology samples which suggests that perturbation or alteration or interruption of, or interference with, the Rho signaling pathway can be a useful therapeutic modality. Examples with specificity for Rho include the DLC1 gene in hepatocellular carcinoma, p-190-A, which is in a region that is altered in gliomas and astrocytomas, GRAF, which has loss of function mutations in leukemia, and LARG, which is found in some gene fusions found in acute myeloid leukemia. Genetically engineered point mutations can activate RhoA and induce cellular transformation in vitro.

Rho kinase inhibitors have widespread potential for use in the treatment of neurodegenerative diseases, particularly if the Rho kinase inhibitors have the property to enhance plasticity and axon regeneration in neurons. However, there is much scientific evidence for a direct link between Rho signaling and neurodegenerative disease. In an animal model of Alzheimer's Disease (AD), there is clear evidence that Rho kinase inhibitors can reduce the pathological hallmarks of the disease.

A trans-4-amino(alkyl)-1-pyridylcarbamoylcyclohexane, designated as Y27632, is a Rho kinase inhibitor and available from Calbiochem. Y27632 is described in U.S. Pat. No. 4,997,834, the entire content of which is incorporated herein by reference. Y27632 has been used to demonstrate that inhibition of Rho kinase is effective in preventing metastasis.

Other compounds are described in U.S. Pat. No. 5,478,838, the entire content of which is incorporated herein by reference.

Rho signaling antagonists can be useful in treatment of hypertension. For example, Y-27632 can relax smooth muscle and increase vascular blood flow. Y-27632 is a small molecule that can enter cells, and is not toxic in rats after oral administration of 30 mg/kg for 10 days. Y-27632 reduces blood pressure in hypertensive rats, but does not affect blood pressure in normal rats.

A number of Rho kinase inhibitors are known. For example, the compound NHM-1152 can act as vascular relaxant in vascular vasospasm. The compound known as hydroxy fasudil may find use in the treatment of stroke after intravenous application and can reduce infarct volume, improve outcomes, can have anti-ischemic properties in vasospastic angina, and inhibits neutrophil migration in ischemic brain. A fasudil compound called HA-1077 is an antivasospasm agent which improves cerebral hemodynamic activity, inhibits production of superoxide anion by neurotrophils, and may find use in the treatment of spinal cord injury, stroke, subarachnoid hemorrhage, and cerebral infarction. U.S. Pat. No. 6,218,410, the disclosure of which is hereby incorporated by reference in its entirety, describes a Rho kinase inhibitor. U.S. patent application Ser. No. 10/022,301 (McKerracher et al) published as U.S. 2002/0119140, the disclosure of which is hereby incorporated by reference in its entirety, describes Rho family antagonists and their use to block inhibition of neurite outgrowth. Canadian Patent applications 2,304,981 (McKerracher et al) and 2,325,842 (McKerracher), the disclosure of each of which is hereby incorporated by reference in its entirety, disclose the use of Rho antagonists such as for example C3 and chimeric C3 proteins as well as substances selected from among known trans-4-amino(alkyl)-1-pyridylcarbamoylcyclohexane compounds or Rho kinase inhibitors for use in the regeneration of axons. C3 inactivates Rho by ADP-ribosylation and can be relatively non-toxic to nerve cells at therapeutically effective doses. U.S. Pat. Nos. 4,857,301, and 5,741,792, the disclosure of each of which is hereby incorporated by reference in its entirety, describes a number of 4-substituted piperidine compounds. U.S. Pat. No. 6,140,333, the disclosure of which is hereby incorporated by reference in its entirety, describes certain piperidine compounds, one of which is a 4-aminomethylpiperidine acylated at the piperidine ring nitrogen by a group containing a carbon adjacent to the carbonyl group to which carbon is attached an aryl group and a hydroxyl group. U.S. Pat. No. 6,020,352, the disclosure of which is hereby incorporated by reference in its entirety, describes the use of certain 1-phenyl-2-piperidinoalkanol derivatives to treat ischemic disorders of the retina and optic nerve.

U.S. Pat. Nos. 4,849,521, 4,584,303, 4,866,077, 4,933,353, and 6,169,097, the disclosure of each of which is hereby incorporated by reference in its entirety, disclose methods to prepare a number of piperidines with substituents attached to one or more of the ring carbon atoms of a piperidine. U.S. Pat. No. 6,545,022, the disclosure of which is hereby incorporated by reference in its entirety, describes a method to prepare certain 4-substituted-4-aminoalkylpiperidines including certain 4-substitutedmethylene-4-aminomethylpiperidines.

SUMMARY OF THE INVENTION

The present invention provides novel 4-substituted piperidine compounds, processes for the preparation of such novel 4-substituted piperidine compounds, and pharmaceutical compositions novel 4-substituted piperidine compounds. These compounds may increase neurite (axon and dendrite) outgrowth in nerve cells on inhibitory substrates, and pharmaceutical compositions may be useful in a method of in vivo treatment of injured, damaged, or diseased nerves in the CNS and PNS when administered to mammals, which method of treatment comprises another aspect of the invention.

During development of a nerve, neurons or nerve cells become assembled into functional networks by growing out axons and dendrites, collectively called neurites. The neurites connect synaptically to those of other neurons, and are important for communication between each other. While many tissues such as muscle, skin, and liver have the ability to repair and regrow after an injury, nerves in the CNS have a very limited ability to repair and regrow after injury. Compounds of the present invention may promote neurite outgrowth and have potential curative effects in nerve injury such as spinal cord injury and traumatic brain injury, and in nerve-related diseases such as Alzheimer's, Parkinson's disease and brain cancer. During nerve development, growing axons of neurons orient themselves and find their way to the appropriate proximal adjacent neurons. Growing axons interact directly with molecules on the surfaces of cells or in the extracellular matrix of the tissues through which they grow. These physical interactions induce the axons to grow in certain directions and repel or inhibit them from growing in others. There also appears to be secreted and released by tissues, diffusible molecules that are similarly attractive or repellant to growing axons. In addition, surface "markers" or recognition molecules on the target cells seem to direct axons to the appropriate region of the target tissue to form synapses.

Growing axons appear to sense attractive or repellant materials, and to orient their growth accordingly. The growing tips of axons are enlarged into more or less conical regions called "growth cones." Growth cones are highly motile structures that extend and retract fine tubes of cytoplasm and membrane called filopodia. The axon elongates as the growth cone moves forward, and new plasma membrane is added into the growth cone. Growth cones in living neurons in tissue culture are active, highly dynamic regions; advancing, retracting, and changing direction constantly.

The present invention relates in one aspect thereor, to compounds and compositions of the general structure of the formula I:

I

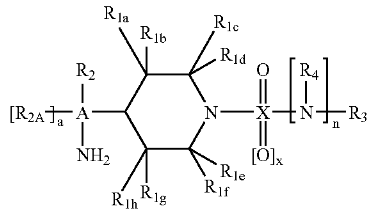

wherein

A may be a carbon, C, or nitrogen, N;

a may be 1 (one) when A is carbon or a may be 0 (zero) when A is nitrogen;

x may be 0 or 1;

X may be carbon or sulfur provided that X may be carbon only when x is 0, and X may be sulfur only when x is 1;

n may be 0 or 1;

each of $R_{1a}$, $R_{1b}$, $R_{1c}$, $R_{1d}$, $R_{1e}$, $R_{1f}$, $R_{1g}$, and $R_{1h}$, which may be a piperidine ring substituent, may be independently selected from the group consisting of:

hydrogen, a C1 (one carbon) to C30 (thirty carbon) alkyl group which may be linear or branched, a C4 (four carbon) to C30 cycloalkylalkyl group, a spirocycloalkyl group which may have a C2 (two carbon) to C5 (five carbon) bridging group, a C3 (three carbon) to C40 (forty carbon) alkenyl group, a C3 to C10 (ten carbon) alkylthioalkyl group (e.g., methylthioethyl), an alkoxy-containing alkyl group (alkoxyalkyl) which may contain at least one oxygen atom and from 2 to 30 carbon atoms, an alkoxy-containing alkenyl group which may have from 3 to 30 carbon atoms and which may contain at least one oxygen atom that may be allylic to or may be further removed from a double bond in the alkenyl group, a 2-poly(2-oxyethyl)ethyl group which may contain from 2 to (about) 30 oxygen atoms which 2-poly(2-oxyethyl)ethyl group may be terminated in a hydroxyl group or a methoxyl group, an aralkyl group which may contain from 7 to 30 carbons (i.e., aryl alkyl e.g., benzyl) wherein the aryl group may be a substituted aryl group, an aralkyl group which may contain from 7 to 30 carbons (C7 to C30) wherein the alkyl portion of the aralkyl may contain an ether group, and an aralkyl group which may contain from 7 to 30 (C7 to C30) carbons and substituted with a linear polyethyleneglycol group which may contain from 3 to 30 oxygen atoms in the form of an omega-hydroxyl-terminated poly(oxyethyl) (or HO-PEG-) group or in the form of an omega-methoxy-terminated poly(oxyethyl) (or $CH_3O$-PEG- or MeO-PEG or MPEG) group, provided that at least four of $R_{1a}$, $R_{1b}$, $R_{1c}$, $R_{1d}$, $R_{1e}$, $R_{1f}$, $R_{1g}$, and $R_{1h}$ may be hydrogen, and at least two of $R_{1a}$, $R_{1b}$, $R_{1g}$, and $R_{1h}$ may be hydrogen and at least two of $R_{1c}$, $R_{1d}$, $R_{1e}$, and $R_{1f}$ may be hydrogen;

$R_2$ and $R_{2A}$ may be independently selected from the group consisting of:

hydrogen, a C1 to C30 alkyl group, i.e., an alkyl group which may be selected from the group consisting of C1 to C30 alkyls, which group may include a subgroup of lower alkyls of from C1 to C10, a C3 to C10 cycloalkyl group, i.e., a cycloalkyl group which may be selected from the group consisting of C3 (three carbons) to C10 (ten carbons) cycloalkyls, which group may include a subgroup of lower cycloalkyls of from C3 to C6 (six carbons), a C4 to C30 cycloalkylalkyl group, i.e., a cycloalkylalkyl group which may be selected from the group consisting of C4 to C30 cycloalkylalkyls, which group may include a subgroup of lower cycloalkylalkyls of C4 (four carbons) to C8 (eight carbons), a C3 to C40 alkenyl group, i.e., an alkenyl group which may be selected from the group consisting of C3 to C40 alkenyls, which group may include a subgroup of lower alkenyls of C3 to C10, a C3 to C40 alkynyl group, i.e., an alkynyl group which may be selected from the group consisting of C3 to C40 alkynyls, which group may include a subgroup of lower alkynyls of C3 to C10, an alkoxy-containing alkyl group containing at least one ether oxygen atom and from 2 to 30 carbon atoms, i.e., an alkoxy-containing or ether-containing alkyl group which may comprise or consist of an alkyl group containing at least one ether oxygen atom and from 2 to 30 carbon atoms, which group may include a subgroup of lower alkoxy groups containing one oxygen atom in the form of an ether oxygen and from 2 to 10 carbon atoms, a hydroxyl-containing alkyl group which may contain 2 to 30 carbon atoms which may contain at least one hydroxyl substituent, i.e., a hydroxyl-containing alkyl group which may comprise an alkyl group from 2 to 30 carbon atoms containing at least one hydroxyl substituent, which group may include lower alkyl groups which may contain one hydroxyl substituent and from 2 to 10 carbon atoms, a hydroxyl-containing alkyl group which may comprise an alkyl group from 4 to 30 carbon atoms which may contain at least one hydroxyl substituent and at least one ether oxygen atom wherein the hydroxyl and ether groups may be separated by at least 2 carbon atoms, which group may include a subgroup of lower alkyl groups which may contain one hydroxyl substituent and from 2 to 10 carbon atoms, an alkoxy-containing alkenyl group which may contain at least one oxygen atom that may be allylic to or more distantly removed from a double bond in the alkenyl group which alkenyl group may contain from 3 to 30 carbon atoms, a 2-poly(2-oxyethyl)ethyl group which may contain from 2 to about 30 oxygen atoms which group may be terminated with a 2-methoxyethyl group ($CH_3O—CH_2CH_2—$) or a 2-hydroxyethyl group (HO—$CH_2$CH2-), an aryl group of 6 to 10 ring carbons (e.g., unsubstituted as in phenyl, naphthyl) which aryl group may be a substituted aryl group which may be an aryl group substituted with a group selected, for example, from the group of lower alkyl, lower cycloalkyl, lower alkoxy, a lower alkenyl, halogen (F—, Cl—, Br—, I—), a perfluoro-lower alkyl group, nitro, cyano, amino, lower alkyl amino, di(lower alkyl) amino, carboxyl (HOOC—), carboxyl-substituted lower alkyl (HOOC— substituted lower alkyl), hydroxy, phenyloxy, a linear polyethyleneglycol group containing, for exmple, from 3 to 30 oxygen atoms in the form of an omega-hydroxyl-terminated poly(oxyethyl) (or HO-PEG-) group or in the form of an omega-methoxy-terminated poly(oxyethyl) (or $CH_3O$-PEG- or MeO-PEG or MPEG) group and combinations thereof, wherein the phenyloxy group may be substituted with lower alkyl, lower alkoxy, lower alkenyl, lower cycloalkyl, perfluoro-lower-alkyl, halogen, and combinations thereof, an aralkyl group containing from 7 to 30 carbons (i.e., aryl alkyl e.g., benzyl) wherein the aryl group may be a substituted aryl group, an aralkyl group which may contain from 7 to 30 carbons (C7 to C30) wherein the alkyl portion of the aralkyl may contain an ether group, and a 1-imidazolyl group which may contain at the 2-, 4-, or 5-position an alkyl, alkoxyalkyl, cycloalkylalkyl, alkoxyalkyl, or a polyethyleneglycol substituent group containing from 3 to 30 oxygen atoms in the form of a peg group or a methoxy-terminated peg group, a 2-imidazolyl group which may contain at the 1-, or 4/5-position an alkyl, alkoxyalkyl, cycloalkylalkyl, alkoxyalkyl, or a polyethyleneglycol substituent group containing from 3 to 30 oxygen atoms in the form of a HO-PEG-group or a methoxy-terminated MPEG group, a 4-imidazolyl group which may contain at the 1- or 2-positions an alkyl, alkoxyalkyl, cycloalkylalkyl, alkoxyalkyl substituents, or a polyethyleneglycol substituent group containing from 3 to 30 oxygen atoms in the form of a hydroxyl-terminated polyethyleneglycol (PEG) group or a methoxy-terminated polyethyleneglycol (MPEG) group, a pyridinyl group which may be selected, for example, from 2-pyridyl or 3-pyridyl or 4-pyridyl and represented by formula (group-i):

(group-i)

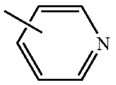

a substituted pyridinyl group selected from 2-pyridyl or 3-pyridyl or 4-pyridyl or 5-pyridyl or 6-pyridyl and represented by formula (group-ii):

(group-ii)

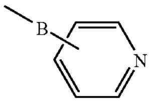

a 1H-indolyl group represented by formula (group-iii):

(group-iii)

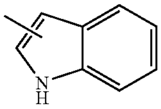

a 1H-indolyl-containing group represented by formula (group-iv):

(group-iv)

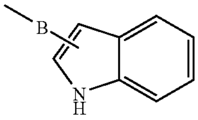

a substituted quinolyl group represented by formula (group-v):

(group-v)

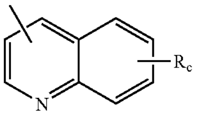

a substituted quinolyl-containing group represented by formula (group-vi):

(group-vi)

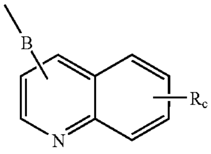

a substituted phenyl group represented by formula (group-vii):

(group-vii)

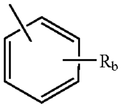

a substituted phenyl-containing (or phenylene) group represented by formula (group-viii):

(group-viii)

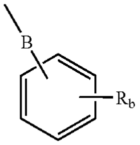

a substituted piperidinyl (or piperidylidinyl) group represented by formula (group-ix):

(group-ix)

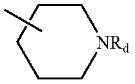

a substituted piperidinyl-containing (or piperidylidinyl) group represented by formula (group-x):

(group-x)

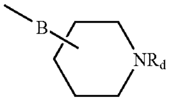

a 1H-pyrrolo[2,3-b]pyridinyl group represented by formula (group-xi):

(group-xi)

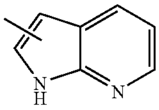

a 1H-pyrrolo[2,3-b]pyridinyl-containing group represented by formula (group-xii):

(group-xii)

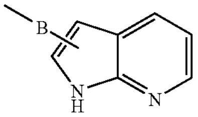

an isoquinolinyl group represented by formula (group-xiii):

(group-xiii)

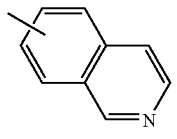

an isoquinolinyl-containing group represented by formula (group-xiv):

(group-xiv)

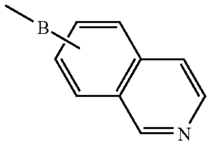

a 5-isoquinolyl group which may contain a hydroxy group substituent;

a 1H-imidazolyl group represented by formula (group-xv):

(group-xv)

a 1H-imidazolyl-containing group represented by formula (group-xvi):

(group-xvi)

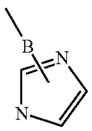

a 1H-indazolyl group represented by formula (group-xvii):

(group-xvii)

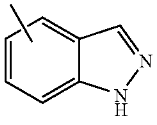

a 1H-indazolyl-containing group represented by formula (group-xviii):

(group-xviii)

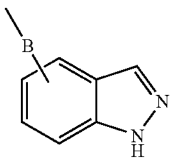

a purinyl group (a 9H-purinyl group) represented by formula (group-xix)

(group-xix)

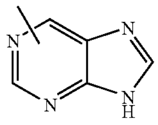

and a purinyl-containing group (or 9H-purinyl-containing group) represented by formula (group-xx):

(group-xx)

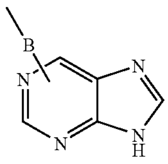

wherein

B may be, for example, an alkylene linking group selected from the group consisting of (a) an unsubstituted straight chain linear alkylene group of from 1 to 20 carbon atoms, i.e., a C1 to C20 unsubstituted straight chain linear alkylene linking group (e.g., methylene, i.e., $—CH_2—$; ethylene, i.e., $—CH_2CH_2—$; trimethylene, i.e., $—CH_2CH_2CH_2—$; tetramethylene, i.e., $—CH_2CH_2CH_2CH_2—$; . . . etc. to; dodecamethylene, i.e., $—CH_2—(CH_2)_{18}—CH_2—$ or $—(CH_2)_{20}—$;), and (b) a branched alkylene group comprising a linear alkylene group of from 1 to 20 carbon atoms that may be substituted by an alkyl group of 1 to 4 carbon atoms (e.g. methylmethylene, i.e., $—C(CH_3)H—$; 1-methylethylene, i.e., $—CH(CH_3)—CH_2—$; 3-ethyl-tetramethylene, $—CH_2—CH_2—C(CH_2CH_3)H—CH_2—$; 2,6-dimethyloctamethylene, i.e., $—CH_2—C(CH_3)H—CH_2—CH_2—CH_2—C(CH_3)H—CH_2—CH_2—$; etc, $R_b$ may be selected from the group consisting of hydrogen (H), alkyl, amino, alkylamino, dialkylamino, $R_c$ may be selected from the group consisting of hydrogen (H), and alkyl, and $R_d$ may selected from the group consisting of hydrogen (H), alkyl, and aralkyl, and when n is 1, $R_3$ and $R_4$ may each independently be selected from the group consisting of:

hydrogen, an aryl group of 6 to 10 ring carbons (e.g., phenyl, naphthyl) which aryl group may be substituted with a group selected from lower alkyl, lower cycloalkyl, lower alkoxy, a lower alkenyl, halogen (F—, Cl—, Br—, I—), a perfluoro-lower alkyl group, nitro, cyano, amino, lower alkyl amino, di(lower alkyl)amino, carboxyl (HOOC—), carboxyl-substituted lower alkyl (HOOC— substituted lower alkyl), hydroxy, phenyloxy, a linear polyethyleneglycol group which may contain from 3 to 30 oxygen atoms in the form of an omega-hydroxyl-terminated poly(oxyethyl) (or HO-PEG-) group or in the form of an omega-methoxy-terminated poly(oxyethyl) (or $CH_3O$-PEG- or MeO-PEG or MPEG) group, and combinations thereof, wherein the phenyloxy group may be substituted with lower alkyl, lower alkoxy, lower alkenyl, lower cycloalkyl, perfluoro-lower-alkyl, halogen, and combinations thereof, an aralkyl group containing from 7 to 30 carbons (e.g. benzyl, benzhydryl) wherein the aryl group may be a substituted aryl group, an aralkyl group which may contain from 7 to 30 carbons (C7 to C30) wherein the alkyl portion of the aralkyl may contain an ether group, and a pyridinyl group selected from 2-pyridyl or 3-pyridyl or 4-pyridyl and represented by formula (group-i):

(group-i)

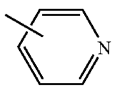

a substituted pyridinyl group selected from 2-pyridyl or 3-pyridyl or 4-pyridyl or 5-pyridyl or 6-pyridyl and represented by formula (group-ii):

(group-ii)

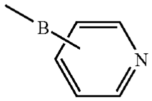

a 1H-indolyl group represented by formula (group-iii):

(group-iii)

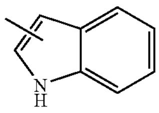

a 1H-indolyl-containing group represented by formula (group-iv):

(group-iv)

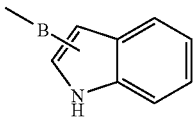

a substituted quinolyl group represented by formula (group-v):

(group-v)

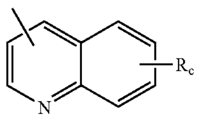

a substituted quinolyl-containing group represented by formula (group-vi):

(group-vi)

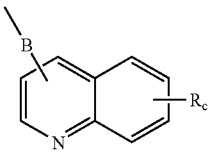

a substituted phenyl group represented by formula (group-vii):

(group-vii)

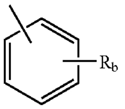

a substituted phenyl-containing (or phenylene) group represented by formula (group-viii):

(group-viii)

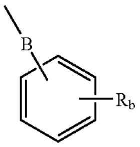

a substituted piperidinyl (or piperidylidinyl) group represented by formula (group-ix):

(group-ix)

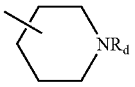

a substituted piperidinyl-containing (or piperidylidinyl) group represented by formula (group-x):

(group-x)

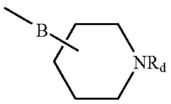

a 1H-pyrrolo[2,3-b]pyridinyl group represented by formula (group-xi):

(group-xi)

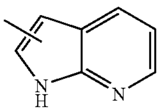

a 1H-pyrrolo[2,3-b]pyridinyl-containing group represented by formula (group-xii):

(group-xii)

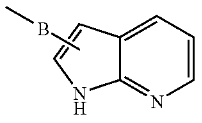

an isoquinolinyl group represented by formula (group-xiii):

(group-xiii)

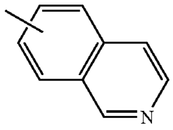

an isoquinolinyl-containing group represented by formula (group-xiv):

(group-xiv)

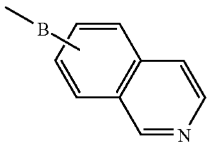

a 1H-imidazolyl group represented by formula (group-xv):

(group-xv)

a 1H-imidazolyl-containing group represented by formula (group-xvi):

(group-xvi)

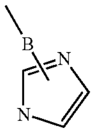

a 1H-indazolyl group represented by formula (group-xvii):

(group-xvii)

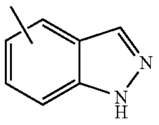

a 1H-indazolyl-containing group represented by formula (group-xviii):

(group-xviii)

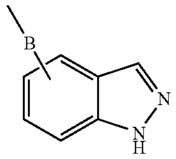

a purinyl group (a 9H-purinyl group) represented by formula (group-xix)

(group-xix)

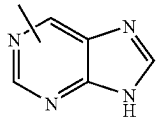

and a purinyl-containing group (or 9H-purinyl-containing group) represented by formula (group-xx):

(group-xx)

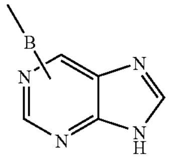

wherein

B may be a C1 to C20 an unsubstituted (straight chain or linear) alkylene group (e.g., methylene, ethylene, trimethylene, tetramethylene, etc.) or may be a C1 to C20 branched alkylene group (e.g. methylene, ethylene, trimethylene, tetramethylene, etc.) substituted by an alkyl group of 1 to 4 carbon atoms, $R_b$ may be selected from the group consisting of hydrogen (H), alkyl, amino, alkylamino, dialkylamino, $R_c$ may be selected from the group consisting of hydrogen (H), and alkyl, and $R_d$ may be selected from the group consisting of hydrogen (H), alkyl, and aralkyl, or $R_3$ and $R_4$ together inclusively with the nitrogen atom from which they are subtended may form a heterocyclic nitrogen-containing ring group, which nitrogen-containing ring group may be a single ring, inclusively with said nitrogen atom, of from 5 to 7 atoms optionally having in the single ring an oxygen atom, a sulfur atom, or an additional nitrogen atom, or which nitrogen-containing ring group may be a fused ring structure, inclusively with said nitrogen atom, of from 8 to 16 atoms, optionally having in the fused ring structure an oxygen atom, a sulfur atom, or an additional nitrogen atom, the heterocyclic nitrogen-containing ring group optionally having a substituent which may be selected from the group consisting of lower alkyl, lower alkenyl, lower alkynyl, lower alkoxyalkyl, lower alkoxy, carboxyl-(lower alkyl) such as carboxylmethyl or $HOOC—CH_2—$, N-[carboxyl-(lower alkyl)]amino such as carboxylmethyl amino or $(HOOC—CH_2)—NH—$, N,N-di(carboxyl-lower alkyl)amino such as N,N-di(carboxylmethyl)amino or (HOOC—$CH_2$)$_2$N—, amino or $H_2N$—, di-(lower alkyl)amino, halogen, and perfluoro-(lower alkyl);

or when n is zero, $R_3$ may be selected from the group consisting of:

an aryl group of 6 to 10 ring carbons (e.g., phenyl, naphthyl) which aryl group may be substituted with a group selected from lower alkyl, lower cycloalkyl, lower alkoxy, a lower alkenyl, halogen (F—, Cl—, Br—, I—), a perfluoro-lower alkyl group, nitro, cyano, amino, lower alkyl amino, di(lower alkyl)amino, carboxyl (HOOC—), carboxyl-substituted lower alkyl (HOOC— substituted lower alkyl), hydroxy, phenyloxy, a linear polyethyleneglycol group which may contain from 3 to 30 oxygen atoms in the form of an omega-hydroxyl-terminated poly(oxyethyl) (or HO-PEG-) group or in the form of an omega-methoxy-terminated poly(oxyethyl) (or $CH_3$O-PEG- or MeO-PEG or MPEG) group, and combinations thereof, wherein the phenyloxy group may be substituted with lower alkyl, lower alkoxy, lower alkenyl, lower cycloalkyl, perfluoro-lower-alkyl, halogen, and combinations thereof, an aralkyl group containing from 7 to 30 carbons (e.g. benzyl, benzhydryl) wherein the aryl group may be a substituted aryl group, and wherein the alkyl portion of the aralkyl may optionally contain an ether group separated from X by at least two carbons, and a heteroaryl group attached directly to X at a carbon of the heteroaryl ring or optionally to X by a group B that may be attached at a carbon of the heteroaryl ring, the heteroaryl group selected from the group consisting of pyridinyl, 1H-indolyl, quinolyl substituted by a group $R_c$ at a carbon that not attached to X or B, piperidinyl substituted with a group $R_d$ at the 1-position of the piperidine ring, 1H-pyrrolo[2,3-b]pyridinyl, isoquinolinyl, 1H-imidazolyl, 1H-indazolyl, and 9H-purinyl, wherein B may be a C1 to C20 linear alkylene group (e.g., methylene, ethylene, trimethylene, tetramethylene, etc.) optionally substituted by an alkyl group of 1 to 4 carbon atoms, $R_c$ may be selected from the group consisting of hydrogen (H), and C1 to C20 alkyl, and $R_d$ may be selected from the group consisting of hydrogen (H), C1 to C20 alkyl, and C7 to C20 aralkyl, provided that in an $R_3$ group a carbon atom attached to X may not contain both a hydroxyl group and an aryl group or may not contain both a hydroxyl group and a heteroaryl group; and a pharmaceutically acceptable salt thereof (i.e., of a compound represented by formula I or I').

In a further aspect, the present invention relates to a compound of formula I' and pharmaceutically acceptable salts thereof:

I'

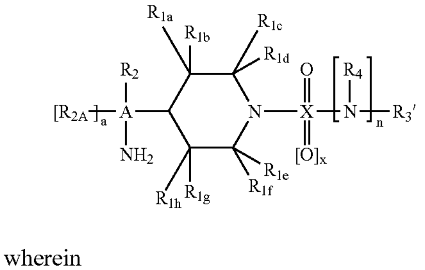

wherein

A may be, for example, a carbon or a nitrogen;

a may be, for example, 0 or 1, wherein, a may be 1 when A is carbon and a may be 0 when A is nitrogen;

x may be, for example, 0 or 1;

X may be, for example, a carbon or a sulfur, provided that X is carbon when x is 0, and/or X is sulfur when x is 1;

n may be, for example, 0 or 1;

each of $R_{1a}$, $R_{1b}$, $R_{1c}$, $R_{1d}$, $R_{1e}$, $R_{1f}$, $R_{1g}$, and $R_{1h}$ may be independently selected from the group consisting of:

hydrogen, a C1 to C30 alkyl group, which may be selected from the group consisting of a linear C1 to C30 alkyl group and a branched C1 to C30 alkyl group, a C4 to C30 cycloalkylalkyl group, a spirocycloalkyl group having, for example, a C2 to C5 bridging group, a C3 to C40 alkenyl group, a C3 to C10 alkylthioalkyl group, an alkoxy-containing alkyl group containing, for example, at least one oxygen atom and which may have of from 2 to 30 carbon atoms, an alkoxy-containing alkenyl group which may have of from 3 to 30 carbon atoms and which may further contain at least one oxygen atom, the oxygen atom may be allylic to or further removed from a double bond in the alkenyl group, a 2-poly(2-oxyethyl)ethyl group which may contain, for example, of from 2 to 30 oxygen atoms the 2-poly(2-oxyethyl)ethyl group may optionally be terminated by a group selected from the group consisting of a hydroxyl group and a methoxyl group, etc., an aralkyl group which may contain, for example, of from 7 to 30 carbons, the aryl group may optionally be substituted (i.e., may be substituted with a group or may be unsubstituted) with a group as defined herein, and an aralkyl group which may contain, for example, of from 7 to 30 carbons, the alkyl portion of the aralkyl may contain, for example, an ether group, for example, at least four of $R_{1a}$, $R_{1b}$, $R_{1c}$, $R_{1d}$, $R_{1e}$, $R_{1f}$, $R_{1g}$, and $R_{1h}$ may be hydrogen, more particularly at least two of $R_{1a}$, $R_{1b}$, $R_{1g}$, and $R_{1h}$ may be hydrogen and at least two of $R_{1c}$, $R_{1d}$, $R_{1e}$, and $R_{1f}$ may be hydrogen;

$R_2$ and $R_{2A}$ may independently be selected from the group consisting of:

hydrogen, a C1 to C30 alkyl group, a C3 to C10 cycloalkyl group, a C4 to C30 cycloalkylalkyl group, a C3 to C40 alkenyl group, a C3 to C40 alkynyl group, an alkoxy-containing alkyl group which may contain at least one ether oxygen atom and may further contain from 2 to 30 carbon atoms, a hydroxyl-containing alkyl group which may contain from 2 to 30 carbon atoms containing, for example, at least one hydroxyl substituent, a hydroxyl-containing alkyl group which may comprise an alkyl group of from 4 to 30 carbon atoms containing, for example, at least one hydroxyl substituent and the alkyl group may further contain, for example, at least one ether oxygen atom, the hydroxyl and ether groups may be separated by at least 1 or at least 2 carbon atoms, an alkoxy-containing alkenyl group which may contain at least one oxygen atom that may be allylic to or may be more distantly removed from a double bond in the alkenyl group, the alkenyl group may contain, for example, from 3 to 30 carbon atoms, a 2-poly(2-oxyethyl)ethyl group which may contain, for example, from 2 to 30 oxygen atoms, the group may optionally be terminated as a 2-methoxyethyl group, a 2-hydroxyethyl group, or a similar group.

an aryl group of 6 to 10 ring carbons which may optionally be substituted with a group selected, for example, from the group consisting of a lower alkyl, a lower cycloalkyl, a lower alkoxy, a lower alkenyl, an halogen, a perfluoro-lower alkyl, a nitro, a cyano, an amino, a lower alkyl amino, a di(lower alkyl)amino, a carboxyl, a carboxyl-substituted lower alkyl, an hydroxy, a phenyloxy, a linear polyethyleneglycol group containing from 3 to 30 oxygen atoms in the form, for example, of an omega-hydroxyl-terminated poly(oxyethyl) (or HO-PEG-) group, in the form of an omega-methoxy-terminated poly(oxyethyl) (or $CH_3O$-PEG- or MeO-PEG or MPEG) group, and combinations thereof, the phenyloxy group may optionally be substituted with a group selected, for example, from the group consisting of a lower alkyl, a lower alkoxy, a lower alkenyl, a lower cycloalkyl, a perfluoro-lower-alkyl, an halogen, and combinations thereof, an aralkyl group which may contain, for example, from 7 to 30 carbons, the aryl group of the aralkyl group may optionally be substituted with such group as defined herein, an aralkyl group which may contain, for example, from 7 to 30 carbons, the alkyl portion of the aralkyl may contain an ether group, and a 1-imidazolyl group which optionally may contain at the 2-, 4-, or 5-position a group such as an alkyl group, an alkoxyalkyl group, a cycloalkylalkyl group, an alkoxyalkyl group, or a polyethyleneglycol substituent group which may contain from 3 to 30 oxygen atoms such as in the form of a peg group or a methoxy-terminated peg group, or similarly, a 2-imidazolyl group which may optionally contain at the 1-, or 4/5-position a group which may be selected, for example, from the group consisting of an alkyl group, an alkoxyalkyl group, a cycloalkylalkyl group, an alkoxyalkyl group, a polyethyleneglycol substituent group which may contain from 3 to 30 oxygen atoms in the form of a HO-PEG-group and a methoxy-terminated MPEG group, a 4-imidazolyl group which may optionally contain at the 1- or 2-positions a group such as (selected from the group consisting of) an alkyl group, an alkoxyalkyl group, a cycloalkylalkyl group, an alkoxyalkyl group, or (and) a polyethyleneglycol group containing, for example, from 3 to 30 oxygen atoms in the form of, for example, a hydroxy-terminated peg group or a methoxy-terminated peg group, and similarly, a pyridinyl group which may be selected from the group consisting of 2-pyridyl, 3-pyridyl and 4-pyridyl and represented by formula (group-i):

(group-i)

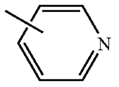

a substituted pyridinyl group which may be selected from the group consisting of substituted-2-pyridyl, 3-pyridyl, 4-pyridyl, 5-pyridyl, 6-pyridyl and represented by formula (group-ii):

(group-ii)

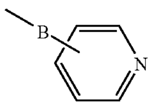

a 1H-indolyl group represented by formula (group-iii):

(group-iii)

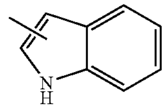

a 1H-indolyl-containing group represented by formula (group-iv):

(group-iv)

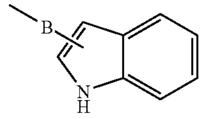

a substituted quinolyl group represented by formula (group-v):

(group-v)

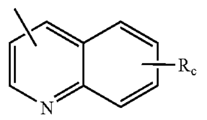

a substituted quinolyl-containing group represented by formula (group-vi):

(group-vi)

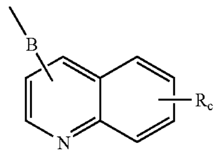

a substituted phenyl group represented by formula (group-vii):

(group-vii)

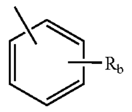

a substituted phenyl-containing (or phenylene) group represented by formula (group-viii):

(group-viii)

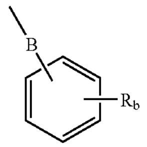

a substituted piperidinyl (or piperidylidinyl) group represented by formula (group-ix):

(group-ix)

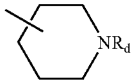

a substituted piperidinyl-containing (or piperidylidinyl) group represented by formula (group-x):

(group-x)

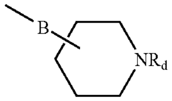

a 1H-pyrrolo[2,3-b]pyridinyl group represented by formula (group-xi):

(group-xi)

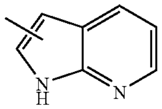

a 1H-pyrrolo[2,3-b]pyridinyl-containing group represented by formula (group-xii):

(group-xii)

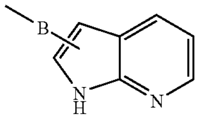

an isoquinolinyl group represented by formula (group-xiii):

(group-xiii)

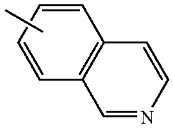

an isoquinolinyl-containing group represented by formula (group-xiv):

(group-xiv)

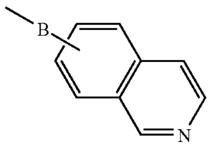

a 5-isoquinolyl group which can contain a hydroxy group substituent;

a 1H-imidazolyl group represented by formula (group-xv):

(group-xv)

a 1H-imidazolyl-containing group represented by formula (group-xvi):

(group-xvi)

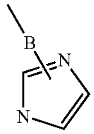

a 1H-indazolyl group represented by formula (group-xvii):

(group-xvii)

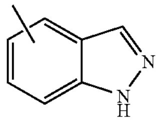

a 1H-indazolyl-containing group represented by formula (group-xviii):

(group-xviii)

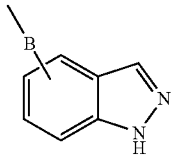

a purinyl group (a 9H-purinyl group) represented by formula (group-xix)

(group-xix)

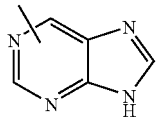

and a purinyl-containing group (or 9H-purinyl-containing group) represented by formula (group-xx):

(group-xx)

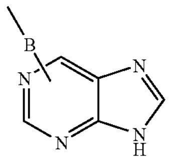

wherein

B may an alkylene linking group which may be selected from the group consisting of an unsubstituted straight chain linear alkylene group of, for example, from 1 to 20 carbon atoms, and a branched alkylene group which may comprise a linear alkylene group of, for example, from 1 to 20 carbon atoms which may be (optionally) substituted by an alkyl group of 1 to 4 carbon atoms;

$R_b$ may be selected, for example, from the group consisting of hydrogen, alkyl, amino, alkylamino, dialkylamino;

$R_c$ may be selected, for example, from the group consisting of hydrogen (H), and alkyl; and $R_d$ may be selected, for example, from the group consisting of hydrogen (H), alkyl, and aralkyl, for example, when n is 1, $R_3$' and $R_4$ may each independently be selected from the group consisting of:

hydrogen, an aryl group of 6 to 10 ring carbons which may optionally be substituted with a group selected from the group consisting of, for example, a lower alkyl, a lower cycloalkyl, a lower alkoxy, a lower alkenyl, an halogen, a perfluoro-lower alkyl, a nitro, a cyano, an amino, a lower alkyl amino, a di(lower alkyl)amino, a carboxyl, a carboxyl-substituted lower alkyl, an hydroxy, a phenyloxy, a linear polyethyleneglycol group which may contain from 3 to 30 oxygen atoms in the form, for example, of an omega-hydroxyl-terminated poly(oxyethyl) (or HO-PEG-) group or in the form of an omega-methoxy-terminated poly(oxyethyl) (or $CH_3O$-PEG- or MeO-PEG or MPEG) group, and similar group and combinations thereof, the phenyloxy group may optionally be substituted with a group which may be selected from the group consisting of a lower alkyl, a lower alkoxy, a lower alkenyl, a lower cycloalkyl, a perfluoro-lower-alkyl, an halogen, and combinations thereof, an aralkyl group which may containing from 7 to 30 carbons, the aryl group may optionally be substituted with a group as defined herein, an aralkyl group which may contain, for example, from 7 to 30 carbons wherein the alkyl portion of the aralkyl may contain an ether group, and a pyridinyl group which may be selected, for example, from the group consisting of 2-pyridyl, 3-pyridyl and 4-pyridyl and represented by formula (group-i):

(group-i)

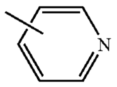

a substituted pyridinyl group which may be selected from the group consisting of substituted-2-pyridyl, 3-pyridyl, 4-pyridyl, 5-pyridyl and 6-pyridyl and represented by formula (group-ii):

(group-ii)

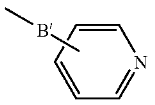

a 1H-indolyl group represented by formula (group-iii):

(group-iii)

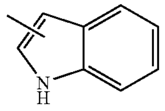

a 1H-indolyl-containing group represented by formula (group-iv):

(group-iv)

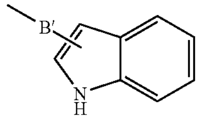

a substituted quinolyl group represented by formula (group-v):

(group-v)

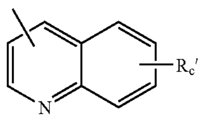

a substituted quinolyl-containing group represented by formula (group-vi):

(group-vi)

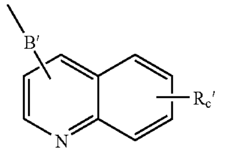

a substituted phenyl group represented by formula (group-vii):

(group-vii)

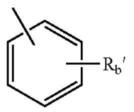

a substituted phenyl-containing (or phenylene) group represented by formula (group-viii):

(group-viii)

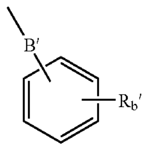

a substituted piperidinyl (or piperidylidinyl) group represented by formula (group-ix):

(group-ix)

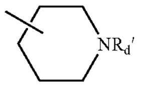

a substituted piperidinyl-containing (or piperidylidinyl) group represented by formula (group-x):

(group-x)

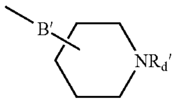

a 1H-pyrrolo[2,3-b]pyridinyl group represented by formula (group-xi):

(group-xi)

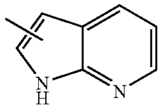

a 1H-pyrrolo[2,3-b]pyridinyl-containing group represented by formula (group-xii):

(group-xii)

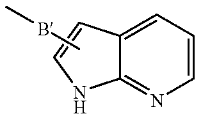

an isoquinolinyl group represented by formula (group-xiii):

(group-xiii)

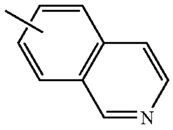

an isoquinolinyl-containing group represented by formula (group-xiv):

(group-xiv)

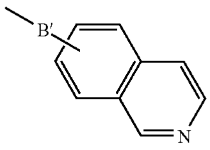

a 1H-imidazolyl group represented by formula (group-xv):

(group-xv)

a 1H-imidazolyl-containing group represented by formula (group-xvi):

(group-xv)

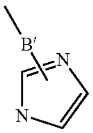

a 1H-indazolyl group represented by formula (group-xvii):

(group-xvii)

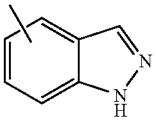

a 1H-indazolyl-containing group represented by formula (group-xviii):

(group-xviii)

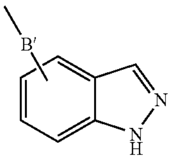

a purinyl group (a 9H-purinyl group) represented by formula (group-xix)

(group-xix)

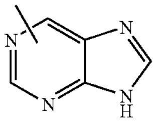

and a purinyl-containing group (or 9H-purinyl-containing group) represented by formula (group-xx):

(group-xx)

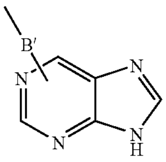

, wherein

B' may be, for example, a C1 to C20 linear or branched alkylene group, $R_b$' may be selected, for example, from the group consisting of hydrogen, alkyl, amino, alkylamino, and dialkylamino, $R_c$' may be selected, for example, from the group consisting of hydrogen and alkyl, and $R_d$' may be selected, for example, from the group consisting of hydrogen, alkyl, and aralkyl, It is to be understood that the B' group of compound of formula I' may be interchangeable with the corresponding B group of compound of formula I, II, III, IV, V, VI, VII, VIII, or IX. In addition, the $R_b$', $R_c$' or $R_d$' groups of compound of formula I' may be interchangeable with the corresponding $R_b$, $R_c$, or $R_d$ groups of compound of formula I, II, III, IV, V, VI, VII, VIII, o IX. Similarly, with other groups such as, for example, B", $R_b$", $R_c$" or $R_d$" etc. which may be interchangeable with corresponding groups of other molecules or compounds describred herein.

or $R_3$' and $R_4$ together inclusively with the nitrogen atom from which they are subtended may form a heterocyclic nitrogen-containing ring group, the nitrogen-containing ring group may be selected, for example, from the group consisting of A) a single ring, inclusively with the nitrogen atom, of from 5 to 7 atoms (e.g., in the ring portion) which may optionally have in the single ring an atom selected, for example, from the group consisting of an oxygen atom, a sulfur atom, and an additional nitrogen atom, and B) a fused ring structure, inclusively with the nitrogen atom, of from 8 to 16 atoms (e.g., in the ring portion), which may optionally have in the fused ring structure an atom which may be selected from the group consisting of an oxygen atom, a sulfur atom, and an additional nitrogen atom, the heterocyclic nitrogen-containing ring group may optionally have a substituent selected, for example, from the group consisting of a lower alkyl, a lower alkenyl, a lower alkynyl, a lower alkoxyalkyl, a lower alkoxy, a carboxyl (lower alkyl), a N-[carboxyl-(lower alkyl)]amino, a N,N-di(carboxyl-loweralkyl)amino, an amino, a di-(lower alkyl)amino, an halogen, and a perfluoro-(lower alkyl);

or when n is zero, $R_3$' may be selected, for example, from the group consisting of:

an aryl group of 6 to 10 ring carbons which may optionally e substituted, an aralkyl group which may contain from 7 to 30 carbons wherein the aryl group may optionally be substituted, and the alkyl portion of the aralkyl optionally may contain an ether group separated from X by, for example, at least two carbons, and a heteroaryl group may be attached directly to X at a carbon of the heteroaryl ring or optionally to X by a group B" that may be attached at a carbon of the heteroaryl ring, the heteroaryl group may be selected, for example, from the group consisting of a pyridinyl, a 1H-indolyl, a quinolyl substituted by a group $R_c$" at a carbon that is not attached to X or B", a piperidinyl substituted with a group $R_d$" at the 1-position of the piperidine ring, a 1H-pyrrolo[2,3-b]pyridinyl, an isoquinolinyl, a 1H-imidazolyl, a 1H-indazolyl, and a 9H-purinyl, wherein B" may be, for example, a C1 to C20 linear alkylene group which may optionally be substituted by an alkyl group of 1 to 4 carbon atoms, $R_c$" may be selected, for example, from the group consisting of hydrogen and C1 to C20 alkyl, and $R_d$" may be selected, for example, from the group consisting of hydrogen, C1 to C20 alkyl, and C7 to C20 aralkyl, and provided that in a $R_3$' group a carbon atom attached to X may not contain both a hydroxyl group and an aryl group or may not contain both a hydroxyl group and a heteroaryl group.

In one aspect, examples of compounds of the invention may be, for example, a substituted piperidine compound of structure I, wherein x is zero, X is carbon, a is one, A is carbon, and n is zero; or a substituted piperidine compound of structure I, wherein x is zero, X is carbon, a is one, A is carbon, each of $R_{1a}$, $R_{1b}$, $R_{1c}$, $R_{1d}$, $R_{1e}$, $R_{1f}$, $R_{1g}$, and $R_{1h}$ is hydrogen, and n is zero; or a substituted piperidine compound of structure I, wherein x is zero, X is carbon, a is one, A is carbon, each of $R_{1a}$, $R_{1b}$, $R_{1c}$, $R_{1d}$, $R_{1e}$, $R_{1f}$, $R_{1g}$, and $R_{1h}$ is hydrogen, one of $R_2$ and $R_{2A}$ is hydrogen and the other is alkyl, and n is zero.

In another aspect, compounds of the invention may be, for example, a substituted piperidine compound of structure I, wherein x is zero, X is carbon, a is one, A is carbon, and n is one; or a substituted piperidine compound of structure I, wherein x is zero, X is carbon, a is one, A is carbon, each of $R_{1a}$, $R_{1b}$, $R_{1c}$, $R_{1d}$, $R_{1e}$, $R_{1f}$, $R_{1g}$, and $R_{1h}$ is hydrogen, and n is one; or a substituted piperidine compound of structure I, wherein x is zero, X is carbon, a is one, A is carbon, each of $R_{1a}$, $R_{1b}$, $R_{1c}$, $R_{1d}$, $R_{1e}$, $R_{1f}$, $R_{1g}$, and $R_{1h}$ is hydrogen, one of $R_2$ and $R_{2A}$ is hydrogen and the other is alkyl, and n is one.

In another aspect, compounds of the invention may be, for example, a substituted piperidine compound of structure I, wherein x is one, X is sulfur, a is one, A is carbon, and n is zero; or a substituted piperidine compound of structure I, wherein x is one, X is sulfur, a is one, A is carbon, each of $R_{1a}$, $R_{1b}$, $R_{1c}$, $R_{1d}$, $R_{1e}$, $R_{1f}$, $R_{1g}$, and $R_{1h}$ is hydrogen, and n is zero; or a substituted piperidine compound of structure I, wherein x is one, X is sulfur, a is one, A is carbon, each of $R_{1a}$, $R_{1b}$, $R_{1c}$, $R_{1d}$, $R_{1e}$, $R_{1f}$, $R_{1g}$, and $R_{1h}$ is hydrogen, one of $R_2$ and $R_{2A}$ is hydrogen and the other is alkyl, and n is zero.

In another aspect, exemplary compounds of the invention may be a substituted piperidine compound of structure I, wherein x is one, X is sulfur, a is one, A is carbon, and n is one; or a substituted piperidine compound of structure I, wherein x is one, X is sulfur, a is one, A is carbon, each of $R_{1a}$, $R_{1b}$, $R_{1c}$, $R_{1d}$, $R_{1e}$, $R_{1f}$, $R_{1g}$, and $R_{1h}$ is hydrogen, and n is one; or a substituted piperidine compound of structure I, wherein x is one, X is sulfur, a is one, A is carbon, each of $R_{1a}$, $R_{1b}$, $R_{1c}$, $R_{1d}$, $R_{1e}$, $R_{1f}$, $R_{1g}$, and $R_{1h}$ is hydrogen, one of $R_2$ and $R_{2A}$ is hydrogen and the other is alkyl, and n is one.

In another aspect, other exemplary compounds of the invention may be a substituted piperidine compound of structure I, wherein x is zero, X is carbon, a is zero, A is nitrogen, and n is zero; or a substituted piperidine compound of structure I, wherein x is zero, X is carbon, a is zero, A is nitrogen, each of $R_{1a}$, $R_{1b}$, $R_{1c}$, $R_{1d}$, $R_{1e}$, $R_{1f}$, $R_{1g}$, and $R_{1h}$ is hydrogen, and n is zero; or a substituted piperidine compound of structure I, wherein x is zero, X is carbon, a is zero, A is nitrogen, each of $R_{1a}$, $R_{1b}$, $R_{1c}$, $R_{1d}$, $R_{1e}$, $R_{1f}$, $R_{1g}$, and $R_{1h}$ is hydrogen, $R_2$ is selected from the group consisting of hydrogen and alkyl, and n is zero.

In another aspect, compounds of the invention may be, for example, a substituted piperidine compound of structure I, wherein x is zero, X is carbon, a is zero, A is nitrogen, and n is one; or a substituted piperidine compound of structure I, wherein x is zero, X is carbon, a is zero, A is nitrogen, each of $R_{1a}$, $R_{1b}$, $R_{1c}$, $R_{1d}$, $R_{1e}$, $R_{1f}$, $R_{1g}$, and $R_{1h}$, is hydrogen, and n is one; or a substituted piperidine compound of structure I, wherein x is zero, X is carbon, a is zero, A is nitrogen, each of $R_{1a}$, $R_{1b}$, $R_{1c}$, $R_{1d}$, $R_{1e}$, $R_{1f}$, $R_{1g}$, and $R_{1h}$ is hydrogen, $R_2$ is selected from the group consisting of hydrogen and alkyl, and n is one.

In another aspect, compounds of the invention may be, for example, a substituted piperidine compound of structure I, wherein x is one, X is sulfur, a is zero, A is nitrogen, and n is zero; or a substituted piperidine compound of structure I, wherein x is one, X is sulfur, a is zero, A is nitrogen, each of $R_{1a}$, $R_{1b}$, $R_{1c}$, $R_{1d}$, $R_{1e}$, $R_{1f}$, $R_{1g}$, and $R_{1h}$ is hydrogen, and n is zero; or a substituted piperidine compound of structure I, wherein x is one, X is sulfur, a is zero, A is nitrogen, each of $R_{1a}$, $R_{1b}$, $R_{1c}$, $R_{1d}$, $R_{1e}$, $R_{1f}$, $R_{1g}$, and $R_{1h}$ is hydrogen, $R_2$ is selected from the group consisting of hydrogen and alkyl, and n is zero.

In another aspect, exemplary compounds of the invention may be a substituted piperidine compound of structure I, wherein x is one, X is sulfur, a is zero, A is nitrogen, and n is one; or a substituted piperidine compound of structure I, wherein x is one, X is sulfur, a is zero, A is nitrogen, each of $R_{1a}$, $R_{1b}$, $R_{1c}$, $R_{1d}$, $R_{1e}$, $R_{1f}$, $R_{1g}$, and $R_{1h}$ is hydrogen, and n is one; or a substituted piperidine compound of structure I, wherein x is one, X is sulfur, a is zero, A is nitrogen, each of $R_{1a}$, $R_{1b}$, $R_{1c}$, $R_{1d}$, $R_{1e}$, $R_{1f}$, $R_{1g}$, and $R_{1h}$ is hydrogen, $R_2$ is selected from the group consisting of hydrogen and alkyl, and n is one.

In another aspect, the invention provides a pharmaceutical composition which may comprise a compound of structure I or I' and a pharmaceutically acceptable carrier therefor; or more particularly a pharmaceutical composition which may comprise a compound of structure I or I' and a pharmaceutically acceptable carrier therefor, wherein the carrier may comprise, for example, a sterile isotonic aqueous solution suitable for injection; or even more particularly a pharmaceutical composition which may comprising a compound of structure I or I' and a pharmaceutically acceptable carrier therefor, wherein the carrier may comprise, for example, a sterile isotonic aqueous solution suitable for injection, and wherein the solution may comprise a buffer salt; or for example, a pharmaceutical composition which may comprise a compound of structure I or I' and a pharmaceutically acceptable carrier therefor, wherein the carrier may comprise a sterile isotonic aqueous solution suitable for injection, wherein the solution may comprise, for example, phosphate buffered saline.

In another embodiment, the invention further relates to a pharmaceutical composition which may comprise a (at least one) substituted piperidine compound (and/or a pharmaceutically acceptable salt thereof) and a pharmaceutically acceptable carrier therefor; wherein the carrier may comprise a sterile isotonic aqueous solution suitable for injection, and wherein the solution may comprise a buffer salt such as phosphate buffered saline.

In another aspect, the invention further relates to a method of treatment of an injury or disease of a nerve of the central nervous system in a mammal which may comprise administration (adminstering) to the mammal of a therapeutically effective amount of a compound of structure I or I'; or more particularly a method of treatment of an injury or disease of a nerve of the central nervous system in a mammal which may comprise administration to the mammal of a therapeutically effective amount of a compound as described herein.

In another aspect, the invention provides a method of treatment of (for treating) an injury or disease of a nerve of the central nervous system in a mammal which may comprise administration to the mammal of a therapeutically effective amount of a pharmaceutical composition comprising a compound of structure I or I' and a pharmaceutically acceptable carrier therefor; or a pharmaceutical composition comprising a compound as described herein and a pharmaceutically acceptable carrier therefor.

In another aspect, the invention provides a method of treatment of a cancer in a mammal which may comprise administration to the mammal of a therapeutically effective amount of a compound of structure I or I'; wich may comprise administration to the mammal of a therapeutically effective amount of a compound described herein.

In another aspect, the invention comprises a method of treatment of a cancer in a mammal which may comprise administration to the mammal of a therapeutically effective amount of a pharmaceutical composition which may comprise a compound of structure I or I' and a pharmaceutically acceptable carrier therefor; or more particularly a pharmaceutical composition which may comprise a compound as described herein and a pharmaceutically acceptable carrier therefor.

In another aspect, the invention comprises a method of treatment of macular degeneration in a mammal which may comprise administration to the mammal of a therapeutically effective amount of a compound of structure I or I'; which may comprise administration to the mammal of a therapeutically effective amount of a compound described herein.

In another aspect, the invention relates to a method of treatment of macular degeneration in a mammal which method may comprise administration to the mammal of a therapeutically effective amount of a pharmaceutical composition which may comprise a compound of structure I or I' and a pharmaceutically acceptable carrier therefor; or a pharmaceutical composition which may comprise a compound as described herein and a pharmaceutically acceptable carrier therefor.

In another aspect, the invention comprises a method of inhibiting the enzyme rho kinase in a cell which method may comprise administration of a compound of structure I or I' to the cell; wherein the cell may reside in a mammal. In a further aspect, the invention comprises a method of inhibiting the enzyme rho kinase in a cell which may comprise administration to a cell of a compound of the invention as described herein; wherein the cell may reside in a mammal.

The present invention also relates to the use of a compound as described herein for treatment of a disease (or an individual having a disease) defined herein.

The present invention further relates to the use of a compound described herein in the manufacture of a pharmaceutical composition for the treatment of a disease or condition as defined herein.

Compounds and compositions such as a pharmaceutical composition of a compound having the structure represented by formula I of I' may comprise all spatial or geometrically related isomers including all cis- and trans-ring-substituted isomers, all optical isomers and epimers and mixtures of optical isomers, racemic mixtures, diastereomers, enantiomers, rotational isomers, mirror images, and comformational isomers, and isomers that may arise in the form of a salt of a compound of formula I or I', such as an acid salt such as a pharmaceutically acceptable acid salt.

In one aspect of the present invention, an exemplary compound of the present invention is a 4-aminoalkylpiperidine amide wherein the piperidine-1-nitrogen may be attached to the carbonyl of the amide, this amide compound represented by formula II, which is, for example, a compound of formula I wherein x may be zero, 0; X may be carbon, C; a may be one, 1; A may be carbon, C; and n may be zero, 0; and wherein $R_{1a}$, $R_{1b}$, $R_{1c}$, $R_{1d}$, $R_{1e}$, $R_{1f}$, $R_{1g}$, $R_{1h}$, $R_2$, $R_{2A}$, and $R_3$ may be as defined above for formula I, and to pharmaceutically acceptable salts thereof.

II

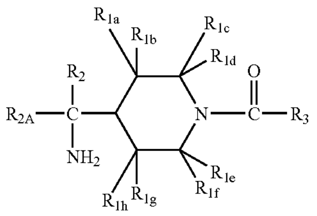

In another aspect of the present invention, a further exemplary compound of the present invention is a urea that incorporates a 4-(aminoalkyl)piperidine wherein the piperidine-1-nitrogen may be attached to the carbonyl of the urea, this urea compound represented by formula III, which is a compound of formula I wherein x may be zero, 0; X may be carbon, C; a may be one, 1; A may be carbon, C; and n may be one, 1; and wherein $R_{1a}$, $R_{1b}$, $R_{1c}$, $R_{1d}$, $R_{1e}$, $R_{1f}$, $R_{1g}$, $R_{1h}$, $R_2$, $R_{2A}$, $R_3$ and $R_4$ may be as defined above for formula I, and to pharmaceutically acceptable salts thereof.

III

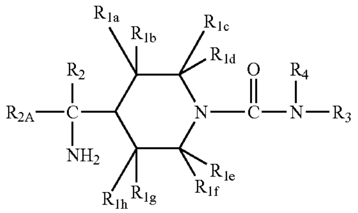

In another aspect of the present invention, an additional exemplary compound of the present invention is a 4-(aminoalkyl)-1-(sulfonyl)piperidine wherein the piperidine-1-nitrogen may be attached to the sulfur of the sulfonyl group, this sulfonylpiperidine compound represented by formula IV, which is a compound of formula I wherein x may be one, 1; X may be sulfur, S; a may be one, 1; A may be carbon, C; and n may be zero, 0; and wherein $R_{1a}$, $R_{1b}$, $R_{1c}$, $R_{1d}$, $R_{1e}$, $R_{1f}$, $R_{1g}$, $R_{1h}$, $R_2$, $R_{2A}$, and $R_3$ may be as defined above for formula I, and to pharmaceutically acceptable salts thereof.

IV

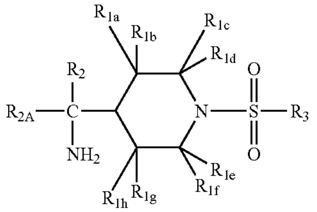

In another aspect of the present invention, a further exemplary compound of the present invention is a 4-(aminoalkyl)-1-piperidine sulfamide, wherein the piperidine-1-nitrogen may be attached to the sulfur of the sulfonyl group, this sulfamide compound represented by formula V, which is a compound of formula I wherein x may be one, 1; X may be sulfur, S; a may be one, 1; A may be carbon, C; and n may be one, 1; and wherein $R_{1a}$, $R_{1b}$, $R_{1c}$, $R_{1d}$, $R_{1e}$, $R_{1f}$, $R_{1g}$, $R_{1h}$, $R_2$, $R_{2A}$, $R_3$, and $R_4$ may be as defined above for formula I, and to pharmaceutically acceptable salts thereof.

V

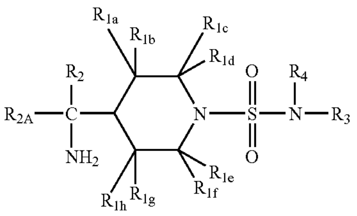

In another aspect of the present invention, another exemplary compound of the present invention is a 4-hydrazinylpiperidine amide, wherein the piperidine-1-nitrogen may be attached to the carbonyl of the amide, this amide compound represented by formula VI, which is a compound of formula I wherein x may be zero, 0; X may be carbon, C; a may be is zero, 0; A may be nitrogen, N; and n may be zero, 0; and wherein $R_{1a}$, $R_{1b}$, $R_{1c}$, $R_{1d}$, $R_{1e}$, $R_{1f}$, $R_{1g}$, $R_{1h}$, $R_2$, and $R_3$ may be as defined above for formula I, and to pharmaceutically acceptable salts thereof.

VI

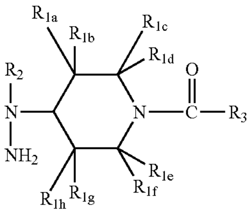

In another aspect of the present invention, an additional exemplary compound of the present invention is a urea that may incorporate a 4-hydrazinylpiperidine in which the piperidine-1-nitrogen may be attached to the carbonyl of the urea, this urea compound represented by formula VII, which is a compound of formula I wherein x may be zero, 0; X is carbon, C; a may be zero, 0; A may be nitrogen, N; and n may be one, 1; and wherein $R_{1a}$, $R_{1b}$, $R_{1c}$, $R_{1d}$, $R_{1e}$, $R_{1f}$, $R_{1g}$, $R_{1h}$, $R_2$, $R_3$, and $R_4$ may be as defined above for formula I, and to pharmaceutically acceptable salts thereof.

VII

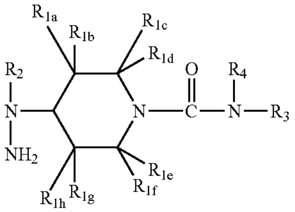

In another aspect of the present invention, a further exemplary compound of the present invention is a 4-hydrazinyl-1-(sulfonyl)piperidine, wherein the piperidine-1-nitrogen may be attached to the sulfur of the sulfonyl group, this sulfonylpiperidine compound represented by formula VIII, which is a compound of formula I wherein x is one, 1; X may be sulfur, S; a may be zero, 0; A may be nitrogen, N; and n may be zero, 0; and wherein $R_{1a}$, $R_{1b}$, $R_{1c}$, $R_{1d}$, $R_{1e}$, $R_{1f}$, $R_{1g}$, $R_{1h}$, $R_2$, and $R_3$ may be as defined above for formula I, and to pharmaceutically acceptable salts thereof.

VIII

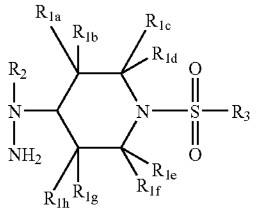

In another aspect of the present invention, an additional exemplary compound of the present invention is a 4-(hydrazinyl)-1-piperidine sulfamide, wherein the piperidine-1-nitrogen may be attached to the sulfur of the sulfonyl group, this sulfamide compound represented by formula IX, which is a compound of formula I wherein x may be one, 1; X may be sulfur, S; a may be zero, 0; A may be nitrogen, N; and n may be one, 1; and wherein $R_{1a}$, $R_{1b}$, $R_{1c}$, $R_{1d}$, $R_{1e}$, $R_{1f}$, $R_{1g}$, $R_{1h}$, $R_2$, $R_3$, and $R_4$ may be as defined above for formula I, and to pharmaceutically acceptable salts thereof.

IX

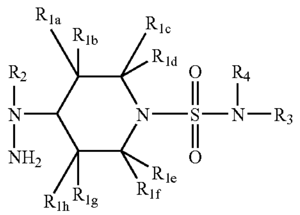

With respect to substitution patterns related to substituents $R_{1a}$, $R_{1b}$, $R_{1c}$, $R_{1d}$, $R_{1e}$, $R_{1f}$, $R_{1g}$, and $R_{1h}$ on the piperidine ring of Formula I at ring positions 2, 3, 5, and 6, and with respect to other aspects of this invention represented by Formulas I', II, III, IV, V, VI, VII, VIII, and IX, the following embodiments I-(i) to I-(xvii) obtain.

I-(i): Example of all Hydrogen

In one embodiment of a compound of formula I, or of a compound of formula I', II, III, IV, V, VI, VII, VIII, or IX, and to pharmaceutically acceptable salts thereof, each of $R_{1a}$, $R_{1b}$, $R_{1c}$, $R_{1d}$, $R_{1e}$, $R_{1f}$, $R_{1g}$, and $R_{1h}$ may be hydrogen.

I-(ii): Example of One Substituent at Position-2

In another embodiment of a compound of formula I, or of a compound of formula I', II, III, IV, V, VI, VII, VIII, or IX, and to pharmaceutically acceptable salts thereof, each of $R_{1a}$, $R_{1b}$, $R_{1e}$, $R_{1f}$, $R_{1g}$, and $R_{1b}$ may be hydrogen, and only one of $R_{1c}$ and $R_{1d}$ may be hydrogen while the other of $R_{1c}$ and $R_{1d}$ may be as defined above but is not hydrogen. In this aspect, a single non-hydrogen substituent as defined above for $R_{1c}$ and $R_{1d}$ may occupy 2-position (or the optically enatiomeric 6-position) of the piperidine ring of formula Ia, and may comprise an equitorial or axial substituent, and may include all enantiomeric mirror images, and relative to the substituent at the 4-position of the piperidine may be equitorial or axial.

I-(iii): Example of One Substituent at Position-3

In another embodiment of a compound of formula I, or of a compound of formula I', II, III, IV, V, VI, VII, VIII, or IX, and to pharmaceutically acceptable salts thereof, each of $R_{1a}$, $R_{1b}$, $R_{1c}$, $R_{1d}$, $R_{1e}$, $R_{1f}$, $R_{1g}$, and $R_{1h}$ may be hydrogen, and only one of $R_{1a}$ and $R_{1b}$ may be hydrogen while the other of $R_{1a}$ and $R_{1b}$ may be as defined above but is not hydrogen. In this aspect, a single non-hydrogen substituent as defined above for $R_{1a}$ and $R_{1b}$ may occupy 3-position (or the optically enantiomeric 5-position) of the piperidine ring of formula Ia, and comprises an equitorial or axial substituent, includes all enantiomeric mirror images, and relative to the substituent at the 4-position of the piperidine may be equitorial or axial.

I-(iv): Example of Two Substituents at Position-2, Geminal

In another embodiment of a compound of formula I, or of a compound of formula I', II, III, IV, V, VI, VII, VIII, or IX, and to pharmaceutically acceptable salts thereof, each of $R_{1a}$, $R_{1b}$, $R_{1e}$, $R_{1f}$, $R_{1g}$, and $R_{1h}$ may be hydrogen, and each of $R_{1c}$ and $R_{1d}$ may be as defined above but is not hydrogen. In this aspect, two non-hydrogen substituents as defined above for $R_{1c}$ and $R_{1d}$ may occupy geminally the 2-position (or in a mirror image sense, the optically enantiomeric 6-position) of the piperidine ring of formula Ia, and may comprise an equitorial and an axial substituent at the 2-position. This embodiment may include all enantiomeric mirror images and geometric isomers relative to the 4-position.

I-(v): Example of Two Substituents at Position-3, Geminal

In another embodiment of a compound of formula I, or of a compound of formula I', II, III, IV, V, VI, VII, VIII, or IX, and to pharmaceutically acceptable salts thereof, each of $R_{1c}$, $R_{1d}$, $R_{1e}$, $R_{1f}$, $R_{1g}$, and $R_{1h}$ may be hydrogen, and each of $R_{1a}$ and $R_{1b}$ may be as defined above but is not hydrogen. In this aspect, two non-hydrogen substituents as defined above for $R_{1a}$ and $R_{1b}$ may occupy geminally the 3-position (or in a mirror image sense, the optically enantiomeric 5-position) of the piperidine ring of formula Ia, and may comprise an equitorial and an axial substituent at the 3-position. This embodiment includes all enantiomeric mirror images and geometric isomers relative to the 4-position.

I-(vi): Example of Two Substituents, One at Position-2 and One at Position-3, Ortho In another embodiment of a compound of formula I, or of a compound of formula I', II, III, IV, V, VI, VII, VIII, or IX, and to pharmaceutically acceptable salts thereof, each of $R_{1e}$, $R_{1f}$, $R_{1g}$, and $R_{1h}$ may be hydrogen, only one of $R_{1a}$ and $R_{1b}$ may be hydrogen while the other of $R_{1a}$ and $R_{1b}$ may be as defined above but is not hydrogen, and only one of $R_{1c}$ and $R_{1d}$ may be hydrogen while the other of $R_{1c}$ and $R_{1d}$ may be as defined above but is not hydrogen. In this aspect, one non-hydrogen substituent as defined above for $R_{1a}$ and $R_{1b}$ may occupy the 3-position and one non-hydrogen substituent as defined above for $R_{1c}$ and $R_{1c}$ may occupy the 2-position (or in a mirror image sense, the respective optically enantiomeric positions 5 and 6) of the piperidine ring of formula Ia. The two substituents may be ortho to each other. The two substituents may be related geometrically as both equitorial, both axial, or one equitorial and one axial. This embodiment includes all enantiomeric mirror images and geometric isomers relative to the 4-position.

I-(vii): Example of Two Substituents, One at Position-2 and One at Position-5, Para In another embodiment of a compound of formula I, or of a compound of formula I', II, III, IV, V, VI, VII, VIII, or IX, and to pharmaceutically acceptable salts thereof, each of $R_{1a}$, $R_{1b}$, $R_{1e}$, and $R_{1f}$ may be hydrogen, only one of $R_{1c}$ and $R_{1d}$ may be hydrogen while the other of $R_{1c}$ and $R_{1d}$ may be as defined above but is not hydrogen, and only one of $R_{1h}$ and $R_{1g}$ may be hydrogen while the other of $R_{1h}$ and $R_{1g}$ may be as defined above but is not hydrogen. In this aspect, one non-hydrogen substituent as defined above for $R_{1c}$ and $R_{1d}$ occupies the 2-position and one non-hydrogen substituent as defined above for $R_{1h}$ and $R_{1g}$ may occupy the 5-position (or in a mirror image sense, the respective optically enantiomeric positions 6 and 3) of the piperidine ring of formula Ia. The two substituents may be para to each other in the 6-membered ring. The two substituents may be related geometrically as both equitorial, both axial, or one equitorial and one axial. This embodiment includes all enantiomeric mirror images and geometric isomers relative to the 4-position.

I-(viii): Example of Two Substituents, One at Position-2 and One at Position-6, Meta In another embodiment of a compound of formula I, or of a compound of formula I', II, III, IV, V, VI, VII, VIII, or IX, and to pharmaceutically acceptable salts thereof, each of $R_{1a}$, $R_{1b}$, $R_{1g}$, and $R_{1h}$ may be hydrogen, only one of $R_{1c}$ and $R_{1d}$ may be hydrogen while the other of $R_{1c}$ and $R_{1d}$ may be as defined above but is not hydrogen, and only one of $R_{1e}$ and $R_{1f}$ is hydrogen while the other of $R_{1e}$ and $R_{1f}$ may be as defined above but is not hydrogen. In this aspect, one non-hydrogen substituent as defined above for $R_{1c}$ and $R_{1d}$ may occupy the 2-position and one non-hydrogen substituent as defined above for $R_{1e}$ and $R_{1f}$ may occupy the 6-position [in a mirror image sense, the 2 and 6 positions may be related optically enantiomeric positions] of the piperidine ring of formula Ia. The two substituents may be meta to each other in the 6-membered ring. The two substituents may be related geometrically as both equitorial, both axial, or one equitorial and one axial. This embodiment includes all enantiomeric mirror images and geometric isomers relative to the 4-position.

I-(ix): Example of Two Substituents, One at Position-3 and One at Position-5, Meta In another embodiment of a compound of formula I, or of a compound of formula I', II, III, IV, V, VI, VII, VIII, or IX, and to pharmaceutically acceptable salts thereof, each of $R_{1c}$, $R_{1d}$, $R_{1e}$, and $R_{1f}$ may be hydrogen, only one of $R_{1a}$ and $R_{1b}$ may be hydrogen while the other of $R_{1a}$ and $R_{1b}$ may be as defined above but is not hydrogen, and only one of $R_{1g}$ and $R_{1h}$ may be hydrogen while the other of $R_{1g}$ and $R_{1h}$ may be as defined above but is not hydrogen. In this aspect, one non-hydrogen substituent as defined above for $R_{1a}$ and $R_{1b}$ may occupy the 3-position and one non-hydrogen substituent as defined above for $R_{1g}$ and $R_{1h}$ may occupy the 5-position [in a mirror image sense, the 3 and 5 positions may be related optically enantiomeric positions] of the piperidine ring of formula Ia. The two substituents may be meta to each other in the 6-membered ring. The two substituents may be related geometrically as both equitorial, both axial, or one equitorial and one axial. This embodiment includes all enantiomeric mirror images and geometric isomers relative to the 4-position.

I-(x): Example of Three Substituents, Two at Position-2 and One at Position-3

In another embodiment of a compound of formula I, or of a compound of formula I', II, III, IV, V, VI, VII, VIII, or IX, and to pharmaceutically acceptable salts thereof, each of $R_{1e}$, $R_{1f}$, $R_{1g}$, and $R_{1h}$ may be hydrogen, only one of $R_{1a}$ and $R_{1b}$ may be hydrogen while the other of $R_{1a}$ and $R_{1b}$ may be as defined above but is not hydrogen, and each of $R_{1c}$ and $R_{1d}$ may be as defined above but is not hydrogen. In this aspect, one non-hydrogen substituent as defined above for $R_{1a}$ and $R_{1b}$ may occupy the 3-position and two non-hydrogen substituents as defined above for $R_{1c}$ and $R_{1d}$ may occupy the 2-position [in a mirror image sense, the 3 and 5 positions may be related optically enantiomeric positions and the 2,2 and 6,6 positions may be related optically enantiomeric positions] of the piperidine ring of formula Ia. Two substituents may be geminal at the 2-position, and one substituent may be ortho to each of the two geminal substituents in the 6-membered ring. The single substituent at $R_{1a}$ or $R_{1b}$ may be either axial or equitorial while $R_{1c}$ may be axial or equitorial while $R_{1d}$ is equitorial or axial, respectively. This embodiment includes all enantiomeric mirror images and geometric isomers relative to the 4-position.

I-(xi): Example of Three Substituents, Two at Position-2 and One at Position-5

In another embodiment of a compound of formula I, or of a compound of formula I', II, III, IV, V, VI, VII, VIII, or IX, and to pharmaceutically acceptable salts thereof, each of $R_{1a}$, $R_{1b}$, $R_{1e}$, and $R_{1f}$ may be hydrogen, only one of $R_{1g}$ and $R_{1h}$ may be hydrogen while the other of $R_{1g}$ and $R_{1h}$ may be as defined above but is not hydrogen, and each of $R_{1c}$ and $R_{1d}$ may be as defined above but is not hydrogen. In this aspect, one non-hydrogen substituent as defined above for $R_{1g}$ and $R_{1h}$ may occupy the 5-position and two non-hydrogen substituents as defined above for $R_{1c}$ and $R_{1d}$ may occupy the 2-position [in a mirror image sense, the 5 and 3 positions may be related optically enantiomeric positions and the 2,2 and 6,6 positions may be related optically enantiomeric positions] of the piperidine ring of formula Ia. Two substituents may be geminal at the 2-position, and one substituent is para to each of the two geminal substituents in the 6-membered ring. The single substituent at $R_{1g}$ or $R_{1h}$ may be either axial or equitorial while $R_{1c}$ may be axial or equitorial while $R_{1d}$ may be equitorial or axial, respectively. This embodiment includes all enantiomeric mirror images and geometric isomers relative to the 4-position.

I-(xii): Example of Three Substituents, Two at Position-2 and One at Position-6

In another embodiment of a compound of formula I, or of a compound of formula I', II, III, IV, V, VI, VII, VIII, or IX, and to pharmaceutically acceptable salts thereof, each of $R_{1a}$, $R_{1b}$, $R_{1g}$, and $R_{1h}$ may be hydrogen, only one of $R_{1e}$ and $R_{1f}$ may be hydrogen while the other of $R_{1e}$ and $R_{1f}$ may be as defined above but is not hydrogen, and each of $R_{1c}$ and $R_{1d}$ may be as defined above but is not hydrogen. In this aspect, one non-hydrogen substituent as defined above for $R_{1e}$ and $R_{1f}$ may occupies the 6-position and two non-hydrogen substituents as defined above for $R_{1c}$ and $R_{1d}$ may occupy the 2-position [in a mirror image sense, the 2,2,6 and 2,6,6 positions may be related optically enantiomeric positions] of the piperidine ring of formula Ia. Two substituents are geminal at the 2-position, and one substituent may be meta to each of the two geminal substituents in the 6-membered ring. The single substituent at $R_{1e}$ or $R_{1f}$ may be either axial or equitorial while $R_{1c}$ may be axial or equitorial while $R_{1d}$ may be equitorial or axial, respectively. This embodiment includes all enantiomeric mirror images and geometric isomers relative to the 4-position.

I-(xiii): Example of Three Substituents, One at Position-2 and Two at Position-3

In another embodiment of a compound of formula I, or of a compound of formula I' II, III, IV, V, VI, VII, VIII, or IX, and to pharmaceutically acceptable salts thereof, each of $R_{1e}$, $R_{1f}$, $R_{1g}$, and $R_{1h}$ may be hydrogen, only one of $R_{1c}$ and $R_{1d}$ may be hydrogen while the other of $R_{1c}$ and $R_{1d}$ may be as defined above but is not hydrogen, and each of $R_{1a}$ and $R_{1b}$ may be as defined above but is not hydrogen. In this aspect, one non-hydrogen substituent as defined above for $R_{1c}$ and $R_{1d}$ may occupy the 2-position and two non-hydrogen substituents as defined above for $R_{1a}$ and $R_{1b}$ may occupy the 3-position [in a mirror image sense, the 2,3,3 and 6,5,5 positions may be related optically enantiomeric positions] of the piperidine ring of formula Ia. Two substituents are geminal at the 3-position, and one substituent may be ortho to each of the two geminal substituents in the 6-membered ring. The single substituent at $R_{1c}$ or $R_{1d}$ may be either axial or equitorial while $R_{1a}$ may be axial or equitorial while $R_{1b}$ is equitorial or axial, respectively. This embodiment includes all enantiomeric mirror images and geometric isomers relative to the 4-position.

I-(xiv): Example of Three Substituents, One at Position-5 and Two at Position-3

In another embodiment of a compound of formula I, or of a compound of formula I', II, III, IV, V, VI, VII, VIII, or IX, and to pharmaceutically acceptable salts thereof, each of $R_{1c}$, $R_{1d}$, $R_{1e}$, and $R_{1f}$ may be hydrogen, only one of $R_{1g}$ and $R_{1h}$ may be hydrogen while the other of $R_{1g}$ and $R_{1h}$ may be as defined above but is not hydrogen, and each of $R_{1a}$ and $R_{1b}$ may be as defined above but is not hydrogen. In this aspect, one non-hydrogen substituent as defined above for $R_{1g}$ and $R_{1h}$ may occupy the 5-position and two non-hydrogen substituents as defined above for $R_{1a}$ and $R_{1b}$ may occupy the 3-position [in a mirror image sense, the 3,3,5 and 5,5,3 positions may be related optically enantiomeric positions] of the piperidine ring of formula Ia. Two substituents may be geminal at the 3-position, and one substituent may be meta to each of the two geminal substituents in the 6-membered ring. The single substituent at $R_{1g}$ or $R_{1h}$ may be either axial or equitorial while $R_{1a}$ may be axial or equitorial while $R_{1b}$ may be equitorial or axial, respectively. This embodiment includes all enantiomeric mirror images and geometric isomers relative to the 4-position.

I-(xv): Example of Three Substituents, One at Position-6 and Two at Position-3

In another embodiment of a compound of formula I, or of a compound of formula I', II, III, IV, V, VI, VII, VIII, or IX, and to pharmaceutically acceptable salts thereof, each of $R_{1c}$, $R_{1d}$, $R_{1g}$, and $R_{1h}$ may be hydrogen, only one of $R_{1e}$ and $R_{1f}$ may be hydrogen while the other of $R_{1e}$ and $R_{1f}$ may be as defined above but is not hydrogen, and each of $R_{1a}$ and $R_{1b}$ may be as defined above but is not hydrogen. In this aspect, one non-hydrogen substituent as defined above for $R_{1e}$ and $R_{1f}$ may occupy the 6-position and two non-hydrogen substituents as defined above for $R_{1a}$ and $R_{1b}$ may occupy the 3-position [in a mirror image sense, the 3,3,6 and 5,5,2 positions may be related optically enantiomeric positions] of the piperidine ring of formula Ia. Two substituents may be geminal at the 3-position, and one substituent may be para to each of the two geminal substituents in the 6-membered ring. The single substituent at $R_{1e}$ or $R_{1f}$ may be either axial or equitorial while $R_{1a}$ may be axial or equitorial while $R_{1b}$ may be equitorial or axial, respectively. This embodiment includes all enantiomeric mirror images and geometric isomers relative to the 4-position.

I-(xvi): Example of Four Substituents, One at Each of Position-2, -3, -5 and -6

In another embodiment of a compound of formula I, or of a compound of formula I', II, III, IV, V, VI, VII, VIII, or IX, and to pharmaceutically acceptable salts thereof, only one of $R_{1a}$ and $R_{1b}$ may be hydrogen, only one of $R_{1c}$ and $R_{1d}$ may be hydrogen, only one of $R_{1e}$ and $R_{1f}$ may be hydrogen, and only one of $R_{1g}$ and $R_{1h}$ may be hydrogen, while the other of $R_{1a}$ and $R_{1b}$ may be as defined above but is not hydrogen, the other of $R_{1c}$ and $R_{1d}$ may be as defined above but is not hydrogen, the other of $R_{1e}$ and $R_{1f}$ may be as defined above but is not hydrogen, and the other of $R_{1g}$ and $R_{1h}$ may be as defined above but is not hydrogen. In this aspect, one non-hydrogen substituent as defined above for each of $R_{1c}$ and $R_{1d}$ may occupy position 2 and one non-hydrogen substituent as defined above for each of $R_{1a}$ and $R_{1b}$ may occupy position 3 and one non-hydrogen substituent as defined above for each of $R_{1g}$ and $R_{1h}$ may occupy position 5 and one non-hydrogen substituent as defined above for each of $R_{1e}$ and $R_{1f}$ may occupy position 6 of the piperidine ring of formula Ia. In this embodiment, any of the four substituents may be axial or equitorial on the piperidine ring. This embodiment includes all enantiomeric mirror images and geometric isomers relative to the 4-position.

I-(xvii): Example of Four Substituents, One at Each of Position-2, -2, -3 and -3

In another embodiment of a compound of formula I, or of a compound of formula I', II, III, IV, V, VI, VII, VIII, or IX, and to pharmaceutically acceptable salts thereof, each of $R_{1e}$, $R_{1f}$, $R_{1g}$ and $R_{1h}$ may be hydrogen, and each of $R_{1a}$, $R_{1b}$, $R_{1c}$, and $R_{1d}$ may be as defined above but is not hydrogen. This embodiment includes all enantiomeric mirror images and geometric isomers relative to the 4-position.

In compounds of formula I, when a substituent other than hydrogen is located at position 2, or position 3 of the piperidine ring, it may be selected from the group consisting of lower alkyl, lower alkylenyl, lower cycloalkylalkyl, lower alkoxyalkyl, aralkyl, PEG and MPEG.

More particularly, in accordance with the present invention the group of formula (group-i) may be 4-pyridinyl represented by formula (group-i-a) or 3-pyridinyl represented by formula (group-i-b);

(group-i-a)

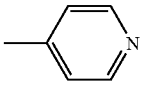

(group-i-b)

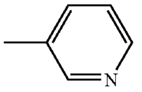

or the group of formula (group-ii) may be 3-pyridinylmethyl represented by formula (group-ii-a), 4-pyridinylmethyl represented by formula (group-ii-b), or 2-pyridinylethyl represented by formula (group-ii-c);

(group-ii-a)

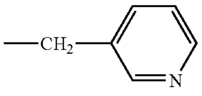

(group-ii-b)

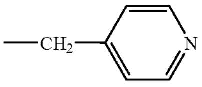

or (group-ii-c)

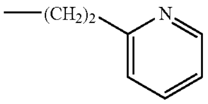

the group of formula (group-iii) may be 5-1H-indolyl represented by formula (group-iii-a);

(group-iii-a)

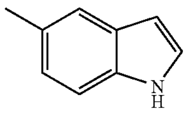

the group of formula (group-iv) may be 2-(3-1H-indolyl) ethyl represented by formula (group-iv-a);

(group-iv-a)

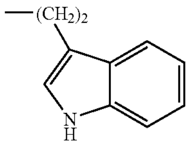

a group of formula (group-v) may be 3-quinolinyl represented by formula (group-v-a), 5-quinolinyl represented by formula (group-v-b), or 4-(2-methylquinolinyl) represented by formula (group-v-c);

(group-v-a)

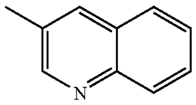

(group-v-b)

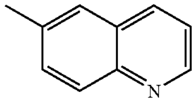

or (group-v-c)

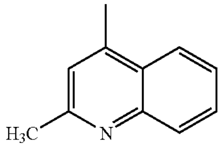

the group of formula (group-viii) may be 4-(N,N-dimethylaminophenyl)methyl represented by formula (group-viii-a);

(group-viii-a)

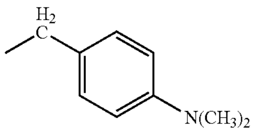

the group of formula (group-ix) may be 4-(N-benzylpiperidinyl) represented by formula (group-ix-a);

(group-ix-a)

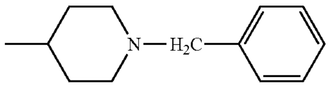

the group of formula (group-xi) may be 4-(1H-pyrrolo[2,3-b]pyridinyl) represented by formula (group-xi-a);

(group-xi-a)

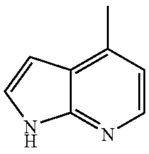

the group of formula (group-xiii) may be 8-isoquinolinyl represented by formula (group-xiii-a);

(group-xiii-a)

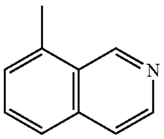

the group of formula (group-xv) may be 2-1H-imidazolyl represented by formula (group-xv-a);

(group-xv-a)

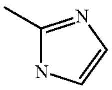

the group of formula (group-xvii) may be 5-(1H-indazolyl) represented by formula (group-xvii-a);

(group-xvii-a)

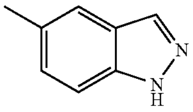

the group of formula (group-xix) may be 6-(9H-purinyl) represented by formula (group-xix-a);

(group-xix-a)

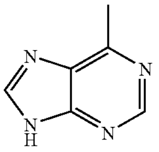

and pharmaceutically acceptable salts thereof, for example, HCl salts which may be represented as ".HCl" in formulas used herein.

In a particular aspect of this invention, referring to exemplary compounds of Formula (I), when A is CH, and X is carbon, and x is zero, and n is zero, the 4-aminomethylpiperidin-1-yl amide represented by formula II obtains as an aspect, wherein $R_1$, $R_2$, and $R_3$ may be as defined above, and pharmaceutically acceptable salts thereof. More particularly compounds of this aspect of the invention may comprise compounds of formula II where in II(a) $R_1$ is H, $R_2$ is propyl, and $R_3$ is 2-pyridinyl (optionally as the hydrochloride salt or dihydrochloride salt).

II

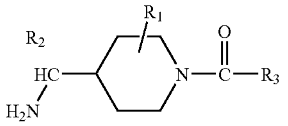

II(a)

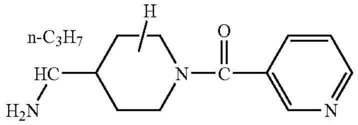

In another particular aspect of this invention, referring to exemplary compounds of Formula (I), when A is CH, and X is carbon, and x is zero, and n is 1, the 4-aminomethylpiperidin-1-yl ($R_3R_4$) urea represented by Formula III obtains as another aspect, wherein $R_1$, $R_2$, $R_3$ and $R_4$ ar may be e as defined above, and pharmaceutically acceptable salts thereof.

III

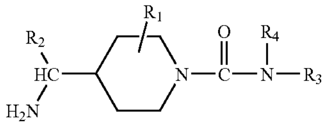

In another particular aspect of this invention, referring to other exemplary compounds of Formula (I), when A is CH, and X is sulfur, and x is 1, and n is 0, the sulfonylpiperidine, e.g., the 4-aminomethyl-1-($R_3$-sulfonyl)piperidine, represented by Formula IV obtains as a further aspect, wherein $R_1$, $R_2$, and $R_3$ may be as defined above, and pharmaceutically acceptable salts thereof. More particularly compounds of this aspect of the invention may comprise compounds of formula IV where in IV(a) $R_1$ is H, $R_2$ is n-propyl, and $R_3$ is 5-isoquinolinyl (optionally as the hydrochloride salt or dihydrochloride salt); and in IV(b) $R_1$ is H, $R_2$ is methyl, and $R_3$ is 5-isoquinolinyl (optionally as the hydrochloride salt or dihydrochloride salt).

IV

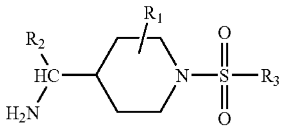

IV(a)

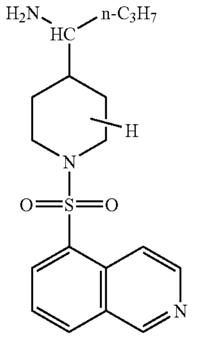

-continued

IV(b)

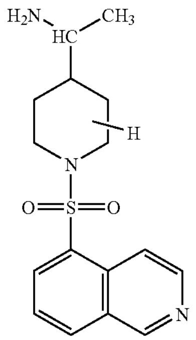

In another particular aspect of this invention, referring to further exemplary compounds of Formula (I), when A is CH, and X is sulfur, and x is 1, and n is 1, the sulfamide, e.g., the 4-aminomethyl-1-piperidine ($R_3R_4$) sulfamide, represented by Formula V obtains as a further aspect, wherein $R_1$, $R_2$, $R_3$ and $R_4$ may be as defined above, and pharmaceutically acceptable salts thereof.

V

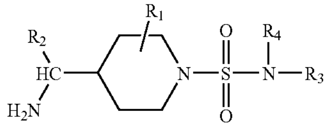

In another particular aspect of this invention, referring to additional exemplary compounds of Formula (I), when A is N, and X is carbon, and x is 0, and n is 0, the amide, e.g., 4-hydrazinylpiperidin-1-yl amide, represented by Formula VI obtains as another aspect, wherein $R_1$, $R_2$, and $R_3$ are as defined above, and pharmaceutically acceptable salts thereof.

More particularly compounds of this aspect of the invention may comprise compounds of formula VI where in VI(a) $R_1$ is H, $R_2$ is n-octyl, and $R_3$ is 4-pyridinyl (optionally as the hydrochloride salt or dihydrochloride salt); in VI(b) $R_1$ is H, $R_2$ is n-propyl, and $R_3$ is 4-pyridinyl (optionally as the hydrochloride salt or dihydrochloride salt); in VI(c) $R_1$ is H, $R_2$ is n-octyl, and $R_3$ is 3-pyridinyl (optionally as the hydrochloride salt or dihydrochloride salt); and in VI(d) $R_1$ is H, $R_2$ is methyl, and $R_3$ is 3-pyridinyl (optionally as the hydrochloride salt or dihydrochloride salt).

VI

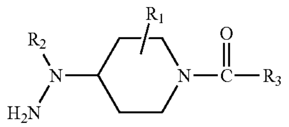

VI(a)

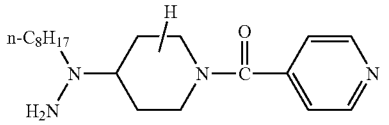

-continued

VI(b)

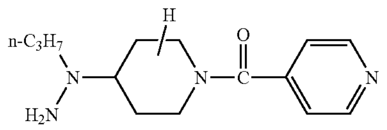

VI(c)

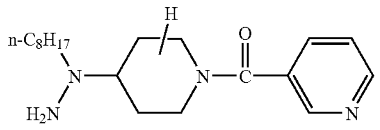

VI(d)

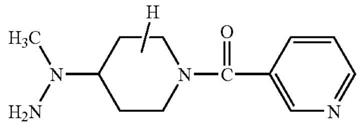

In another particular aspect of this invention, referring to further exemplary compounds of Formula (I), when A is N, and X is carbon, and x is 0, and n is 1, the urea, e.g., the 4-hydrazinylpiperidin-1-yl ($R_3R_4$) urea, represented by Formula VII obtains as an additional aspect, wherein $R_1$, $R_2$, $R_3$ and $R_4$ may be as defined above, and pharmaceutically acceptable salts thereof.

VII

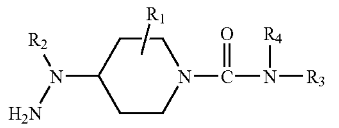

In another particular aspect of this invention, referring to exemplary compounds of Formula (I), when A is N, and X is sulfur, and x is 1, and n is 0, the sulfonylpiperidine, e.g., the 4-hydrazinyl-1-($R_3$-sulfonyl)piperidine, represented by Formula VIII obtains as another aspect, wherein $R_1$, $R_2$, and $R_3$ may be as defined above, and pharmaceutically acceptable salts thereof. More particularly compounds of this aspect of the invention may comprise compounds of formula VIII where in VIII(a) $R_1$ is H, $R_2$ is n-octyl, and $R_3$ is 5-isoquinolinyl (optionally as the hydrochloride salt or dihydrochloride salt); in VIII(b) $R_1$ is H, $R_2$ is n-propyl, and $R_3$ is 5-isoquinolinyl (optionally as the hydrochloride salt or dihydrochloride salt); and in VIII(c) $R_1$ is H, $R_2$ is methyl, and $R_3$ is 5-isoquinolinyl (optionally as the hydrochloride salt or dihydrochloride salt).

VIII

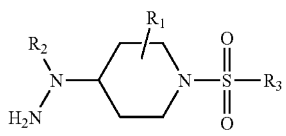

-continued

VIII(a)

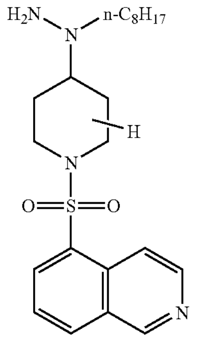

VIII(b)

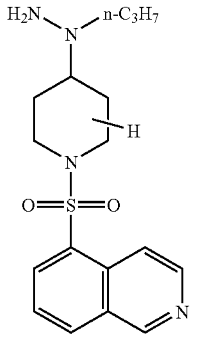

VIII(c)

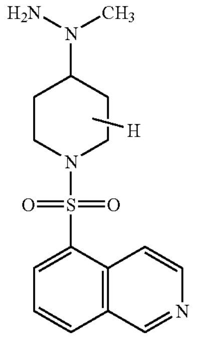

In another particular aspect of this invention, referring to Formula (I), when A is N, and X is sulfur, and x is 1, and n is 1, the piperidine sulfamide, e.g., the 4-hydrazinyl-1-piperidine ($R_3R_4$) sulfamide, represented by Formula IX obtains as an aspect, wherein $R_1$, $R_2$, $R_3$ and $R_4$ may be as defined above, and pharmaceutically acceptable salts thereof.

IX

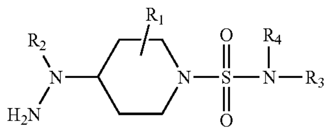

Additional examples of compounds of this invention include the following represented by structure formulas AM-1 to AM-39 and H-1 to H-12, and pharmaceutically acceptable salts thereof.

-continued
AM-1
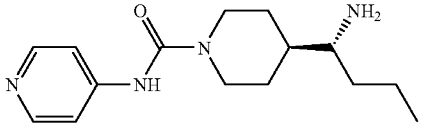
AM-2
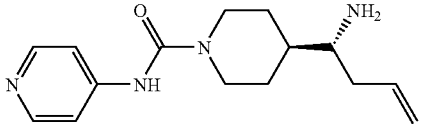
AM-3
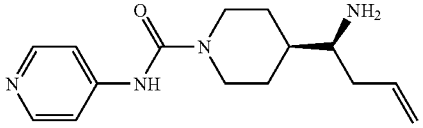
AM-4
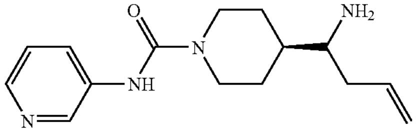
AM-5
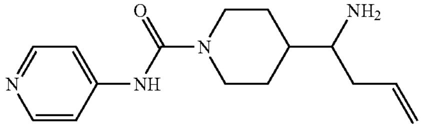
AM-6
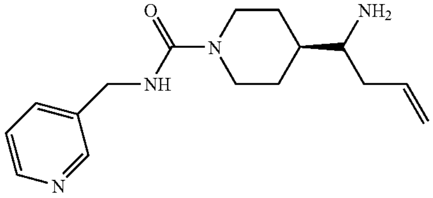
AM-7
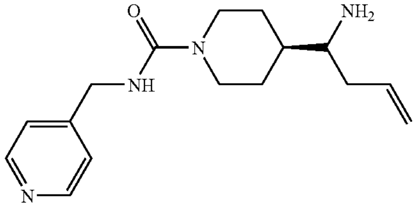
AM-8
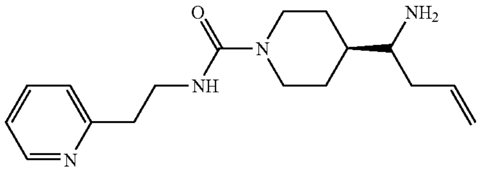
AM-9
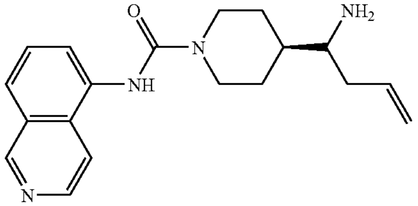
AM-10
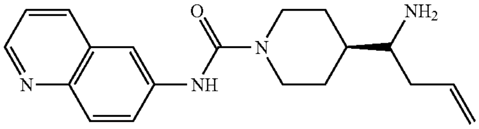
AM-11
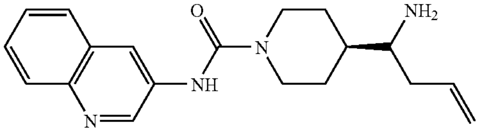
AM-12
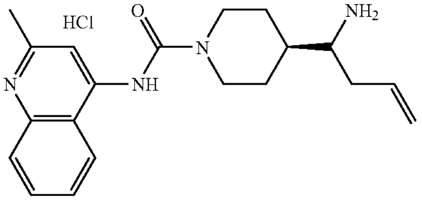
AM-13
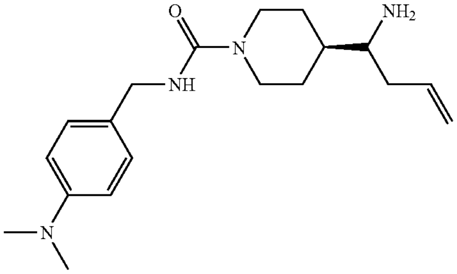
AM-14
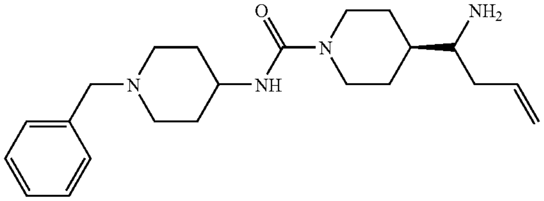
AM-15
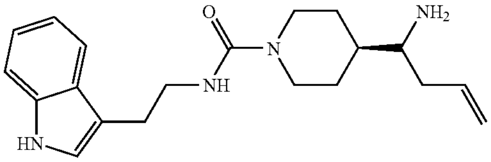
AM-16
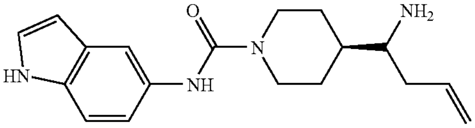
AM-17
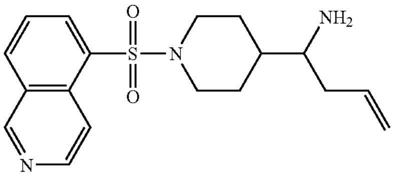

-continued
AM-18
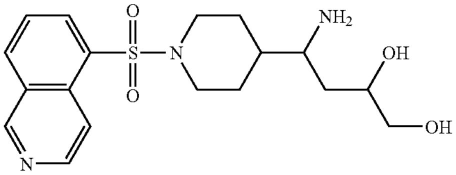
AM-19
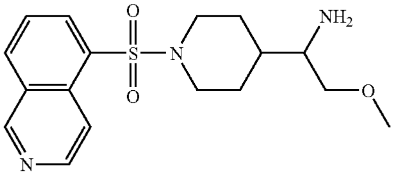
AM-20
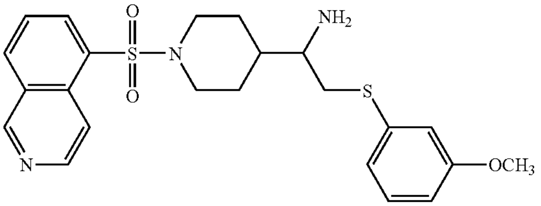
AM-21
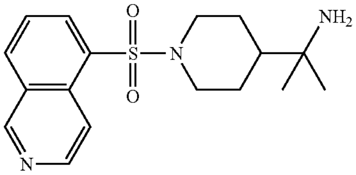
AM-22
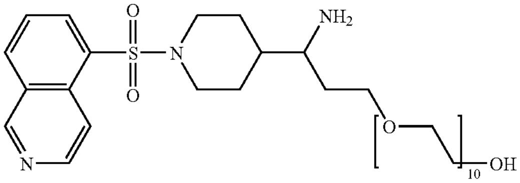
AM-23
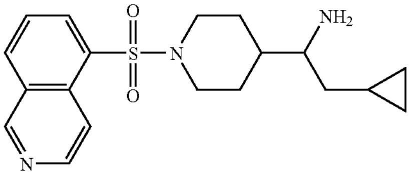
AM-24
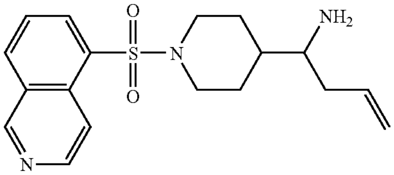
AM-25
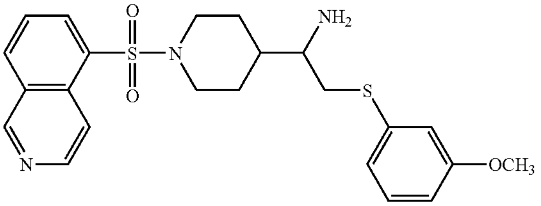
-continued
AM-26
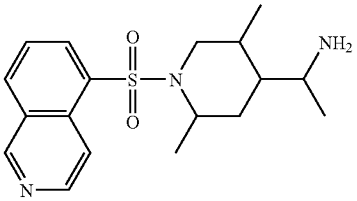
AM-27
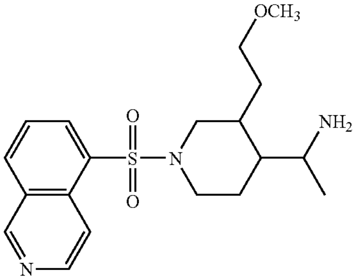
AM-28
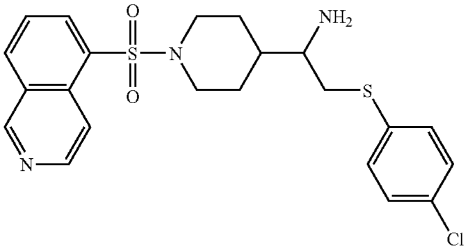
AM-29
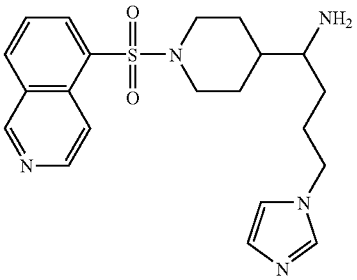
AM-30
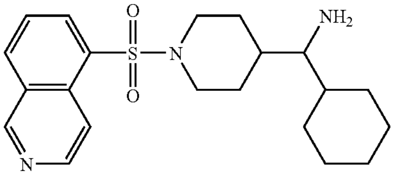
AM-31
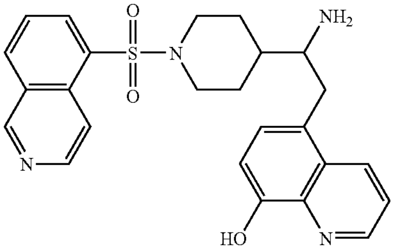

-continued
AM-32
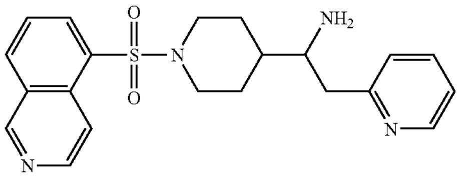
AM-33
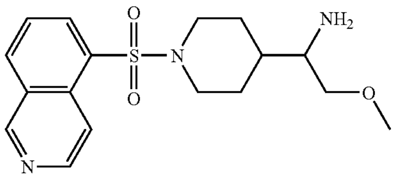
AM-34
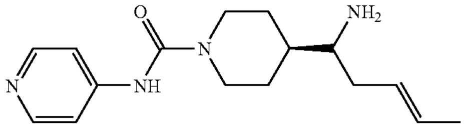
AM-35
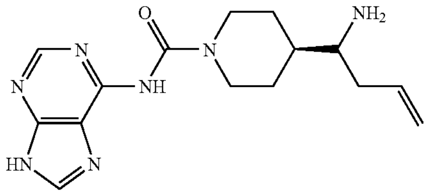
AM-36
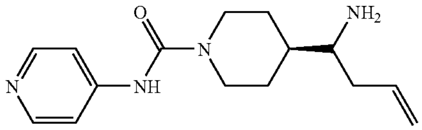
AM-37
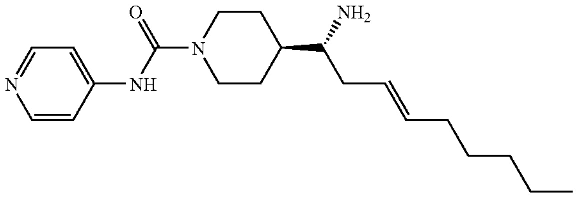
AM-38
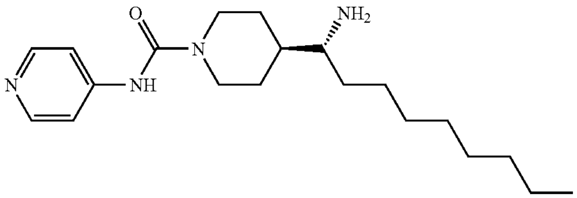
AM-39
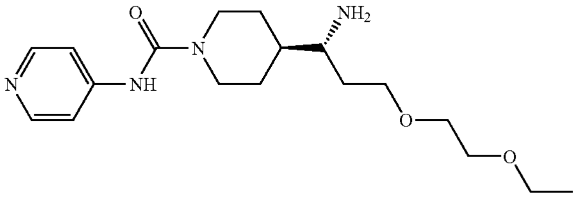
-continued
H-1
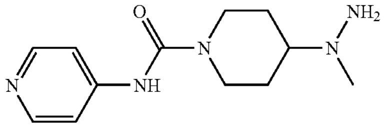
H-2
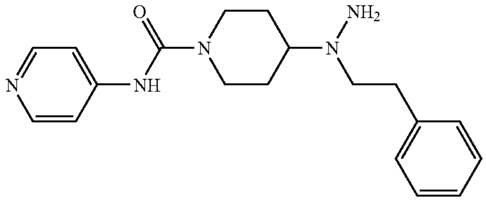
H-3
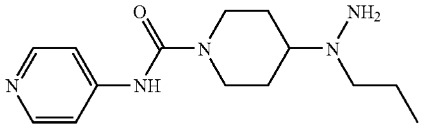
H-4
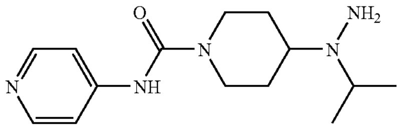
H-5
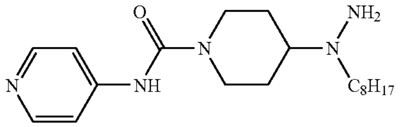
H-6
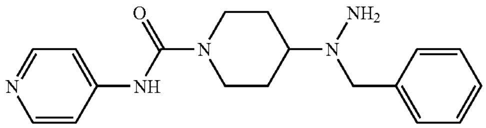
H-7
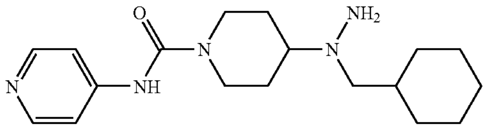
H-8
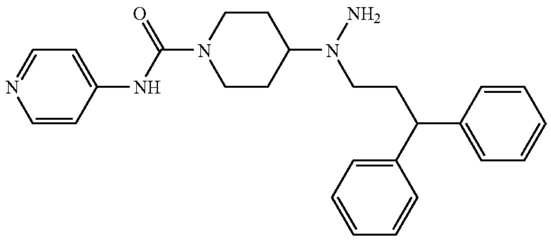
H-9
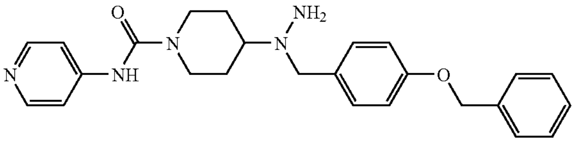

-continued

H-10

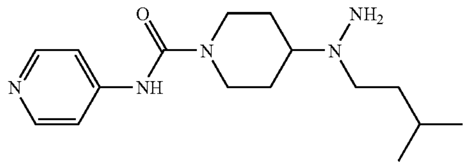

H-11

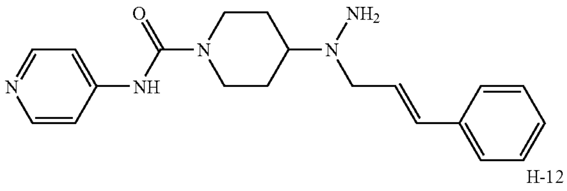

H-12

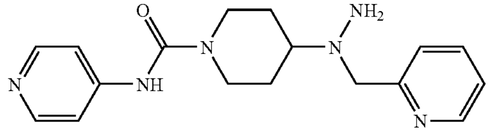

In one aspect, an alkyl group may refer to a C1 to C30 alkyl group which may be a linear, a branched or a cyclic alkyl group, examples of which include methyl, ethyl, propyl, butyl, isobutyl, pentyl, isopentyl, hexyl, isohexyl, heptyl, octyl, 3-ethylhexyl, 4-ethylhexyl, nonyl, decyl, undecyl, dodecyl, cyclohexyl, cyclopropyl, octadecyl, tetradecanyl, hexadecanyl, icosanyl, docosanyl, tetracosanyl, hexocosanyl, octacosanyl.

In one aspect, an alkyl substituent group may be a linear or branched alkyl having 1 to 10 carbon atoms, such as for example methyl, ethyl, propyl, isopropyl, butyl, isobutyl, sec-butyl, tert-butyl, pentyl, hexyl, heptyl, octyl, nonyl, decyl and the like, and more such as an alkyl having 1 to 4 carbon atoms.

In one aspect, a cycloalkyl substituent may have 3 to 7 carbon atoms such as for example cyclopropyl, cyclobutyl, cyclopentyl, cyclohexyl, cycloheptyl and the like.

In one aspect, a cycloalkylalkyl group may be a cycloalkyl-ring-substituted cycloalkylalkyl group such as an alkylcycloalkylalkyl group and alkyloxycycloalkylalkyl group, for example, a C4 to C30 cycloalkylalkyl group such as, for example, cyclopropylmethyl, 2-cyclopropylethyl, 3-cyclopropylpropyl, 2-cyclohexylethyl, 4-cyclopropylbutyl, 2-methylcyclopentylmethyl, 4-ethylcyclohexylmethyl, 2-(4-ethylcyclohexyl)ethyl, 4-isopropylcyclohexylmethyl, 4-decalinylcyclohexylmethyl, 2-bicyclo[4.4.0]decylmethyl; 2,2-dimethylcyclopropylmethyl, 2,3-dimethylcyclopropylmethyl, 3-(4-methoxyethoxycyclohexyl)propyl, and 4-(4-ethoxycyclohexyl)methylcyclohexylmethyl.

In one aspect, a cycloalkylalkyl may contain the above-mentioned cycloalkyl group having 3 to 7 carbon atoms and an alkyl moiety that is a linear or branched alkyl having 1 to 6 carbon atoms (e.g., methyl, ethyl, propyl, isopropyl, butyl, pentyl, hexyl and the like), such as for example cyclopropylmethyl, cyclobutylmethyl, cyclopentylmethyl, cyclohexylmethyl, cycloheptylmethyl, cyclopropylethyl, cyclopentylethyl, cyclohexylethyl, cycloheptylethyl, cyclopropylpropyl, cyclopentylpropyl, cyclohexylpropyl, cycloheptylpropyl, cyclopropylbutyl, cyclopentylbutyl, cyclohexylbutyl, cycloheptylbutyl, cyclopropylhexyl, cydopentylhexyl, cyclohexylhexyl, cycloheptylhexyl and the like.

In one aspect, a spirocycloalkyl group may be a C2 to C5 bridging alkylene group in which the ends of the alkylene group are attached to the same carbon atom in a ring to which they are commonly bound, such as for example an ethylidene group which forms a 3-membered ring with the commonly bound ring carbon; a propylidene group which forms a 4-membered ring with the commonly bound ring carbon; a butylidene group which forms a 5-membered ring with the commonly bound ring carbon. Optionally the spiro group may be substituted with a lower alkyl group, a lower alkoxy group, a lower thioalkyl group, or a lower alkylamino group.

In one aspect, an alkenyl group may contain from 1 to 11 double bonds including a C3 to C40 alkenyl group which may be a linear, branched, cyclic in which the cyclic group may be saturated or unsaturated and/or substituted with a lower alkyl group, cycloalkyl-containing alkenyl group which may be linear or branched, and which may contain cis- and/or trans double bonds, examples of which include allyl, cis-but-2-enyl, trans-but-2-enyl, cis- and trans-pent-2-enyl, pent-3-enyl, isopentenyl, hex-2-enyl, hex-3-enyl, isohexenyl, hept-6-enyl, oct-2-enyl, isopropenylhexyl, 4-isopropenylcyclohexylmethyl, 9-hexadecenyl, cis-9-octadecenyl, 11-octadecenyl, cis,cis-9,12-octadecadienyl, 9,12,15-octadecatrienyl, 6,9,12-octadecatrienyl, 9,11,13-octadecatrienyl, 8,11-icosadienyl, 5,8,11-icosatrienyl, 5,8,11,14-icosatetraenyl, cis-15-tetracosenyl, and carotenyl.

In one aspect, an alkoxy-containing alkyl group may be one wherein the alkyl group is defined as above, and may contain from one to 6 oxygen atoms and from 2 to 30 carbon atoms, such as methoxymethyl, 2-methoxyethyl, 2-ethoxyethyl, 3-ethoxylpropyl, 2-(2-(2-(2-methoxyethoxy)ethoxy)ethoxy)ethyl.

In one aspect, a 2-poly(2-oxyethyl)ethyl group may be a PEG group polyether such as a poly(2-oxyethyl)oxyethyl-group containing from 2 to about 30 oxygen atoms, which PEG group may be terminated in a hydroxy group (PEG-OH) or in a methoxy group (PEG-OMe) or in an ethoxy group (PEG-OEt), such as for example, 2-ethoxyethyl, 2-(2-methoxyethyl)oxyethyl, 4-methoxycylcohexylmethyl, 10-methoxy-5,8-dioxydec-2-enyl, and a 2-(omega-methoxy-(polyoxyethyl)oxyethyl group containing from 3 to 30 oxygen atoms.

In one aspect, an aralkyl group may contain an aryl group and an alkyl moiety wherein the alkyl may have 1 to 4 carbon atoms, such as for example a phenylalkyl group such as benzyl, 1-phenylethyl, 2-phenylethyl, 3-phenylpropyl, 4-phenylbutyl and the like. An exemplary aralkyl group may contain a substituted aryl group as described herein.

In one aspect, a substituent of an optionally substituted phenyl ring and on the ring of an optionally substituted aralkyl may be halogen, including chlorine, bromine, fluorine and iodine; alkyl as described above; alkoxy, which may be a linear or branched alkoxy having 1 to 6 carbon atoms, such as for example methoxy, ethoxy, propoxy, isopropoxy, butoxy, isobutoxy, sec-butoxy, tert-butoxy, pentyloxy, hexyloxy and the like; alkylthio, which may be a linear or branched alkylthio group having 1 to 6 carbon atoms, such as for example methylthio ($CH_3S$—), ethylthio ($CH_3CH_2S$—), propylthio ($CH_3CH_2CH_2S$—), isopropylthio, butylthio ($CH_3CH_2CH_2CH_2S$—), isobutylthio, sec-butylthio, tert-butylthio, pentylthio ($CH_3CH_2CH_2CH_2CH_2S$—), hexylthio ($CH_3CH_2CH_2CH_2CH_2CH_2S$—) and the like; aralkyl as described above; fluorinated alkyl, wherein the alkyl is as described above but in which hydrogen atoms are replaced by fluorine atoms from 1 to all of the hydrogens (i.e., perfluoroalkyl), such as for example fluoromethyl, difluoromethyl, trifluoromethyl, 2,2,2-trifluoroethyl, 2,2,3,3,3-pentafluoropropyl and the like); nitro; amino; cyano; azide; and the like.

In one aspect, an exemplary substituent of an optionally substituted ring of a cycloalkyl and of an optionally substituted ring of cycloalkylalkyl may be chlorine and fluorine; alkyl as described above; alkoxy, which may be a linear or branched alkoxy having 1 to 6 carbon atoms, such as for example methoxy, ethoxy, propoxy, isopropoxy, butoxy, isobutoxy, sec-butoxy, tert-butoxy, pentyloxy, hexyloxy and the like; alkylthio, which may be a linear or branched alkylthio group having 1 to 6 carbon atoms, such as for example methylthio ($CH_3S$—), ethylthio ($CH_3CH_2S$—), propylthio ($CH_3CH_2CH_2S$—), isopropylthio, butylthio ($CH_3CH_2CH_2CH_2S$—), isobutylthio, sec-butylthio, tert-butylthio, pentylthio ($CH_3CH_2CH_2CH_2CH_2S$—), hexylthio ($CH_3CH_2CH_2CH_2CH_2CH_2S$—) and the like; aralkyl as described above; fluorinated alkyl, wherein the alkyl is as described above but in which hydrogens are substituted by fluorine atoms from 1 to all of the hydrogens (i.e., perfluoroalkyl), such as for example fluoromethyl, difluoromethyl, trifluoromethyl, 2,2,2-trifluoroethyl, 2,2,3,3,3-pentafluoropropyl and the like)); nitro; amino; cyano; azide; and the like.

In one aspect, a heterocyclic group formed by $R_3$ and $R_4$ in combination together with the adjacent nitrogen atom, wherein such a heterocycle may optionally have, in the ring, an oxygen atom, a sulfur atom or an optionally substituted nitrogen atom is for example selected from the group consisting of a 5-membered ring, a 6-membered ring, 5-membered ring fused to a 5-membered ring, a 5-membered ring fused to a 6-membered ring, and a 6-membered ring fused to a 6-membered ring, each optionally substituted with a substituent group as described herein. Examples of heterocyclic rings comprising $R_3$ and $R_4$ in combination together with the adjacent nitrogen atom include 1-pyrrolidinyl, piperidino, 1-piperazinyl, morpholino, thiomorpholino, 1-imidazolyl, 2,3-dihydrothiazol-3-yl, imidazol-2-yl, thiazol-2-yl, oxazol-2-yl, imidazolin-2-yl, 3,4,5,6-tetrahydropyridin-2-yl, 3,4,5,6-tetrahydropyrimidin-2-yl, 1,3-oxazolin-2-yl, 1,3-thiazolin-2-yl or optionally substituted benzoimidazol-2-yl, benzothiazol-2-yl, benzoxazol-2-yl and the like having a substituent such as halogen, alkyl, alkoxy, haloalkyl (e.g., fluoroalkyl, chloroalkyl, bromoalkyl, iodoalkyl), nitro, amino, phenyl, aralkyl and the like, wherein substituents halogen, alkyl, alkoxy, haloalkyl and aralkyl are as defined above. The substituent of the optionally substituted nitrogen atom may be alkyl, aralkyl, haloalkyl and the like as described above.

In one aspect, the amino group subtended from A of formula I may be acylated as an amide by an alkanoyl having 2 to 6 carbon atoms (e.g., acetyl, propionyl, butyryl, valeryl, pivaloyl and the like), benzoyl or phenylalkanoyl wherein the alkanoyl moiety may have 2 to 4 carbon atoms (e.g., phenylacetyl, phenylpropionyl, phenylbutyryl and the like).

In one aspect, alkylamino may refer to an amino group that may be substituted by one or two alkyl moieties, the alkyl moiety of such alkylamino having linear or branched alkyl having 1 to 6 carbon atoms, such as for example methylamino, ethylamino, propylamino, isopropylamino, butylamino, isobutylamino, sec-butylamino, tert-butylamino, pentylamino, hexylamino and the like.

In one aspect, acylamino may be that wherein the acyl moiety is an alkanoyl having from 2 to 6 carbon atoms, benzyl, or phenylalkanoyl where the alkanoyl has 2 to 4 carbon atoms, and the like, for example acetylamino, propionylamino, butyrylamino, valerylamino, pivaloylamino, benzoylamino, phenylacetylamino, phenylpropionylamino, phenylbutyrylamino and the like.

In one aspect, alkylthio may refer to an alkyl moiety attached to a sulfur atom (as a thioether), wherein the alkyl moiety may be a linear or branched alkyl having 1 to 6 carbon atoms, such as for example methylthio, ethylthio, propylthio, isopropylthio, butylthio, isobutylthio, sec-butylthio, tert-butylthio, pentylthio, hexylthio, and the like.

In one aspect, aralkyloxy may refer to an aralkyl ether wherein the alkyl moiety may have from 1 to 4 carbon atoms, such as for example benzyloxy, 1-phenylethyloxy, 2-phenylethyloxy, 3-phenylpropyloxy, 4-phenylbutyloxy and the like.

In one aspect, aralkylthio may refer to an aralkylthio moiety attached to a sulfur atom (as a thioether), wherein the alkyl moiety may have from 1 to 4 carbon atoms, such as for example benzylthio, 1-phenylethylthio, 2-phenylethylthio, 3-phenylpropylthio, 4-phenylbutylthio and the like.

In one aspect, alkylcarbamoyl may refer to a carbamoyl group that is mono- or di-substituted by an alkyl having from 1 to 4 carbon atoms, such as for example methylcarbamoyl, dimethylcarbamoyl, ethylcarbamoyl, diethylcarbamoyl, propylcarbamoyl, dipropylcarbamoyl, butylcarbamoyl, dibutylcarbamoyl and the like.

In one aspect, hydroxyalkyl may refer to an alcohol-containing alkyl group wherein the alkyl group may be a linear or branched alkyl of from 1 to 6 carbon atoms which may be substituted by 1 to 3 hydroxy —OH groups, such as for example hydroxymethyl, 2-hydroxyethyl, 1-hydroxyethyl, 3-hydroxypropyl, 4-hydroxybutyl and the like.

In one aspect, aminoalkyl may refer to an amine-substituted alkyl group wherein the alkyl may be a linear or branched alkyl of from 1 to 6 carbon atoms, such as for example aminomethyl, 2-aminoethyl, 1-aminoethyl, 3-aminopropyl, 4-aminobutyl, 5-aminopentyl, 6-aminohexyl and the like.

In one aspect, alkylaminoalkyl or dialkylaminoalkyl may refer to, respectively, a monoalkyl-substituted or dialkyl-substituted aminoalkyl wherein the alkyl may have from 1 to 4 carbon atoms, such as for example methylaminomethyl, dimethylaminomethyl, ethylaminomethyl, diethylaminomethyl, propylaminomethyl, dipropylaminomethyl, butylaminomethyl, dibutylaminomethyl, 2-dimethylaminoethyl, 2-diethylainioethyl and the like.

In one aspect, an alkyl of a carbamoylalkyl may be a linear or branched alkyl having 1 to 6 carbon atoms substituted by carbamoyl, such as for example carbamoylmethyl, 2-carbamoylethyl, 1-carbamoylethyl, 3-carbamoylpropyl, 4-carbamoylbutyl, 5-carbamoylpentyl, 6-carbamoylhexyl and the like.

In one aspect, an alkyl of a phthalimidoalkyl may be a linear or branched alkyl having 1 to 6 carbon atoms, which is substituted by phthalimide, such as for example, phthalimidomethyl, 2-phthalimidoethyl, 1-phthalimidoethyl, 3-phthalimidopropyl, 4-phthalimidobutyl, 5-phthalimidopentyl, 6-phthaimidohexyl and the like.

In one aspect, an alkylene group may be a linear or branched alkylene having 1 to 6 carbon atoms, for example methylene (—$CH_2$—); ethylene (—$CH_2CH_2$—); trimethylene (—$CH_2CH_2CH_2$—) which may be also propylene; tetramethylene (—$CH_2CH_2CH_2CH_2$—) which is also butylene; pentamethylene (—$CH_2CH_2CH_2CH_2CH_2$—) which may be also pentylene; hexamethylene (—$CH_2CH_2CH_2CH_2CH_2CH_2$—) which may also be hexylene, and the like.

In one aspect, an alkenylene may be a linear or branched alkenylene having 2 to 6 carbon atoms and at least one —C═C— or double bond, such as for example vinylene, propenylene, butenylene, pentenylene and the like.

In one aspect, at $R_3$ (and $R_4$) of formula I or I' and related formulas (e.g., II to IX), a heterocycle group may be a monocyclic heterocycle group such as for example pyridine, pyrimidine, pyridazine, triazine, pyrazole, triazole and the like.

In one aspect, at $R_3$ (and $R_4$) of formula I or I' and related formulas (e.g., II to IX), a heterocycle group may be a fused ring heterocycle group such as for example pyrrolopyridine including 1H-pyrrolo[2,3-b]pyridine, 1H-pyrrolo[3,2-b]pyridine, and 1H-pyrrolo[3,4-b]pyridine; pyrazolopyridine including 1H-pyrazolo[3,4-b]pyridine and 1H-pyrazolo[4,3-b]pyridine; imidazopyridine including 1H-imidazo[4,5-b]pyridine; pyrrolopyrimidine including 1H-pyrrolo[2,3-d]pyrimidine, 1H-pyrrolo[3,2-d]pyrimidine, and 1H-pyrrolo[3,4-d]pyrimidine; pyrazolopyrimidine including 1H-pyrazolo[3,4-d]pyrimidine, and pyrazolo[1,5-a]pyrimidine, 1H-pyrazolo[4,3-d]pyrimidine; imidazopyrimidine including imidazol[1,2-a]pyrimidine and 1H-imidazo[4,5-d]pyrmidine; pyrrolotriazine including pyrrolo[1,2-a]-1,3,5-triazine and pyrrolo[2,1-f]-1,2,4-triazine; pyrazolotriazine including pyrazolo[1,5-a]-1,3,5-triazine; triazolopyridine including 1H-1,2,3-triazolo[4,5-b]pyridine; triazolopyrimidine including 1,2,4-triazolo[1,5-a]pyrimidine, 1,2,4-triazolo[4,3-a]pyrimidine, and 1H-1,2,3-triazolo[4,5-d]pyrimidine; cinnoline; quinazoline; quinoline; isoquinoline; pyridopyridazine including pyrido[2,3-c]pyridazine; pyridopyrazine including pyrido[2,3-b]pyrazine; pyridopyrimidine including pyrido[2,3-d]pyrimidine, and pyrido[3,2-d]pyrimidine; pyrimidopyrimidine including pyrimido[4,5-d]pyrimidine, and pyrimiido[5,4-d]pyrimidine; pyrazinopyrimidine including pyrazino[2,3-d]pyrimidine; naphthyridine including 1,8-naphthyridine; tetrazolopyrimidine including tetrazolo[1,5-a]pyrimidine; thienopyridine including thieno[2,3-b]pyridine; thienopyrimidine including thieno[2,3-d]pyrimidine; thiazolopyridine including thiazolo[4,5-b]pyridine, and thiazolo[5,4-b]pyridine; thiazolopyrimidine including thiazolo[4,5-d]pyrimidine, and thiazolo[5,4-d]pyrimidine; oxazolopyridine including oxazolo[4,5-b]pyridine and oxazolo[5,4-b]pyridine; oxazolopyrimidine including oxazolo[4,5-d]pyrimidine, and oxazolo[5,4-d]pyrimidine; furopyridine including furo[2,3-b]pyridine, and furo[3,2-b]pyridine; furopyrimidine including furo[2,3-d]pyrinidine, and furo[3,2-d]pyrimidine; 2,3-dihydropyrrolopyridine including 2,3-dihydro-1H-pyrrolo[2,3-b]pyridine, and 2,3-dihydro-1H-pyrrolo[3,2-b]pyridine; 2,3-dihydropyrrolopyrimidine including 2,3-dihydro-1H-pyrrolo[2,3-d]pyrimidine, and 2,3-dihydro-1H-pyrrolo[3,2-d]pyrimidine; 5,6,7,8-tetrahydropyiido[2,3-d]pyrimidine; 5,6,7,8-tetrahydro-1,8-naphthyridine; and 5,6,7,8-tetrahydroquinoline; 2,3-dihydro-2-oxopyrrolopyridine; 2,3-dihydro-2,3-dioxopyrrolopyridine; 7,8-dihydro-7-oxo-1,8-naphthyridine; 5,6,7,8-tetrahydro-7-oxo-1,8-naphthyridine, and the like.

The heterocycle rings may be substituted by a substituent such as halogen; alkyl; alkoxy; aralkyl; haloalkyl such as perfluoroalkyl; nitro; amino; alkylamino; cyano; aminoalkyl; alkylaminoalkyl; dialkylaminoalkyl; azide; carboxyl (HOOC—); carboxylalkyl; carbamoyl; alkylcarbamoyl; alkoxyalkyl including methoxymethyl, methoxyethyl, methoxypropyl, ethoxymethyl, ethoxyethyl, ethoxypropyl, and the like; and an optionally substituted hydrazine, wherein the substituent of the optionally substituted hydrazine includes alkyl as defined above in one aspect, aralkyl as defined above in one aspect, nitro, cyano and the like, and include for example methyl hydrazino, ethyl hydrazino, benzyl hydrazine, and the like.

In one aspect of the invention, the term "lower alkyl" designates C1 to C10 alkyl which may be straight or branched, such as methyl, ethyl, propyl, isopropyl, butyl, isobutyl, pentyl, hexyl, heptyl, octyl, nonyl, and decyl. More particularly, the term "lower alkyl" designates C1 to C6 alkyl which may be straight or branched, such as methyl, ethyl, propyl, isopropyl, butyl, isobutyl, pentyl, or hexyl. Halogenated lower alkyl groups may be perfluorinated lower alkyl groups such as trifluoromethyl.

The term "lower alkenyl" designates a C3 to C10 straight or branched alkyl group which contains a double bond, such as 2-propenyl, 2-butenyl, 2-pentenyl, 2-hexenyl, 2-methyl-2-propenyl, 3-methyl-2-butenyl, 2-heptenyl, 2-octenyl, isooctenyl, 2-nonenyl, or 2-decenyl.

The term "heteroaryl group" refers to an aromatic heterocyclic group which does not contain a saturated carbon atom in the heterocyclic ring. Heteroaryl groups may include group-i, group-iii, group-v, group-xi, group-xiii, group-xv, group-xvii, and group-xix as described herein.

The term "lower alkadienyl" designates a C5 to C10 straight or branched alkyl group containing two double bonds, such as 2,4-pentadienyl, 2-methyl-2,4-pentadienyl, 2,4-hexadienyl, 2,4-heptadienyl, 2,4-octadienyl, 2,4-nonadienyl, or 2,4-decadienyl.

The term "lower alkynyl" designates a C3 to C10 straight or branched alkyl group containing a triple bond, such as 2-propynyl, 2-butynyl, 2-pentynyl, 2-hexynyl or 4-methyl-2-pentynyl, 2-heptynyl, 2-octynyl, 2-nonynyl, or 2-decynyl.

Where a phenyl group is substituted with halogen, lower alkyl, or lower alkoxy, they may be mono-, di- or tri-substituted, and when they are di- or tri-substituted the substituents may be the same or different.

The term "lower alkoxy" designates oxy to which is attached a lower alkyl group.

Example of groups include methoxy and ethoxy.

Compounds according to the present invention may be synthesized by a number of methods such as according to the following non-limiting methods and reaction schemes. Useful protecting groups for nitrogen-containing groups such as amines, oxygen-containing groups such as alcohols, sulfur-containing groups such as thiols, and the like are known in the art and may be found, for example, in Greene et al., Protective Groups in Organic Synthesis, Second Edition, John Wiley and Sons, 1991.

Method 1:

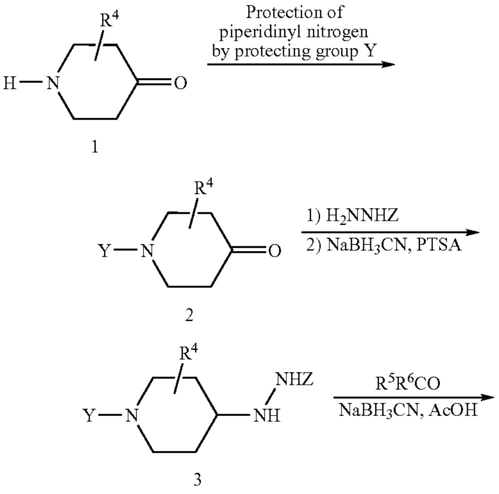

1

2

3

-continued

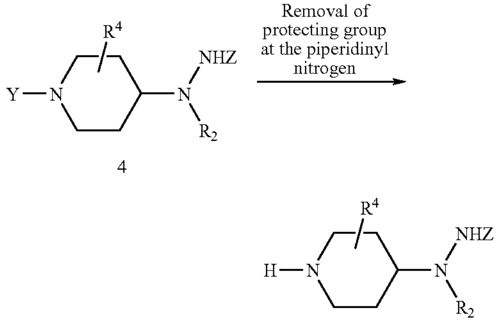

4

5

-continued

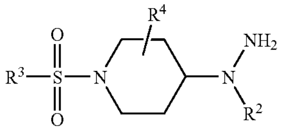

VIII

Referring to the scheme for Method 1, an oxopiperidine, sometime herein referred to as a piperidin-4-one, 1, is protected at the piperidinonyl nitrogen with an appropriate protecting group, for example, with a benzyloxycarbonyl protecting group, or a tert-butyloxycarbonyl protecting group, etc. according to well known methods using commercially available (Sigma-Aldrich) reagents to provide an N-protected piperidin-4-one, 2. The N-protected piperidin-4-one, 2, is reacted with a suitably protected hydrazine (useful compounds include, for example, tert-butylcarbazide, benzylcarbazide, etc. designated $H_2NNHZ$ in step "1)" of Method 1) to provide a resulting hydrazone. The resulting hydrazone is then reduced such as by treating the hydrazone with for example, sodium cyanoborohydride and p-toluene sulfonic acid or other suitable reducing medium to provide the hydrazine, 3. Reductive amination between the hydrazine, 3, and the carbonyl group in an aldehyde such as, for example, formaldehyde, propionaldehyde, octylaldehyde, and the like as a precursor to $R_2$ in formula I, or reductive amination between the hydrazine, 3, and the carbonyl group in a ketone such as acetone, methyl ethyl ketone, etc. as a precursor to $R_2$ in formula I wherein $—R_2$ comprises the $—CR^5R^6$ segment of the aldehyde or ketone, is performed using a suitable reducing reagent medium such as with sodium cyanoborohydride in the presence of acetic acid, to give a hydrazine, 4 containing a protecting group, Y. The protecting group, Y, at the piperidinyl nitrogen in structure 4 is removed to afford a compound of formula 5.

Method 2:

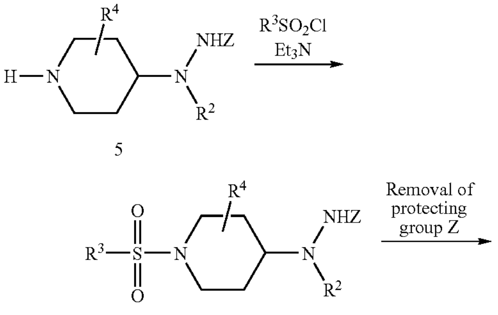

5

6

Referring to the scheme for Method 2, amine 5 is coupled with a sulfonyl chloride, for example with 5-isoquinolinesulfonyl chloride, with 3-pyridinesulfonyl chloride, etc. in the presence of triethylamine to give the corresponding Z-protecting group-containing-sulfonylpiperidine 6, which is deprotected by removal of the Z-protecting group to give a compound of formula VIII.

Method 3:

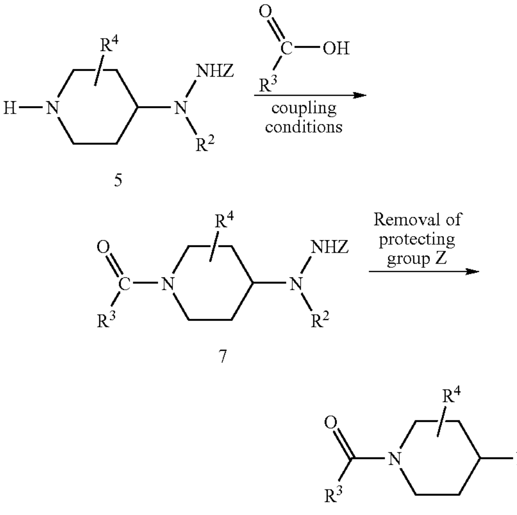

5

7

VI

Referring to the scheme for Method 3, amine 5 is coupled with a carboxylic acid for example such as isonicotic acid or nicotinic acid, etc., or with a carboxylic acid equivalent (anhydride, N-hydroxysuccinimide ester, acid chloride, etc.) using suitable coupling conditions (e.g. dehydration with a carbodiimide) to provide the corresponding Z-protecting-group-containing-amide, 7, which is deprotected by removal of the Z-protecting group to give an amide compound of formula VI.

Method 4:

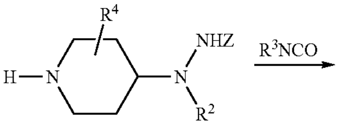

5

-continued

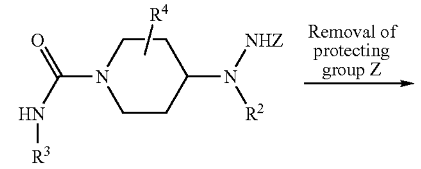

8

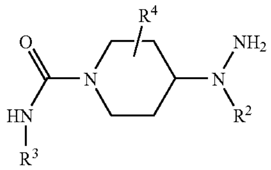

VII

Referring to the scheme for Method 4, amine 5 is reacted with an isocyanate such as 4-pyridineisocyanate, or phenylisocyanate, etc., to provide the corresponding Z-protecting-group-containing-urea, 8, which is deprotected by removal of the Z-protecting group to give a urea compound of formula VII.

Method 5:

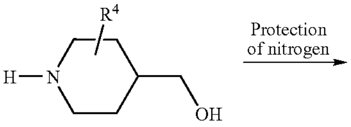

9

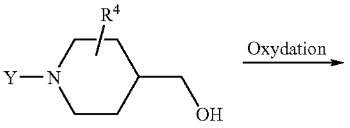

10

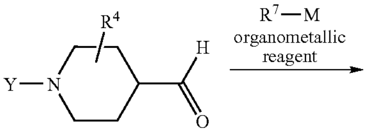

11

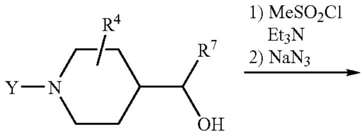

12

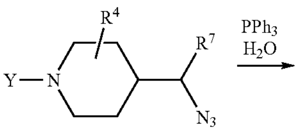

13

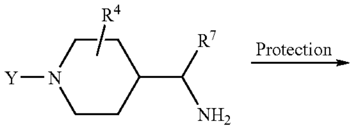

14

-continued

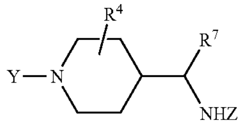

15

Referring to the scheme for Method 5, the piperidine nitrogen in a 4-hydroxymethylpiperidine, 5, is protected with a suitable protecting group such as benzyloxycarbonyl, tert-butyloxycarbonyl, etc. to give a compound of formula 10, which 10 is then oxidized for example using pyridinium chlorochromate, Dess-Martin periodinane, etc. to give aldehyde, 11. Addition of an organometallic reagent such as a Grignard reagent, a cuprate, a borane, etc., to aldehyde 11, provides an alcohol, 12. The alcohol functional group is activated by conversion to a more active leaving group such as a sulfonate ester or halide by means of methanesulfonate, toluenesulfonate, bromide, etc. An azide 13 is prepared by alcohol activation as a suitable leaving group, for example, by acylation of alcohol 12 using methanesulfonyl chloride and triethylamine followed by displacement with azide ion. Reduction of azide 13 may be done with an appropriate reducing agent such as triphenylphosphine and water, etc. to give an amine 14. The amine group in amine 14 is then protected to afford a compound of formula 15.

Method 6:

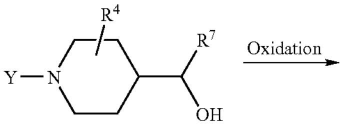

12

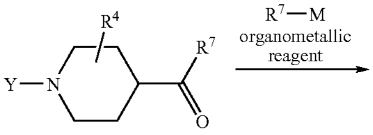

16

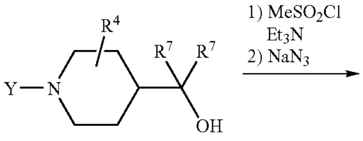

17

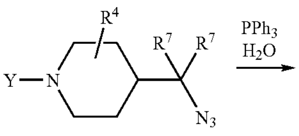

18

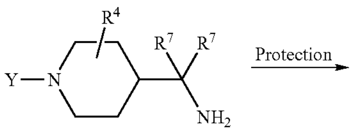

19

-continued

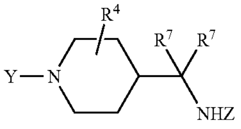

20

Referring to the scheme for Method 6, the piperidine alcohol 12 is oxidized for example with pyridinium chlorochromate, Dess-Martin periodinane, etc., to give a ketone, 16. Addition of an organometallic reagent such as a Grignard reagent, a cuprate, a borane, etc. to the ketone 16 gives an alcohol 17. The alcohol functional group is activated by conversion to a more active leaving group such as a sulfonate ester or halide by means of methanesulfonate, toluenesulfonate, bromide, etc. An azide 18 is prepared by alcohol activation as a suitable leaving group, for example, by acylation of alcohol 17 using methanesulfonyl chloride and triethylamine followed by displacement with azide ion. Reduction of azide 18 may be done with an appropriate reducing agent such as triphenylphosphine and water, etc. to give an amine 19. The amine group in amine 19 is then protected to afford a compound of formula 20.

Method 7:

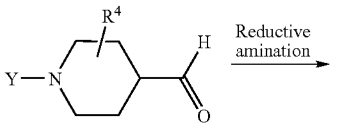

11

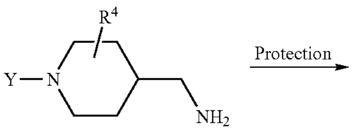

21

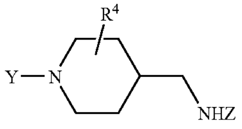

22

Referring to the scheme for Method 7, reductive amination of a piperidine aldehyde 11 using for example, sodium cyanoborohydride and ammonium acetate in the presence of acetic acid gives an amine 21. The amino group of 21 is then protected with suitable protecting group such as with a tert-butyloxycarbonyl, benzyloxycarbonyl, etc. to give an amine-protected compound of formula 22.

Method 8:

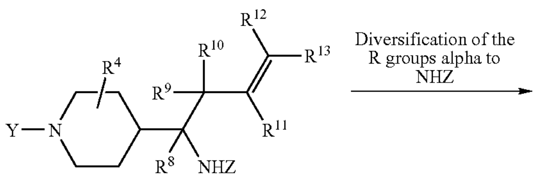

23

-continued

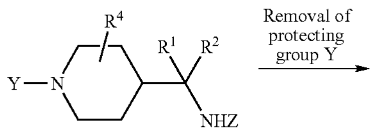

24

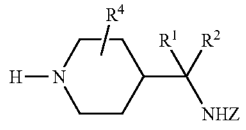

25

Referring to the scheme for Method 8, a compounds of formula 25 is obtained by reacting a compound of formula 23 with a reagent known and used for cross olefin metathesis such as a so-called first or second generation of ruthenium organometallic complexes, etc. or with an organic reagent used for cross-coupling reactions such as a palladium organometallic complex, a boronic acid, etc. and by subsequent treatment of resulting products such as by reduction, oxidation, halogenation, and other functional group manipulation, etc. to provide compound 24. Deprotection of compound 24 affords a compound of formula 25.

Method 9:

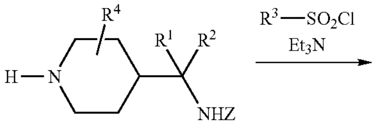

25

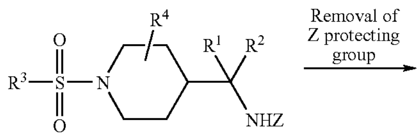

26

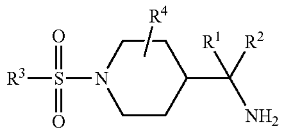

IV

Referring to the scheme for Method 9, an amine 25 is reacted with a sulfonyl chloride such as 5-isoquinolinesulfonyl chloride, 3-pyridinesulfonyl chloride, etc., in the presence of a base such as triethylamine to give a sulfonylpiperidine, 26. The amino nitrogen is then deprotected by removal of the Z group to afford a compound of formula IV.

Method 10:

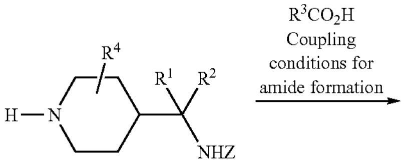

25

-continued

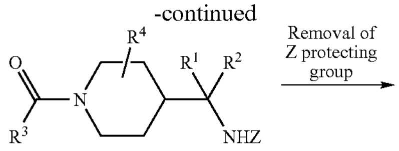

27

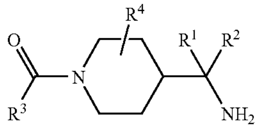

II

Referring to the scheme for Method 10, an amine 25 is coupled with a carboxylic acids such as isonicotic acid, nicotinic acid, etc., or with an activated carboxylic acid equivalent such as a carboxylic acid chloride, anhydride, active ester (e.g., N-hydroxysuccinimde ester, etc.), using suitable coupling conditions such as in the presence of a carbodiimide (e.g., dicyclohexylcarbodiimide when a carboxylic acid is used) to give the corresponding amide 27. The amino nitrogen is then deprotected by removal of the Z group to afford a compound of formula II.

Method 11:

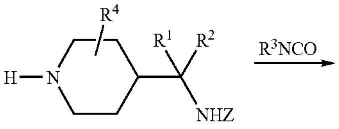

25

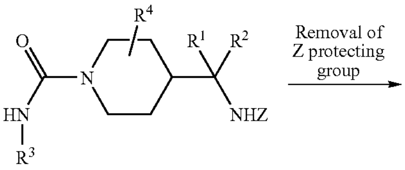

28

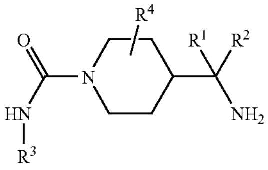

III

Referring to the scheme for Method 11, an amine 25 may be reacted with an isocyanate such as 4-pyridineisocyanate, phenylisocyanate, etc. to give a urea 28. The amino nitrogen is then deprotected by removal of the Z group to afford a compound of formula III.

Method 12

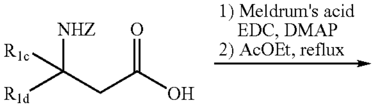

29

-continued

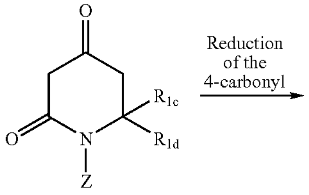

30

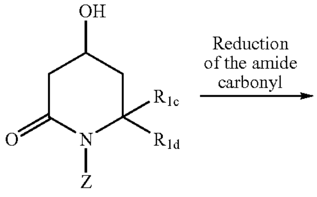

31

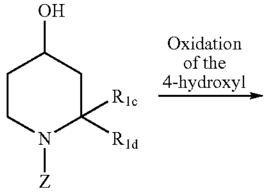

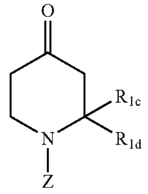

32 $2_{c,d}$

Referring to the scheme for Method 12, a β-amino acid 29 is condensed with a 2,2-dialkyl-1,3-dioxane-4,6-dione such as for example Meldrum's acid (2,2-dimethyl-1,3-dioxane-4,6-dione which is a malonic acid cyclic isopropylidene ester) in presence of 1-(3-dimethylaminopropyl)-3-ethylcarbodiimide hydrochloride [i.e., EDC] and 4-(dimethylamino)pyridine [i.e., DMAP] followed by cyclisation in a warm solvent such as ethyl acetate at about 80° C. to give a dioxopiperidine 30 in which substituents alpha to nitrogen in 29 become substituents at position 2 in the piperidin-4-one represented by formula 2c,d. Reduction of the 4-carbonyl group in 30 with a suitable reducing agent such as sodium borohydride or sodium cyanoborohydride affords the hydroxy lactam (cyclic amide) of formula 31. The amide or lactam carbonyl group may be further reduced for example by treating 30 with borane methyl sulfide to give a hydroxypiperidine 32. The hydroxyl group of the alcohol 32 is then oxidized for example with pyridinium chlorochromate, or Dess-Martin periodinane which is also known as 1,1,1-tris(acetyloxy)-1,1-dihydro-1,2-benziodoxol-3-(1H)-one, etc., to afford a piperidin-4-one, 2c,d, in which R1c and R1d are methyl groups from Meldrum's acid as a non-limiting example.

Method 13

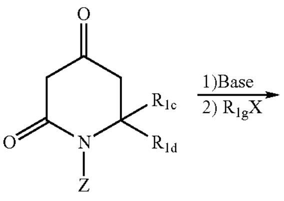

30

-continued

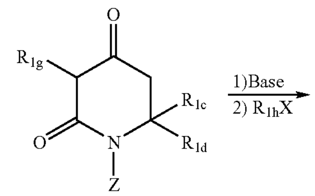

33

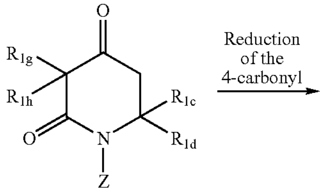

34

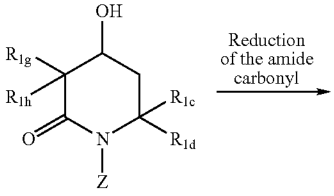

35

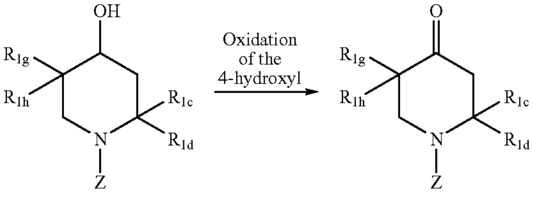

36

$2_{c,d,g,h}$

Referring to the scheme for Method 13, a dioxopiperidine 30 is treated with a base such as sodium bis(trimethylsilyl) amide, NaH, etc. to form a stabilized anion (in an enolization step) which is then reacted with an electrophilic reagent such as an alkyl halide etc. (in an alkylation step) to afford a the 2,2,5-trisubstituted dioxopiperidine compound of formula 33. A second enolization-alkylation procedure is done under similar reaction conditions to give the 2,2,5,5-tetrasubstituted dioxopiperidine 34. Reduction of the carbonyl ketone group in 34 with an appropriate reducing agent such as $NaBH_4$, $NaBH_3CN$, etc., affords an alcohol of formula 35 which is reduced further with for example borane dimethyl sulfide to give an alcohol 36. The alcohol 36 is oxidized with a suitable oxidant such as pyridinium chlorochromate, Dess-Martin periodinane, etc., to give 4-oxopiperidine $2_{c,d,g,h}$.

Method 14

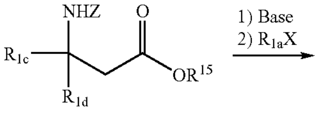

29

-continued

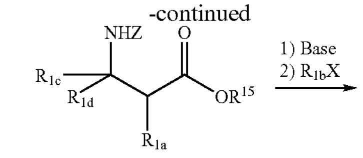

37

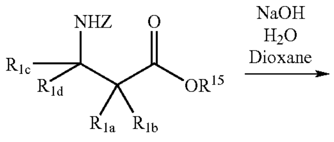

38

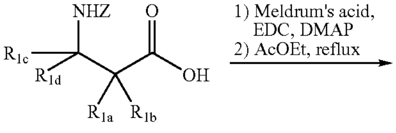

39

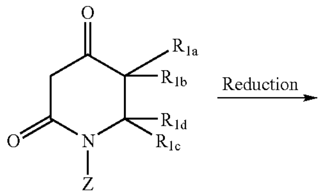

40

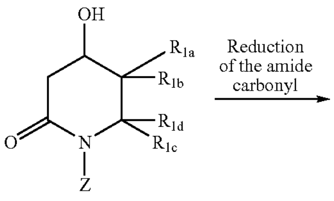

41

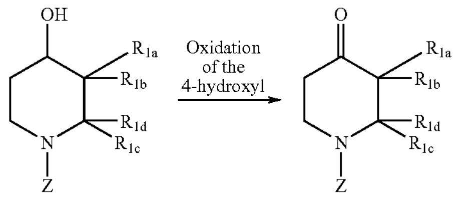

42

$2_{a,b,c,d}$

Referring to the scheme for Method 14, an N-protected (such as with a Z group) amino ester 29 is substituted alpha to the carbonyl group of the ester by a procedure using a base to form an anion at the carbon alpha to the carbonyl followed by treatment with an electrophilic reagent such as an alkyl halide which acts as an alkylating agent to provide a compound of structure 37. Compound 37 may be similarly treated with base and another (or the same) alkylating agent such as an alkyl halide to provide a compound 38, for example by using similar conditions to those in method 13. Esters 37 and 38 are converted to piperidine analogs such as piperidinedione 40, the hydroxyl-containing lactam 41, the 4-hydroxypiperidine 42, and the piperidin-4-one 2a,b,c,d be using reaction conditions such as those conditions described in method 12. For example, amino ester 38 is hydrolyzed with sodium hydroxide in water containing a miscible solvent such as dioxane to give an amino acid 39. A compound of formula 29 is condensed with Meldrum's acid in presence of 1-(3-dimethylaminopropyl)-3-ethylcarbodiimide hydrochloride and 4-(dimethylamino)pyridine followed by cyclization for example at an elevated temperature above room temperature such as about 80° C. in a solvent such as ethyl acetate to give a dioxopiperidine 40. Selective reduction of the ketone group in dioxopiperidine 40 with a reducing agent such as sodium borohydride or sodium cyanoborohydride affords a compound of formula 41. The amide carbonyl group of compound 41 is reduced with a suitable reducing agent such as with borane methyl sulfide complex to give the 4-hydroxypiperidine 42. The hydroxyl group of the 4-hydroxypiperidine of formula 42 is oxidized using an appropriate oxidizing agent such as pyridinium chlorochromate, Dess-Martin periodinane, and the like to afford piperidin-4-one $2_{a,b,c,d}$.

Method 15

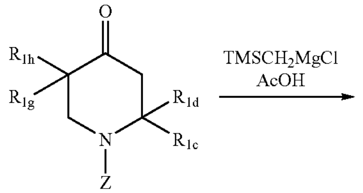

$2_{c,d,g,h}$

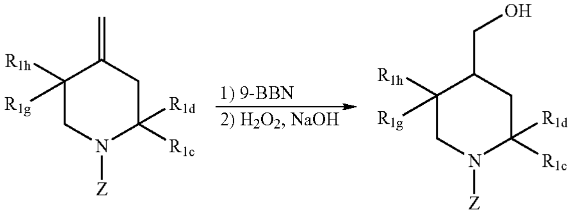

43

$10_{c,d,g,h}$

Referring to the scheme for Method 15, piperidin-4-one $2_{a,b,c,d}$ in which the piperidine-1-nitrogen is protected for example by a Z group, is treated with a reagent suitable for the introduction of an olefin methylene at the piperidine 4-position such as the Grignard reagent derived from trimethylsilylmethyl chloride, i.e., $TMSCH_2MgCl$ or trimethylsilylmethyl magnesium chloride, which with acetic acid (AcOH) affords an alkene of formula 43. Hydroboration of alkene 43 with for example 9-borabicyclo[3.3.1]nonane or 9-BBN followed by an oxidation with a suitable oxidizing agent such as a peroxide such as hydrogen peroxide ($H_2O_2$) and sodium hydroxide (NaOH) gives a piperidinemethanol or 4-hydroxymethylpiperidine, $10_{c,d,g,h}$.

Method 16

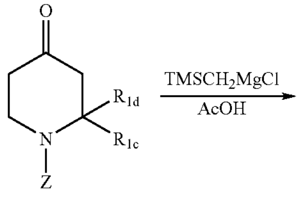

$2_{c,d}$

-continued

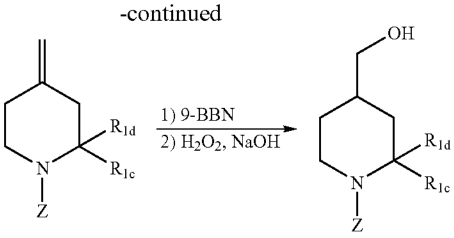

44

$10_{c,d}$

Referring to the scheme for Method 16, N-protected piperidin-4-one (sometimes referred to as an N-protected oxopiperidine) $2_{c,d}$ is treated with (trimethylsilylmethyl) magnesium chloride and acetic acid in a manner similar to that described in Method 15 to afford an alkene of formula 44, a 4-methylenepiperidine. Hydroboration of alkene 44 with a hydroborating agent such as 9-borabicyclo[3.3.1]nonane (9-BBN) and an acid such as acetic acid (AcOH) followed by an oxidation with a suitable oxidizing agent such as hydrogen peroxide and sodium hydroxide gives a piperidinemethanol $10_{c,d}$.

Method 17

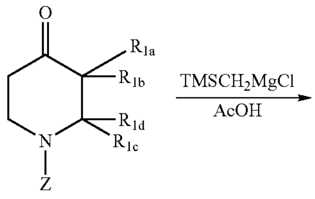

$2_{a,b,c,d}$

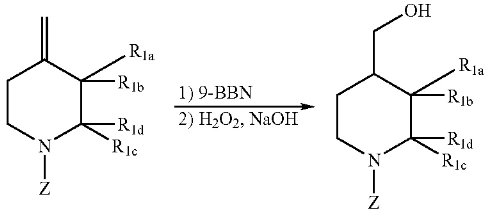

34

$10_{a,b,c,d}$

Referring to the scheme for Method 17, N-protected piperidin-4-one (sometimes referred to as an N-protected oxopiperidine) $2_{a,b,c,d}$ is converted to an olefin 45 for example by treatment with trimethylsilylmethyl magnesium chloride and acetic acid to afford an alkene of formula 45. Hydroboration of alkene 45 with 9-borabicyclo[3.3.1]nonane or 9-BBN followed by an oxidation with a suitable oxidizing agent such as with hydrogen peroxide and sodium hydroxide gives a 4-hydroxymethylpiperidine or piperidine-4-methanol $10_{a,b,c,d}$.

Method 18

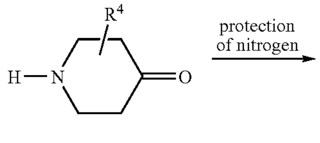

-continued

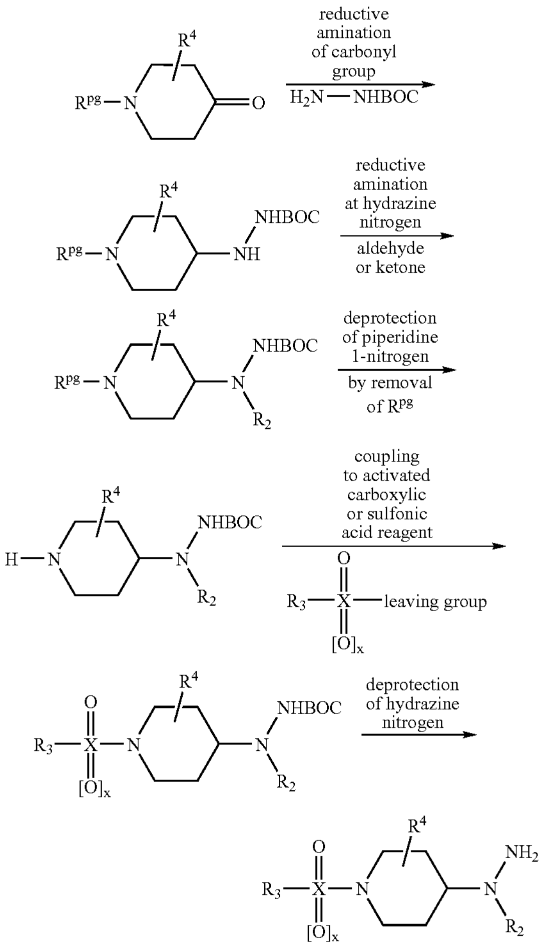

Referring to the scheme for Method 18, wherein $R^4$ represents any of $R_{1a}$ to $R_{1h}$ in formula I, the nitrogen of the piperidin-4-one is protected with a suitable protecting group known in the art, represented by $R^{pg}$, (e.g., benzyoxycarbonyl, etc.) and the carbonyl group at the piperidin-4-one is reductively aminated by a hydrazine which is blocked at one nitrogen (e.g., t-butoxycarbonyl or BOC as an illustrative group). The resulting 4-(blocked hydrazinyl)-1-(blocked)piperidine is reductively aminated with for example an aldehyde or ketone (e.g., with sodium cyanoborohydride) to introduce an $R_2$ group at the hydrazine nitrogen as shown. The nitrogen of the piperidine ring is then unblocked to remove the $R^{pg}$ protecting group (e.g., hydrogenation in the presence of palladium on carbon) to liberate the secondary amine. The piperidine with the free secondary amine is then reacted with an $R_3$-containing sulfonyl or carbonyl compound activated for reaction by the presence of a leaving group (e.g., as an acid halide) or otherwise dehydratively coupled (such as with a carbodiimide) to form an amide or sulfonamide. The blocking group at the hydrazine is then removed (e.g., HCl) to provide an amide or sulfonamide according to formula I. Alternatively, the piperidine with the free secondary amine may be reacted with an $R_3$-containing isocyanate to provide a urea. The blocking group at the hydrazine is then removed to provide a urea according to formula I.

Method 19

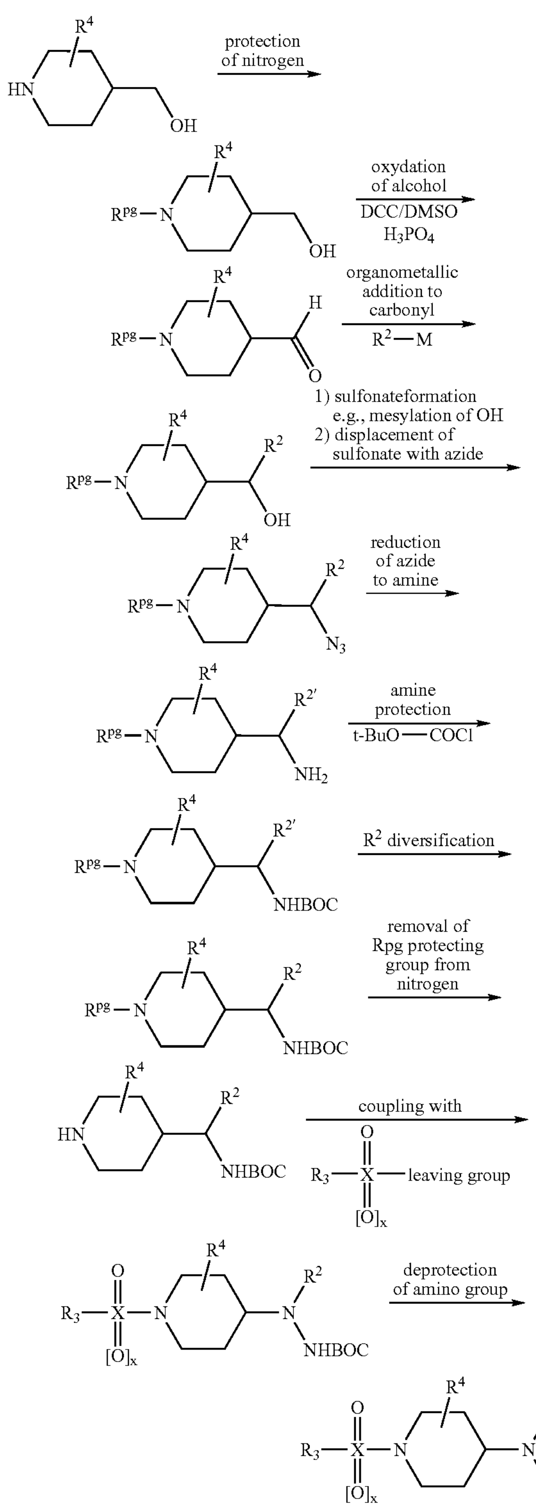

Referring to the scheme for Method 19, wherein $R^4$ represents any of $R_{1a}$ to $R_{1h}$ in formula I, the nitrogen of the 4-hydroxymethylpiperidine is protected with a suitable protecting group known in the art, represented by $R^{pg}$, (e.g., benzyoxycarbonyl, benzyl etc.), and the alcohol OH is oxidized (e.g., dichlorochromate as DCC, dimethyl sulfoxide as DMSO, and phosphoric acid as $H_3PO_4$) to provide an 1-N-protected piperidine-4-carboxaldehyde. The aldehyde is treated with an organometallic reagent (e.g., Grignard reagent, cuprate, etc.) to add an $R^2$ group to the carbon of the carbonyl group with concomitant production of a hydroxyl group from the carbonyl group. The hydroxyl group is activated for displacement (e.g., sulfonate with methanesulfonyl chloride as mesyl chloride to produce a mesylate, or toluenesulfonyl chloride as tosyl chloride to produce a tosylate, etc.), and the sulfonate is then displaced with azide ion to produce an azide, —$N_3$. The azide is reduced (e.g., catalytic hydrogenation) to provide a primary amine group which is then protected with a protecting group (e.g., t-butoxycarbonyl or BOC). The group $R^2$ may than be optionally diversified, and the protecting group at the piperidine nitrogen removed (e.g., for benzyl using Pd/C, HCOOH, MeOH) to provide a 1-H-piperidine-containing compound. This piperidine with the free secondary amine is then reacted with an $R_3$-containing sulfonyl or carbonyl compound activated for reaction by the presence of a leaving group (e.g., as an acid halide) or otherwise dehydratively coupled (such as with a carbodiimide) to form an amide or sulfonamide. The blocking group at the 4-alkylamine nitrogen is then removed (e.g., HCl) to provide an amide or sulfonamide according to formula I. Alternatively, the piperidine with the free secondary amine may be reacted with an $R_3$-containing isocyanate to provide a urea. The blocking group at the 4-alkylamine nitrogen is then removed to provide a urea according to formula I.

For a compound of this invention or for a mixture of enantiomeric or diastereomeric compounds of this invention, an enantiomerically enriched component comprising a compound of this invention or a diastereomerically enriched component comprising a compound of this invention or an enantiomerically pure compound of this invention or a diastereomerically pure compound of this invention may be prepared for example by employing chiral reagents such as chiral organometallic reagents for example according to method 5 and 6 described herein; or may be obtained from a mixture comprising such compounds for example by use of chiral resolution techniques using selective crystallization of one isomer from a mixture of isomers, and/or by use of a chromatographic purification technique which employs a chiral substance bound to a solid support using methods and skills known in the art.

A variety of substituted piperidines which may be useful in the preparation of the compounds of the present invention are known and/or available from a number of sources, such as from Sigma/Aldrich Chemical Co. Examples of piperidines and acid salts of piperidines which may be useful in the preparation of compounds of the present invention include piperidine and acid salts of piperidine such as piperidine hydrochloride, 4-amino-1-benzylpiperidine, 1-acetyl-3-methylpiperidine, delta-valerolactam or 2-piperidinone, 3-methylpiperidine, (2S)-2-methylpiperidine, 4-methylpiperidine, 1-piperidinamine, 4-piperidinamine, 4-hydroxypiperidine or 4-piperidinol, 3-hydroxypiperidine or 3-piperidinol, 1-piperidinecarbonitrile or 1-cyanopiperidine, bicyclic piperidines such as 3-azabicyclo[3.1.0]hexanes such as 3-azabicyclo[3.1.0]hexane-2,4-dione, quinuclidine which may be oxidized at a carbon atom on the 1-azabicyclo [2.2.2]octane structure, tropane or 8-methyl-8-azabicyclo [3.2.1]octane, 1-azabicyclo[2.2.2]octan-3-amine such as (3R)-1-azabicyclo[2.2.2]octan-3-amine, 3-azabicyclo[3.1.0] hexane-2-carboxylic acid such as (1S,2S,5R)-3-azabicyclo [3.1.0]hexane-2-carboxylic acid, 3-azabicyclo[3.1.0]hexane-2-carboxylic acid such as cis-3-azabicyclo[3.1.0]hexane-2-carboxylic acid or (1R,2S,5S)-3-azabicyclo[3.1.0]hexane-2-carboxylic acid, (1R,2S,5S)-3-azabicyclo[3.1.0]hexane-2-carboxylic acid, 3-quinuclidinol or quinuclidin-3-ol, tropinone or 8-methyl-8-azabicyclo[3.2.1]octan-3-one, tropine or (1R,5S)-8-methyl-8-azabicyclo[3.2.1]octan-3-ol, 2-methylquinuclidin-3-ol, 4-methyl-1-propylpiperidine, N-methyl-1-piperidinecarboxamide, N,N-dimethyl(2-piperidinyl)methanamine, decahydroquinoline such as cis-decahydroquinoline or trans-decahydroquinoline, perhydroisoquinoline or decahydroisoquinoline, glutarimide or 2,6-piperidinedione, 1-methyl-2-piperidinone, 1-methyl-4-piperidinone, 1-piperidinecarbaldehyde, cis-2,6-dimethylpiperidine, (2R,6S)-2,6-dimethylpiperidine, 2-ethylpiperidine, 3,5-dimethylpiperidine, cis-3,5-dimethylpiperidine, trans-3,5-dimethylpiperidine, 3,5-dimethylpiperidine as a mixture of cis and trans isomers, 1-ethylpiperidine, 2,6-dimethylpiperidine as cis and/or trans isomers, 4-piperidinone oxime, 1-nitrosopiperidine, 4-piperidinylmethanamine or 4-aminomethylpiperidine, 3-hydroxy-2-piperidinone, 2-piperidinemethanol or 2-piperidinylmethanol, 4-piperidinemethanol or 4-piperidinylmethanol, 1-methyl-4-piperidinol, 3-piperidinemethanol or 3-piperidinylmethanol, 1-methyl-3-piperidinol, (2E)-2-piperidinylidenecyanamide, 1-piperidinylacetonitrile, 1-ethyl-4-piperidinone, 1-ethyl-4-methylpiperidine, 2-propylpiperidine or racemic (±)-coniine or (+)-coniine or (−)-coniine, 4-propylpiperidine, 5-ethyl-2-methylpiperidine, 3-piperidinecarboxamide, 1-piperidinecarboxamide, 4-piperidinecarboxamide, 1-amino-2,6-dimethylpiperidine or 2,6-dimethyl-1-piperidinamine, 1-methyl-4-(methylamino)piperidine or N, 1-dimethyl-4-piperidinamine, N,N-dimethyl-4-piperidinamine, 1-amino-cis-2,6-dimethylpiperidine or (2R,6S)-2,6-dimethyl-1-piperidinamine, 1-ethyl-3-piperidinamine, 2-piperidinoethylamine or 2-(1-piperidinyl)ethanamine, 1-hydroxy-2,6-piperidinedione, 2-piperidinecarboxylic acid or DL-pipecolinic-carboxylic acid, isonipecotic acid or 4-piperidinecarboxylic acid, 3-piperidinecarboxylic acid or nipecotic acid or (±)-nipecotic acid or optically pure isomer thereof such as (S)-(+)-nipecotic acid or (3S)-3-piperidinecarboxylic acid, DL-pipecolinic acid such as the tetrahydrate or 2-piperidinecarboxylic acid, DL-pipecolic acid or 2-piperidinecarboxylic acid, D-pipecolic acid or (2R)-2-piperidinecarboxylic acid, (R)-(−)-nipecotic acid or (3R)-3-piperidinecarboxylic acid, L-pipecolic acid or (2S)-2-piperidinecarboxylic acid, 1-(2-hydroxyethyl)piperidine or 2-(1-piperidinyl)ethanol, 1-methyl-2-piperidinemethanol or (1-methyl-2-piperidinyl)methanol, 2-piperidineethanol or 2-(2-piperidinyl)ethanol, 1-ethyl-3-piperidinol, 2-(4-piperidinyl)ethanol, 4-chloro-1-methylpiperidine, 3-aminopiperidine as an acid salt such as the dihydrochloride or 3-piperidinamine hydrochloride, 3-hydroxypiperidine such as (R)-(+)-3-hydroxypiperidine hydrochloride or (3R)-3-piperidinol hydrochloride, 4-hydroxypiperidine such as an acid salt such as 4-hydroxypiperidine hydrochloride or 4-piperidinol hydrochloride, 3-hydroxypiperidine such as an acid salt such as 3-hydroxypiperidine hydrochloride or 3-piperidinol hydrochloride, Michael addition compounds such as 1-piperidinepropionitrile or 3-(1-piperidinyl)propanenitrile, 1-(2-methyl-1-propenyl)piperidine, 1-acetyl-4-piperidinone or 1-acetyl-4-piperidone, 1-propyl-4-piperidone or 1-propyl-4-piperidinone, 1-acetyl-4-methylpiperidine, 1-acetyl-3-methylpiperidine, 1-isopropyl-4-piperidinone, 2,6-dimethyl-1-piperidinecarbaldehyde, 3-(1-piperidinyl)-1-propanamine, 1,4-dioxa-8-azaspiro[4.5]decane, methyl isonipecotate or methyl 4-piperidinecarboxylate, 1-(1-piperidinyl)-2-propanol, 4-piperidinylmethanamine, 4-piperidinecarboxamide, N~1~-(4-piperidinylmethyl)-1,2-ethanediamine, 4-(ethylamino)-4-piperidinecarboxamide, 1-isopentyl-4-piperidinecarboxamide, 1-pentyl-4-piperidinecarboxamide, 3-aminoquinuclidine such as a salt such as a dihydrochloride or 1-azabicyclo[2.2.2]oct-3-ylamine dihydrochloride, N-phenylquinuclidin-3-amine, 4-(dimethylamino)-4-piperidinecarboxamide hydrochloride, 1-hexyl-4-piperidinecarboxamide, tert-butyl 4-(aminomethyl)-1-piperidinecarboxylate, N-benzylquinuclidin-3-amine, 4-anilino-4-piperidinecarboxamide, 4-(cyclohexylamino)-4-piperidinecarboxamide, 1-phenyl-1,3,8-triazaspiro[4.5]decan-4-one, N-[(4-phenyl-4-piperidinyl)methyl]acetamide, 1-benzyl-4-(methylamino)-4-piperidinecarboxamide, 1-benzyl-4-(ethylamino)-4-piperidinecarboxamide, 1-benzyl-4-(isopropylamino)-4-piperidinecarboxamide, 1-benzyl-4-(propylamino)-4-piperidinecarboxamide, 1-benzyl-4-(1-pyrrolidinyl)-4-piperidinecarboxamide, (1-benzyl-4-phenyl-4-piperidinyl)methylformamide, 4-anilino-1-benzyl-4-piperidinecarboxamide, N-[(1-benzyl-4-phenyl-4-piperidinyl)methyl]acetamide, and 1-benzyl-4-(4-toluidino)-4-piperidinecarboxamide.

Compounds of the present invention may demonstrate Rho kinase inhibitory action in mammalian cells such as in nerve cells in vitro and when administered to a mammal as a pharmaceutical composition in vivo, and may find use as agents to induce neurite regeneration in damaged nerve cells and in damaged nerve tissue or nerve site injury.

The term “nerve injury site” refers to a site of traumatic nerve injury or of traumatic nerve damage, or of nerve injury or nerve damage or nerve abnormality caused by disease, particularly in a mammal. In one aspect a nerve injury may comprise a completely severed nerve, wherein a normally occurring nerve is severed or broken into at least two residual nerve parts comprising segments of the original nerve, and wherein the distance between the cells at the end of one part of the severed nerve is from about 1 micrometer to about 1000 micrometers. In another aspect a nerve injury may comprise a partially severed nerve, wherein a normally occurring nerve is from about 1% to about 99% severed or broken at the site of injury to the original nerve, and wherein the original nerve remains from about 1% to about 99% in tact at the site of damage to the nerve. A nerve injury site may occur in a single nerve (e.g., in a sciatic nerve) or in a nerve tract or in a nerve structure comprised of many nerves (e.g., a nerve injury site may comprise a damaged region of the spinal cord). A nerve injury site may be in the central nervous system (e.g., in the brain and/or spinal cord) or in a peripheral nervous system or in any region of nerve in need of repair. A nerve injury site may form as a result of damage caused by stroke. A nerve injury site may be located in the brain and comprise damage to brain tissue which may occur, for example, as a result of a surgical procedure wherein a portion of normally connected brain tissue is cut or severed completely or partially into at least two parts or domains, or as a result of surgical removal of a brain tumor or as a result of therapy such as radiation therapy or chemotherapy such as may occur in the presence of or following removal of a cancerous lesion. A nerve injury site may result from stroke, Parkinson’s disease, Alzheimer’s disease, amyotrophic lateral sclerosis (ALS), diabetes, or any other type of neurodegenerative disease.

The compounds of this invention may be useful in the treatment of Alzheimer’s disease. Alzheimer’s disease is a progressive neurodegenerative disorder. A characteristic pathological feature of AD is the accumulation of extracellular deposits of amyloid. Amyoid plaques result from the aggregation of amyloid-β peptides (Aβ), which are formed by processing of amyloid precursor protein (APP) by β- and γ-secretases. Studies with non-steroidal anti-inflammatory drugs (NSAIDs) which are known to reduce inflammation have shown a link between inflammation and Rho signaling (e.g., Zhou et al. Science 302, 1215-1217, 2003). Only NAIDs that acted as Rho inhibitors could lower Aβ formation in vivo. In addition, the Rho kinase inhibitor Y-27632 reduced the formation of amyloid aggregations in vitro and amyloid plaques in vivo.

NSAIDs may reduce pathological Aβ and lower the risk of developing AD (McGeer et al., 1990; Lancet 335, 1037. Weggen et al., 2001 Nature 414, 212-216). Rho kinase inhibitors of this invention should also have an ability to reduce pathological Aβ (see Zhou et al. Science 302, 1215-1217, 2003). Importantly, Rho kinase inhibitors are expected to be much more effective than NSAIDs when used in the therapeutic treatment of AD.

Rho kinase acts on another pathway important in disease progression, which is the formation of neurofibrillary tangles that are present in neuritic plaques. Neurofibrillary tangles, a hallmark of AD, are composed of hyperphosphorylated forms of the protein called Tau, which is a microtubule-associate protein (see Lee et al., 2001 Ann Rev. Neurosci. 24:1121). Rho activates two of the kinases that phosphorylate Tau (Sayas et al, 2002 J. Neurosci. 22:6863). In this regard, Rho kinase inhibitors of this invention should reduce neurofibrillary tangle formation because non-phosphorylated forms of Tau do not form tangles. Rho kinase inhibitors of this invention may be effective not only for use in the treatment of AD, but also for use in the treatment of prefrontal dementias that are characterized pathologically by Tau tangle formation, the taupathies.

In addition, hypercholesterolemia is commonly treated with a class of drugs called statins, which are competitive inhibitors of 3-hydroxy-3-methylglutaryl coenzyme A (HMG-CoA) reductase. Statins may reduce serum levels of cholesterol and low density lipoproteins (LDL). A significant reduction in the prevalence of AD has been observed in patients taking statins (Lancet 2000; 356(9242): 1627-31). Statins may act in a manner similar to Rho kinase inhibitors to reduce signaling by active Rho (Kato et al (2004) Biochem. Biophys. Acta. 1689:267). Rho kinase inhibitors of this invention may be effective drugs for use in the treatment of AD and for use to lower the risk in a patient of developing AD.

Compounds of the present invention may find use in the treatment of disease symptoms, for example, of hypertension, angina pectoris, cerebrovascular contraction, asthma, peripheral circulation disorder, immature birth, arteriosclerosis, cancer, inflammation, immune disease, autoimmune disease, AIDS, bacterial infection of digestive tract, osteoporosis, retinopathy, brain function disorder, traumatic brain injury, spinal cord injury, and the like.

Cancer includes bone marrow leukemia, lymphocytic leukemia, gastric cancer, colon cancer, lung cancer, pancreatic cancer, liver cancer, cancer of esophagus, ovarian cancer, breast cancer, skin cancer, cervical cancer, orchioncus, neuroblastoma, urinary epithelial cancer, multiple myeloma, uterine cancer, melanoma, cerebral tumor and cancer of the central nervous system, and the like; anti-cancer means inhibition of formation, infiltration, metastasis, growth and the like of tumors such as those mentioned above. The pathological progression of cancer involves abnormal cell growth which may result in the formation of tumors, and increased cell motility which may cause invasive properties and metastasis. Rho A, B, and C, all of which activate Rho kinase, play a role in both tumor development and metastatic progression by regulating the growth and motility of cells. For example, cultured fibroblasts transfected with active Rho develop alterations in morphology and grow at higher densities than untransfected cells (del Peso et al, 1997 Oncogene.

15:3047-57). A useful model to evaluate anti-proliferative activity of compounds of the invention in vivo comprises a subcutaneous (s.c.) tumor model. In this model, human cancer cells are seeded into in mice by a subcutaneous injection. Typically immune-compromised mouse cell lines are used, such as CD-1 nude mice, to prevent a graft rejection response.

An immune disease includes allergic diseases, rejection in organ transplantation and the like.

An autoimmune disease includes articular rheumatism, systemic lupus erythematodes, Sjogren's disease, multiple sclerosis, myasthenia gravis, type I diabetes, endocrine ophthalmopathy, primary biliary cirrhosis, Crohn's disease, glomerulonephritis, sarcoidosis, psoriasis, pemphigus, hyoplastic anemia, essential thrombocytopenic purpura, and the like.

Bacterial infection of digestive tract means various diseases caused by the invasion of *Salmonella*, dysentery *bacillus*, intestinal pathogenic *Escherichia coli* and the like into intestinal mucosa epithelial cells.

Retinopathy means angiopathic retinopathy, arteriosclerosis retinopathy, central angiospastic retinopathy, central serous retinopathy, circinate retinopathy, diabetic retinopathy, dysproteinemic retinopathy, hypertensive retinopathy, leukemic retinopathy, lipemic retinopathy, proliferative retinopathy, renal retinopathy, toxemic retinopathy of pregnancy, and the like.

Brain function disorder includes psychotic condition related to or caused by cerebral hemorrhage, cerebral thrombus, cerebral embolus, subarachnoid hemorrhage, transient cerebral ischemic stroke, hypertensive encephalopathy, cerebral arteriosclerosis, subdural hematoma, extradural hematoma, cerebral hypoxia, cerebral edema, cerebritis, cerebral tumor, external injury in head, mental disease, poisoning caused by a drug metabolite, drug poisoning, temporal respiratory arrest, deep anesthesia during operation, physical disorder and the like, and sequelae, decreased attention, hyperactivity, logopathy, delayed mental development, lethe, dementia (inclusive of wandering, nocturnal delirium, aggressive behavior and the like associated with dementia) caused by the above-mentioned diseases.

A compound of the present invention may be effective as a pharmaceutical agent, particularly as an agent for the prophylaxis and treatment of these diseases caused by Rho or which are mediated by inhibition of Rho kinase, such as a therapeutic agent for treatment of hypertension, a therapeutic agent for treatment of angina pectoris, a suppressive agent for treatment of cerebrovascular contraction, a therapeutic agent for treatment of asthma, a therapeutic agent for treatment of peripheral circulation disorder, a prophylactic agent for treatment of immature birth, a therapeutic agent for treatment of arteriosclerosis, an anti-cancer drug for treatment of cancer, an anti-inflammatory agent for treatment of an inflammatory disease, an immunosuppressant for treatment of an autoimmune disease, a therapeutic agent for treatment of autoimmune disease, a therapeutic agent for treatment of AIDS, a contraceptive, a prophylactic agent of digestive tract infection, a therapeutic agent for treatment of osteoporosis, a therapeutic agent for treatment of retinopathy, a therapeutic agent for treatment of damage to the brain caused by brain cancer, and a therapeutic agent for treatment of spinal cord injury. A compound of formula I or I' or pharmaceutically acceptable saltd thereof according to this invention may be formulated for administration in a pharmaceutically acceptable carrier in accordance with known techniques, for example, those described in Remington, The Science And Practice of Pharmacy (9th Ed. 1995) that is incorporated herein by reference in its entirety.

The present invention also provides for a "pharmaceutical composition" comprising a compound in accordance with the present invention (namely, a compound of formula (I) (II), (IIa), etc. including pharmaceutically acceptable salts thereof) and a pharmaceutically acceptable carrier. A "pharmaceutical composition" may comprise one or more such compounds of the present invention. It is to be understood herein that the expression "pharmaceutical composition" refers to a composition which comprises a therapeutically effective amount(s) of active agent(s) wherein the active agent comprises a compound in accordance with the present invention, namely a compound of formula (I) (II), (IIa), etc. including pharmaceutically acceptable salts thereof. A "therapeutically effective amount" as used herein refers to that amount which provides a therapeutic effect for a given condition and administration regimen.

The term "pharmaceutically acceptable carrier" is to be understood herein as referring to any substance that may, medically, be acceptably administered to a patient, together with a compound of this invention, and which does not undesirably affect the pharmacological activity thereof; a "pharmaceutically acceptable carrier" may thus be for example a pharmaceutically acceptable member(s) selected from the group comprising or consisting of diluents, preservatives, solubilizers, emulsifiers, adjuvant, tonicity modifying agents, buffers as well as any other physiologically acceptable vehicle.

Such pharmaceutically acceptable carriers include carriers known in the art such as for example, phosphate buffer solution such as 0.01 M to 0.1 M phosphate buffer and for example 0.05 M phosphate buffer or phosphate buffered saline, and 0.8% saline solution. Additionally, such pharmaceutically acceptable carriers may be aqueous or non-aqueous solutions, suspensions, and emulsions. Such solutions, suspensions, and emulsions may be aqueous. Examples of non-aqueous solvents include propylene glycol, polyethylene glycol, vegetable oils such as olive oil or soybean oil, and pharmaceutically acceptable organic esters such as ethyl oleate which are suitable for use in injectable formulations. Aqueous carriers may include water, alcoholic/aqueous solutions, emulsions or suspensions, including saline and buffered media. Parenteral vehicles may include sodium chloride solution, Ringer's dextrose, dextrose and sodium chloride, lactated Ringer's or fixed oils. Intravenous vehicles may include fluid and nutrient replenishers, electrolyte replenishers such as those based on Ringer's dextrose, and the like. Preservatives and other additives may also be present, such as, for example, antimicrobials, antioxidants, collating agents, inert gases and the like. Formulations of compounds of this invention may be performed, for example, in the absence of oxygen, such as in an inert atmosphere for example nitrogen or argon. Liquids used in the preparation of formulation compositions of this invention may be sparged with an inert gas prior to use to substantially remove unwanted dissolved gases such as air and oxygen. Additionally such compositions may more particularly be liquids or lyophilized or otherwise dried formulations and include diluents of various buffer content (e.g., Tris-HCl, acetate, phosphate), pH and ionic strength; additives such as albumin or gelatin which may prevent absorption of an active compound of this invention to a surface such as glass, pharmaceutically acceptable detergents (e.g., Tween 20, Tween 80, Pluronic F68, bile acid salts); solubilizing agents (e.g., glycerol, polyethylene glycerol); anti-oxidants (e.g., ascorbic acid, sodium metabisulfite); preservatives (e.g., thimerosal, benzyl alcohol, parabens); bulking substances or tonicity modifiers (e.g., lactose, mannitol). The active agent may for example be associated with liposomes, emulsions, microemulsions, micelles, unilamellar or multilamellar vesicles, erythrocyte ghosts, or spheroplasts. The carrier element of such compositions may be chosen with an eye to influence the physical state, solubility, stability, rate of in vivo release, and rate of in vivo clearance. The compositions of this invention may comprise controlled or sustained release compositions and may comprise a compound of this invention formulated in lipophilic depots (e.g., fatty acids, waxes, oils). The pharmaceutical composition may be formulated so as to able to be administered or for administration to a patient in need of treatment parenterally, paracancerally, transmucosally, transdermally, intramuscularly, intravenously, intradermally, subcutaneously, intraperitonealy, intraventricularly, intracranially intratumorally or more particularly, directly at a central nervous system (CNS) lesion site or a peripheral nervous system (PNS) lesion site.

Compositions of this invention that are intended for injectable or implantable use into a mammal may be sterilizable, for example by filtration through a membrane or filter intended for such use, by irradiation for example by irradiation derived from a radioisotope or by ultraviolet irradiation, or by thermal sterilization such as by steam sterilization (e.g., at 121° C. for an effective time such as about 15 minutes or more) or by thermal sterilization in the absence of steam. An injectable composition of this invention, may comprise, for example, an a unit dose amount of a compound of this invention, may be filled into a container such as a vial or a syringe or a pharmaceutically acceptable plastic bag, and for example, under an inert atmosphere such as nitrogen or argon and the like or under a substantially inert atmosphere such as an atmosphere consisting essentially of nitrogen or argon and the like, sealed for example with a stopper and crimp cap for a vial, and sterilized.

In one aspect of this invention, a method of treatment of a mammal may comprise administration by a route selected from parenteral, paracanceral, transmucosal, transdermal, intramuscular, intravenous, intradermal, subcutaneous, intraperitoneal, intraventricular, intracranial, intratumoral, or more particularly, directly at a central nervous system (CNS) lesion site or at a peripheral nervous system (PNS) lesion site, of a compound of this invention in a pharmaceutically acceptable carrier.

Compositions of this invention that are intended for injectable or implantable use into a mammal may comprise a kit of parts. A kit of parts of this invention may comprise two parts, wherein for example, one part of such kit may comprise a dried composition of this invention, for example such as a lyophilized formulation of a compound of this invention, sealed in a first vessel, for example such as vial or a compartment of a syringe, and another part of such kit may consist of a sterile aqueous solution, for example such as sterile water or buffered water, sealed in a second vessel, wherein the aqueous solution in the second vessel may be in an amount suitable for addition to the lyophilized formulation in the first vessel suitable to form an injectable unit dosage form of the compound of this invention, may be uniformly dissolved or dispersed in the aqueous medium. Transfer of aqueous medium between vessels may be via syringe or cannula or the like and done in a fashion to minimize contamination by ambient microbials. The unit dosage form prepared according to this invention may be administered by injection. Optionally, the kit of parts may comprise a third part which may be a container or a packaging material shaped in a manner suitable to hold the other parts of the kit in proximity prior to and optionally during rehydration or even during administration of the formulation of this invention. The third part of the kit for example may comprise a first socket or cradle of a size suitable to hold, optionally firmly or permanently, the first vessel of the kit, and a second socket or cradle of a size suitable to hold, optionally firmly or permanently, the second vessel of the kit, and may optionally comprise a cannula for use in transfer of the aqueous medium from the second vessel to the first vessel.

The compounds according to the present invention include where applicable and desired, pharmaceutically acceptable salts (e.g. pharmaceutically acceptable ammonium salts such as for example acid addition salts). Thus, for example, compounds of the formula (I), (II), (Ia), (IIa), etc., where appropriate and/or desired may be obtained as or converted to pharmaceutically acceptable acid addition salts thereof according to any conventional manner. The acid for forming pharmaceutically acceptable acid addition salts may be suitably selected from inorganic acids (e.g. hydrochloric acid, hydrobromic acid, sulfuric acid, phosphoric acid, and the like) and organic acids (e.g. acetic acid, methanesulfonic acid, maleic acid, fumaric acid, and the like). These salts may be converted to the corresponding free base according to a conventional manner, for example, by reacting with an alkali such as sodium hydroxide or potassium hydroxide. The compound of the formula (I) (II), (IIa), etc., when appropriate or desired may also be converted to a quaternary ammonium salt thereof. If a compound of the formula (I), (II), (Ia), (Ia), etc., is a compound having a carboxyl group as a substituent, the carboxyl group may be converted to a salt, such as a salt comprising a metal ion (e.g. sodium, potassium, calcium, aluminum) or amino acid ion (e.g. lysine, ornithine). In the case where a compound of the formula (I) (II), (IIa), etc., comprises an acid function (e.g. carboxyl group) then where appropriate and/or desired such compound may be obtained as or converted to a salt comprising a pharmaceutically acceptable metal ion (e.g. alkali metal ion e.g., sodium ion, or alkaline earth metal ion, e.g., calcium ion).

Pharmaceutically acceptable acids for use in the preparation of a pharmaceutically acceptable acid addition salt of a compound of this invention include and be selected from the group consisting of acetic acid, benzenesulfonic acid, benzoic acid, bicarbonic acid, bitartaric acid, calcium dihydrogenedetic acid, camphorsulfonic acid, carbonic acid, citric acid, dodecylsulfonic acid, edetic acid, 1,2-ethanedisulfonic acid, estolic acid, ethanesulfonic acid, 2-ethylsuccinic acid, fumaric acid, glucoheptonic acid, glubionic acid, gluconic acid, glutamic acid, glycollylarsanilic acid, hexylresorcinic acid, hydrobromic acid, hydrochloric acid, hydroxynaphthoic acid, 3-hydroxynaphthoic acid, hydriodic acid, 2-hydroxyethanesulfonic acid, isethionic acid, lactic acid, lactobionic acid, laurylsulfuric acid, levulinic acid, malic acid, maleic acid, mandelic acid, methanesulfonic acid, mucic acid, naphthalenesulfonic acid, nitric acid, pamoic acid, embonic acid, pantothenic acid, phosphoric acid, polygalacturonic acid, propionic acid, salicylic acid, saccharic acid, stearic acid, subacetic acid, succinic acid, sulfamic acid, sulfuric acid, tannic acid, tartaric acid, theoclic acid, 8-chlorotheophyllinic acid, triethiodic acid, and combinations thereof.

Pharmaceutically acceptable acids for use in the preparation of a pharmaceutically acceptable salt of a compound of this invention may be selected from the group consisting of adipic, alginic, aminosalicylic, anhydromethylenecitric, arecoline, aspartic, hydrogensulfuric, camphoric, digluconic, hydrogensuccinic, glycerophosphoric, hydrofluoric, methylenebis(salicylic), napadisylic, 1,5-naphthalenedisulfonic, pectinic, persulfuric, phenylethylbarbituric, picric, propionic, thiocyanic, toluenesulfonic, and undecanoic acid, and combinations thereof.

Acids such as hydroxynapthoic, napadisylic, naphthalenesulfonic, pamoic may reduce water solubility of a compound of this invention.

In the preparation of a pharmaceutical formulation according to the invention, a compound of formula I or mixture of compounds of formula I or I' which may include one or more physiologically acceptable salts thereof, is typically admixed with, inter alia, a pharmaceutically acceptable carrier. The carrier may be a solid or a liquid, or both, and may be formulated with the compound of formula I as a unit-dose formulation, for example, a tablet or an injectable suspension or an injectable solution, which may contain from 0.01 percent to 99 percent, or from 0.5 percent to 95 percent, by weight of the compound or mixture of compounds of formula I.

The method of administration of a formulation of this invention may be selected from the group consisting of oral, rectal, topical, buccal, sub-lingual, vaginal, parenteral, subcutaneous, intramuscular, intradermal, intravenous, topical, transdermal, transmucosal, inhalation, subdural injection, implantation at a lesion site of a nerve, controlled release from a depot or matrix implanted or injected at a site of damage of a nerve, and combinations thereof. The most suitable route in any given case will depend on the nature and severity of the condition being treated, particularly when the condition is cancer. When the cancer is systemic, an injectable formulation may be used. When a solid tumor is present in a tissue, an injectable formulation may be used. Other formulations may comprise topical and inhalation formulations.

The compounds of this invention may be formulated in pharmaceutically acceptable dosage forms such as for injectable use, for oral use, for inhalation use, for transdermal use, for transmembrane use, and the like. Formulations suitable for oral administration may be presented in discrete units or dosage forms, such as capsules, cachets, lozenges, tablets, pills, powders, granules, chewing gum, suspensions, solutions, and the like. Each dosage form contains a predetermined amount of a compound of this invention. Solutions and suspensions of a compound of this invention or a pharmaceutically acceptable salt thereof may be in an aqueous liquid, such as buffered with a pharmaceutically acceptable pH buffer, or in non-aqueous liquid such as DMSO, or be prepared as an oil-in-water or water-in-oil emulsion. Injectable dosage forms may be sterilized in a pharmaceutically acceptable fashion, for example by steam sterilization of an aqueous solution sealed in a vial under an inert gas atmosphere at 120° C. for about 15 to 20 minutes, or by sterile filtration of a solution through a 0.2 or smaller pore-size filter, optionally followed by a lyophilization step, or by irradiation of a composition containing a compound of the present invention by means of emissions from a radionuclide source.

Formulations of a compound of this invention or a pharmaceutically acceptable salt thereof may be prepared by any suitable method of pharmacy. An exemplary method may comprise the step of bringing into association, for example by mixing, by dissolution, by suspension, by blending, by granulation, and the like, a compound of this invention or a pharmaceutically acceptable salt thereof and a pharmaceutically acceptable carrier such as a liquid, for example a liquid consisting of water, an aqueous solution of a pharmaceutically acceptable buffer, an aqueous solution of a pharmaceutically acceptable alcohol, a pharmaceutically acceptable oil such as an edible oil such as a triglyceride or mixture of triglycerides of natural sources such as an edible plant oil, an emulsion of a pharmaceutically acceptable oil in an aqueous medium comprising water, and which aqueous medium may contain one or more pharmaceutically acceptable excipients such as an excipient selected from the group consisting of a pH buffering agent, a matrix forming sugar, a pharmaceutically acceptable polymer, a pharmaceutically acceptable tonicity modifying agent, a surface modifier or surfactant useful to form micelles or to form liposomes or to form emulsions, and the like. Useful pharmaceutically acceptable excipients may be found in the Handbook of Pharmaceutical Excipients, second Edition, ed. Wade et al, 1994, which is incorporated by reference.

The compound of this invention or a pharmaceutically acceptable salt thereof may also be combined in solid form with pharmaceutically acceptable excipients such as ingredients used in tablet formation such as release agents and compressing agents, silica, cellulose, methyl cellulose, hydroxypropylcellulose (HPC), polyvinylpyrolidinone (PVP), gelatin, acacia, magnesium stearate, sodium lauryl sulfate, mannitol, lactose, colorants, dyes, and formed into a dosage form such as a tablet, capsule, caplet, pill, powder, granule, and the like. Optionally, the tablet or related dosage form may be coated with a polymer coating such as an enteric and/or moisture barrier polymer coating such as may be applied by spraying, spray drying, or fluid bed drying methods.

The compound of this invention or a pharmaceutically acceptable salt thereof may be combined in an aqueous or aqueous-organic, or an organic liquid solvent together with one or more pharmaceutically acceptable excipient and then dried, for example in an inert or non-oxidizing atmosphere by spray drying, lyophilization, fluid bed drying, or evaporation to form a solid in which the compound of this invention or a pharmaceutically acceptable salt thereof is imbibed or uniformly dispersed or suspended. The formulations of the invention may be prepared by admixing, such as by uniformly and intimately admixing, a compound of this invention or a pharmaceutically acceptable salt thereof, with a liquid or with a finely divided solid carrier or matrix-forming excipient or mixture of excipients, then, if necessary, shaping the resulting mixture into a dosage form suitable for the intended use such. For example, a tablet may be prepared by compressing or molding a powder or granules or granulates containing a compound of this invention or a pharmaceutically acceptable salt thereof, optionally with one or more accessory ingredients. Compressed tablets may be prepared by compressing in a tablet press a mixture of a compound of this invention or a pharmaceutically acceptable salt thereof together with one or more pharmaceutically acceptable excipient materials, which mixture may be in a free-flowing form such as a powder or granules optionally mixed with a pharmaceutically acceptable material selected from the group consisting of a binder, a lubricant, an inert diluent, a surface active agent, a dispersing agent, and combinations thereof. Molded tablets may be made by molding, in a tablet mold machine, a solid powdered mixture of a compound of this invention or a pharmaceutically acceptable salt thereof together with one or more pharmaceutically acceptable excipient, which mixture is moistened with an inert liquid binder such as water or alcohol.

A formulation suitable for buccal or sub-lingual administration to a patient in need of treatment by compound of this invention or a pharmaceutically acceptable salt thereof may include a lozenge such as a lozenge comprising compound of this invention or a pharmaceutically acceptable salt thereof in a flavored base such as sucrose, acacia, tragacanth, and the like; and a pastille comprising a compound of this invention or a pharmaceutically acceptable salt thereof in an inert base such as gelatin, glycerin, sucrose, acacia, and the like.

A composition containing a compound of this invention or a pharmaceutically acceptable salt thereof for implantation in a mammal proximal to a damaged nerve or proximal to a nerve lesion site may be prepared in sterile form by imbibition of a compound of this invention or a pharmaceutically acceptable salt thereof, optionally as a solution or suspension in a pharmaceutically acceptable carrier or solvent into a matrix forming excipient or a depot for the compound, the concentration of the compound and the matrix of shape and dimensions suitable for its intended use. A useful composition comprises a compound of the present invention or a salt thereof in a gel foam absorbable gelatin that may be swollen with a sterile aqueous isotonic fluid containing the compound (for example a gel foam may be Gelfoam® from Pharmacia & Upjohn) for use in implantation proximal to a lesion site of a nerve.

The therapeutically effect concentration of a Rho kinase antagonist compound of this invention or of a pharmaceutically acceptable salt thereof in a dosage form for use to administer the compound to a mammal depends on the activity (e.g., as measured by its $LC_{50}$ concentration in an in vitro cell assay to determine its activity as a Rho kinase antagonist agent) and on the bioavailability of the compound in vivo. The amount of a compound of this invention or a pharmaceutically acceptable salt thereof in a suitable dosage form may be at least a therapeutically effective amount of the compound or salt thereof. The amount of the compound may be, for example, in the range from about 0.01% by weight to about 50% by weight of the dosage form, or from 0.1% to 40% by weight. Additional concentrations may be selected from the group consisting of 0.1% to 5% by weight (percent by weight), 0.1% to 10% by weight, 0.1% to 20% by weight, 1% to 10% by weight, and 1% to 15% by weight of the dosage form. Depending on the dosage form, pharmaceutically acceptable excipients and solvents such as water may make up the remainder of the dosage form weight. Excipients such as sugars (lactose, mannitol, sucrose, and the like, and also non-reducing sugars); polymers such as polyvinylpyrrolidone, poly(vinyl alcohol), gelatin, pharmaceutically acceptable cellulose derivatives, silica, dextrins, cyclodextrins which may form inclusion complexes to enhance solubility and bioavailability of a compound of this invention may be useful in solid oral dosage forms.

A formulation of the present invention that is suitable for parenteral administration may comprise a sterile aqueous solution, and a non-aqueous solution in an organic solvent safe for injection of a compound of this invention or a pharmaceutically acceptable salt thereof of this invention. Useful injectable dosage forms containing a compound of this invention or a pharmaceutically acceptable salt thereof of this invention may be isotonic with the blood of the intended recipient. Tonicity of the dosage form may be adjusted and/or maintained by addition of pharmaceutically acceptable for injection water-soluble excipients such as sugars, buffer salts, and combinations thereof. These dosage forms may optionally contain antioxidants, buffers, bacteriostats, and dissolved solutes that render the formulation isotonic with the blood of the intended recipient. Aqueous and non-aqueous sterile suspensions may include pharmaceutically acceptable suspending agents and thickening agents. Formulations of this invention may be presented in unit-dose or multi-dose containers. For example, for injectable use, a formulation may be sealed in an ampoule or vial, for example, sealed in oxygen-free form such as in a vial under an inert oxygen-free gas such as nitrogen or argon or other non-reactive gas, or a mixture of non-reactive gases. In another embodiment, a dosage form of this invention may be stored in a freeze-dried or lyophilized form as an anhydrous solid or as a solid containing a small quantity of water, for example from 0.01% to about 5% by weight of the dried dosage form, which dosage form then requires the addition of a sterile liquid carrier, for example, isotonic aqueous saline solution, and optionally buffered to between about pH 5 to pH 9, or between pH 6 and pH 8, or by addition of water-for-injection immediately prior to use. Extemporaneous injection solutions and suspensions may be prepared from sterile powders, granules and tablets of the kind previously described.

A formulation of this invention containing a compound of this invention or a pharmaceutically acceptable salt thereof and which is suitable for rectal administration may be presented as a unit dose suppository. A suppository dosage form containing compound of this invention or a pharmaceutically acceptable salt thereof may be prepared by admixing a compound of this invention or a pharmaceutically acceptable salt thereof with one or more conventional pharmaceutically acceptable solid carriers, for example, such as cocoa butter, to form a mixture containing a compound of this invention or a pharmaceutically acceptable salt thereof, and then shaping the resulting mixture.

A formulation of this invention suitable for topical application such as to skin or to tumor margins after resection of a tumor may be in the form of an ointment, a cream, a lotion, paste, gel, spray, aerosol, oil, or a combination thereof. A pharmaceutically acceptable carrier in this embodiment may be selected from the group consisting of petroleum jelly, white petrolatum, lanoline, glycerol, cetyl alcohol and the like, glyceryl stearate, isopropyl palmitate, stearyl alcohol, synthetic beeswax, hexylene glycol, phosphoric acid, propylene glycol stearate, a polyethylene glycol, a polyethylene glycol ether or ester, an alcohol, a transdermal penetration enhancer, a bioabsorbable polymer such as a poly(lactic acid), a poly(glycolic acid), a copolymer of lactic acid and glycolic acid, a bioabsorbable gelatin such as a gelfoam, a phospholipid, and combinations thereof.

A formulation of this invention suitable for transdermal administration of a compound of this invention or a pharmaceutically acceptable salt thereof may be presented as a discrete patch dosage form. The patch may be adapted to remain in intimate contact with the epidermis or stratum corneum of a recipient for a prolonged period of time such as from 8 hours to about 48 hours or longer. A formulation suitable for transdermal administration may also be delivered by an iontophoretic delivery mechanism such as by using an applied voltage difference between two portions of the dosage form, each of which is in contact with the skin of a patient.

A therapeutically effective dosage of a compound of this invention or a pharmaceutically acceptable salt thereof, the use of which is in the scope of present invention, may vary from one compound to another compound, and from patient to patient, and may depend upon factors such as the age of the patient and the diagnosed condition of the patient and the route of delivery of the dosage form to the patient. A therapeutically effective dose and frequency of administration of a dosage form may be determined in accordance with routine pharmacological procedures known to those skilled in the art. Dosage amounts and frequency of administration may vary or change as a function of time and particular condition being treated. For example, a dosage of from about 0.1 to 1000 mg/kg, or from about 1 to about 100 mg/kg, may be suitable for treatment of a cancer such as breast or brain cancer, particularly after removal of a tumor wherein the pharmaceutical dosage form of the compound or Rho kinase inhibitor or agent may be administered to the residual tissue at the residual margins of the excised tumor. When used to treat a damaged nerve in the central nervous system, administration may be by injection into cerebrospinal fluid as a solution or as a suspension suitable for sustained release from the injected pharmaceutical dosage form such as from a vesicle. Administration may be made to nerve cells by injection at the lesion site of a damaged nerve such as by injection such as microinjection through the dura mater, through the arachnoid mater, through the pia mater.

Compositions of this invention when administered to a nerve or to a nerve cell may penetrate into a nerve cell by crossing the outer membrane of the nerve cell from the external environment of the cell into the internal environment (e.g., fluids or membranes) of the cell. A compound of this invention may induce axon regeneration and growth in a nerve cell and may induce growth of axons across the scar tissue of a lesion in a damaged or injured or crushed nerve.

Compositions of this invention when administered to a mammal may be useful in the treatment of spinal cord injury, traumatic spinal cord injury, spinal cord crush injury, or lesion in the spinal nerves, stroke, human immunodeficiency virus (HIV) dementia, prion diseases, Parkinson's disease, Alzheimer's disease, multiple sclerosis, traumatic brain injury, and glaucoma, and in therapy of cancer especially in the prevention of tumor metastasis and regrowth of tumors after in excise margins after surgical removal of a tumor.

In one aspect, a compound of the present invention is a Rho kinase inhibitor compound, and may be used as a therapeutically active agent, in the preparation of a medicine useful for treatment of a disease in which inhibition of Rho kinase may have a therapeutically beneficial or palliative or curative effect, or may halt or slow the rate of progression of a disease or prolong patient life, or reduce discomfort or reduce or eliminate symptoms of a disease.

In one embodiment, a compound of the present invention may be a therapeutically active agent that may be useful to stimulate axon growth in nerve cells and nerve cell connectivity across a lesion site in a damaged nerve.

In another embodiment, a compound of the present invention may be a therapeutically active agent that may be useful to prevent or inhibit apoptosis or cell death following ischemia in the CNS.

In another embodiment, a compound of the present invention may be a therapeutically active agent that may be useful for treatment of a victim of stroke or a victim of a neurodegenerative disease.

In another embodiment, a compound of the present invention may be a therapeutically active agent that may be useful for treatment of Alzheimer's disease.

In another embodiment, a compound of the present invention may be a therapeutically active agent that may be useful to promote repair of nerve cells in diseases that are neurodegenerative, which diseases include but are not limited to stroke, traumatic brain injury, Parkinson's disease, Alzheimer's disease and ALS.

In another embodiment, a compound of the present invention may be a therapeutically active agent that may be useful to treat diseases of the eye such as glaucoma.

In another embodiment, a compound of the present invention may be a therapeutically active agent that may be useful to treat diseases related to abnormalities in smooth muscle relaxation such as hypertension, asthma, and vascular disease as well as penile erectile dysfunction.

In one aspect, a dosage of a compound of this invention or a pharmaceutically acceptable salt thereof may be from about 20 to about 35 mg/kg to have therapeutic efficacy.

In one aspect, a compound of this invention may be in the form of a pharmaceutically acceptable salt, such as a protonated amine form or a deprotonated carboxylate or other acid form. Intravenous dosage forms may sometimes be up to about 20 mg/kg of a Rho kinase inhibitor of this invention. A dosage from about 30 mg/kg to about 50 mg/kg may be employed for oral administration. A dosage from about 20 mg/kg to 30 mg/kg may be employed for intramuscular injection. The frequency of administration of a dosage form of this invention may be once, or twice, or three times, or four times per day. A useful duration of treatment of a patient may be from about one or two days, up to five or seven days, up to two or three weeks, or until symptoms of a disease state in a patient are essentially controlled.

The relative activity of a compound of this invention as a Rho kinase inhibitor may be determined in a Rho kinase inhibitor tissue culture bioassay system. A Rho kinase inhibitor activity bioassay may also be used to identify Rho kinase inhibitor compounds of this invention that may be effective in promoting axon regeneration in spinal cord injury, stroke or neurodegenerative disease. A Rho kinase inhibitor activity bioassay may also be useful to identify compounds of this invention that are active in stimulating neurite outgrowth in nerve cells, such as for example, on an axon-growth-inhibitory substrate such as myelin.

Neurons do not grow neurites on inhibitory myelin substrates. When neurons are placed on inhibitory substrates in tissue culture, the neurons remain rounded. When an effective Rho kinase inhibitor compound is added to the neurons, the neurons are able to grow neurites on myelin substrates. The time, designated "T-myelin" that it takes for neurons to grow neurites after the addition of a Rho kinase inhibitor compound is about the same as the time, designated "T-permissive", that it takes for neurons to grow neurites if the neurons are plated on a growth permissive substrate such as laminin or polylysine. Time T-myelin and time T-permissive usually may range from about 20 hours to about 60 hours in a neuron cell culture. An assessment of resulting neurite growth on the cultured neurons may be scored by visual means.

A quantitative assessment of neurite growth may be performed, wherein, after a time (T-myelin) such as 1 to 2 days, the neurite length on cultured neurons may be measured in separate cultures that are grown as follows.

These separate neuron cell cultures all contain neurons of the same cell type in each culture and may comprise, for example, the following sets of neuron cultures:

neuron culture set a) as one or more control neuron cultures, wherein, in each control culture, neurons are plated on an inhibitory myelin substrate, and wherein the neurons are not treated with a Rho kinase inhibitor compound, and wherein the cultured neurons are allowed to grow for time T-myelin;

neuron culture set b) as one or more positive control neuron cultures, wherein, in each control culture, neurons are plated on a permissive substrate, for example on a polylysine substrate, and wherein the neurons are not treated with a Rho kinase inhibitor compound, and wherein the cultured neurons are allowed to grow for time T-myelin;

neuron culture set c) which comprises a number of separate neuron cultures each grown in a manner analogous to those of neuron culture set a), and wherein the neuron cultures in the set c) are separately treated with a standard size single bolus aliquot of a solution containing a given test concentration of a Rho kinase inhibitor compound of this invention, wherein the given test concentration may be selected from the group consisting of separate logarithmically decreasing diluted concentrations of said compound in a solvent comprising DMSO, which logarithmically decreasing concentrations may be achieved by starting with a relatively high first concentration of the Rho kinase inhibitor compound such as a 1 molar solution or a 0.1 molar solution of the compound in DMSO, [a standard size aliquot of which added to a first neuron culture of set c) at a start time T-zero], and creating a sequential dilution series of solutions of decreasing test concentrations of said compound by a process involving a 10-fold dilution of the first concentration to form a second concentration that may be 0.1 times the concentration of the first concentration [a standard size aliquot of which added to a second neuron culture of set c) at a start time T-zero], diluting the second concentration by a factor of 10 with for example PBS to form a third concentration that may be 0.1 times the concentration of the second concentration of said compound [a standard size aliquot of which added to a third neuron culture of set c) at a start time T-zero], and so on to achieve a logarithmic dilution range comprising from 3 to 12 dilutions, and wherein, after time T-zero, each of the cultured neurons may be allowed to grow for time T-myelin; and neuron culture set d) which comprises a number of separate neuron cultures each grown in a manner analogous to those of neuron culture set b), and wherein the neuron cultures in the set d) are separately treated as in set c) with a standard size single bolus aliquot form a dilution series of a solution containing the Rho kinase inhibitor compound of this invention employed in set c), and wherein, after time T-zero of addition of aliquots to the cultures in the set, each of the cultured neurons may be allowed to grow for time T-myelin.

At the end of the time T-myelin, each of the neuron cultures from sets a), b), c) and d) may be examined microscopically to determine by measurement the median length and number of axons that have grown on the neurons.

A rapid assay may also be used to assess the ability of a Rho kinase inhibitor of this invention to promote neurite outgrowth on neurons. In this assay, NG108 nerve cells are plated on a plastic (such as polystyrene) in the presence or absence of the test substance such as a Rho kinase inhibitor of this invention. Qualitatively, a more effective Rho kinase inhibitor will promote more rapid neurite outgrowth than a less effective Rho kinase inhibitor. An ineffective Rho kinase inhibitor will not promote neurite outgrowth. The relative efficacy may be assessed by fixing the cultures at a time 5 hours after plating on plastic, and thereafter counting the number of NG108 cells that have grown neurites. Rho kinase inhibitors differ from growth factors in their ability to promote neurite outgrowth. Growth factors, such as nerve growth factor (NGF) are not able to overcome growth inhibition by myelin. The tissue culture experiments described herein are all performed in the presence of the growth factor BDNF (brain-derived neurotropic factor) for retinal ganglion cells, or NGF for PC-12 cells, or cAMP for NG108 cells. Growth factors may transiently prevent apoptosis in vivo, but because growth factors are unable to promote neurite growth on growth inhibitory substrates, growth factors do not promote robust neurite regeneration.

A compound of the present invention may be identified as a Rho kinase inhibitor by a process comprising:

a) expressing, in Hela cells or another suitable cell type by transfection, recombinant Rho kinase that may be tagged with a specific tag such as a myc epitope tag, or with a GST tag or with any other suitable tag for which an antibody may be obtained for subsequent immunoprecipitation use;

b) homogenizing said cells and purifying the expressed specifically tagged Rho kinase so obtained from residual cell homogenates using immunoprecipitation with one of more antibody directed against the specific tag (e.g., an antibody to a myc tag or an antibody to a GST tag, respectively); (purified Rho kinase may alternatively be purchased from Upstate Biotechnology Inc.)

c) recovering the immunoprecipitates of tagged Rho kinase from b) and incubating them with a radionuclide labeled [32P] ATP and histone type 2 as a substrate in the presence or absence of test compound such as a Rho kinase inhibitor of this invention;

d) isolating the histone or phosphorylated histone, and d) determining by detection of emissions from the phosphorous radionuclide if the histone is phosphorylated on not phosphorylated, wherein phosphorylation activity of the Rho kinase (i.e. phosphorylation of histone) is blocked in the presence of a test compound, and in the absence of a Rho kinase inhibitor, the Rho kinase phosphorylates histone, and in the presence of a Rho kinase inhibitor the phosphorylation activity of Rho kinase (i.e. phosphorylation of histone) is blocked, and as such identifies the compound as a Rho kinase antagonist.

Rho kinase inhibition by a compound of this invention may be determined by use of any other known procedures such as by using commercially available screening methods.

Rho kinase antagonists of this invention may be used to treat spinal cord injury to promote functional repair of damaged nerve structures.

Rho kinase antagonists of this invention may be used to treat neurodegenerative diseases such as Alzheimer's disease and Parkinson's disease where penetration of the drug to the affected neuronal population may be required for effective treatment. Such penetration may be by diffusion, by pharmacokinetic distribution, by perfusion, or by direct placement such as by implantation or injection, of a pharmaceutical composition of a compound of this invention.

Rho kinase inhibitors of this invention will also be of benefit for the treatment of stroke and traumatic brain injury.

Compounds of this invention which are Rho kinase antagonists may be useful in the treatment of cancer, for example by mitigating or preventing or reducing cancer cell migration. Rho kinase antagonist compounds are also useful in the treatment of disease involving smooth muscle, such as vascular disease, hypertension, asthma, and penile dysfunction.

In one aspect, for treatment of spinal cord injury, a Rho kinase inhibitor compound of this invention may be used in conjunction with cell transplantation. Many different cell transplants have been extensively tested for their potential to promote regeneration and repair, including, but not restricted to, Schwann cells, fibroblasts modified to express growth factors, fetal spinal cord transplants, macrophages, embryonic or adult stem cells, and olfactory ensheathing glia. A Rho kinase inhibitor compound of this invention may be administered to a patient in conjunction with one or more neurotrophins, one or more apoptosis inhibitors, or one or more other agents that prevent cell death. A Rho kinase inhibitor compound of this invention may be used in conjunction with cell adhesion molecules such as L1, laminin, and artificial growth matrices that promote axon growth. A Rho kinase inhibitor compound of this invention may also be used in conjunction with the administration of a monoclonal or polyclonal antibody such as monoclonal antibody IN-1 that blocks growth inhibitory protein substrates to promote axon growth, or a Rho kinase inhibitor compound of this invention may also be used in conjunction with administration of a therapeutic vaccine.

The present invention in an aspect relates to pharmaceutical compositions containing, as an active ingredient, a compound of formula (I) (II) etc., an isomer thereof, or a pharmaceutically acceptable salt (e.g., an acid addition salt) thereof. Such pharmaceutical compositions may be useful as antihypertensive agents, as therapeutic agents for angina pectoris, as therapeutic agents for asthma, as agents for improving peripheral circulation, and the like.

The compound of formula (I), (II), etc., isomers thereof and pharmaceutically acceptable salts thereof of the present invention may have coronary and cerebral blood flow increasing action as well as renal and peripheral artery blood flow increasing action. The blood flow increasing action may last over a long period of time ranging from about one minute to as long as about 1 hour, or to as long as about 6 hours, or to as long as about 12 hours, or to as long as about 24 hours, or to as long as about 48 hours, or to as long as about one week, or longer, and antihypertensive action may be very strong such as sufficient to alter an abnormal blood flood condition in a patient to normal levels during the time of lasting action or of therapeutic efficacy of the compound, optionally until a subsequent dose of the compound is administered to a patient in need of treatment. Accordingly, a compound of the present invention may be useful as an antihypertensive agent and as an agent for the prevention and treatment of diseases in circulatory organs such as in treatment of diseases in coronary, cerebral, renal and peripheral arteries. A compound of the present invention may be an effective agent for the prophylaxis and/or treatment of diseases such as hypertension, angina pectoris, cerebrovascular contraction, asthma, peripheral circulation disorder, immature birth, arteriosclerosis, cancer, inflammation, immune disease, autoimmune disease, AIDS, fertilization and nidation of fertilized egg, osteoporosis, retinopathy, brain function disorder, bacterial infection of digestive tract and the like.

The present invention in an aspect relates to the provision of a compound that may act as a Rho kinase inhibitor. A Rho kinase inhibitor compound of the present invention may exhibit an antihypertensive action, an anti-angina pectoris action, a cerebrovascular contraction suppressive action, an anti-asthma action, a peripheral circulation improving action, an immature birth preventive action, an anti-arteriosclerosis action, an anti-cancer action, an anti-inflammatory action, an immunosuppressive action, an autoimmune disease improving action, an anti-AIDS action, a preventive action on fertilization and nidation of fertilized egg, an osteoporosis treating action, a retinopathy treating action, a brain function improving action, a preventive action on bacterial infection of digestive tract. A Rho kinase inhibitor compound of the present invention may be useful as a pharmaceutical agent, particularly as a therapeutic agent of hypertension, a therapeutic agent of angina pectoris, a suppressive agent of cerebrovascular contraction, a therapeutic agent of asthma, a therapeutic agent of peripheral circulation disorder, a prophylactic agent of immature birth, a therapeutic agent of arteriosclerosis, an anti cancer drug, an anti-inflammatory agent, an immunosuppressant, a therapeutic agent of autoimmune disease, an anti-AIDS drug, a therapeutic agent of osteoporosis, a therapeutic agent of retinopathy, a brain function improving drug, a contraceptive and a prophylactic agent of digestive tract infection.

A compound of this invention which inhibits Rho kinase may be useful as a reagent for the study of the enzymes Rho and Rho kinase and as a diagnostic agent in the diagnosis of diseases in which inhibition or antagonism of Rho and/or Rho kinase has a perturbing effect on the outcome or symptom of the disease.

This invention comprises a pharmaceutical agent containing a compound of the present invention.

This invention comprises in further aspects, a pharmaceutical agent comprising a compound of the present invention, which may be, for example, a therapeutic agent useful for treatment of at least one condition or disease selected from the group consisting of a spinal cord injury, a stroke, a neurodegenerative disease, glaucoma, hypertension, angina pectoris, a cerebrovascular abnormality wherein the agent may be a suppressive agent of cerebrovascular contraction, asthma, a peripheral circulation disorder, arteriosclerosis, a cancer wherein the agent may be an anti-cancer drug, inflammation wherein the agent may be an anti-inflammatory agent, a disease or condition relating to a tissue or organ implantation or graft wherein the agent may be an immunosuppressant, an autoimmune disease, AIDS wherein the agent may an anti-AIDS or anti-HIV (human immunodeficiency) drug, osteoporosis, retinopathy, functional abnormalities of the brain wherein the agent may be, for example, a brain-function-improving drug, immature birth wherein the agent may be a prophylactic agent of immature birth, a contraceptive agent wherein the agent may be, for example, useful for prevention or reversal of nidation of a fertilized egg, and a prophylactic agent useful in the treatment of an infection of the digestive tract.

This invention comprises a pharmaceutical composition containing a therapeutically effective amount of a compound of the present invention and as desired a pharmaceutically acceptable additive.

This invention comprises a reagent containing a compound of the present invention.

This invention comprises a diagnostic containing a compound of the present invention.

This invention comprises a pharmaceutical agent containing a compound of the formula (I), (II), etc., an isomer thereof, and/or a pharmaceutically acceptable salt thereof, which may be, for example, a therapeutic agent of at least one disease selected from the group consisting of hypertension, angina pectoris, cerebrovascular contraction, asthma and peripheral circulation disorder, which disease is related to Rho kinase activity.

This invention comprises a pharmaceutical agent containing a compound of the formula (I), (II), etc., an isomer thereof, and/or a pharmaceutically acceptable acid addition salt thereof, which may be, for example, at least one therapeutic agent selected from the group consisting of a therapeutic agent of arteriosclerosis, an anti-cancer drug, an anti-inflammatory agent, an immunosuppressant, a therapeutic agent of autoimmune disease, an anti-AIDS drug, a therapeutic agent of osteoporosis, a therapeutic agent of retinopathy, a brain function improving drug, a prophylactic agent of immature birth, a contraceptive and a prophylactic agent of digestive tract infection.

This invention comprises a method of treatment of a disease or injury that may be treatable by the in vivo inhibition of the enzyme Rho kinase, wherein the disease may be, for example, at least one disease selected from the group consisting of hypertension, angina pectoris, cerebrovascular contraction, asthma, a peripheral circulation disorder, arteriosclerosis, cancer, an inflammation, an immune disease, an autoimmune disease, AIDS, osteoporosis, retinopathy, a brain function disorder, immature birth, fertilization and nidation of fertilized egg and infection of digestive tract, the method may comprise administration to a patient of a pharmaceutically effective amount of a compound or pharmaceutical composition of this invention.

This invention comprises a method of treatment of at least one disease selected from the group consisting of hypertension, angina pectoris, cerebrovascular contraction, asthma and a peripheral circulation disorder, which are caused by Rho kinase, and arteriosclerosis, cancer, inflammation, immune disease, autoimmune disease, AIDS, osteoporosis, retinopathy, brain function disorder, immature birth, fertilization and nidation of fertilized egg and infection of digestive tract, which method comprises administering a pharmaceutically effective amount of a compound of the formula (I), (II), etc., an isomer thereof and/or a pharmaceutically acceptable salt thereof.

This invention comprises the use of a compound of the present invention, for the production of a therapeutic agent or medicine useful for the treatment of a disease treatable by inhibiting Rho kinase.

The present invention in an aspect relates to pharmaceutical compositions containing, as an active ingredient, a compound of formula (I) (II) etc., an isomer thereof, or a pharmaceutically acceptable salt (e.g., an acid addition salt) thereof. Such pharmaceutical compositions may be useful as antihypertensive agents, as therapeutic agents for angina pectoris, as therapeutic agents for asthma, as agents for improving peripheral circulation, and the like.

The compound of formula (I), (II), etc., isomers thereof and pharmaceutically acceptable salts thereof of the present invention may have coronary and cerebral blood flow increasing action as well as renal and peripheral artery blood flow increasing action. The blood flow increasing action may last over a long period of time ranging from about one minute to as long as about 1 hour, or to as long as about 6 hours, or to as long as about 12 hours, or to as long as about 24 hours, or to as long as about 48 hours, or to as long as about one week, or longer, and antihypertensive action may be very strong such as sufficient to alter an abnormal blood flood condition in a patient to normal levels during the time of lasting action or of therapeutic efficacy of the compound, optionally until a subsequent dose of the compound may be administered to a patient in need of treatment. Accordingly, a compound of the present invention may be useful as an antihypertensive agent and as an agent for the prevention and treatment of diseases in circulatory organs such as in treatment of diseases in coronary, cerebral, renal and peripheral arteries.

A compound of the present invention may be an effective agent for the prophylaxis and/or treatment of diseases such as hypertension, angina pectoris, cerebrovascular contraction, asthma, peripheral circulation disorder, immature birth, arteriosclerosis, cancer, inflammation, immune disease, autoimmune disease, AIDS, fertilization and nidation of fertilized egg, osteoporosis, retinopathy, brain function disorder, bacterial infection of digestive tract and the like.

The present invention in an aspect relates to the provision of a compound that may act as a Rho kinase inhibitor. A Rho kinase inhibitor compound of the present invention may exhibit an antihypertensive action, an anti-angina pectoris action, a cerebrovascular contraction suppressive action, an anti-asthma action, a peripheral circulation improving action, an immature birth preventive action, an anti-arteriosclerosis action, an anti-cancer action, an anti-inflammatory action, an immunosuppressive action, an autoimmune disease improving action, an anti-AIDS action, a preventive action on fertilization and nidation of fertilized egg, an osteoporosis treating action, a retinopathy treating action, a brain function improving action, a preventive action on bacterial infection of digestive tract. A Rho kinase inhibitor compound of the present invention may be useful as a pharmaceutical agent, particularly as a therapeutic agent of hypertension, a therapeutic agent of angina pectoris, a suppressive agent of cerebrovascular contraction, a therapeutic agent of asthma, a therapeutic agent of peripheral circulation disorder, a prophylactic agent of immature birth, a therapeutic agent of arteriosclerosis, an anti cancer drug, an anti-inflammatory agent, an immunosuppressant, a therapeutic agent of autoimmune disease, an anti-AIDS drug, a therapeutic agent of osteoporosis, a therapeutic agent of retinopathy, a brain function improving drug, a contraceptive and a prophylactic agent of digestive tract infection.

A compound of this invention which inhibits Rho kinase may be useful as a reagent for the study of the enzymes Rho and Rho kinase and as a diagnostic agent in the diagnosis of diseases in which inhibition or antagonism of Rho and/or Rho kinase has a perturbing effect on the outcome or symptom of the disease.

This invention comprises a pharmaceutical agent containing a compound of the present invention.

This invention comprises a pharmaceutical agent comprising a compound of the present invention, which may be, for example, a therapeutic agent useful for treatment of at least one condition or disease selected from the group consisting of a spinal cord injury, a stroke, a neurodegenerative disease, glaucoma, hypertension, angina pectoris, a cerebrovascular abnormality wherein the agent may be a suppressive agent of cerebrovascular contraction, asthma, a peripheral circulation disorder, arteriosclerosis, a cancer wherein the agent may be, for example, an anti-cancer drug, inflammation wherein the agent may be, for example, an anti-inflammatory agent, a disease or condition relating to a tissue or organ implantation or graft wherein the agent may be, for example, an immunosuppressant, an autoimmune disease, AIDS wherein the agent may be an anti-AIDS or anti-HIV (human immunodeficiency) drug, osteoporosis, retinopathy, functional abnormalities of the brain wherein the agent may be a brain-function-improving drug, immature birth wherein the agent may be a prophylactic agent of immature birth, a contraceptive agent wherein the agent may be useful for prevention or reversal of nidation of a fertilized egg, and a prophylactic agent useful in the treatment of an infection of the digestive tract.

This invention comprises a pharmaceutical composition containing a therapeutically effective amount of a compound of the present invention and as desired a pharmaceutically acceptable additive.

This invention comprises a reagent containing a compound of the present invention.

This invention comprises a diagnostic containing a compound of the present invention.

This invention comprises a pharmaceutical agent containing a compound of the formula (I), (II), etc., an isomer thereof, and/or a pharmaceutically acceptable salt thereof, which may be a therapeutic agent of at least one disease selected from the group consisting of hypertension, angina pectoris, cerebrovascular contraction, asthma and peripheral circulation disorder, which disease is related to Rho kinase activity.

This invention comprises a pharmaceutical agent containing a compound of the formula (I), (II), etc., an isomer thereof, and/or a pharmaceutically acceptable acid addition salt thereof, which may be, for example, at least one therapeutic agent selected from the group consisting of a therapeutic agent of arteriosclerosis, an anti-cancer drug, an anti-inflammatory agent, an immunosuppressant, a therapeutic agent of autoimmune disease, an anti-AIDS drug, a therapeutic agent of osteoporosis, a therapeutic agent of retinopathy, a brain function improving drug, a prophylactic agent of immature birth, a contraceptive and a prophylactic agent of digestive tract infection.

This invention comprises a method of treatment of a disease or injury that may be treatable by the in vivo inhibition of the enzyme Rho kinase, wherein the disease may be, for example, at least one disease selected from the group consisting of hypertension, angina pectoris, cerebrovascular contraction, asthma, a peripheral circulation disorder, arteriosclerosis, cancer, an inflammation, an immune disease, an autoimmune disease, AIDS, osteoporosis, retinopathy, a brain function disorder, immature birth, fertilization and nidation of fertilized egg and infection of digestive tract, the method comprising administration to a patient of a pharmaceutically effective amount of a compound or pharmaceutical composition of this invention.

This invention comprises a method of treatment of at least one disease selected from the group consisting of hypertension, angina pectoris, cerebrovascular contraction, asthma and a peripheral circulation disorder, which are caused by Rho kinase, and arteriosclerosis, cancer, inflammation, immune disease, autoimmune disease, AIDS, osteoporosis, retinopathy, brain function disorder, immature birth, fertilization and nidation of fertilized egg and infection of digestive tract, which method comprises administering a pharmaceutically effective amount of a compound of the formula (I), (II), etc., an isomer thereof and/or a pharmaceutically acceptable salt thereof.

This invention comprises the use of a compound of the present invention, for the production of a therapeutic agent or medicine useful for the treatment of a disease treatable by inhibiting Rho kinase.

While the compositions and methods of this invention will be generally described in terms of or be directed at repair in the CNS, the inventive compositions and techniques described herein may be extended to use in many other diseases including, but not restricted to, cancer, metastasis, hypertension, cardiac disease, stroke, diabetic neuropathy, and neurodegenerative disorders such as stroke, Alzheimer's disease, Parkinson's disease, amyotrophic lateral sclerosis (ALS). Treatment with a compound of the present invention including a pharmaceutically acceptable salt thereof, (e.g. Rho kinase inhibitors) may be used to enhance the rate of axon growth of nerves such as peripheral nerves and thereby be effective for repair of damaged peripheral nerves after surgery, for example after reattaching severed limbs or after prostate surgery. Also, treatment with a compound of the present invention including a suitable salt thereof, may be effective for the treatment of various peripheral neuropathies (such as diabetic neuropathy) because of its axon growth promoting effects.

The compounds and compositions of this invention may find use as Rho kinase inhibitors and may find use to treat a traumatically damaged nervous system in a mammal. The compositions and methods of this invention may also be applied to treatment of diseases and cell damage arising from disease states and causes, such as during stroke, multiple sclerosis, HIV dementia, Parkinson's disease, Alzheimer's disease, traumatic brain injury, prion diseases or other diseases of the CNS where axons are damaged in the CNS environment, and includes those disease states identified herein.

A substituted piperidine compound of the present invention, which is a Rho kinase inhibitor and which may be cell membrane permeable may be useful as a pharmaceutical agent in the therapeutic treatment of a disease where inhibition of Rho kinase activity may be useful.

A substituted piperidine compound of the present invention, which is a Rho kinase inhibitor, which is cell membrane permeable, and which comprises a diagnostically useful moiety such as a radionuclide, a fluorescence emitting chromophore such as an infrared or visible light fluorescence emitting chromophore may be useful as a diagnostic agent for example to detect the cause and/or effect of inhibition of Rho kinase activity in a cell, particularly in a cell where inhibition of rho kinase may be involved in a disease process or desired for repair of injury in a cell such as a nerve cell proximal to a lesion in a damaged or diseased nerve.

The compounds of the present invention may affect smooth muscle and endothelial cells and may find useful application in a variety of therapeutic aspects such use on stents, as coated stents to prevent restenosis.

In one aspect, the compounds and compositions of the present invention may find use in repair in a mammal of a component of a nervous system such as a central nervous system (CNS) lesion site or a peripheral nervous system (PNS) lesion site, in axon regeneration and/or axon sprouting, in neurite growth and/or protection from neurodegeneration and ischemic damage.

In another aspect, the compounds and compositions of the present invention target intracellular signaling mechanisms involving Rho and the Rho kinase for promoting axon regeneration and axon growth.

In another aspect, the compounds and compositions of the present invention may promote axon growth on growth in nerve cells on inhibitory substrates surrounding nerves in the CNS and may promote repair of nerves in an injured CNS.

In another aspect, the compounds and compositions of the present invention may stimulate or promote regeneration of injured, cut, crushed, or otherwise damaged axons, i.e. the site of a nerve lesion and invention may stimulate or promote regeneration of axons across a nerve lesion.

Rho kinase inhibitors of this invention may find therapeutic use in the treatment of cancer and of malignant transformations and abnormal proliferation of cells. Rho kinase inhibitors of this invention may be useful in therapeutic treatment of hypertension, asthma, pulmonary vasoconstriction, vascular disease, penile erectile dysfunction, glaucoma, malignant cell transformation, prostate cancer metastasis, hepatocellular carcinoma and metastasis, fibrosis or organs such as liver and kidney, cardioprotection and allograft survival, and cerebral vasospasm.

The compounds or Rho kinase inhibitors in accordance with the present invention provide an improved alternative with respect to known Rho kinase inhibitors such as Rho kinase inhibitory Y27632. A compound or inhibitor in accordance with the present invention, when compared with Y27632, may exhibit different and improved kinase inhibition profiles and/or may also promote more neurite outgrowth on growth inhibitory substrates.

It is an advantage that the compounds and compositions of the present invention inhibit the activity of Rho kinase. These compounds and compositions may be advantageous over proteins and peptides such as C3 which inhibit the activity of Rho kinase and which may generate an immune response in vivo because the substituted piperidines may not generate an unwanted immune response. It is a further advantage that the compounds of this invention are cell permeable. It is another advantage of this invention that the novel compounds and compositions disclosed herein may promote repair of nerve cells and of nerve structure when applied to an injured mammalian central nervous system.

Compounds and compositions of this invention may promote neurite growth on growth inhibitory substrates.

Although the novel compounds and compositions of the present invention may be useful to facilitate regeneration of axons and in neuroprotection, it is to be understood that the compounds and compositions may be exploited in other contexts as shall be mentioned herein, including with respect to treatment of diseases such as cancers.

The compounds and compositions of this invention may be useful in the treatment and repair of injured, damaged, or diseased nerves in the CNS and in the PNS. In the brain and spinal cord of the CNS, the compounds and compositions of this invention may be useful in the treatment and repair of injured, damaged, or diseased nerves selected from the group consisting of cranial nerves, cervical spinal nerves, thoracic spinal nerves, lumbar spinal nerves, sacral spinal nerves, coccygeal spinal nerves, suboccipital nerve, nerves of the gray ramus communicans, nerves of the white ramus communicans and combinations thereof. The compounds and compositions of this invention may be useful in the treatment and repair of injured, damaged, or diseased nerve ganglia. The compounds and compositions of this invention may be useful in the treatment and repair of injured, damaged, or diseased spinal nerve fibers belonging to the somatic nerve system, to the sympathetic or splanchnic nerve system, to nerve fibers connecting these systems with each other, and combinations thereof. The compounds and compositions of this invention may be useful in the treatment and repair of injured, damaged, or diseased nerve cells selected from unipolar nerve cells, the cells of Dogiel, and multipolar cells. Administration of the compounds and compositions of this invention may be directly to a nerve, for example, by administration below the pia mater covering, below the covering of dura mater sheath, or by administration directly into the cerebrospinal fluid in brain ventricles, in the spinal canal, or in the spinal cord. Administration of the compounds and compositions of this invention to a nerve may be by administration to a nerve in need of treatment residing under meninges membranes, including under dura mater tissue, arachnoid mater, and pia mater. Administration of the compounds and compositions of this invention to a nerve may be accomplished by administration to the vascular component of the pia mater. Administration of the compounds and compositions of this invention to a nerve may be by administration to a nerve in need of treatment residing in the epidural space.

Compounds and compositions of the present invention may be useful in the treatment and therapy of neurodegenerative diseases of the CNS, with diseases associated with cell death, and with diseases and trauma associated with axonal loss. Representative diseases and trauma of the CNS include stroke, human immunodeficiency virus (HIV) dementia, prion diseases, Parkinson's disease, Alzheimer's disease, multiple sclerosis, traumatic brain injury, and glaucoma, and others. Compounds and compositions of the present invention may be useful to stimulate growth of axons from the injured, damaged, diseased or an otherwise abnormal neuronal population.

It is in to be understood herein for example that the compound formulae (i.e. formula (I), (II), (I') etc.) referred to herein, each includes, each and every individual compound (including the isomers thereof) described thereby as well as each and every possible class or sub-group or sub-class of compounds; thus it is to be understood that such individual compounds or classes or sub-classes are inherently defined herein in every and any possible manner whatsoever; it is thus for example to be understood that the definitions herein with respect to any such individual compound, class or sub-class include both positive as well as negative or exclusionary definitions i.e. the definitions herein incorporate any and all definitions that may be worded as positively including particular individual compounds, classes or sub-classes and/or as excluding particular individual compounds, classes or sub-classes or combinations thereof; for example an exclusionary definition for the formulae (e.g. (I), etc.) may read as follows: "provided that X is carbon when x is 0, and X is sulfur when x is 1".

BRIEF DESCRIPTION OF THE FIGURES

FIG. 10 shows microphotographs of HUVEC tube formation after plating on fibronectin alone (control), on fibronectin with E-23a, 10 and 50 μM. Tube formation is substantially reduced relative to control in the presence of E-23a.

FIG. 12 is a histogram showing the effects of E-23a and Tranilast on endothelial cell migration in the presence of VEGF in the bottom chamber of a Boyden chamber.

EXAMPLES

Figure 1:
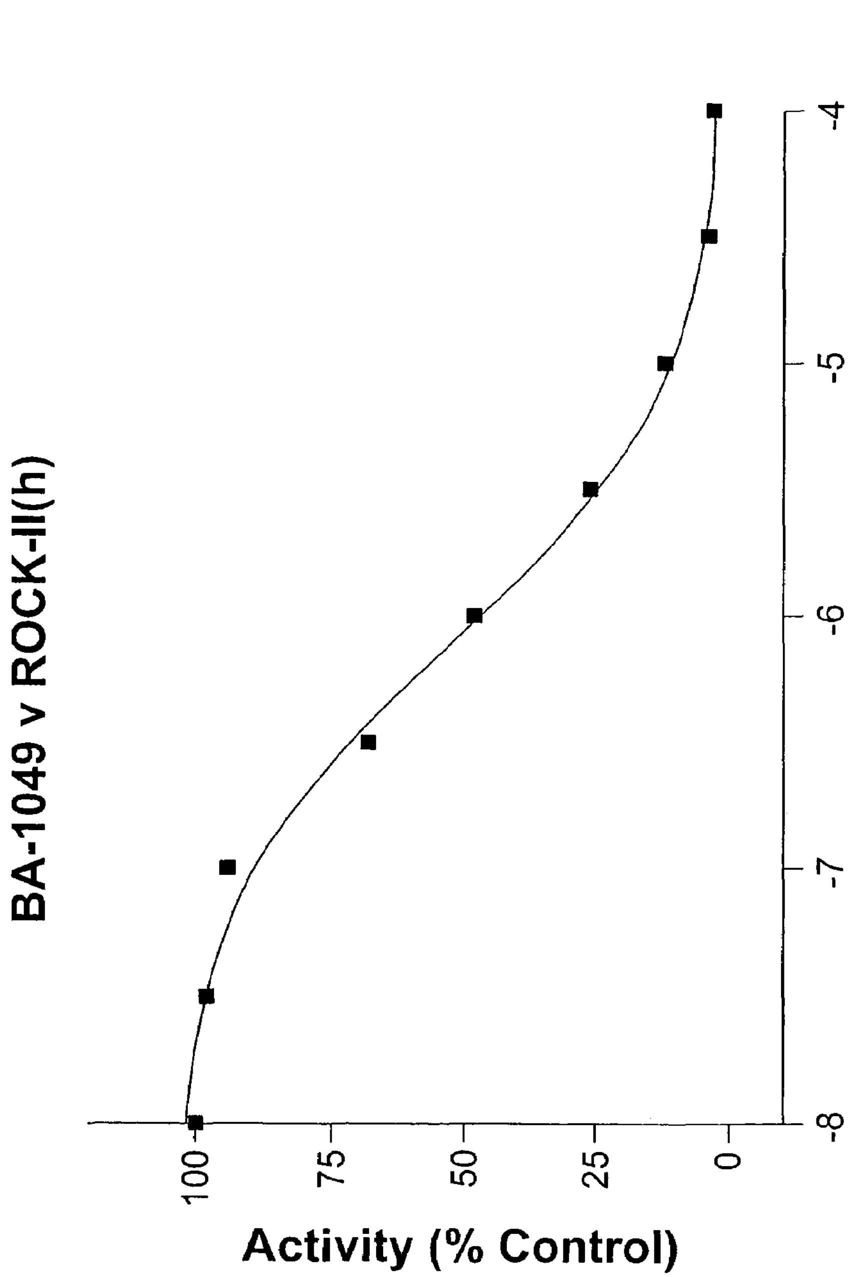
FIG. 1 is a plot of rho kinase inhibitor activity (ROCKII) (y-axis) as a percent of activity in a control incubation of a compound of this invention, BA-1049 (compound E-23a), versus log10 molar concentration x-axis), which data were used to calculate an $IC_{50}$ value of 791 nM.

The following examples illustrate the wide range of potential applications of the present invention and are not intended to limit its scope. Modifications and variations can be made therein without departing from the spirit and scope of the invention. Although any methods and materials similar or equivalent to those described herein can be used in the practice for testing the present invention, exemplary compounds, methods and materials are described.

Unless otherwise noted, all chemicals were purchased from Aldrich Chemicals Inc. and used without further purification. Solvents (N,N-dimethylformamide (DMF), dichloromethane (DCM), diethyl ether, acetonitrile, tetrahydrofuran (THF)) were dried by filtration through neutral alumina columns of a solvent dispensing system. Column chromatography was performed on 230-400 Mesh silica gel. Proton nuclear magnetic resonance ($^1$H NMR) spectra were recorded on Bruker ARX400 and AV400 spectrometers in deuterated chloroform ($CDCl_3$) or methanol ($CD_3OD$). Chemical shifts are reported in ppm (δ units) relative to residual solvent signals. Coupling constants (J) are reported in Hertz (Hz).

Preparations of compounds of this invention are illustrated in a non-limiting manner below in which preparation of compounds with the following structures is outlined. These compounds are numbered E-1, E-2, etc., wherein the E designates a compound related to the synthetic examples described below.

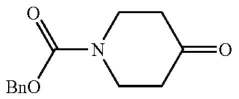

E-1

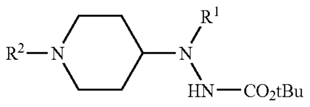

E-3: $R^1$ = H, $R^2$ = $CO_2CH_2Ph$
E-4a: $R^1$ = $C_8H_{17}$, $R^2$ = $CO_2CH_2Ph$
E-4b: $R^1$ = $C_3H_7$, $R^2$ = $CO_2CH_2Ph$
E-4c: $R^1$ = $CH_3$, $R^2$ = $CO_2CH_2Ph$
E-5a: $R^1$ = $C_8H_{17}$, $R^2$ = H
E-5b: $R^1$ = $C_3H_7$, $R^2$ = H
E-5c: $R^1$ = $CH_3$, $R^2$ = H

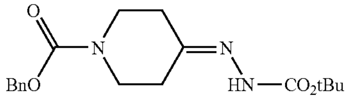

E-2

-continued

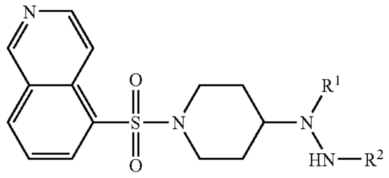

E-6a: $R^1$ = $C_8H_{17}$, $R^2$ = $CO_2tBu$
E-6b: $R^1$ = $C_3H_7$, $R^2$ = $CO_2tBu$
E-6c: $R^1$ = $CH_3$, $R^2$ = $CO_2tBu$
E-7a: $R^1$ = $C_8H_{17}$, $R^2$ = H
E-7b: $R^1$ = $C_3H_7$, $R^2$ = H
E-7c: $R^1$ = $CH_3$, $R^2$ = H

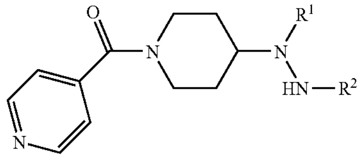

E-8a: $R^1$ = $C_8H_{17}$, $R^2$ = $CO_2tBu$
E-8b: $R^1$ = $C_3H_7$, $R^2$ = $CO_2tBu$
E-9a: $R^1$ = $C_8H_{17}$, $R^2$ = H
E-9b: $R^1$ = $C_3H_7$, $R^2$ = H

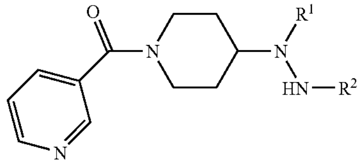

E-10a: $R^1$ = $C_8H_{17}$, $R^2$ = $CO_2tBu$
E-10b: $R^1$ = $CH_3$, $R^2$ = $CO_2tBu$
E-11a: $R^1$ = $C_8H_{17}$, $R^2$ = H
E-11b: $R^1$ = $CH_3$, $R^2$ = H

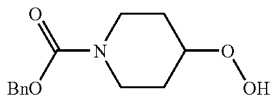

E-12

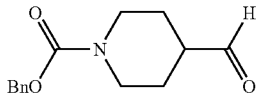

E-13

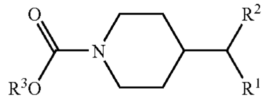

E-14a: $R^1$ = OH, $R^2$ = $CH_3$, $R^3$ = $CH_2Ph$
E-14b: $R^1$ = OH, $R^2$ = CH2CH═CH2, $R^3$ = $CH_2Ph$
E-15a: $R^1$ = OMs, $R^2$ = $CH_3$, $R^3$ = $CH_2Ph$
E-15b: $R^1$ = OMs, $R^2$ = CH2CH═CH2, $R^3$ = $CH_2Ph$
E-16a: $R^1$ = $N_3$, $R^2$ = $CH_3$, $R^3$ = $CH_2Ph$
E-16b: $R^1$ = $N_3$, $R^2$ = CH2CH═CH2, $R^3$ = $CH_2Ph$
E-17a: $R^1$ = $NH_2$, $R^2$ = $CH_3$, $R^3$ = $CH_2Ph$
E-17b: $R^1$ = $NH_2$, $R^2$ = CH2CH═CH2, $R^3$ = $CH_2Ph$

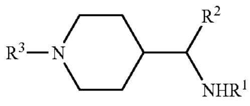

E-18a: $R^1$ = $CO_2tBu$, $R^2$ = $CH_3$, $R^3$ = $CO_2CH_2Ph$
E-18b: $R^1$ = $CO_2tBu$, $R^2$ = CH2CH═CH2, $R^3$ = $CO_2CH_2Ph$
E-19a: $R^1$ = $CO_2tBu$, $R^2$ = $CH_3$, $R^3$ = H
E-19b: $R^1$ = $CO_2tBu$, $R^2$ = $C_3H_7$, $R^3$ = H

-continued

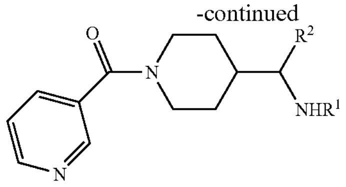

E-20: $R^1 = CO_2tBu$, $R^2 = C_3H_7$
E-21: $R^1 = H$, $R^2 = C_3H_7$

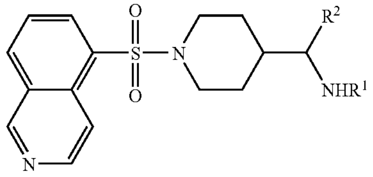

E-22a: $R^1 = CO_2tBu$, $R^2 = CH_3$
E-22b: $R^1 = CO_2tBu$, $R^2 = C_3H_7$
E-23a: $R^1 = H$, $R^2 = CH_3$
E-23b: $R^1 = H$, $R^2 = C_3H_7$

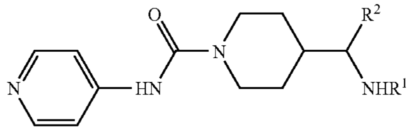

E-24: $R^1 = CO_2tBu$, $R^2 = CH_3$
E-25: $R^1 = H$, $R^2 = CH_3$

Example 1

N-Benzyloxycarbonyl-4-oxopiperidine (E-1)

A stirred solution of 4-oxopiperidine hydrochloride monohydrate (1.0 g, 6.5 mmol) in dry dichloromethane (DCM, 40 mL) was cooled to 0° C., treated with diisopropylethylamine (3.40 mL, 19.5 mmol), stirred for five minutes, treated over 20 minutes with benzyl chloroformate (1.54 mL, 10.7 mmol) over 20 minutes, allowed to warm to room temperature and stirred for two hours. The mixture was partitioned between DCM (25 mL) and water (15 mL). The layers were separated and the aqueous phase was extracted with DCM (2×25 mL). The combined organic phases were washed with brine (1×15 mL), dried over $Na_2SO_4$ and evaporated to a residue that was purified by column chromatography using a gradient of 20 to 40% EtOAc in hexanes as eluant. Evaporation of the collected fractions gave carbamate E-1 (1.20 g, 85%) as a clear oil: HRMS calc'd for $C_{13}H_{15}NO_3$ ($M^+$): 233.1051, found: 233.1048; $^1H$ NMR ($CDCl_3$) δ 2.43 (s, 4H), 3.78 (d, 4H, J=5.96), 5.16 (s, 2H), 7.35 (m, 5H).

Example 2

N-Benzyloxycarbonyl-4-[(N"-(tert-butyloxycarbonyl)hydrazono]piperidine (E-2)

To a stirred solution of N-benzyloxycarbonyl-4-oxopiperidine (E-1, 1.02 g, 4.65 mmol) in dry toluene (25 mL), tert-butyl carbazate (616 mg, 4.65 mmol) was added at room temperature. The mixture was stirred for 5 minutes, allowed to stand at room temperature for 24 hours, treated with $Na_2SO_4$ (1 g), stirred at room temperature for 3 hours and filtered. The filtrate was evaporated to give quantitatively the hydrazone E-2 as an oil which was used in the next step without further purification: HRMS calcd for $C_{18}H_{26}N_3O_4$ [$(MH)^+$]: 348.1923, found: 348.1935, $^1H$ NMR ($CDCl_3$) δ 1.48 (s, 9H), 2.35 (m, 2H), 2.51 (m, 2H), 3.62 (m, 4H), 5.13 (s, 2H), 7.33 (m, 5H), 7.77 (br s, 1H).

Example 3

N-Benzyloxycarbonyl-4-[N"-(tert-butyloxycarbonyl)hydrazino]piperidine (E-3)

A stirred solution of N-benzyloxycarbonyl-4-[(N"-(tert-butyloxycarbonyl)hydrazono]piperidine (E-2, 1.56 g, 4.49 mmol) in dry tetrahydrofuran (THF, 7.5 mL) at room temperature was treated with sodium cyanoborohydride (353 mg, 5.61 mmol) followed by bromocresol green (2 mg). The mixture was stirred vigorously at room temperature, treated with a solution of p-toluenesulfonic acid (773 mg, 4.49 mmol) in dry THF (8 mL) over two hours in order to maintain a green colored mixture. The reaction was partitioned between EtOAc (25 mL) and brine (20 mL). The phases were separated and the aqueous phase was extracted with EtOAc (3×10 mL). The combined organic phases were washed with $NaHCO_3$ sat. (2×15 mL) and brine (1×15 mL), dried over $Na_2SO_4$ and evaporated to a residue, that was suspended in dioxane (10 mL), treated slowly with aqueous sodium hydroxide (1 N, 3 mL), stirred for 5 minutes at room temperature and partitioned between EtOAc (25 mL) and water (5 mL). The phases were separated and the aqueous phase was extracted with EtOAc (1×10 mL). The combined organic phases were washed with brine (1×10 mL), dried over $Na_2SO_4$ and evaporated to a residue, that was purified by column chromatography using a gradient of 30 to 45% EtOAc in hexanes as eluant to give the hydrazine E-3 (931 mg, 61%) as a white solid: m.p.: 122-124° C.; HRMS calcd for $C_{18}H_{28}N_3O_4$ [$(MH)^+$]:350.2079, found: 350.2079; $^1H$ NMR ($CDCl_3$) δ 1.29 (m, 2H), 1.45-1.51 (m, 10H), 1.79 (m, 2H), 2.94 (m, 3H), 4.06 (s, 2H), 5.11 (s, 2H), 6.14 (s, 1H), 7.34 (m, 5H).

Example 4

N-Benzyloxycarbonyl-4-[N"-(tert-butyloxycarbonyl)-N'-(1'-octyl)hydrazino]piperidine (E-4a)

A stirred solution of N-benzyloxycarbonyl-4-[N"-(tert-butyloxycarbonyl)-hydrazino]piperidine (E-3, 225 mg, 0.65 mmol) in dry acetonitrile (4 mL) at room temperature was treated with octanal (494 μL, 3.16 mmol) followed by sodium cyanoborohydride (82 mg, 1.4 mmol), stirred at room temperature for 15 minutes, treated with acetic acid to reach a pH around 6 (about 30 μL/100 mg of E-3, 68 μL), and stirred for 5 hours. During the course of the reaction, small aliquots of acetic acid (5 μL/100 mg of E-3, 13 μL) were added to maintain a reaction pH around 6. The reaction was partitioned between water (4 mL) and EtOAc (20 mL). The phases were separated and the aqueous phase was extracted with EtOAc (2×20 mL). The combined organic phases were washed with brine (1×15 mL), dried over $Na_2SO_4$, and evaporated to a residue, that was purified by column chromatography using 30% EtOAc in hexanes as eluant to give the corresponding hydrazine E-4a (210 mg, 70%) as a clear oil: HRMS calcd for $C_{26}H_{44}N_3O_4$ [$(MH)^+$]: 462.3318, found: 462.3316; $^1H$ NMR ($CDCl_3$) δ 0.87 (t, 3H, J=5.88), 1.25 (s, 11H), 1.43-1.52 (m, 13H), 1.80 (m, 2H), 2.67 (m, 2H), 2.81 (m, 2H), 4.16 (br s, 2H), 5.11 (s, 2H), 5.32 (s, 1H), 7.34 (m, 5H).

Example 5

N-Benzyloxycarbonyl-4-{[N"-(tert-butyloxycarbonyl)-N'-(1'-propyl)]hydrazino}piperidine (E-4b)

Following the procedure described above employing propanal (684 μL, 9.48 mmol) N-benzyloxycarbonyl-4-[N"-(tert-butyloxycarbonyl)hydrazino]piperidine (E-3, 680 mg, 1.95 mmol) reacted to give 465 mg (66%) of the corresponding hydrazine E4b as an oil: HRMS calcd for $C_{21}H_{33}N_3O_4$ ($M^+$): 392.2549, found: 392.2547; $^1H$ NMR ($CDCl_3$) δ 0.90 (t, 3H, J=7.6), 1.42 (m, 13H), 1.79 (m, 2H), 2.64 (m, 2H), 2.81 (m, 3H), 4.15 (m, 2H), 5.10 (s, 2H), 5.33 (brs, 1H), 7.31 (m, 5H).

Example 6

N-Benzyloxycarbonyl-4-{[N"-(tert-butyloxycarbonyl)-N'-(1'-methyl)]hydrazino}piperidine (E-4c)

Following the procedure described above employing formaldehyde (889 μL, 11.0 mmol), N-benzyloxycarbonyl-4-[N"-(tert-butyloxycarbonyl)hydrazino]piperidine (E-3, 800 mg, 2.29 mmol) reacted to give 589 mg (71%) of the corresponding hydrazine E4c as an oil: HRMS calcd for $C_{19}H_{29}N_3O_4$ ($M^+$): 363.2158, found: 363.2162; $^1H$ NMR ($CDCl_3$) δ 1.23 (m, 11H), 1.79 (m, 2H), 2.58 (s, 3H), 2.70 (m, 1H), 2.84 (m, 2H), 4.10 (m, 2H), 5.09 (s, 2H), 5.56 (br s, 1H), 7.32 (m, 5H).

Example 7

4-{[N"-(tert-butyloxycarbonyl)-N'-(1'-octyl)]hydrazino}piperidine (E-5a)

A stirred solution of N-benzyloxycarbonyl-4-{[N"-(tert-butyloxycarbonyl)-N'-(1"-octyl)]hydrazino}piperidine (E4a, 200 mg, 0.430 mmol) in methanol (15 mL) at room temperature was treated with palladium-on-carbon (10% wt, 24 mg) and stirred under $H_2$ (1 atmosphere) for 12 hours. The reaction was filtered on Celite® and the filtrate was evaporated to dryness to give E-5a (125 mg, 89%), which was used in the next step without further purification: HRMS calcd for $C_{18}H_{37}N_3O_2$ ($M^+$): 328.2964, found: 328.2962; $^1H$ NMR ($CDCl_3$): δ 0.87 (t, 3H, J=6.28), 1.26 (m, 12H), 1.43 (s, 12H), 1.84 (d, 2H, J=11.36), 2.64 (m, 5H), 3.16 (d, 2H, J=12.16), 5.29 (s, 1H).

Example 8

4-{[N"-(tert-butyloxycarbonyl)-N'-(1'-propyl)]hydrazino}piperidine (E-5b)

Following the procedure described above for the synthesis of E-5a, N-benzyloxycarbonyl-4-{[N"-(tert-butyloxycarbonyl)-N'-(1'-propyl)]hydrazino}piperidine (E-4b, 180 mg, 0.470 mmol) was hydrogenated to give 103 mg (83%) of hydrazine E-5b which was obtained as an oil: HRMS calcd for $C_{13}H_{27}N_3O_2$ ($M^+$): 257.2089, found: 257.2094; $^1H$ NMR ($CDCl_3$): δ 0.84 (m, 3H), 1.35 (m, 11H), 1.88 (m, 2H), 2.01 (m, 2H), 2.64 (m, 2H), 2.98 (m, 3H), 3.43 (m, 2H), 5.95 (br s, 1H), 9.06 (br s, 1H).

Example 9

4-{[N"-(tert-butoxycarbonyl)-N'-(methyl)]hydrazino}piperidine (E-5c)

Following the procedure described above for the synthesis of E-5a, N-benzyloxycarbonyl-4-{[N"-(tert-butyloxycarbonyl)-N'-(1'-methyl)]hydrazino}piperidine (E-4c, 140 mg, 0.390 mmol) was hydrogenated to give 76 mg (86%) of hydrazine E-5c as an oil: m/z (FAB) 230.2 [$(MH)^+$]; $^1H$ NMR ($CDCl_3$): δ 1.40 (s, 9H), 1.91 (m, 2H), 2.09 (m, 2H), 2.62 (s, 3H), 2.94 (m, 1H), 3.04 (m, 2H), 3.46 (m, 2H), 6.24 (br s, 1H), 9.07 (br s, 1H).

Example 10

N-(5'''-isoquinolinesulfonyl)-4-{[N"-(tert-butyloxycarbonyl)-N'-(1'-octyl)]hydrazino}piperidine (E-6a)

A stirred solution of 4-{[N"-(tert-butyloxycarbonyl)-N'-(1'-octyl)]hydrazino}piperidine (E-5a, 50 mg, 0.15 mmol) in 3 mL of dry DCM at room temperature was treated with triethylamine (63 μL, 0.45 mmol) and 5-isoquinoline sulfonyl chloride (82 mg, 0.3 mmol). The reaction was stirred for 18 hours, diluted with DCM (5 mL) and washed with a saturated aqueous solution of $NaHCO_3$ (1×2 mL), water (1×5 mL) and brine (1×2 mL). The organic phase was dried over $Na_2SO_4$ and evaporated to residue that was purified by column chromatography using an eluant of 2% MeOH in DCM to give 32 mg (40%) of compound E-6a as an oil: HRMS calcd for $C_{26}H_{42}O_4N_4S$ ($M^+$): 519.2998, found: 519.2997; $^1H$ NMR ($CDCl_3$) δ 0.87 (t, 3H, J=6.68), 1.23 (m, 10H), 1.41-1.53 (m, 11H), 1.58 (m, 2H), 1.87 (d, 2H, J=11.12), 2.67 (m, 5H), 3.84 (d, 2H, J=1.56), 5.27 (br s, 1H), 7.77 (t, 1H, J=7.8), 8.27 (d, 1H, J=8.16), 8.43 (d, 1H, J=7.24), 8.69 (m, 2H), 9.42 (br s, 1H).

Example 11

N-(5'''-isoquinolinesulfonyl)-4-{[N"-(tert-butyloxycarbonyl)-N'-(1'-propyl)]hydrazino}piperidine (E-6b)

Following the procedure described above for the synthesis of E-6a, 4-{[N"-(tert-butyloxycarbonyl)-N'-(1'-propyl)]hydrazino}piperidine (E-5b, 60 mg, 0.23 mmol) was reacted to give 44 mg (42%) of compound E-6b as an oil: $^1H$ NMR ($CDCl_3$) δ 0.83 (t, 3H, J=7.28), 1.41 (m, 14H), 1.83 (d, 2H, J=12.6), 2.58 (m, 5H), 3.85 (d, 2H, J=11.4), 7.85 (t, 1H, J=8.16), 8.43 (t, 2H, J=7.28), 8.60 (d, 2H, J=6.48), 9.39 (s, 1H).

Example 12

N-(5'''-isoquinolinesulfonyl)-4-{[N"-(tert-butyloxycarbonyl)-N'-(1'-methyl)]hydrazino}piperidine (E-6c)

Following the procedure described above for the synthesis of E-6a, 4-{[N"-(tert-butyloxycarbonyl)-N'-(1'-methyl)]hydrazino}piperidine (E-5c, 50 mg, 0.20 mmol) was reacted to give 35 mg (38%) of compound E-6c as an oil: HRMS calcd for $C_{20}H_{29}O_4N_4S$ [$(MH)^+$]: 421.1909, found:

419.1904; $^1$H NMR ($CDCl_3$) δ 1.39 (s, 9H), 1.53 (m, 2H), 1.86 (d, 2H, J=11.2), 2.54 (m, 4H), 2.68 (m, 2H), 3.76 (m, 2H), 5.46 (br s, 1H), 7.70 (t, 1H, J=7.64), 8.21 (d, 1H, J=8.12), 8.36 (d, 1H, J=7.36), 8.50 (m, 1H), 8.83 (br s, 1H), 9.36 (br s, 1H).

Example 13

N-(5'''-isoquinolinesulfonyl)-[N'-(1'-octyl)hydrazino] piperidine dihydrochloride (E-7; BA-1041)

A solution of N-(5'''-isoquinolinesulfonyl)-4-{[N''-(tert-butyloxycarbonyl)-N'-(1'-octyl)]hydrazino}piperidine (E-6a, 30 mg, 0.06 mmol) in methanol (1.5 mL) was cooled to 0° C. then treated dropwise with a solution of HCl in MeOH (5.6 M, 3 mL). The mixture was warmed to room temperature, stirred for four hours and evaporated to dryness to give 23 mg (90%) of the corresponding hydrochloric salt E-7a: m/z (FAB) 419.4 [$(MH)^+$]; $^1$H NMR ($CD_3OD$) δ 0.90 (t, 3H, J=6.84), 1.35 (m, 12H), 1.84 (m, 4H), 2.11 (d, 2H, J=9.96), 2.82 (q, 2H, J=6.24), 3.13 (m, 2H), 4.08 (q, 2H, J=3.48), 8.22 (t, 1H, J=7.64), 8.84 (m, 3H), 9.20 (d, 1H, J=6.6), 10.01 (s, 1H).

Example 14

N-(5'''-isoquinolinesulfonyl)-4-[N'-(1'-propyl)hydrazino]piperidine dihydrochloride (E-7b; BA-1042)

Following the procedure described above for the synthesis of E-7a, N-(5-isoquinolinesulfonyl)-4-{[N''-(tert-butyloxycarbonyl)-N'-(1'-propyl]hydrazino}piperidine (E-6b, 14 mg, 0.030 mmol) was deprotected to give 10 mg (86%) of compound E-7b as an oil: m/z (FAB) 349.2 [$(MH)^+$]; $^1$H NMR ($CD_3OD$) δ 0.97 (t, 3H, J=6.4), 1.63-1.89 (m, 4H), 2.07 (m, 2H), 2.77 (t, 2H, J=1H), 3.14 (m, 2H), 3.31 (s, 3H), 4.08 (d, 2H, J=11.92), 8.18 (t, 1H, J=7.88), 8.79 (m, 3H), 9.13 (d, 1H, J=7.12), 9.93 (s, 1H).

Example 15

N-(5'''-isoquinolinesulfonyl)-4-[N'-(1'-methyl)hydrazino]piperidine dihydrochloride (E-7c; BA-1043)

Following the procedure described above for the synthesis of E-7a, N-(5'''-isoquinolinesulfonyl)-4-{[N''-(tert-butyloxycarbonyl)-N'-(1'-methyl]hydrazino}piperidine (E-6c, 23 mg, 0.050 mmol) was deprotected to give 15 mg (86%) of hydrochloric salt E-7c as a yellow solid: m/z (FAB) 321.2 [$(MH)^+$]; $^1$H NMR ($CD_3OD$) δ 1.75 (m, 2H), 2.11 (m, 2H), 2.76 (t, 2H, J=10.6), 2.87 (s, 3H), 4.06 (d, 2H, J=11.04), 8.20 (t, 1H, J=7.92), 8.82 (m, 3H), 9.17 (d, 1H, J=6.88), 9.98 (s, 1H).

Example 16

N-(4'''-pyridinecarbonyl)-4-{[N''-(tert-butyloxycarbonyl)-N'-(1'-octyl)]hydrazino}piperidine (E-8a)

To a stirred solution of 4-[N''-(tert-butyloxycarbonyl)-N'-(1'-octyl)hydrazino]piperidine (E-5a, 23 mg, 0.07 mmol) in dimethyl formamide (2 mL), DIEA (74 μL, 0.42 mmol) and 2-(1H-benzotriazole-1-yl)-1,1,3,3-tetramethyluronium tetrafluoroborate (TBTU, 91 mg, 0.28 mmol) were added at room temperature followed by isonicotinic acid (35 mg, 0.28 mmol). The mixture was stirred overnight. The volatiles were removed under reduced pressure and the residue was partitioned between EtOAc (10 mL) and aqueous 1N sodium hydroxide (2 mL) with vigorous stirring for 2 minutes. The two phases were separated and the organic phase was washed with water (3×5 mL) and brine (3 mL), dried over $Na_2SO_4$, and evaporated to a residue that was purified by column chromatography using 1% methanol in $CHCl_3$ to give the corresponding amide E-8a as an oil: m/z (MAB) 432.4 ($M^+$); $^1$H NMR ($CDCl_3$) δ 0.87 (t, 3H, J=7), 1.26 (m, 11H), 1.54 (m, 11H), 1.59 (m, 1H), 1.78 (d, 1H, J=11), 1.95 (d, 1H, J=10.6), 2.71 (m, 2H), 3.05 (m, 3H), 3.64 (d, 1H, J=13.4), 4.56 (d, 1H, J=11.2), 5.28 (s, 1H), 7.28 (d, 2H, J=5.76), 8.69 (m, 2H).

Example 17

N-(4'''-pyridinecarbonyl)-4-{[N''-(tert-butyloxycarbonyl)-N'-(1'-propyl)]hydrazino}piperidine (E-8b)

Following the procedure described above for the synthesis of E-8a, 4-{[N''-(tert-butyloxycarbonyl)-N'-(1'-propyl)]hydrazino}piperidine (E-5b, 46 mg, 0.18 mmol) was reacted to give 25 mg (46%) of amide E-8b as a yellow oil: m/z (MAB) 362.2 ($M^+$); $^1$H NMR ($CDCl_3$) δ 0.91 (t, 3H, J=7.28), 1.44 (m, 13H), 1.82 (m, 1H), 1.97 (m, 1H), 2.71 (m, 2H), 3.01 (m, 3H), 3.64 (d, 1H, J=13.5), 4.56 (d, 1H, J=12.2), 5.33 (br s, 1H), 7.28 (d, 2H, J=5.28), 8.68 (m, 2H).

Example 18

N-(4'''-pyridinecarbonyl)-4-[N'-(1'-octyl)hydrazino] piperidine dihydrochloride (E-9a; BA-1044)

A stirred solution of N-(4-pyridin)-4-{[N''-(tert-butyloxycarbonyl)-N'-(1'-octyl)]hydrazino}piperidine (E-8a, 12 mg, 0.03 mmol) in methanol (500μL) was cooled to 0° C., treated dropwise with a solution of HCl in MeOH (5.6 M, 1.5 mL), warmed to room temperature and stirred for four hours and evaporated to dryness to give 8 mg (89%) of hydrochloric salt E-9a as a yellow solid: HRMS calcd for $C_{19}H_{32}ON_4$ ($M^+$): 332.2562, found: 332.2564; $^1$H NMR ($CD_3OD$) δ 0.91 (t, 3H, J=6.96), 1.18 (m, 13H), 1.85 (m, 3H), 2.02 (m, 1H), 2.18 (m, 1H), 3.01 (t, 1H, J=12.7), 3.28 (m, 2H), 3.66 (d, 1H, J=7), 4.78 (d, 1H, J=12.1), 8.19 (d, 2H, J=5.48), 9.01 (d, 2H, J=5.36).

Example 19

N-(4'''-pyridinecarbonyl)-4-[N'-(1'-propyl)hydrazino] piperidine dihydrochloride (E-9b; BA-1045)

Following the procedure described above for the synthesis of E-9a, N-(4-pyridin)-4-{[N''-(tert-butyloxycarbonyl)-N'-(1'-propyl)]hydrazino}piperidine (E-8b, 24 mg, 0.070 mmol) was reacted to give 15 mg (88%) of hydrochloric salt E-9b as a yellow solid: HRMS calcd for $C_{14}H_{22}ON_4$ ($M^+$): 262.1794, found: 262.1803; $^1$H NMR ($CD_3OD$) δ 1.02 (t, 3H, J=7.4), 1.82 (m, 3H), 2.02 (m, 1H), 2.20 (m, 1H), 3.01 (t, 1H, J=12.7), 3.16 (m, 2H), 3.31 (q, 2H, J=11.6), 3.58 (m, 1H), 3.67 (d, 1H, J=13.8), 4.77 (d, 1H, J=13.4), 8.19 (d, 2H, J=6.24), 9.01 (d, 2H, J=6.16).

Example 20

N-(3'''-pyridinecarbonyl)-4-{[N''-(tert-butyloxycarbonyl)-N'-(1'-octyl)]hydrazino}piperidine (E-10a)

To a stirred solution of 4-{[N''-(tert-butyloxycarbonyl)-N'-(1'-octyl)]hydrazino}piperidine (E-5a, 60 mg, 0.18 mmol) in dimethylformamide (9 mL), DIEA (160 μL, 0.900 mmol) and TBTU (176 mg, 0.540 mmol) were added at room temperature followed by nicotinic acid (67 mg, 0.54 mmol). The mixture was stirred overnight at room temperature. The volatiles were removed under reduced pressure and the residue was partitioned between EtOAc (20 mL) and aqueous sodium hydroxide 1 N (4 mL) with vigorous stirring for 2 minutes. The two phases were separated and the organic phase was washed with water (3×10 mL) and brine (6 mL), dried over $Na_2SO_4$, and evaporated to a residue that was purified by column chromatography using a gradient of 1 to 3% methanol in $CHCl_3$ to give 45 mg (56%) of the amide E-10a as an oil:

HRMS calcd for $C_{20}H_{40}O_3N_4$ ($M^+$): 432.3101, found: 432.3109; $^1H$ NMR ($CDCl_3$) δ 0.87 (t, 3H, J=6.96), 1.25 (m, 9H), 1.43 (m, 14H), 1.85 (m, 2H), 2.70 (m, 2H), 3.07 (m, 3H), 3.74 (m, 1H), 4.56 (m, 1H), 5.35 (br s, 1H), 7.37 (m, 1H), 7.75 (d, 1H, J=7.68), 8.65 (br s, 2H).

Example 21

N-(3'''-pyridinecarbonyl)-4-{[N''-(tert-butyloxycarbonyl)-N'-(1'-methyl)]hydrazino}piperidine (E-10b)

Following the procedure described above for the synthesis of E-10a, 4-{[N''-(tert-butyloxycarbonyl)-N'-(1'-methyl)]hydrazino}piperidine (E-5c, 52 mg, 0.23 mmol) was reacted to give 25 mg (34%) of amine E-10b as a oil: HRMS calcd for $C_{17}H_{26}O_3N_4$ $(M)^+$: 334.2005, found: 334.2007; $^1H$ NMR ($CDCl_3$) δ 1.43 (m, 12H), 1.59 (m, 1H), 1.83 (m, 1H), 1.95 (m, 1H), 2.63 (s, 3H), 2.83 (m, 1H), 3.07 (m, 1H), 3.73 (m, 1H), 4.52 (m, 1H), 7.36 (m, 1H), 7.74 (d, 1H, J=7.8), 8.65 (br s, 2H).

Example 22

N-(3'''-pyridinecarbonyl)-4-[N'-(1'-octyl)hydrazino]piperidine dihydrochloride (E-11a; BA-1046)

A stirred solution of N-(3-pyridin)-4-{[N''-(tert-butyloxycarbonyl)-N'-(1'-octyl)]hydrazino}piperidine (E-10a, 45 mg, 0.10 mmol) in methanol (1 mL) was cooled to 0° C. then treated dropwise with a solution of HCl in MeOH (5.6 M, 2 mL). The mixture was warmed to room temperature, stirred for four hours and evaporated to dryness to give 30 mg (86%) of the hydrochloric salt E-11a as a yellow solid: m/z (FAB) 333.3 [$(MH)^+$]; $^1H$ NMR ($CDCl_3$) δ 0.90 (t, 3H, J=6.92), 1.34 (m, 11H), 1.77 (m, 4H), 2.05 (m, 2H), 2.99 (m, 1H), 3.17 (m, 2H), 3.47 (m, 1H), 3.79 (m, 1H), 4.76 (m, 1H), 8.17 (m, 1H), 8.71 (d, 1H, J=7.68), 8.96 (d, 1H, J=5.16), 9.07 (s, 1H).

Example 23

N-(3'''-pyridinecarbonyl)-4-[N'-(1'-methyl)hydrazino]piperidine dihydrochloride (E-11b; BA-1047)

Following the procedure described above for the synthesis of E-11a, N-(3-pyridin)-4-{[N''-(tert-butyloxycarbonyl)-N'-(1'-methyl)]hydrazino}piperidine (E-10b, 18 mg, 0.05 mmol) was deprotected to give 10 mg (83%) of hydrochloric salt E-11b as a brown solid: m/z (FAB) 235.3 [$(MH)^+$]; $^1H$ NMR ($CDCl_3$) δ 1.81 (m, 2H), 2.06 (m, 1H), 2.21 (m, 1H), 2.94 (s, 3H), 3.03 (m, 1H), 3.43 (m, 2H), 3.80 (m, 1H), 4.76 (m, 1H), 8.21 (m, 1H), 8.75 (d, 1H, J=7.24), 8.98 (m, 1H), 9.11 (br s, 1H).

Example 24

N-Benzyloxycarbonyl-4-(hydroxymethyl)piperidine (E-12)

A stirred solution of 4-hydroxymethylpiperidine (2.0 g, 17.4 mmol) in dry dichloromethane (DCM, 100 mL) was cooled to 0° C., treated with triethylamine (4.8 mL, 34.8 mmol) followed by benzyl chloroformate (3.7 mL, 34.8 mmol), allowed to warm to room temperature and stirred for two hours. The mixture was partitioned between DCM (50 mL) and water (30 mL). The layers were separated and the aqueous phase was extracted with DCM (2×50 mL). The combined organic phases were washed with brine (1×30 mL), dried over $Na_2SO_4$ and evaporated to a residue, that was purified by column chromatography using a gradient of 70 to 100% EtOAc in hexanes as eluant to give 3.85 g (89%) of E-12 as clear oil: $^1H$ NMR ($CDCl_3$) δ 1.17 (m, 2H), 1.72 (m, 3H), 2.15 (br s, 1H), 2.78 (t, 2H, J=12.24), 3.47 (d, 2H, J=6.04), 4.20 (d, 2H, J=11.68), 5.12 (s, 2H), 7.33 (m, 5H).

Example 25

N-Benzyloxycarbonyl-4-(formyl)-piperidine (E-13)

A stirred suspension of N-(benzyloxycarbonyl)-4-hydroxymethyl)-piperidine (E-12, 2 g, 8 mmol) and Celite™ (4 g) in dry DCM (120 mL) at room temperature was treated with pyridinium chlorochromate (3.5 g, 16.0 mmol), stirred for 3 hours, and filtered on Celite™. The filtrate was evaporated to a dark residue which was purified by column chromatography using a gradient of 25 to 50% EtOAc in hexane as eluant to give 1.5 g (75%) of aldehyde E-13 as a clear oil which was immediately used in the next step: $^1H$ NMR ($CDCl_3$) δ 1.43 (dd, 2H, J=10), 1.78 (m, 2H), 2.31 (m, 1H), 2.91 (t, 2H, J=10.6), 3.96 (m, 2H), 5.05 (s, 2H), 7.24 (m, 5H), 9.52 (s, 1H).

Example 26

(R,S)-N-benzyloxycarbonyl-4-[1'-(hydroxy)ethyl]piperidine (E-14a)

A solution of N-(benzyloxycarbonyl)-4-(formyl)-piperidine (E-13, 1 g, 4 mmol) in diethyl ether ($Et_2O$, 40 mL) was cooled to −78° C., treated with methylmagnesium bromide in $Et_2O$ (3M, 3.2 mL, 9.6 mmol) over 20 minutes, stirred at −78° C. for two hours and partitioned between $Et_2O$ (100 mL) and $NH_4Cl$ saturated (15 mL). The phases were separated and the aqueous phase was extracted with $Et_2O$ (2×20 mL). The combined organic phases were washed with brine (1×30 mL), dried over $Na_2SO_4$ and evaporated to a residue that was purified by column chromatography using a gradient of 35 to 50% EtOAc in hexane as eluant to give 715 mg (67%) of the alcohol E-13 as an oil: HRMS calcd for $C_{15}H_{21}O_3N$ ($M^+$): 263.1521, found: 263.1526; $^1H$ NMR ($CDCl_3$) δ 1.18 (d, 3H, J=6.32), 1.25 (m, 2H), 1.44 (m, 1H), 1.63 (d, 1H, J=12.6), 1.85 (d, 1H, J=13), 2.75 (t, 2H, J=12.4), 3.59 (m, 1H), 4.25 (d, 2H, J=10.1), 5.13 (s, 2H), 7.33 (m, 5H).

Example 27

(R,S)-N-benzyloxycarbonyl-4-[1'-(hydroxy)but-3'-enyl]piperidine (E-14b)

A solution of N-(benzyloxycarbonyl)-4-(formyl)-piperidine (E-13, 1.5 g, 6.3 mmol) in $Et_2O$ (60 mL) was cooled at −78° C. treated with allylmagnesium bromide in $Et_2O$ (1M, 12.5 mL, 12.5 mmol) over 20 minutes, stirred for two hours and was partitioned between $Et_2O$ (100 mL) and $NH_4Cl$ saturated (15 mL). The two phases were separated and the aqueous phase was extracted with $Et_2O$ (2×20 mL). The combined organic phases were washed with brine (1×30 mL), dried over $Na_2SO_4$ and evaporated to a residue that was purified by column chromatography using a gradient of 25 to 45% EtOAc in hexane as eluant to give 1.25 g (71%) of the alcohol E-14b as a yellow oil: HRMS calcd for $C_{17}H_{23}O_3N$ ($M^+$): 289.1677, found: 289.1676; $^1H$ NMR ($CDCl_3$) δ 1.22 (m, 2H), 1.55 (m, 2H), 1.79 (d, 1H, J=12.7), 2.06 (m, 1H), 2.28 (m, 1H), 2.64 (m, 3H), 3.36 (m, 1H), 4.19 (m, 2H), 5.07 (m, 4H), 5.82 (tt, 1H, J=6.32), 7.30 (m, 5H).

Example 28

(R,S)-N-benzyloxycarbonyl-4-[1'-methanesulfonyloxy)ethyl]piperidine (15a)

A solution of (R,S)-N-benzyloxycarbonyl-4-[1'-(hydroxy)ethyl]piperidine (E-14a, 700 mg, 2.66 mmol) in DCM (100 mL) was cooled to 0° C., treated with methanesulfonyl chloride (412 μL, 5.32 mmol) and triethylamine (1.1 mL, 7.98 mmol), stirred for one hour, warmed to room temperature and stirred for two hours. The reaction mixture was diluted with DCM (100 mL) and washed with 1M $NaH_2PO_4$ (2×50 mL) and brine (1×25 mL). The organic phase was dried over $Na_2SO_4$ and evaporated to a residue that was purified by column chromatography using 40% EtOAc in hexanes to give 747 mg (82%) of mesylate E-15a as an oil: HRMS calcd for $C_{16}H_{23}O_5NS$ $(M)^+$: 341.1297, found: 341.1302; $^1H$ NMR ($CDCl_3$) δ 1.27 (m, 2H), 1.39 (d, 3H, J=3.28), 1.73 (m, 3H), 2.74 (m, 2H), 2.98 (s, 3H), 4.24 (m, 2H), 4.61 (m, 1H), 5.11 (s, 2H), 7.33 (m, 5H).

Example 29

(R,S)-N-benzyloxycarbonyl-4-[1'-(methanesulfonyloxy)but-3'-enyl]piperidine (E-15b)

Following the procedure described above for the synthesis of E-15a, (R,S)-N-benzyloxycarbonyl-4-[1'-(hydroxy)but-3'-enyl]-piperidine (E-14b, 1.0 g, 3.5 mmol) was converted to 997 mg (79%) of the corresponding mesylate E-15b as an oil: $^1H$ NMR ($CDCl_3$) δ 1.23 (m, 2H), 1.64 (m, 1H), 1.76 (m, 2H), 2.45 (m, 2H), 2.69 (m, 2H), 2.95 (s, 3H), 4.21 (m, 2H), 4.54 (d, 1H, J=5.24), 5.12 (m, 4H), 5.78 (tt, 1H, J=9.84), 7.28 (m, 5H).

Example 30

(R,S)-N-benzyloxycarbonyl-4-(1'-azido-ethyl)piperidine (E-16a)

A stirred solution of (R,S)-N-benzyloxycarbonyl-4-[1'-methanesulfonyloxy)ethyl]piperidine (E-15a, 740 mg, 2.17 mmol) in DMF (50 mL) was treated with sodium azide (417 mg, 6.51 mmol), heated to 80° C. and stirred overnight. The volatiles were removed under reduced pressure and the residue was suspended in $Et_2O$, washed with water (2×50 mL) and brine (1×25 mL). The organic phase was dried over $Na_2SO_4$ and evaporated to 350 mg (56%) of azide E-16a as an oil. Azide was sufficiently pure to be used in the next step without further purification: HRMS calcd for $C_{15}H_{20}O_2N_4$ ($M^+$): 288.1586, found: 288.1588; $^1H$ NMR ($CDCl_3$) δ 1.24 (m, 5H), 1.45 (m, 1H), 1.61 (m, 1H), 1.78 (d, 1H, J=12.9), 2.72 (m, 2H), 3.28 (m, 1H), 4.24 (m, 2H), 5.12 (s, 2H), 7.35 (m, 5H).

Example 31

(R,S)-N-benzyloxycarbonyl-4-(1'-azido-but-3'-enyl)piperidine (E-16b)

Following the procedure described above for the synthesis of E-16a, (R,S)-N-benzyloxycarbonyl-4-[1'-(methanesulfonyloxy)but-3'-enyl]piperidine (E-15b, 990 mg, 2.70 mmol) was converted to 655 mg (77%) of the azide E-16b as an oil: HRMS calcd for $C_{17}H_{23}O_2N_4$ [$(MH)^+$]: 315.1821, found: 315.1816; $^1H$ NMR ($CDCl_3$) δ 1.22 (m, 2H), 1.53 (m, 2H), 1.70 (d, 1H, J=17.3), 2.26 (m, 2H), 2.66 (m, 2H), 3.12 (m, 1H), 4.19 (m, 2H), 5.12 (m, 4H), 5.75 (m, 1H), 7.29 (m, 5H).

Example 32

(R,S)-N-benzyloxycarbonyl-4-(ethan-1'-amino)piperidine (E-17a)

A solution of (R,S)-N-benzyloxycarbonyl-4-(1'-azido-ethyl)piperidine (E-16a, 350 mg, 1.21 mmol) in THF (25 mL) at room temperature was treated with triphenylphosphine (639 mg, 2.43 mmol) and water (217 μL, 12.1 mmol), heated overnight at 45° C., diluted with $Et_2O$ (100 mL), washed with water (2×50 mL), dried over $Na_2SO_4$ and evaporated to 270 mg (85%) of amine E-17a as an oil. The amine was sufficiently pure to be use in the next step without further purification: $^1H$ NMR ($CDCl_3$) δ 1.05 (d, 3H, J=8.6), 1.25 (m, 3H), 1.48-1.71 (m, 4H), 2.71 (m, 3H), 4.21 (br s, 2H), 5.13 (s, 2H), 7.46 (m, 5H).

Example 33

(R,S)-N-benzyloxycarbonyl-4-(but-3'-en-1'-amine)piperidine (E-17b)

Following the procedure described above for the synthesis of E-17a, (R,S)-N-benzyloxycarbonyl-4-(1'-azido-but-3'-enyl)piperidine (E-16b, 650 mg, 2.07 mmol) was converted to 488 mg (82%) of the amine E-17b as an oil: $^1H$ NMR ($CDCl_3$) δ 1.24 (m, 2H), 1.67 (m, 3H), 1.98 (m, 2H), 2.26 (m, 1H), 3.73 (m, 3H), 3.73 (t, 1H, J=6.16), 4.25 (br s, 2H), 5.14 (m, 4H), 5.78 (m, 1H), 7.31 (m, 5H).

Example 34

(R,S)-N-(benzyloxycarbonyl)-4-[N∝-(tert-butyloxycarbonyl)-ethan-1'-amino]piperidine (E-18a)

A stirred solution of (R,S)-N-benzyloxycarbonyl-4-(ethan-1'-amino)piperidine (E-17a, 300 mg, 1.14 mmol) in a mixture of dimethoxyethane and water (1:1 v:v, 30 mL) at room temperature was treated with sodium carbonate (127 mg, 1.19 mmol) and sodium bicarbonate (100 mg, 1.19 mg) followed by di-tert-butyl dicarbonate (285 mg, 1.3 mmol). The mixture was stirred overnight at room temperature, and partitioned between $NH_4Cl$ sat. (10 mL) and EtOAc (30 mL). The phases were separated and the aqueous phase was extracted with EtOAc (2×25 mL). The combined organic phases were washed with brine (1×15 mL), dried over $Na_2SO_4$ and evaporated to a residue that was purified by column chromatography using an eluant of 30% EtOAc in hexane to give 212 mg (51%) of carbamate E-18a as an oil:

HRMS calcd for $C_{20}H_{30}O_4N_2$ ($M^+$): 362.2205, found: 263.2205; $^1$H NMR ($CDCl_3$) δ 1.07 (d, 3H, J=9.04), 1.20 (m, 1H), 1.43 (m, 10H), 1.66 (m, 2H), 2.69 (m, 2H), 3.48 (m, 2H), 4.28 (m, 2H), 4.36 (m, 1H), 5.11 (s, 2H), 7.35 (m, 5H).

Example 35

(R,S)-N-benzyloxycarbonyl-4-[N'-(tert-butyloxycarbonyl)-but-3'-en-1'amino]piperidine (E-18b)

Following the procedure described above for the synthesis of E-18a, (R,S)-N-benzyloxycarbonyl-4-(but-3'-en-1'-amino)piperidine (580 mg, 2.01 mmol) was reacted to give 476 mg (61%) of carbamate E-18b as an oil: HRMS calcd for $C_{22}H_{32}O_4N_2$ ($M^+$): 388.2362, found: 388.2364; $^1$H NMR ($CDCl_3$) δ 1.24 (m, 2H), 1.42 (s, 9H), 1.55 (m, 1H), 1.67 (m, 2H), 2.08 (m, 1H), 2.25 (m, 1H), 2.72 (m, 2H), 3.56 (m, 1H), 4.22 (m, 2H), 4.37 (m, 1H), 5.12 (m, 4H), 5.75 (m, 1H), 7.31 (m, 5H).

Example 36

(R,S)-4-[N'-(tert-butyloxycarbonyl)ethan-1'-amino]piperidine (E-19a)

A stirred solution of (R,S)-N-(benzyloxycarbonyl)-4-[N'-(tert-butyloxycarbonyl)-ethan-1'-amino]piperidine (E-18a, 65 mg, 0.17 mmol) in methanol (5 mL) at room temperature was treated with palladium-on-carbon (10% wt, 7 mg) and stirred under $H_2$ (1 atmosphere) for 12 hours. The reaction was filtered on Celite® and the filtrate was evaporated to dryness to give E-19a (37 mg, 95%), which was used in the next step without further purification: HRMS calcd for $C_{12}H_{24}O_2N_2$ ($M^+$): 228.1838, found: 228.1839; $^1$H NMR ($CDCl_3$) δ 1.08 (d, 3H, J=3.88), 1.39 (s, 9H), 1.65 (m, 2H), 1.80 (m, 2H), 2.81 (m, 3H), 3.48 (m, 2H), 3.58 (m, 1H), 4.47 (br s, 1H), 9.22 (br s, 1H).

Example 37

(R,S)-4-[N'-(tert-butyloxycarbonyl)butan-1'-amino]piperidine (E-19b)

Following the procedure described above for the synthesis of E-19a, (R,S)-N-benzyloxycarbonyl-4-[N'-(tert-butyloxycarbonyl)-but-3'-en-1'amino]piperidine (E-18b, 120 mg, 0.31 mmol) was converted to 77 mg (97%) of E-19b as an oil: HRMS calcd for $C_{14}H_{28}O_2N_2$ ($M^+$): 256.2151, found: 256.2163; $^1$H NMR ($CDCl_3$) δ 0.86 (t, 3H, J=6.64), 1.24 (m, 3H), 1.38 (m, 10H), 1.68 (m, 3H), 1.82 (m, 2H), 2.80 (m, 2H), 3.47 (m, 3H), 4.38 (d, 1H, J=8.88), 9.14 (br s, 1H).

Example 38

(R,S)-N-(3"-pyridinecarbonyl)-4-[N'-(tert-butyloxycarbonyl)-butan-1'-amino]piperidine (E-20)

A stirred solution of (R,S)-4-[N'-(tert-butyloxycarbonyl) butan-1'-amino]piperidine (E-19b, 40 mg, 0.16 mmol) in dimethylformamide (5 mL), was treated with DIEA (140 µL, 0.80 mmol) and 2-(1H-benzotriazole-1-yl)-1,1,3,3-tetramethyluronium tetrafluoroborate (TBTU, 156 mg, 0.48 mmol) followed by nicotinic acid (60 mg, 0.48 mmol) and stirred overnight at room temperature. The volatiles were removed under reduced pressure and the residue was partitioned between EtOAc (15 mL) and aqueous 1N sodium hydroxide (2 mL) with vigorous stirring for 2 minutes. The two phases were separated and the organic phase was washed with water (3×10 mL) and brine (6 mL), dried over $Na_2SO_4$, and evaporated to a residue that was purified by column chromatography using a gradient of 2 to 5% methanol in $CHCl_3$ to give 31 mg (55%) of amide E-20 as an oil: HRMS calcd for $C_{20}H_{31}O_3N_3$ ($M^+$): 361.2365, found: 361.2357; $^1$H NMR ($CDCl_3$) δ 0.90 (t, 3H, J=6.92), 1.30 (m, 4H), 1.42 (m, 11H), 1.64 (m, 2H), 1.73 (m, 1H), 2.73 (m, 1H), 3.01 (m, 1H), 3.51 (m, 1H), 3.73 (m, 1H), 4.30 (d, 1H, J=9.56), 4.76 (m, 1H), 7.35 (m, 1H), 7.73 (d, 1H, J=7.48), 8.65 (s, 2H).

Example 39

(R,S)-N-(3"-pyridinecarbonyl)-4-[butan-1'-amino]piperidine dihydrochloride (E-21; BA-1048)

A stirred solution of (R,S)-N-(3"-pyridinecarbonyl)-4-[N'-(tert-butyloxycarbonyl)-butan-1'-amino]piperidine (E-20, 25 mg, 0.07 mmol) in methanol (500 µL) was cooled to 0° C., treated dropwise with a solution of HCl in MeOH (5.6 M, 1.5 mL), warmed to room temperature, stirred for four hours and evaporated to dryness to give 15 mg (83%) of hydrochloric salt E-21 as a white solid: m/z (FAB) 262.2 [$(MH)^+$]; $^1$H NMR ($CD_3OD$) δ 0.96 (t, 3H, J=7.12), 1.36-1.68 (m, 8H), 1.85 (m, 1H), 1.99 (m, 1H), 2.99 (t, 1H, J=11.9), 3.17 (m, 1H), 3.69 (m, 1H), 4.69 (d, 1H, J=12.1), 8.19 (t, 1H, J=7.56), 8.72 (d, 1H, J=7.72), 8.95 (d, 1H, J=5.4), 9.06 (s, 1H).

Example 40

(R,S)-N-(5"-isoquinolinesulfonyl)-4-[N'-(tert-butyloxycarbonyl)ethan-1'-amino]piperidine (E-22a)

A stirred solution of (R,S)-4-[N'-(tert-butyloxycarbonyl)-ethan-1'-amino]piperidine (E-19a, 25 mg, 0.11 mmol) in 2 mL of dry DCM at room temperature was treated with triethylamine (46µL, 0.33 mmol) and 5-isoquinoline sulfonyl chloride (60 mg, 0.22 mmol). The reaction was stirred for 18 hours, diluted with DCM (5 mL), washed with a saturated aqueous solution of $NaHCO_3$ (1×2 mL), water (1×5 mL) and brine (1×2 mL). The organic phase was dried over $Na_2SO_4$ and evaporated to a residue that was purified by column chromatography using an eluant of 2% MeOH in DCM to give 19 mg (48%) of E-22a as an oil: $^1$H NMR ($CDCl_3$) δ 1.02 (d, 3H, J=9.12), 1.26 (m, 3H), 1.40 (s, 9H), 1.71 (m, 2H), 2.46 (t, 2H, J=11.3), 3.37 (m, 1H), 3.90 (d, 2H, J=12.0), 4.28 (d, 1H, J=7.68), 7.72 (t, 1H, J=7.6), 8.22 (d, 1H, J=8.2), 8.38 (d, 1H, J=7.24), 8.53 (d, 1H, J=5.6), 8.67 (d, 1H, J=5.72), 9.36 (br s, 1H).

Example 41

(R,S)-N-(5"-isoquinolinesulfonyl)-4-[N'-(tert-butyloxycarbonyl)-butan-1'-amino]piperidine (E-22b)

Following the procedure described above for the synthesis of E-22a, (R,S)-4-[N'-(tert-butyloxycarbonyl)-butan-1'-amino]piperidine (E-37, 45 mg, 0.17 mmol) was converted to 29 mg (37%) of E-22b as an oil: HRMS calcd for $C_{23}H_{34}O_4N_3S$ [$(MH)^+$]: 448.2270, found: 448.2262; $^1$H NMR ($CDCl_3$) δ 0.85 (t, 3H, J=6.65), 1.31 (m, 6H), 1.39 (m, 10H), 1.67 (m, 2H), 2.45 (t, 2H, J=11.3), 3.41 (m, 1H), 3.90 (d, 2H, J=11.4), 4.24 (d, 1H, J=9.41), 7.71 (t, 1H, J=7.56), 8.21 (d, 1H, J=8.16), 8.36 (d, 1H, J=7.4), 8.51 (d, 1H, J=5.64), 8.67 (d, 1H, J=4.64), 9.35 (s, 1H).

Example 42

(R,S)-N-(5"-isoquinolinesulfonyl)-4-[ethan-1'-amino]piperidine dihydrochloride (E-23a; BA-1049)

A solution of (R,S)-N-(5-isoquinolinesulfonyl)-4-[N'-(tert-butyloxycarbonyl)-ethyl-1'-amino]piperidine (E-22a, 15 mg, 0.04 mmol) in MeOH (500μL) was cooled at 0° C., treated with a solution of HCl in MeOH (5.6 M, 1.5 mL), warmed to room temperature, stirred for fours hours and evaporated to dryness to give 9 mg (82%) of hydrochloric salt E-23a as a white solid: m/z (FAB) 320.2 [($MH^+$)]; $^1H$ NMR ($CD_3OD$) δ 1.24 (d, 3H, J=9.01), 1.42 (m, 2H), 1.62 (m, 1H), 1.83 (m, 2H), 2.64 (m, 2H), 3.16 (m, 1H), 4.01 (m, 2H), 8.20 (m, 1H), 8.81 (m, 3H), 9.21 (m, 1H), 10.00 (m, 1H).

Example 43

(R,S)-N-(5"-isoquinolinesulfonyl)-4-[butan-1'-amino]piperidine dihydrochloride (E-23b; BA-1050)

Following the procedure described above for the synthesis of E-23a, (R,S)-N-(5"-isoquinolinesulfonyl)-4-[N'-(tert-butyloxycarbonyl)-butan-1'-amino]piperidine (E-22b, 25 mg, 0.06 mmol) was converted to 16 mg (84%) of hydrochloric salt E-23b as a white solid: m/z (FAB) 348.2 [($MH^+$)]; $^1H$ NMR ($CD_3OD$) δ 0.92 (t, 3H, J=7.12), 1.23-1.67 (m, 6H), 1.70 (m, 1H), 1.76 (t, 2H, J=11.2), 2.58 (t, 2H, J=12), 3.03 (m, 1H) 3.96 (d, 2H, J=10.5), 8.17 (t, 1H, J=7.96), 8.76 (d, 2H, J=7.44), 8.81 (d, 1H, J=8.22), 9.17 (d, 1H, J=6.84), 10.00 (s, 1H).

Example 44

(R,S)-N-[(4-pyridyl)aminocarbonyl]-4-[N'-(tert-butyloxycarbonyl)ethan-1'-amino]piperidine (E-24)

A solution of (R,S)-4-[N'-(tert-butyloxycarbonyl)-ethan-1'-amino]piperidine (E-19a, 65 mg, 0.3 mmol) in THF (7 mL) was treated with 4-pyridyl isocyanate (72 mg, 0.6 mmol) and heated at refluxed for 5 hours. The solvent was removed under reduced pressure and the residue was purified by column chromatography using an eluant of 7% MeOH in $CHCl_3$ to give 89 mg (89%) of E-24 as an oil: $^1H$ NMR ($CDCl_3$) δ 1.06 (d, 3H, J=6.8), 1.21 (m, 2H), 1.41 (s, 9H), 1.49 (m, 1H), 1.65 (d, 1H, J=12.8), 1.72 (d, 1H, J=12.7), 2.78 (t, 2H, J=12.8), 3.53 (m, 1H), 4.16 (d, 2H, J=12.7), 4.56 (d, 1H, J=8.6), 7.36 (d, 2H, J=6.24), 7.72 (s, 1H), 8.33 (d, 2H, J=6.16).

Example 45

(R,S)-N-[(4-pyridyl)aminocarbonyl]-4-[ethan-1'-amino]piperidine dihydrochloride (E-25; BA-1051)

A solution of (R,S)-N-[(4-pyridyl)aminocarbonyl]-4-[N'-(tert-butyloxycarbonyl)ethan-1'-amino]piperidine (E-24, 10 mg, 0.03 mmol) in MeOH (500 μL) was cooled to 0° C., treated with a solution of HCl in MeOH (5.5 M, 1.5 mL), warmed to room temperature, stirred for fours hours and evaporated to dryness to give 6 mg (84%) of hydrochloric salt E-25 as a white solid: $^1H$ NMR ($CD_3OD$) δ 1.31 (d, 3H, J=6.72), 1.46 (m, 2H), 1.85 (m, 3H), 2.99 (t, 2H, J=12.96), 3.19 (m, 1H), 4.36 (d, 2H, J=13.6), 8.02 (d, 2H, J=7.08), 8.47 (d, 2H, J=7.04).

Example 46

Preparation of Human Rho Kinase (ROK) Expressed in COS Cells

ROK has been prepared and cDNAs cloned from a number of sources and the cloning of human p160-ROK cDNA (p160-ROCKI) has been reported (Ishizaki et al., 1996, EMBO J. 15: 1885; U.S. Pat. No. 5,906,819). Overexpression of human Rho kinase in mammalian cells provides a convenient, easily renewed source of ROK activity. ROK is available as a clone in pCAG-myc-p160 (Ishizaki et al., 1997, FEBS Lett. 404: 118). The myc tag in this expression plasmid allows for purification using immunological techniques.

Transfection-quality DNA is prepared from *E. coli* (DH5α or XL1-Blue) containing the pCAG-myc-p160myc-727 (Ishizaki et al., 1997) using a midi-kit (Qiagen). This construct expresses ROK activity in a constitutive fashion and yields a polypeptide of about 98 kDa. COS cells (available from the ATCC, American Type Culture Collection) are plated and grown overnight. The expression vector DNA is introduced using lipofectamine (Qiagen), followed by an 18-hour incubation. The following steps are performed on ice. The transfected cells are washed with pre-cooled PBS, then lysed with buffer containing a cocktail of protease and phosphatase inhibitors (20 mM Tris-HCl (pH=7.5), 1 mM EDTA, 1 mM EGTA, 5 mM $MgCl_2$, 25 mM NaF, 10 mM β glycerophosphate, 5 mM sodium pyrophosphate, 0.2 mM phenylmethylsulfonyl fluoride, 2 mM dithiothreitol, 0.2 mM sodium vanadate, 0.05% Triton X-100, 0.1 μM calyculin A). The cells are scraped into 1.5 mL Eppendorf tubes and centrifuged at 10,000 g for 10 min. The supernatant is transferred to a fresh tube and the pellet discarded. Anti-myc antibody (9E10; Sigma #M5546) is added, and the tube rotated for 2 hours at 4° C. Protein G-Sepharose (Sigma, #P3296) prewashed in lysis buffer is added and the incubation and rotation continued for another 2 hours. The suspension is then centrifuged at 1,000 g for 5 min and the pellet is washed 3 times with lysis buffer and once with ROK kinase buffer (50 mM Hepes-NaOH (pH=7.4), 10 mM MgCl2, 5 mM MnCl2, 2 mM dithiothreitol, 0.02% Brij 35). The pellet is suspended in ROK kinase buffer to give a standard enzyme product of immobilized ROK.

ROK can also be purchased commercially.

Example 47

Evaluation of Compounds of this Invention as Inhibitors of Rho Kinase (ROK) Activity The ability of compounds of this invention to inhibit ROK activity may be tested in a cell-free assay system using recombinant ROK enzyme, radioactive ATP, and Myelin basic Protein (MBP; purchased from Upstate, Lake Placid, N.Y.). MBP is a highly phosphorylated protein, is inexpensive to buy in purified form, is phosphorylated by ROK, and is used as the assay substrate for phosphorylation. Measurement of Rho-associated kinase (ROK) activity is important to determine the potency of novel inhibitors. MBP is a substrate for ROK and a number of other protein kinases, making it useful both to quantitate ROK activity and to indicate the potency and specificity of novel inhibitors for ROK. Conditions can be adjusted for analysis of other substrates. The assay is modified as necessary to provide optimal buffer and incubation conditions to check $IC_{50}$ (Inactivation concentration 50%) values for other protein kinases to provide an index of specificity for ROK kinase. Other protein kinases that are used to assess specificity for ROK include PKCα, PKA, PKN, and MLCK.

Example 48

Kinase Assay

ROCK II (purchased from Upstate, Lake Placid, N.Y.) activity is assayed in 20 mM MOPS, pH 7.2, 25 mM β-glycerophosphate, 5 mM EGTA, 1 mM sodium orthovanadate, 1 mM dithiothreitol with dephosphorylated myelin basic protein (MBP, 0.2 mg/ml) as substrate with or without addition of a reference Rho kinase inhibitor. Activity assay reactions are performed for 30 min at 30° C. in 50 μl volumes using radiolabeled [32P] ATP (from Perkin-Elmer). The concentrations of ATP and magnesium chloride are 100 μM and 75 mM respectively. Assay reactions are initiated by adding Mg2+/ATP to each reaction mixture and are terminated by spotting 40 μl of each reaction mixture onto phosphocellulose paper (P81 paper, Whatman), followed by washes in 0.75% phosphoric acid to remove ATP followed by drying. The spotted paper is placed in scintillation cocktail and counted to measure 32P incorporation. Radioactivity is measured using a scintillation counter. Percent activity for a particular concentration of inhibitor is calculated as 100*(a−b)/(c−b), where a=cpm (enzyme+inhibitor), b=cpm (autophosphorylation of substrate and kinase) and c=cpm (enzyme−inhibitor). A dose-response chart is prepared for each inhibitor compound evaluated, then an $IC_{50}$ (inhibitor concentration at 50% inhibition) determination is made as a measure of the potency of the compound as an inhibitor of Rho kinase. A plot of the log of concentration of test inhibitor compound (x axis) and the percent inhibition of kinase activity (y axis) is prepared. The curve can be interpolated to estimate the concentration at which each compound demonstrates 50% inhibition of Rho kinase. Experiments are done in duplicate or triplicate. ROCK II and dephosphorylated myelin basic protein (MBP) can be purchased from Upstate (Lake Placid, N.Y.). ATP is from Boehringer Mannheim and [γ-32P] ATP is from Perkin-Elmer. ROCK-II(h) is human ROCK-II.

One unit of Rho kinase can be defined as the amount of rho kinase required to incorporate 1 pmol of phosphate per minute into a substrate at 30° C.

Compounds of this invention can be evaluated (Upstate Ltd. in United Kingdom) for their relative ability to inhibit Rock II kinase and to determine the respective concentration required to achieve 50% inhibition of Rok-II kinase activity ($IC_{50}$ value).

Compounds of this invention can be evaluated for kinase inhibition activity as solutions in 100% DMSO at a concentration of 10 μM added to GSK3β(h) and to ROCK-II(r) with ATP present at a concentration of 100 μM. Samples of compounds of this invention can be tested at 10 μM.

Samples can also be tested at 10 μM against cSRC(h), JNK1α1(h), MAPK2(h), PKA(b), PKCα(h), PKBα(h), and Fyn(h) with ATP at 100 μM.

Samples can also be tested at 10 μM against CDK5/p35(h), JNK1α1(h), MAPK1(h), PKA(b), PKCα(h), PRK2(h), ROCK-II(r), GSK313β(h), PKBα(h), and Fyn(h) with ATP at 100 μM.

Kinase assay can be reported as Activity (% control) using the following equation:

$$\text{Activity (\% control)} = \frac{\text{Mean for test sample } (cpm) - \text{blank } (cpm)}{\text{Mean for control } (cpm) - \text{blank } (cpm)} \times 100$$

Results obtained for the bioassay can be analyzed using Microsoft® Excel e.g., 2002 Version SP-2.

The data can be presented as relative ROCK kinase inhibition at a reference compound concentration of 3.5 uM and at 35 μM, wherein 0 signifies complete inhibition under the ATP concentration tested (100 μM). ROCK kinase activity is the opposite of ROCK kinase inhibition, and is compared with the GSKB kinase activity.

$IC_{50}$ values can be determined for compounds of this invention using for example an ATP concentration of 100 μM. Kinase inhibitors frequently compete with ATP binding and are ATP-competitive. Drug concentration required for 50% inhibition ($IC_{50}$) depends on the concentration of ATP used in the assays.

An $IC_{50}$ value for a compound of this invention can be determined from a plot of concentration of compound of this invention versus kinase activity of ROCK-II(h). The $IC_{50}$ value for a compound of this invention can be expressed in units of micromolar, nanomolar, picomolar, and the like.

The $IC_{50}$ value obtained for the dihydrochloride addition salt of compound IV(b) of this invention, which is sometimes referred to herein as compound BA-1049, was found to be 791 nM from a plot of rho kinase inhibitor activity as a percent of control versus $\log_{10}$ concentration in an assay to measure the inhibition of the human Rho kinase enzyme, ROCK-II(h) the method described herein.

Concentration and activity as % (percent) of control data are presented in Table 1. In the table, the concentration of the rho kinase inhibitor is micromolar, CPM is counts per minute, and SD is standard deviation. The rho kinase inhibitor activity was tested in duplicate. In each case, the kinase activity is expressed as a percentage of that in control incubations. $IC_{50}$ values were derived by PRISM at Upstate. ATP concentration was 100 micromolar.

TABLE 1

Concentration vs activity data to calculate $IC_{50}$ on BA-1049 v ROCKII(h)

| [Final] μM | CPM | Mean | CPM-Blank | % Control | SD* | Activity (% Control) |
|---|---|---|---|---|---|---|
| 0.01 | 9489 | 9891 | 8813 | 96 | 6 | 100 |
| | 10292 | | 9616 | 104 | | |
| 0.03 | 8602 | 9664 | 7926 | 86 | 16 | 98 |
| | 10725 | | 10049 | 109 | | |
| 0.1 | 8598 | 9322 | 7922 | 86 | 11 | 94 |
| | 10046 | | 9370 | 102 | | |
| 0.3 | 6409 | 6927 | 5733 | 62 | 8 | 68 |
| | 7444 | | 6768 | 74 | | |
| 1 | 4773 | 5032 | 4097 | 45 | 4 | 48 |
| | 5290 | | 4614 | 50 | | |
| 3 | 3018 | 3105 | 2342 | 25 | 1 | 26 |
| | 3191 | | 2515 | 27 | | |
| 10 | 1428 | 1787 | 752 | 8 | 6 | 12 |
| | 2145 | | 1469 | 16 | | |
| 30 | 1013 | 1033 | 337 | 4 | 0 | 4 |
| | 1053 | | 377 | 4 | | |

TABLE 1-continued

| Concentration vs activity data to calculate $IC_{50}$ on BA-1049 v ROCKII(h) | | | | | | |
|---|---|---|---|---|---|---|
| [Final] µM | CPM | Mean | CPM-Blank | % Control | SD* | Activity (% Control) |
| 100 | 716 | 927 | 40 | 0 | 3 | 3 |
| | 1138 | | 462 | 5 | | |
| Control | 10017 | 9202 | 9341 | 102 | 3 | 100 |
| | 9566 | | 8890 | 97 | | |
| | 9776 | | 9100 | 99 | | |
| | 10155 | | 9479 | 103 | | |
| Blank | 429 | 677 | / | / | / | / |
| | 924 | | | | | |

*NB. Where n = 2, the value reported here is actually range/2.

Reaction conditions used in the kinase assays are described in the following.

FIG. 1 is a plot of rho kinase inhibitor activity (ROCKII) (y-axis) as a percent of activity in a control incubation of a compound of this invention, BA-1049 (compound E-23a), versus log10 molar concentration x-axis), which data were used to calculate an $IC_{50}$ value of 791 nM.

Figure 2:
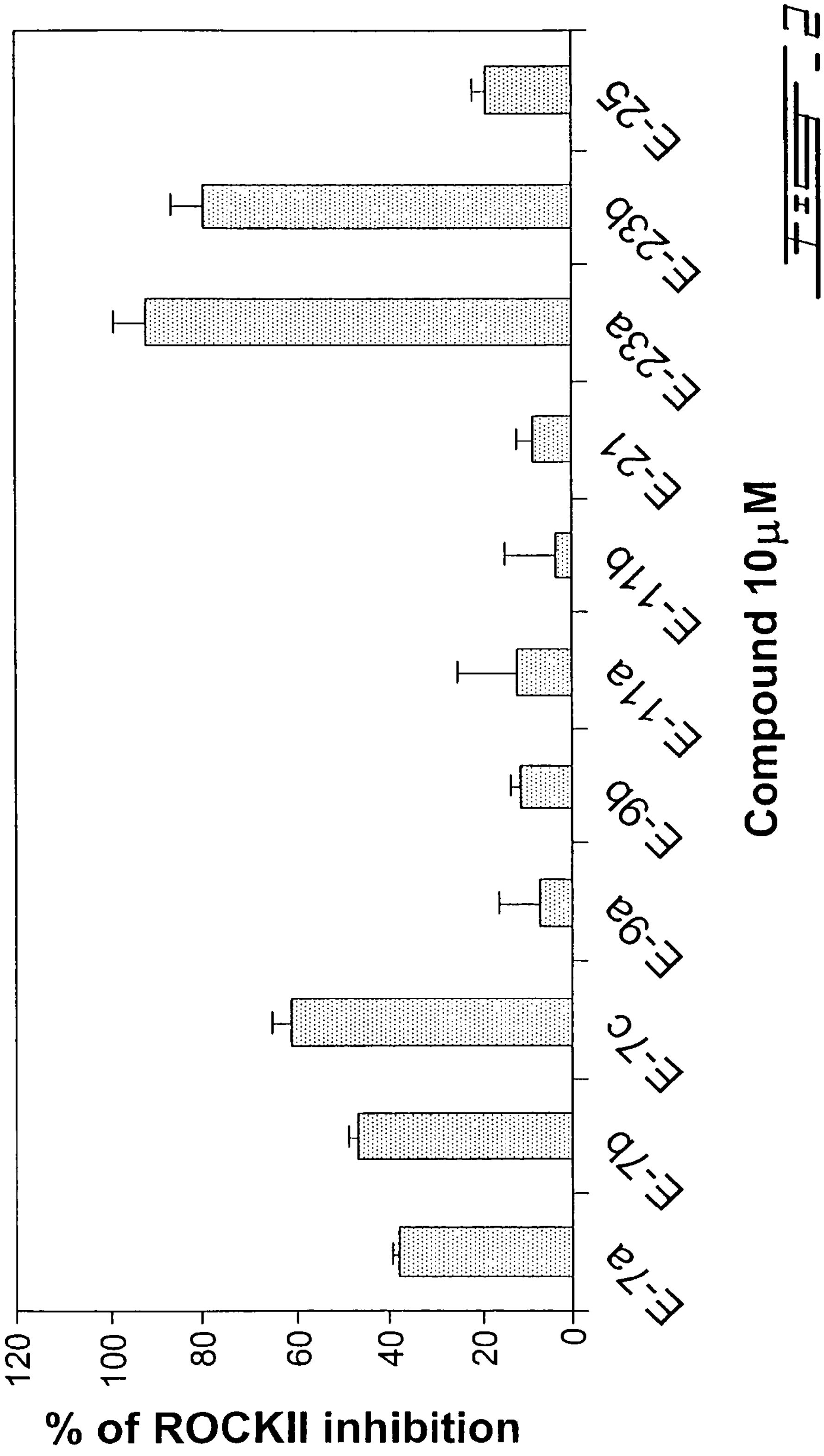
FIG. 2 is a plot of inhibition of ROCKII activity by compounds E-7a to E-25 at 100 μM. Experiments were done in duplicate. ATP was present at 100 μM in the assay.

FIG. 2 is a plot of inhibition of ROCKII activity by compounds E-7a to E-25 at 10 µM. Experiments were done in duplicate. ATP was present at 100 µM in the assay.

Figure 3:
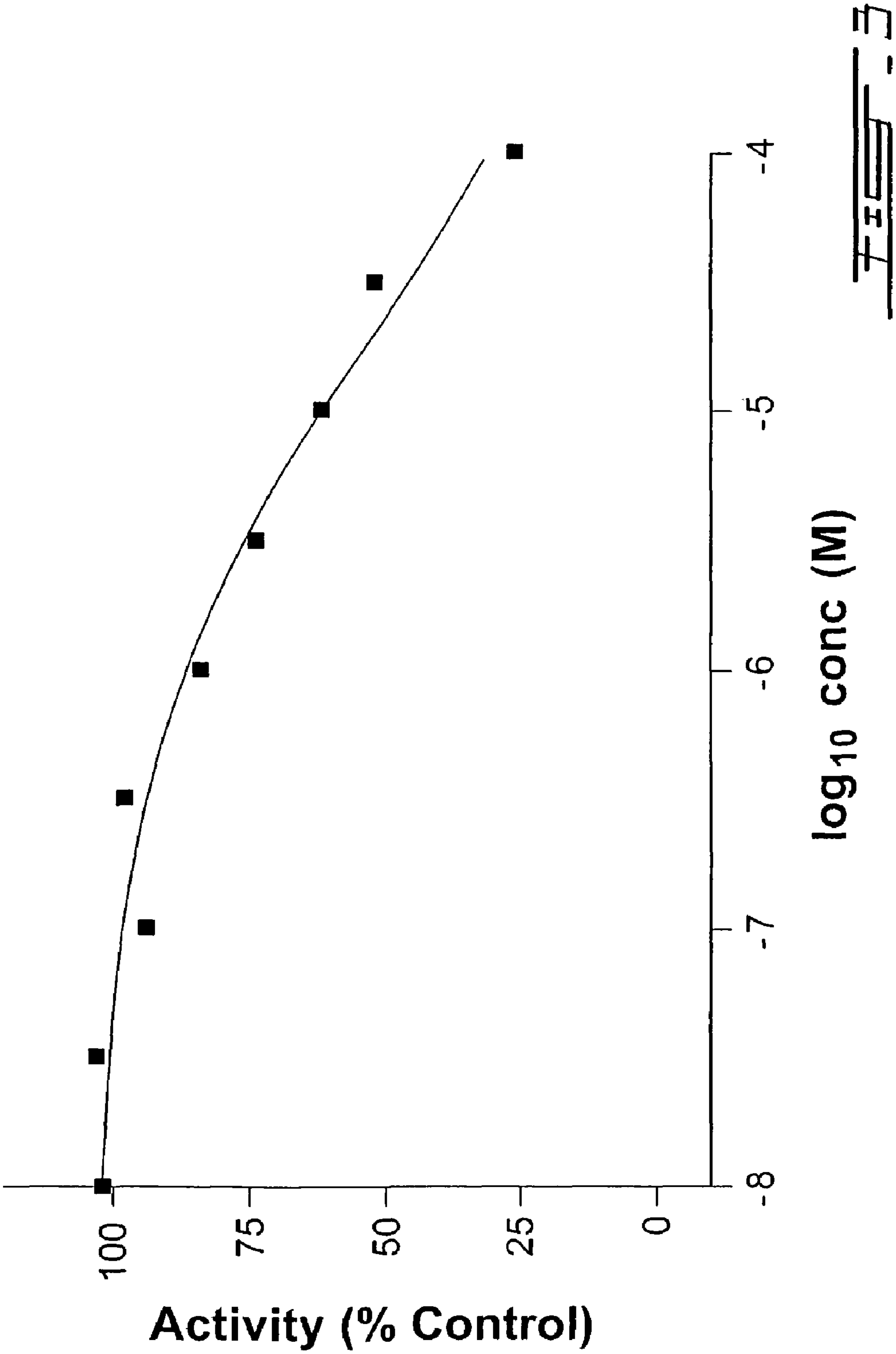
FIG. 3 is an $IC_{50}$ plot of rho kinase inhibitor activity (ROCKI) (y-axis) as a percent of activity in a control incubation of a compound of this invention, BA-1049 (compound E-23a), versus log10 molar concentration x-axis), which data were used to calculate an $IC_{50}$ value of 20.6 micromolar (μM). Experiments were done in duplicate. ATP was present at 100 μM in the assay.

FIG. 3 is an $IC_{50}$ plot of rho kinase inhibitor activity (ROCKI) (y-axis) as a percent of activity in a control incubation of a compound of this invention, BA-1049 (compound E-23a), versus log10 molar concentration x-axis), which data were used to calculate an $IC_{50}$ value of 20.6 micromolar (µM). Experiments were done in duplicate. ATP was present at 100 µM in the assay.

Figure 4:
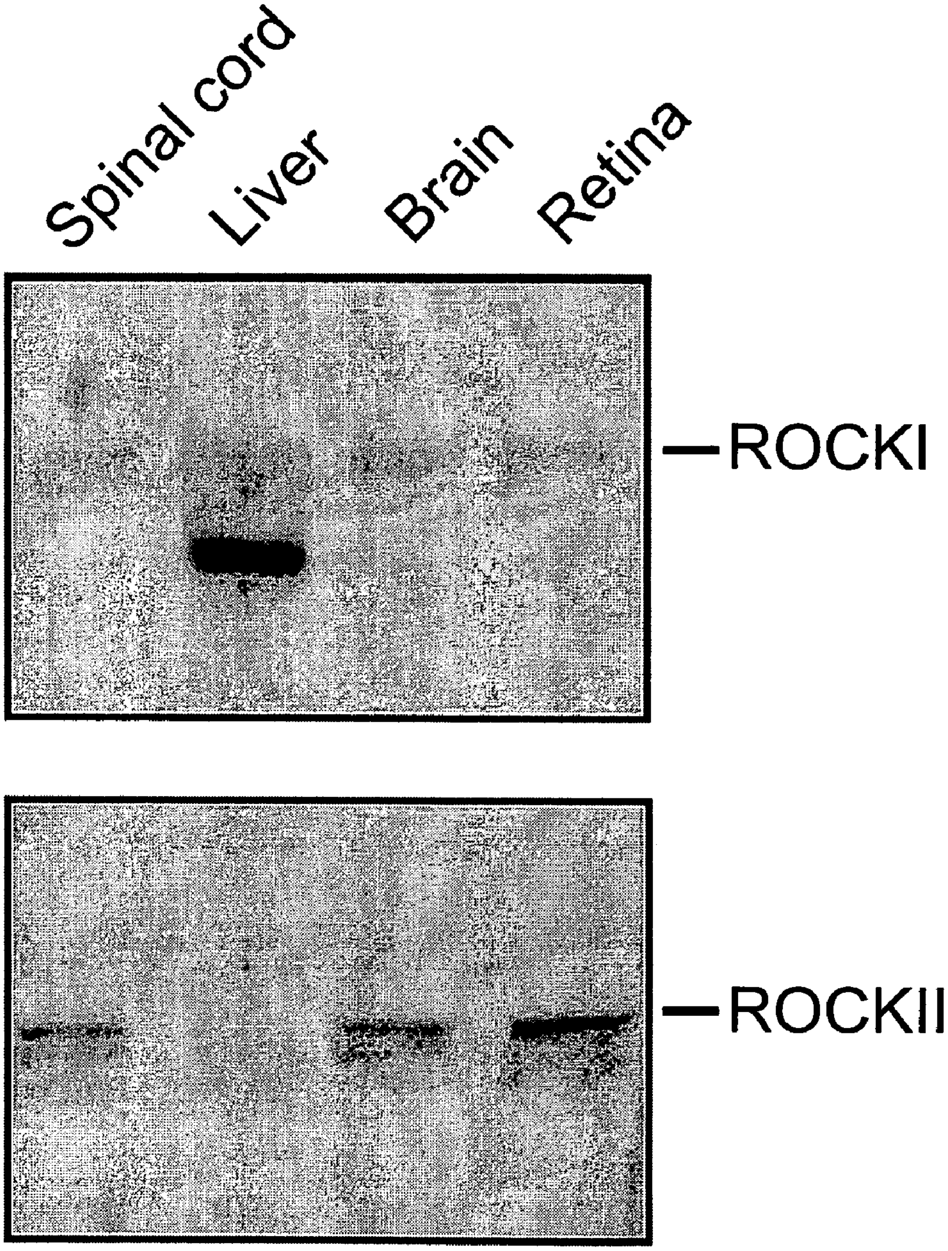
FIG. 4 is a Western blot showing patterns of expression of ROCKI and ROCKII in spinal cord, liver, brain and retina. Proteins were extracted from rat spinal cord, liver, brain or retina; 20 μg was loaded on 7% SDS-PAGE. Specific protein expression was revealed by Western blot using antibodies specific to ROCKI or ROCKII (Santa Cruz Biotechnology Inc.). The results show that ROCKII I is expressed in spinal cord, brain and retina. By contrast, ROCKI is more highly expressed in liver.

FIG. 4 is a Western blot showing patterns of expression of ROCKI and ROCKII in spinal cord, liver, brain and retina. Proteins were extracted from rat spinal cord, liver, brain or retina; 20 µg was loaded on 7% SDS-PAGE. Specific protein expression was revealed by Western blot using antibodies specific to ROCKI or ROCKII (Santa Cruz Biotechnology Inc.). The results show that ROCKII I is expressed in spinal cord, brain and retina. By contrast, ROCKI is more highly expressed in liver.

Figure 5:
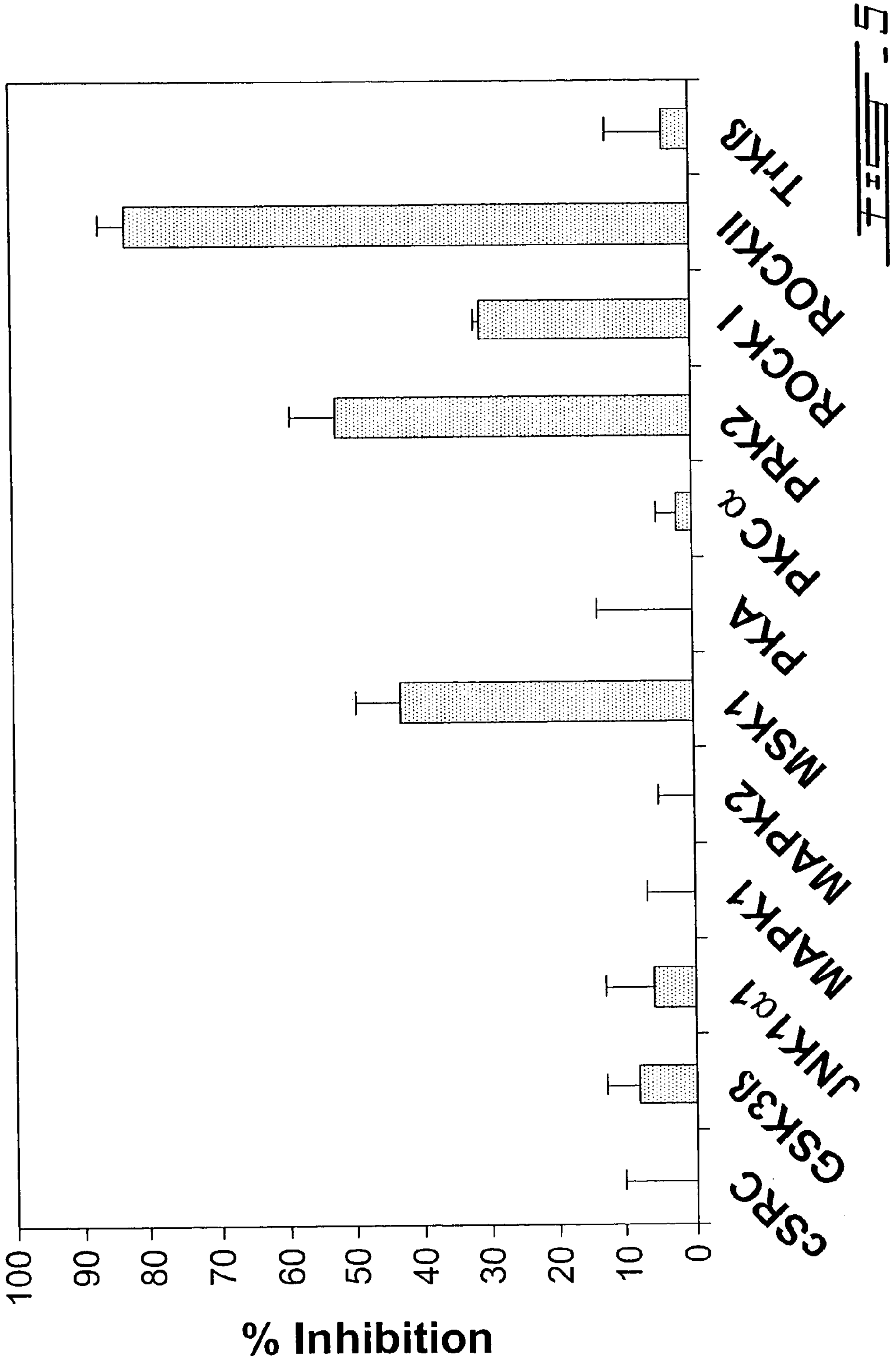
FIG. 5 is a histogram showing kinase selectivity of compound E-23a at 10 μM tested against different kinase substrates: cSRC, GSK3B, JNK1alpha1, MAPK1, MAPK2, MSK1, PKA, PKC alpha, PRK2, ROCKI, ROCKII, and Trkb. E-23a inhibits ROCKII by 83%. E-23a inhibits ROCK I by 31%. E-23a inhibits MSK1 by 43%. E-23a inhibits PRK2 by 52%. The values were expressed in a percentage of inhibition of each kinase. Experiments were done in duplicate. ATP was present at 100 μM in the assay.

FIG. 5 is a histogram showing kinase selectivity of compound E-23a at 10× tested against different kinase substrates: cSRC, GSK3B, JNK1alpha1, MAPK1, MAPK2, MSK1, PKA, PKC alpha, PRK2, ROCKI, ROCKII, and Trkb. E-23a inhibits ROCKII by 83%. E-23a inhibits ROCK I by 31%. E-23a inhibits MSK1 by 43%. E-23a inhibits PRK2 by 52%. The values were expressed in a percentage of inhibition of each kinase. Experiments were done in duplicate. ATP was present at 100 µM in the assay.

Table 2 shows the reaction conditions used for the different kinases tested.

TABLE 2

| Reaction conditions, buffer and substrate used for kinase assays. | | |
|---|---|---|
| Kinase | Reaction Buffer | Substrate |
| ROCK-I | 8 mM MOPS pH 7.0<br>0.2 mM EDTA | 30 µM KEAKEKRQEQIAKRRRLSSLRASTSKSGGSQK |
| ROCK-II | 50 mM Tris pH 7.5<br>0.1 mM EGTA | 30 µM KEAKEKRQEQIAKRRRLSSLRASTSKSGGSQK |
| JNKα1 | 50 mM Tris pH 7.5<br>0.1 mM EGTA,<br>0.1% β-mercaptoethanol | 3 µM AFT2 (Iron sensing transcription factor) |
| cSRC | 8 mM MOPS pH 7.0<br>0.2 mM EDTA | 250 µM KVEKIGEGTYGVVYK (Cdc2 peptide) |
| MAPK1 | 25 mM Tris pH 7.5<br>0.02 mM EGTA | 250 µM Peptide (proprietary) |
| MAPK2 | 25 mM Tris pH 7.5<br>0.02 mM EGTA | 0.33 mg/mL myelin basic protein |
| PKCα | 20 mM HEPES pH 7.4<br>0.03% Triton X-100<br>0.1 mg/mL phosphatidylserine<br>10 µg/mL diacylglycerol | 0.1 mg/mL Histone H1 |
| MSK1 | 8 mM MOPS pH 7.0<br>0.2 mM EDTA | 30 µM GRPRTSSFAEGKK |
| GSK3β | 8 mM MOPS pH 7.0<br>0.2 mM EDTA | 20 µM YRRAAVPPSPSLSRHSSPHQS(p)EDEEE |
| PRK2 | 50 mM Tris pH 7.5<br>0.1 mM EGTA<br>0.1, % β-mercaptoethanol | 30 µM AKRRRLSSLRA |
| TrkB | 8 mM MOPS pH 7.0<br>0.2 mM EDTA | 0.1 mg/mL poly(Glu, Tyr) 4:1 |
| PKA | 8 mM MOPS pH 7.0<br>0.2 mM EDTA | 30 µM LRRASLG (Kemptide) |

Example 49

Bioassay to Determine Neurite Outgrowth-Promoting Activity

A rapid bioassay is used to determine the effect of a test compound on the stimulation of neurite growth in vitro. A neuronal cell line, NG108-15 (ATCC HB-12317), is maintained in culture in Dulbecco's minimal essential medium (DMEM) supplemented with 10% fetal bovine serum (FBS), Penicillin/Streptomycin and HAT supplement (Gibco/BRL). For the bioassay, the cells are collected by trypsinisation and resuspended in DMEM supplemented with 5% FBS, Penicillin/Streptomycin, HAT supplement and 0.25 mg/ml cAMP, adjusted to 1.0×104 cells/ml. The cells are plated into wells of a 96 well plate at 100 μls (1000 cells)/well. Cells are incubated 4 hours at 37° C. and 5% CO2 in the presence of a test molecule of this invention or in the presence of a reference compound (such as Cethrin™) at a concentration of 1000 cells per well of a 96-well plate in a final volume of 100 μl.

After incubation, cells are fixed by adding 35 μl of 16% PFA and 5.4 μl of 2.5% glutaraldehyde to the media in each well. The wells are stained with cresyl violet 0.05% solution at a concentration of 100 μl/well for 15 min. Cells with neurites (length ≧one cell body) are counted using an inverted light microscope. The percent neurite outgrowth is determined by calculating the ratio of the number of cells with neurites to the total number of counted cells (time 100%).

Figure 6:
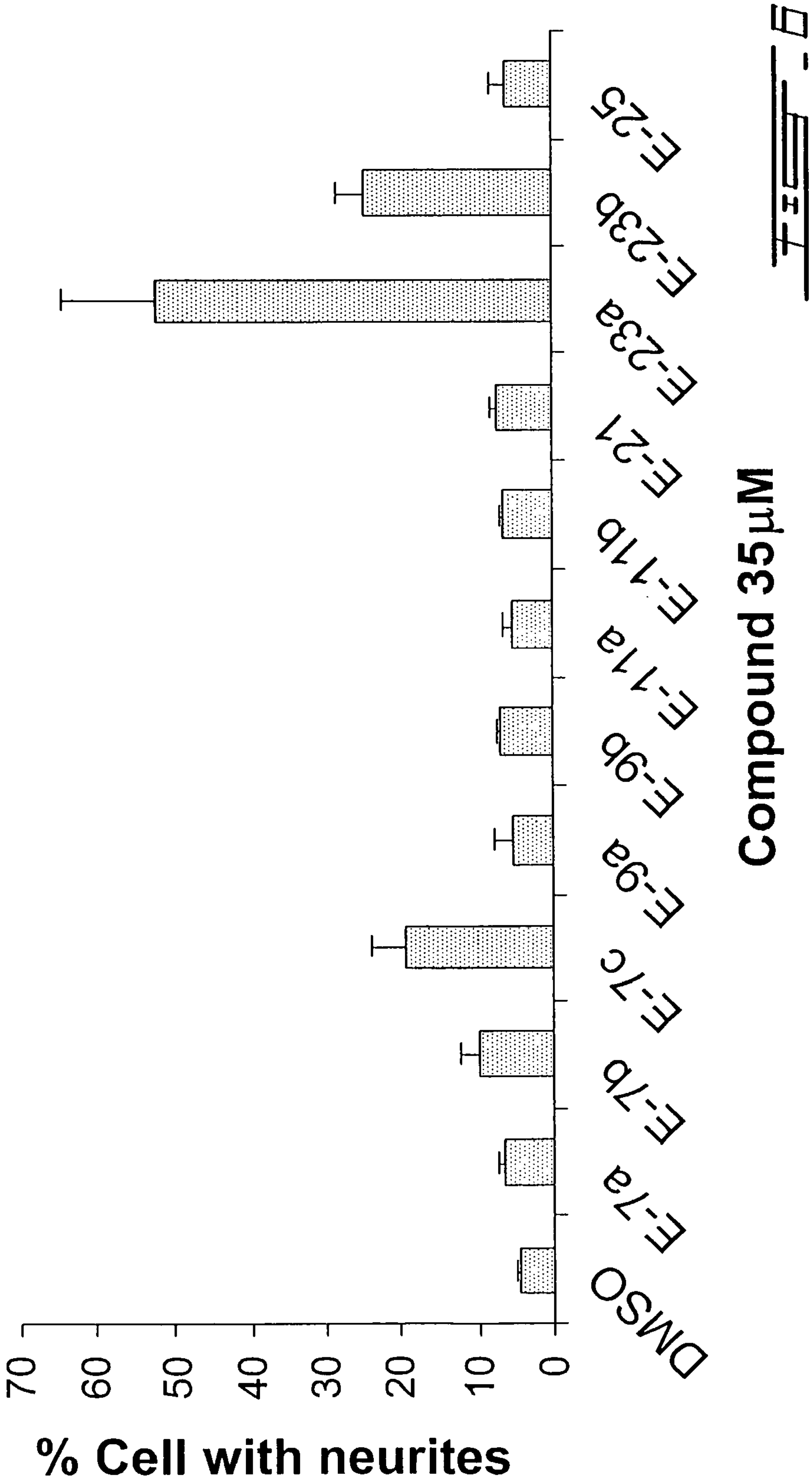
FIG. 6 is a histogram that shows the results of an experiment to examine neurite outgrowth after treatment of cell cultures of NG-108 cells with compounds E-7 to E-25 at a concentration of 35 μM. The percentage of cells with neurites for compounds E-7a to E-25 at 35 μM. The experiment was performed in triplicate. Cells ($1\times10^4$ cells/mL) were incubated in the presence of DMSO 0.35% (control) or test compound (35 μM) dissolved in DMSO for 4 h. The percent of cells with neurites was determined from counts of cells with neurites longer than 1 cell body diameter.

FIG. 6 is a histogram that shows the results of an experiment to examine neurite outgrowth after treatment of cell cultures of NG-108 cells with compounds E-7 to E-25 at a concentration of 35 μM. The percentage of cells with neurites for compounds E-7a to E-25 at 35 μM. The experiment was performed in triplicate. Cells ($1\times10^4$ cells/mL) were incubated in the presence of DMSO 0.35% (control) or test compound (35 μM) dissolved in DMSO for 4 h. The percent of cells with neurites was determined from counts of cells with neurites longer than 1 cell body diameter.

Example 50

Bioassay on Plastic to Determine Relative Neurite Outgrowth Observable in NG108 Cells Treated with a Compound of this Invention Each compound of this invention is tested in triplicate at two concentrations: 3.5 μM and 35 μM prepared from a 7.35 weight % DMSO solution diluted with phosphate buffered saline (PBS). 20 μL of the samples are added to 400 μL of NG108 cell suspension for a final volume of 420 μL. This way the final concentration of DMSO in culture is 0.35%. DMSO does not have an effect on cell morphology at this concentration after microscope observation of cells treated with DMSO in PBS is compared to observation of cells to which only PBS in culture media is added.

The neurite outgrowth observed in NG108 cells treated with a compound of this invention is expressed as percent of neurite outgrowth obtained for a reference control for both 3.5 μM and 35 μM concentrations.

To compare the neurite outgrowth caused by each compound of this invention, bioassay results can be expressed as % of the effect of control compound for a given concentration.

Neurite outgrowth compared to a negative control (fold increase) is determined using the following equation:

$$\frac{\text{Neurite outgrowth}}{\text{(fold increase)}} = \frac{\text{\% Neurite outgrowth for test sample}}{\text{Net \% Neurite outgrowth for vehicle control}}$$

Percent net neurite outgrowth at 35 micromolar concentrations are presented in Table 3 together with percent Rock inhibition at 10 micromolar for three compounds designated BA-1043, BA-1049, and BA-1050. Compound BA-1043 is a dihydrochloride addition salt of compound VIII(c), a compound of this invention. Compound BA-1049 is a dihydrochloride addition salt of compound IV(b), a compound of this invention. Compound BA-1050 is a dihydrochloride addition salt of compound IV(a), a compound of this invention. It should be noted that percent Rock activity is equal to 100% minus percent Rock inhibition.

TABLE 3

Net neurite outgrowth and percent Rock inhibition observed in compounds BA-1043, BA-1049, and BA-1050 of this invention.

| Compound | Percent Net Neurite Outgrowth at 35 micromolar | Percent Rock inhibition at 10 micromolar |
|---|---|---|
| BA-1043 | 15.2 | 61 |
| BA-1049 | 39.0 | 97 |
| BA-1050 | 20.2 | 79 |

Example 51

Bioassay on Growth Inhibitory Myelin-Associated Glycoprotein (MAG) Substrates, and the Ability of a Compound of this Invention to Induce Growth of Neurites on Cells when Plated on Inhibitory Substrates PC-12 cells (ATCC CRL-1721) typically extend neurites in response to NGF, but when plated on inhibitory substrates, this outgrowth is inhibited and the cells remain round.

A compound of this invention is able to overcome growth inhibition by MAG. On MAG substrates in the absence of a Rho kinase inhibitor, a nerve cell remains round and is unable to extend neurites. When a compound of this invention which exhibits Rho kinase inhibition activity and can penetrate a nerve cell membrane to reach the Rho kinase residing inside a nerve cell is added to a culture medium of nerve cells, the compound can overcome growth inhibition by MAG, the cells differentiate and grew long neurites (greater in length than the average diameter a nerve cell in the culture. MAG is an inhibitory protein present in the CNS, and the receptor to MAG is a common receptor shared by the other major myelin-derived inhibitors Nogo and Oligodendrocyte myelin glycoprotein. The MAG receptor is called Nogo-66 receptor, or NgR.

A compound of this invention can overcome growth inhibition by nogo-66 receptor-dependent mechanisms. A compound of this invention should be effective in promoting growth of neurites in nerve cells in the central nervous system when administered to a local lesion site of a damaged or diseased nerve, which site has a growth inhibitory environment.

PC12 cells, obtained from the American Type Culture Collection, are grown in Dulbecco's modified eagle's medium (DMEM) with 10% horse serum and 5% fetal bovine serum (FBS). To evaluate compounds for their ability to overcome growth inhibition by MAG substrate, PC12 cells are collected by detaching with trypsin-EDTA (0.05%), then resuspended in DMEM, 1% FBS, and 50 ng/ml nerve growth factor before plating on MAG substrates. MAG used for substrates is purified from myelin after extraction in 1% octylglucoside and separation by ion exchange chromatography (McKerracher et al. 1994, Neuron 13:805-811). Test substrates are prepared as uniform substrates in 96-well plates by drying overnight in the laminar flow hood (Nalge Nunc, Naperville, Ill.). The plates are precoated with polylysine (100 μg/ml) for 3 hours at 37° C., then washed and dried approximately 1 hour. MAG is prepared as a substrate by drying down 8 μg of protein overnight. After plating on the MAG substrate, the cells are grown at 37° C. for two days in the presence or absence of test compound of this invention to allow time for neurite growth. Polylysine substrates are used as a positive control.

Quantitative analysis of the ability of a compound to overcome growth inhibition by MAG of neurite outgrowth is accomplished with the aid of Northern Eclipse software (Empix Imaging, Mississauga, Ontario). The ratio of the number of neurons that grow neurites to total number of neurons observed is calculated as the percentage of neurite growth. Data analysis and statistics can be done using Microsoft Excel. Experiments can be performed in triplicate.

Example 52

Cell Survival After Axotomy

Transection of the optic nerve (ON) in an adult rat, as a model of fiber tract lesion in the adult mammalian CNS, results in delayed, mainly apoptotic death of 80-90% of retinal ganglion cells (RGCs) within 14 days post-lesion. Because of good surgical accessibility of the retina and the optic nerve, the retino-tectal projection represents not only a convenient model to study the molecular mechanisms underlying neuronal death but also serves as a suitable system for investigating potential neuroprotective agents in vivo.

The ability of a compound of this invention to support RGC cell survival after optic nerve injury can be tested. A single injection of a pharmaceutical composition of the compound can be made in the eye, and at a later time, such as one week later, cell survival can be assessed. Three animals can be examined for each treatment group.

Multiple or chronic application of a compound of this invention may be effective to rescue injured retinal ganglion cells.

Example 53

Retrograde Labeling of Retinal Ganglion Cells

Experiments can be performed on adult female CD rats (180-200 g; Charles River, Canada). Animals are cared for according to the Canadian Council on Animal Care. Rats can be under general anesthesia with isofluorane connected to a Moduflex Access anesthesia machine during experimental procedures. Ophthalmic eye ointment (Polysporin) can be applied to prevent corneal desiccation. Retinal ganglion cells (RGCs) can be retrogradely labeled with Fluorogold (Fluorochrome, Inc., Denver, Colo., U.S.A; 2% in 0.9% NaCl aqueous solution containing 10% dimethyl sulfoxide) applied with a small piece of gel foam on the surface of right superior colliculus (SC). All rats can be pre-labeled with Fluorogold one week prior to optic nerve lesion.

Example 54

Optic Nerve Transection and Drug Administration

One week after Fluorogold application, the left optic nerve can be transected 1 mm from the eye. The optic nerve can be accessed within the orbit by making an incision parasagitally in the skin covering the superior rim of the orbit bone, by means of micro scissors taking care to leave the supraorbital vein intact. Following subtotal resection or reflection of the lacrimal gland using blunt preparation, the superior extraocular muscles can be spread with a small retractor or suture 6-0 silk to keep both hands free. The superior orbital contents can be dissected and the rectus muscles can be reflected laterally. When the optic nerve is exposed, the surrounding dura mater sheath can be cut longitudinally to avoid cutting blood vessels while revealing the optic nerve. There are blood vessels on pia and optic nerve. The pia mater sheath can be lifted and a lateral incision can be made to expose the optic nerve. It is important not to cut the optic nerve before cutting the pia. When pia is cut, the optic nerve can be moved gently to dislodge it from its sheath so that the scissors can be slipped under it to cut it. It is important to not pull the nerve at this point to avoid compromising the blood supply. When the optic nerve is well exposed, small scissors can be slid tangentially under optic nerve, making sure to see their end on other side of the nerve, then the nerve can be cut with one clean cut at 1 mm from the eye. Scissor blades can be used as a reference to estimate the 1 mm distance. In a group of animals assigned to receive intravitreal injection after axotomy, the compounds of interest (i.e., compounds of this invention) can be injected into the vitreous space. The eye can be punctured at the superior nasal retina area with a 30 gauge needle and then a Hamilton syringe can be used to inject about 10 micrograms in about 5 microlitres of volume of a test compound over a 1 minute period. The needle can be removed after one minute. Once injection is completed, tissue adhesive (Indermil) can be used to seal the overture. Lens injury, which can negatively effect survival of the RGCs, is to be avoided.

A binocular microscope can be used to view the eye during injection. The skin can be closed with staples (auto clips) and the integrity of the retinal vasculature can be evaluated by a postoperative ophthalmoscopy using a water-covered microscope slide. Rats with compromised vasculature are not to be included in the experimental results. The animals are then returned to the cage and closely monitored until awakened. Seven days after axotomy, animals can be killed by injecting an overdose of Chloral hydrate intraperitoneally, and then can be fixed by perfusion with 4% paraformaldehyde (PFA), 0.1 M phosphate buffer. The eyes can be removed carefully transecting the ocular muscles with scissors and forceps. The eyes can be fixed in 4% PFA and the cornea can be punctured to allow entrance of PFA to the posterior pole of the eye. The retina can be then separated carefully from the eye bulb and can be flat-mounted on a glass slide incising the tissue according to the four retinal quadrants. RGCs can be examined under a fluorescence microscope with an UV filter (365/420). The number of fluorescent RGCs can be counted on 12 standard areas (0.45×0.35 mm each) located beside the optic nerve head and at 1.35 and 2.7 mm from the optic disc in each of the retinal quadrants.

Example 55

In Vivo Evaluation of a Compound of this Invention

Compounds in accordance with the present invention may be used to promote axon growth on inhibitory substrates in vitro and/or in vivo. To examine the ability of a compound of this invention to promote axon regeneration in vivo, the regeneration of retinal ganglion cell axons can be examined in the optic nerve in a mammal after intravitrial injection of a pharmaceutically acceptable solution of the compound. A pharmaceutically acceptable solution of a compound of this invention can be injected in the vitreous of rats immediately after an optic nerve crush that transects all of the retinal ganglion cell (RGC) axons. Two weeks later the animals cholera toxin B subunit can be injected in the eye to anterogradely label the regenerating RGC axons. The next day the animals can be killed, perfused with saline, and the optic nerves can be removed for sectioning. Longitudinal sections of the optic nerve can be reacted for anti-cholera toxin immunoreactivity to observe the anterogradely labeled fibers. RGC axons can be observed after treatment with a compound of this invention, and distances of axon growth are expected to exceed 500 μm. No observable axon regeneration is expected in buffer-treated control animals.

Rats can be anesthetized with isoflorane (2.4%) and the head can be shaved. To make microcrush lesions, the left optic nerve can be exposed by a supraorbital approach, the optic nerve sheath can be slit longitudinally, the optic nerve can be lifted out from the sheath and can be crushed about 1 mm from the globe by constriction with a 10.0 suture to be held for 60 seconds. Immediately after optic nerve crush a test solution containing a compound of this invention in a pharmaceutically acceptable carrier solution or a buffer control (phosphate buffered saline) can be injected into the vitreous in the amount of about 100 micrograms of compound in a volume of about 5 microliters. After 2 weeks, all rats can be given an intravitreal injection of 5 μl 1% cholera toxin β subunit (CTB; List Biological Labs, Campbell, Calif.) 24 hr before subsequent perfusion with PFA. Optic nerves can be dissected, can be post-fixed 1 hr in PFA, can be cryoprotected overnight in 30% sucrose and can be frozen at −70° C. in OCT (Canlab, Montreal, PQ). Longitudinal cryostat sections of optic nerves can be cut at 14 μm and can be mounted on Superfrost Plus slides (Fisher, Montreal, PQ). Retinal ganglion cell axons can be labeled by CTB and can be detected by immunohistochemistry for CTB using a goat anti-choleragenoid (List Biological Labs), a biotinylated rabbit anti-goat (Vector Labs., Burlingame, Calif.) and DTAF-conjugated streptavidin (Jackson Labs., West Grove, Pa.).

It is anticipated that in a longitudinal section of an optic nerve treated with a compound of this invention, at the site of the lesion regenerating axons will be found to extend past the lesion site while in a longitudinal section of a control optic nerve, axons will not be found to regenerate past the site of the lesion.

Example 56

Determination of Anti-Proliferative Effects of a Compound of this Invention for Cancer Cells (a) Thymidine Uptake Assay The antiproliferative effects of a compound of this invention can be evaluated using a thymidine uptake assay that can employ several different human cancer cell lines grown in culture such as HEC-1B human adnocarcinoma, SK-MEL-1 human malignant melanoma, and Caco-2 human colorectal adenocarcinoma. The cells can be seeded in a 96 well plate and after 2 hours the cells can be treated with a solution containing DMSO of a compound of this invention or with a control solution. The control solution can be PBS as a negative control, or the control solution can be complete medium plus DMSO vehicle (at 0.1% or 1%). A solution of a compound of this invention can be added at three different concentrations, for example, at 1 μM, at 10 μM, or at 100 μM. Each control solution and test solution can be plated in triplicate for each cell line. The plate can be incubated at 37° C. with 5% CO2 in a humidified atmosphere for approximately 54 hours. A volume of 0.02 ml of radioisotopic (tritium-containing) $^3$H-methyl thymidine which can contain about 1.0 μCi can be added to each well. The culture can be incubated a further 18 hours. Using an automated cell harvester, the cells from each well can be aspirated onto a glass microfiber filter. The cells can be broken with distilled water to leave mainly the DNA on the filter. Each filter can be placed in a scintillation counter (TopCount NXT). At appropriate settings for the 3H, each filter can be counted for one minute. The results can be expressed as CPM (counts per minute).

Cancer is characterized by the uncontrolled division of a population of cells which, most typically, leads to the formation of one or more tumors. Rho kinase is inhibited by compounds of this invention. The small GTPase Rho is up-regulated in certain cancers, such as malignant melanoma and breast cancer. Up-regulation of Rho can activate Rho kinase. Inactivation of Rho kinase is expected to reduce or cure malignancy.

It is expected that a compound of this invention when tested for example at concentrations of 100 μM, 10 μM, and 1 μM can reduce cell proliferation of SK-MEL-1 cells, a human malignant melanoma cell line. It is expected that a most compound of this invention can substantially completely arrest cell proliferation of tumor cells such as SK-MEL-1 melanoma cells and such as HEC-1B human endometrial adenocarcinoma cancer cells, and reduce cell migration, and potentially reduce metastasis of cancerous lesions and malignant tumors.

(b) AlamarBlue™ Assay

Another method to study the anti-proliferative effect of a compound of this invention comprises use of an Alamar Blue assay. For this assay, cells are thawed and passaged at least one time before the experiment. Cells are grown in a culture dish in media supplemented with serum and supplements appropriate for the test cell line. When they reach logarithmic growth, the cells are trypsinized to detach them from the culture dish and are counted. The cell pellet is resuspended and adjusted to 2-5×10$^4$ cells/ml. A 96-well microplate is used for the experiment and cells are plated at a density of 1000 to 5000 cells/well in 100 μL of growth media. The seeding density is noted to ensure that the cells in the control wells are not overgrown after the total incubation time. The microplates are placed in the cell culture incubator at 37° C., 5% $CO_2$ and 100% relative humidity for 18-20 h, then examined by phase contrast microscopy to check for even growth across the plate. Fresh media of 100 μl is added with the test reagent, and one control receives media alone. After drug addition, microplates are incubated for an additional 24 to 96 h. One to four hours before the end of incubation, 20 μL of AlamarBlue™ reagent is added to the wells that already contain 200 μL of culture medium, and the plate is incubated for 1-4 h at 37° C., 5% $CO_2$ and 100% relative humidity. At the end of the incubation period, the fluorescence intensity is read with a 96-well microplate reader (excitation 530-560 nm; emission 590 nm), with bottom reading. The fluorescence generated in the AlamarBlue™ assay can be stopped and stabilized by the addition of 3% SDS. A volume of 50 μl per 100 μl of original culture medium is used. The plate is then be stored at ambient temperature for up to 24 h before recording data, provided that the contents are protected from light and covered to prevent evaporation.

For each concentration of test article, a % growth is calculated using the following equation, wherein $T_0$=fluorescence units at the time of test article addition (time 0)

C=fluorescence units for control (no test article)

$T_i$=fluorescence unit for test article (different dilution)

$$\%\ \text{Growth} = \left[\frac{(Ti - To)}{(C - To)}\right] \times 100$$

Figure 7:
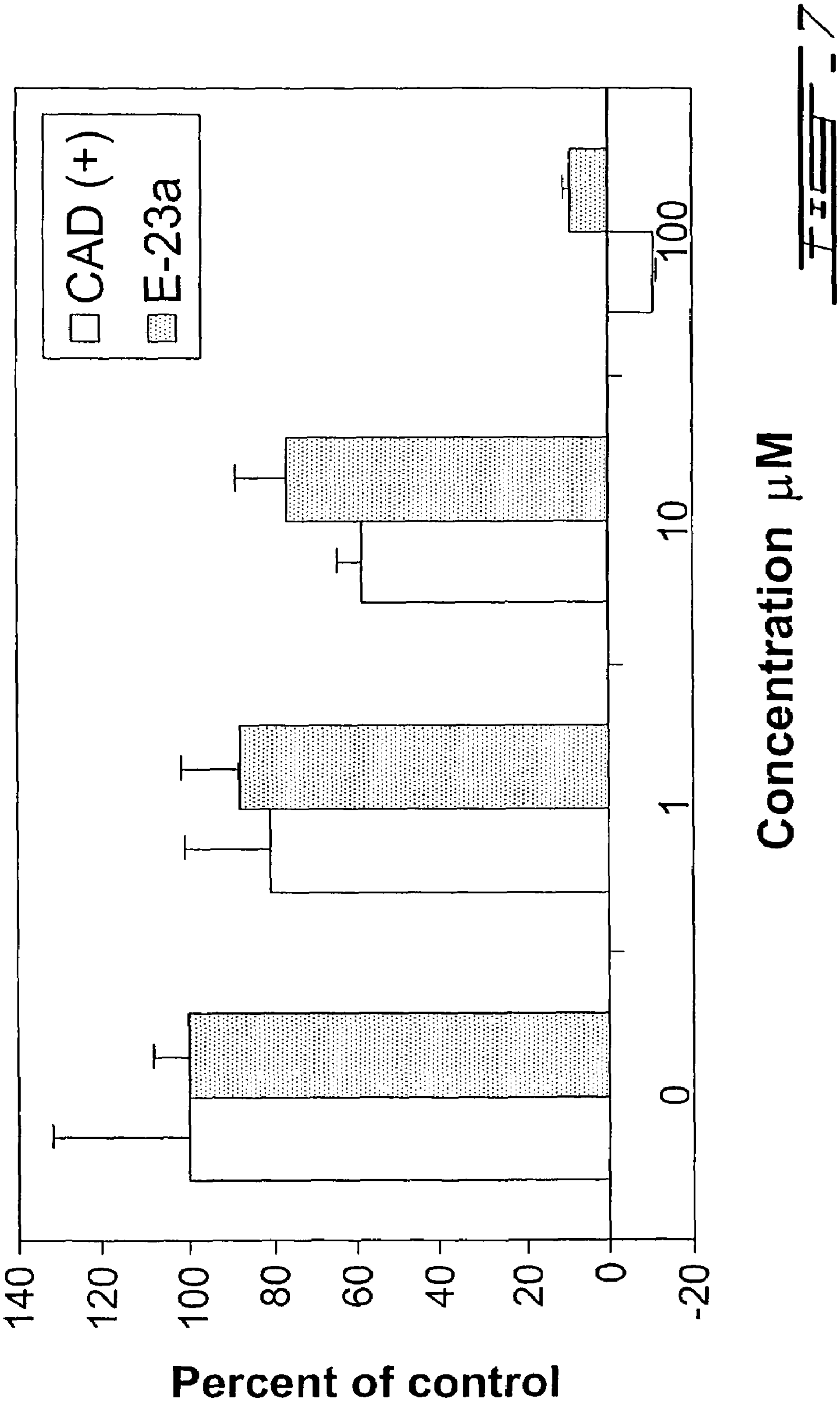
FIG. 7 shows the reduced proliferation of HEC-1B cells expressed as a percentage of control cells (Y-axis) after incubation for 72 hours in the presence of different concentrations of E-23a x-axis). Cadmium sulfate hydrate (CAD) was used as a positive control. Following treatment, the rate of proliferation was measured using the Alamar Blue assay.

FIG. 7 shows the reduced proliferation of HEC-1B cells expressed as a percentage of control cells (Y-axis) after incubation for 72 hours in the presence of different concentrations of E-23a x-axis). Cadmium sulfate hydrate (CAD) was used as a positive control. Following treatment, the rate of proliferation was measured using the Alamar Blue assay.

Example 57

Method to Study the Effect of Compounds of this Invention on Proliferation of Cancer Cells The anti-proliferative effects of a compound of this invention can be tested by a thymidine uptake assay with several different human cancer cell lines grown in culture such as HEC-1B human adnocarcinoma, SK-MEL-1 human malignant melanoma, and Caco-2 human colorectal adenocarcinoma. The cells are seeded in a 96 well plate and after 2 hours the cells are treated with a compound of this invention or with a control solution. The control solutions are (a) PBS as a negative control, and (b) complete medium plus DMSO vehicle (at 0.1% or 1%). A compound of this invention is added at three different concentrations: 1 μM, 10 μM or 100 μM. Each control solution and test solution is plated in triplicate for each cell line. The plate is incubated at 37° C. with 5% $CO_2$ in a humidified atmosphere for approximately 54 hours. A volume of 0.02 mL of 3H-methyl thymidine containing about 1.0 μCi is added to each well. The culture is incubated a further 18 hours. Using an automated cell harvester the cells from each well are aspirated onto a glass microfiber filter. The cells are broken with distilled water to leave mainly the DNA on the filter. Each filter is placed in a scintillation counter (TopCount NXT). At appropriate scintillation counter settings for the $^3H$, each filter is counted for one minute. The results can be expressed as CPM (counts per minute).

Rho kinase inhibitors have potential therapeutic use in cancer. The intracellular enzyme Rho kinase is activated by the intracellular enzyme Rho, and Rho kinase inhibitors block Rho signaling. A number of Rho family regulatory proteins in which mutations have been found in clinical oncology suggest that perturbation of Rho signaling can be useful as a therapeutic modality, for example, in preventing metastasis and to treat various forms of malignant transformation.

The relative anti-proliferative effects of a compound of this invention versus a control compound such as Y-27632 can be evaluated using a thymidine uptake assay, which provides a relative measure of DNA synthesis. A useful compound of this invention can block or inhibit cell proliferation, for example of human malignant melanocarcinoma cells, compared to that observed using only vehicle (DMSO) and PBS controls.

Example 58

Determination of Effect of a Compound of the Invention on the Reduction of Solid Tumor Size after Transplantation of Human Tumor Cells in Mice An in vivo model to test anti-proliferative activity of test compounds is a subcutaneous (s.c.) tumor model. In this model, human cancer cells are seeded into mice by a subcutaneous injection. Typically immune-compromised mouse cell lines are used, such as CD-1 nude mice, to prevent a graft rejection response. The test compound is administered as a formulation in a pharmaceutically acceptable vehicle suitable for injection use, such as isotonic phosphate buffered saline (PBS), by injection into the tumor. Different dosing schedules can be tested and compared with mice receiving injection of vehicle control. Before implantation into an animal, tumor cells are expanded in their specific tissue culture medium. Medium is changed 2 to 3 times per week. They are split 1:5 to 1:10 with mild trypsinisation (e.g., using an overlay of 0.05% typsin-0.02% EDTA solution left for 1-2 minute). Fresh media is then added to the flask and cell aliquots are transferred to new flasks. Cells are always injected into mice at the log stage of their growth. Useful cells are, for example, Caki cells which are a human renal cancer line. The number of cells is a function of the cell line used and proliferation rate. Cells are injected subcutaneously into the right flank region of immunocompromised mice (nude mice) in a total volume of 0.05 ml using a 1 ml syringe with 261/2 gauge needle. Injection site is disinfected with alcohol 70% before injection. Usually by day 4, or longer, depending on cell number and cell line injected, a visible and palpable subcutaneous nodule develops at the injection site. The tumor growth is monitored twice a week. Tumor volume is determined with a digital caliper and calculated using the formula: $width^2 \times length \times 0.5$. The length is taken at the basis of the tumors between the two most distant points of the tumor mass, whereas the width is measured right-angled to the length. All measurements are performed on individual animals and then used to calculate tumor volume. When tumors have reached a mean volume of 125 $mm^3$, treatment is started. Mice are randomized into control and treated groups, with n=5-10 animals in each group. Animals are identified in a permanent manner by small incision (notch, flap, or punch hole) at the ear level. Subcutaneous tumors are injected centrotumoraly with test and vehicle articles, with a dose volume of 20 μl to 100 μl. Tumor volume and animal body weight are recorded twice a week.

Figure 8:
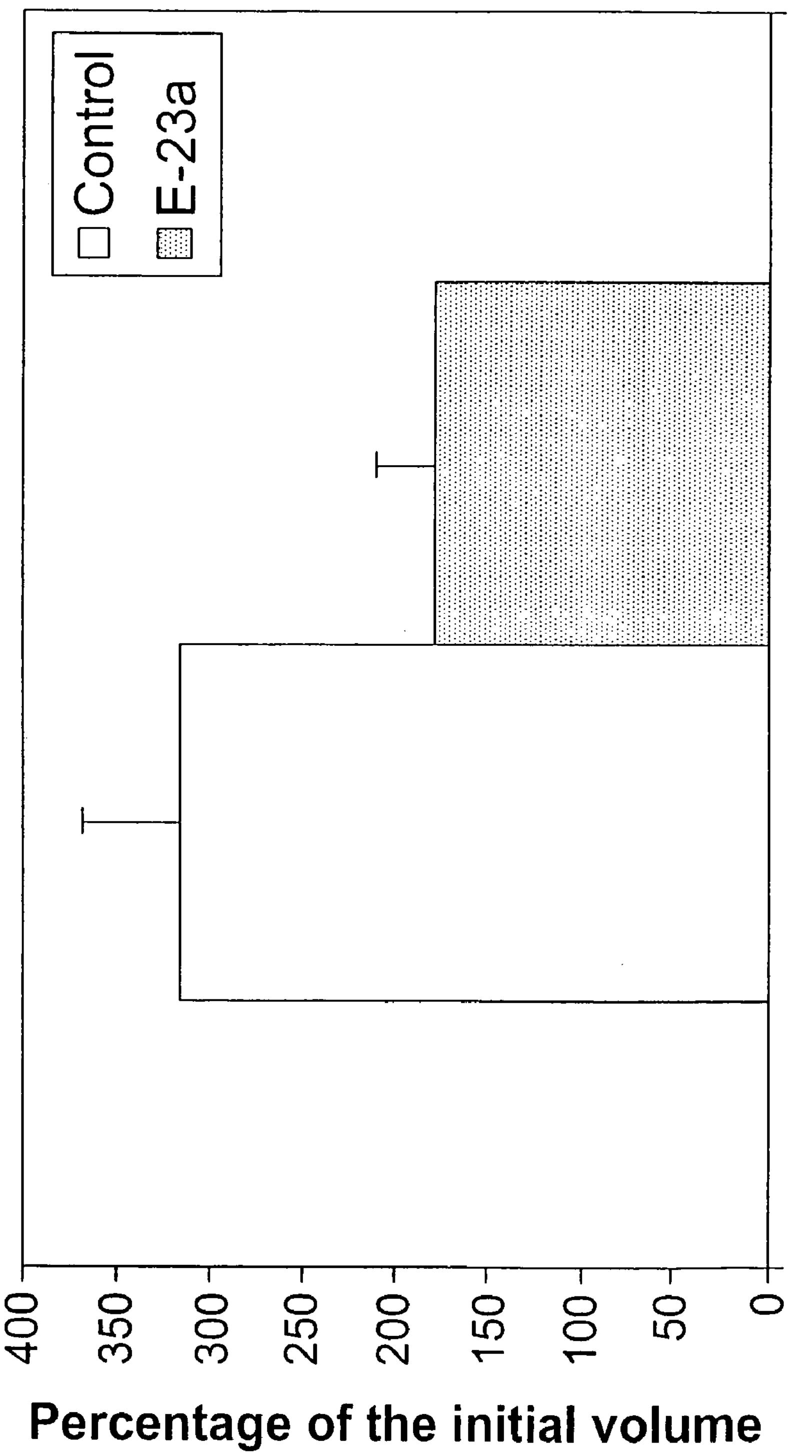
FIG. 8 shows the effect of E-23a on reducing rate of growth of tumor size relative to a control. The effect on tumor size change of administration of the compound of the invention, E-23a, and of administration of control vehicle are expressed as a percentage of the respective initial tumor volumes which were determined at the beginning of the treatment schedule.

FIG. 8 shows the effect of E-23a on reducing rate of growth of tumor size relative to a control. Caki cells, which are a human renal cancer line were grown in tissue culture. At logarithmic phase of growth, $5 \times 10^6$ cells in 50 to 200 μl were injected subcutaneously in nude mice. When tumors had formed, the control tumors were injected with 50 μL of PBS and the treated tumors were injected with 50 μL PBS with 40 μM of E-23a every day for two weeks. Tumors were evaluated after 2 weeks of treatment after the final injection. The effect on tumor size change of administration of the compound of the invention, E-23a, and of administration of control vehicle are expressed as a percentage of the respective initial tumor volumes which were determined at the beginning of the treatment schedule. The experiment was performed with 7 mice (control) and 6 mice treated with E-23a. The mean tumor size increase observed in tumors treated with E23a in PBS was approximately 156% of initial tumor volume versus an increase of 304% of initial tumor volume in tumors treated with control vehicle.

Example 59

Determination of Anti-Angiogenesis Activity of Compounds

To measure the effect of a compound (drug) of this invention on the proliferation of vascular endothelial cells, HUVEC cells (human umbilical vein endothelial cells) are used. Endothelial cells (HUVEC) are maintained in an appropriate culture medium (e.g., EBM-2 with supplements; EBM=Endothelial Basal Medium), and cells at a logarithmic growth phase are trypsinized as described by Clonetics™ Umbilical Vein Endothelial Cell Systems (Cambrex Bio Science Walkersville, Inc.), the instructions of which are incorporated herein by reference. The number of passages of HUVEC cells is carefully monitored and experiments are done between will cells that have been passed in culture 4 to 5 times. After centrifugation, the cell pellet is resuspended in complete medium, and 2000 cells/well are plated on a 96-well microplate (surface: 0.32 $cm^2$) in 100 µl of medium. After 18 h, 100 µl of medium and 20 µl of AlamarBlue™ (Medicorp Inc., Montreal, Quebec, Canada) is added for 2 to 4 h. This plate is used for the measurement of the cell population, by AlamarBlue™, at the time of test article (drug) addition (T0). Aliquots of 100 µl of test article (drug) at drug concentrations achieved by the appropriate dilution are added to the appropriate well already containing 100 µl of medium. After drug addition, the microplates are incubated for an additional 1 to 96 h at 37° C. with 5% $CO_2$ and at 100% relative humidity. Four (4) hours before the end of incubation, 20 µL of AlamarBlue™ solution is added to each of the wells which already contain 200 µl of culture medium. The plates are further incubated for 4 h at 37° C. with 5% $CO_2$ at 100% relative humidity. The fluorescence intensity is measured with an ELISA plate reader (excitation wavelength: 530-560 nm; emission wavelength: 590 nm). Tranilast (N-(3',4'-dimethoxycinnamoyl)anthranilic acid) (Calbiochem; EMD Biosciences, Inc) acts as a potent inhibitor of VEGF- (Vascular Endothelial Growth Factor) and vascular permeability factor-induced angiogenesis and collagen synthesis. Tranilast inhibits VEGF- and PMA-stimulated PKC activity in capillary endothelial cells without affecting the VEGF binding or VEGF receptor phosphorylation. Tranilast is used as a positive control.

Figure 9:
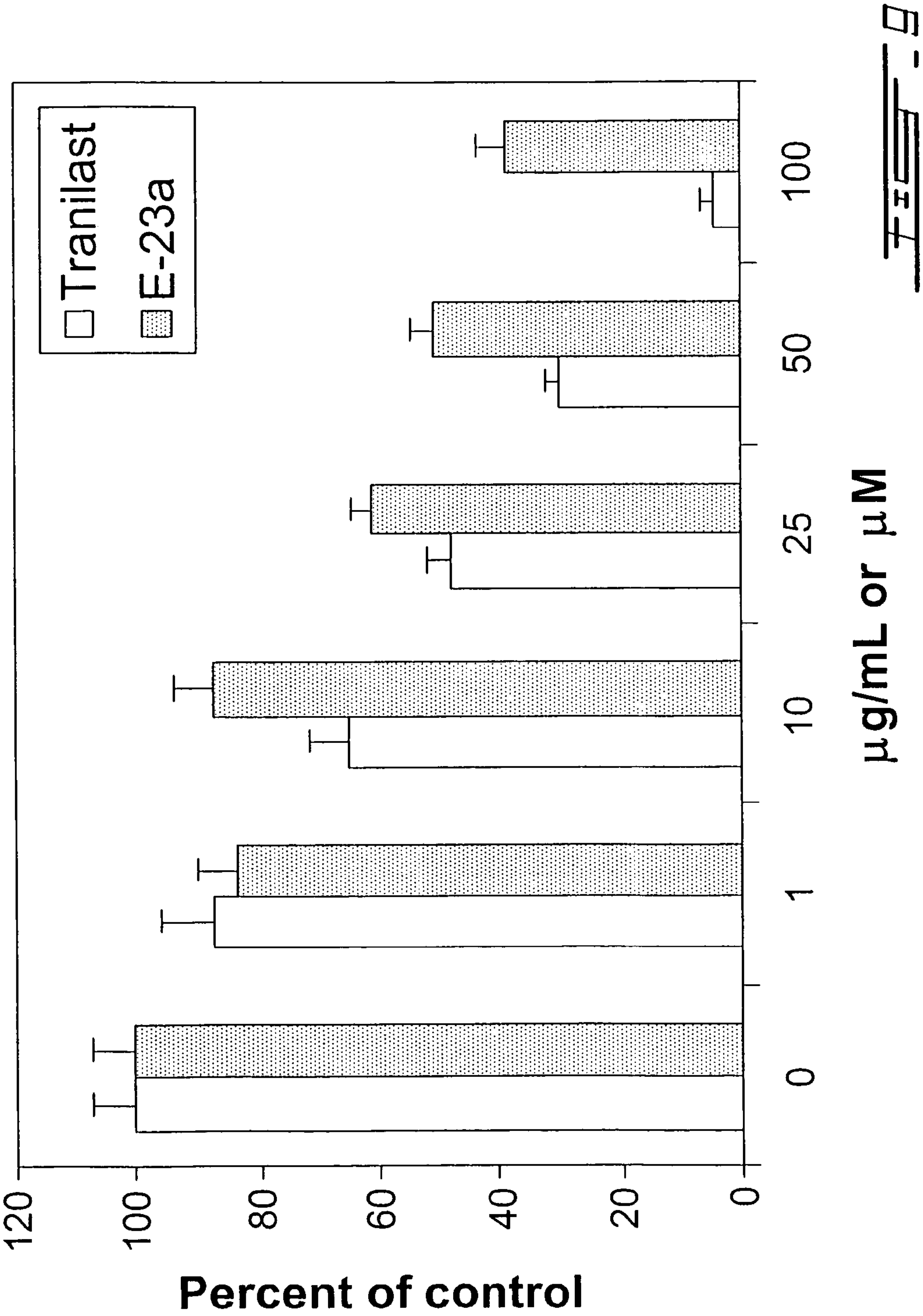
FIG. 9 shows the relative anti-proliferative effect as a percent of control of compound E-23a and of tranilast as a function of concentration on human endothelial cells.

FIG. 9 shows the relative anti-proliferative effect as a percent of control of compound E-23a and of tranilast as a function of concentration (1, 10, 25, 50, and 100 µg/mL or 1, 10, 25, 50, and 100 µM) on human endothelial cells (HUVEC cells). Two thousand HUVEC cells were incubated for 72 h with different concentrations of E-23a or tranilast, a positive control. Following treatment, the rate of proliferation was measured using Alamar Blue. Results are presented as mean±SD for two separate experiments done in triplicate.

HUVEC cells will form capillary tubes when plated on protein substrates composed of proteins found in the extracellular matrix. Typical substrates useful for experiments with HUVEC cells are Matrigel, fibronectin or collagen. Matrigel is composed of several proteins that make up the extracellular matrix. Extracelluar matrix substrates can be plated in tissue culture dishes as 3-dimensional cell culture substrates. Another reagent that can be used as a substrate is ECMatrix™ (Chemicon International, Temecula, Calif.), a reconstituted basement membrane matrix of proteins derived from the Engelbreth Holm-Swarm (EHS) mouse tumor. This substrate gels rapidly at 22-35° C. Thus, ECMatrix™ is thawed overnight on ice or in +4° C. A 96-well plate is pre-chilled, and 100µl of the ECMatrix solution is added to each well. The plate is incubated at 37° C. for at least one hour to allow the matrix solution to solidify. The HUVEC cells are harvested and resuspended in a standard cell growth media supplemented with endothelial cell growth supplements. The presence of serum (0.5-10%) is optional. EGM (endothelial cell growth media) can be used. The HUVEC cells are plated at a density of $5\times10^3$ to $1\times10^4$ cells per well onto the surface of the polymerized ECMatrix™, and then incubated overnight in a tissue-culture incubator. Cellular network structures are fully developed by 12 to 18 h, with the first signs apparent after 5-6 h. After 24 h, the cells begin to undergo apoptosis. To study the effect of anti-angiogenic factors, they can be added at the time of cell plating. Optional tissue culture vary depending on the cell type, age, and media growth conditions. The tubes are inspected under an inverted light microscope at 40×-200× magnification. Since there is a lack of contrast of the cellular networks, the cultures can be stained with any of the common cell staining procedures such as Diff-Quick or Wright-Giemsa or crystal-violet. The total capillary tube length measurement method is used to quantify the results. The total length of all the capillary tubes in several (3-10) view-fields is measured by Northern Eclipse software.

Figure 10:
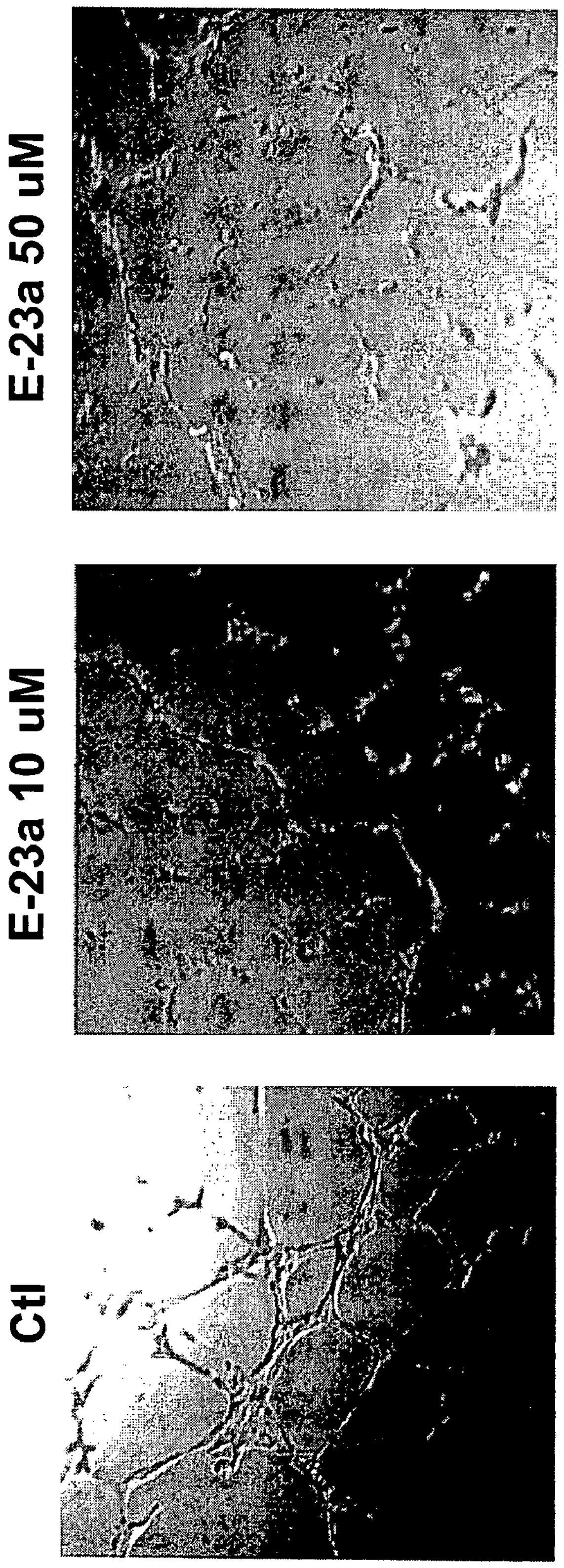

FIG. 10 shows microphotographs of HUVEC tube formation after plating on ECMatrix™ alone (Ctl or control), on ECMatrix™ with 10 µM of E-23a, and on ECMatrix™ with 50 µM of E-23a. Tube formation was revealed under microscope at 4× magnification. Photos are representative of 5 separate experiments. Tube formation is substantially reduced relative to control in the presence of E-23a.

Figure 11:
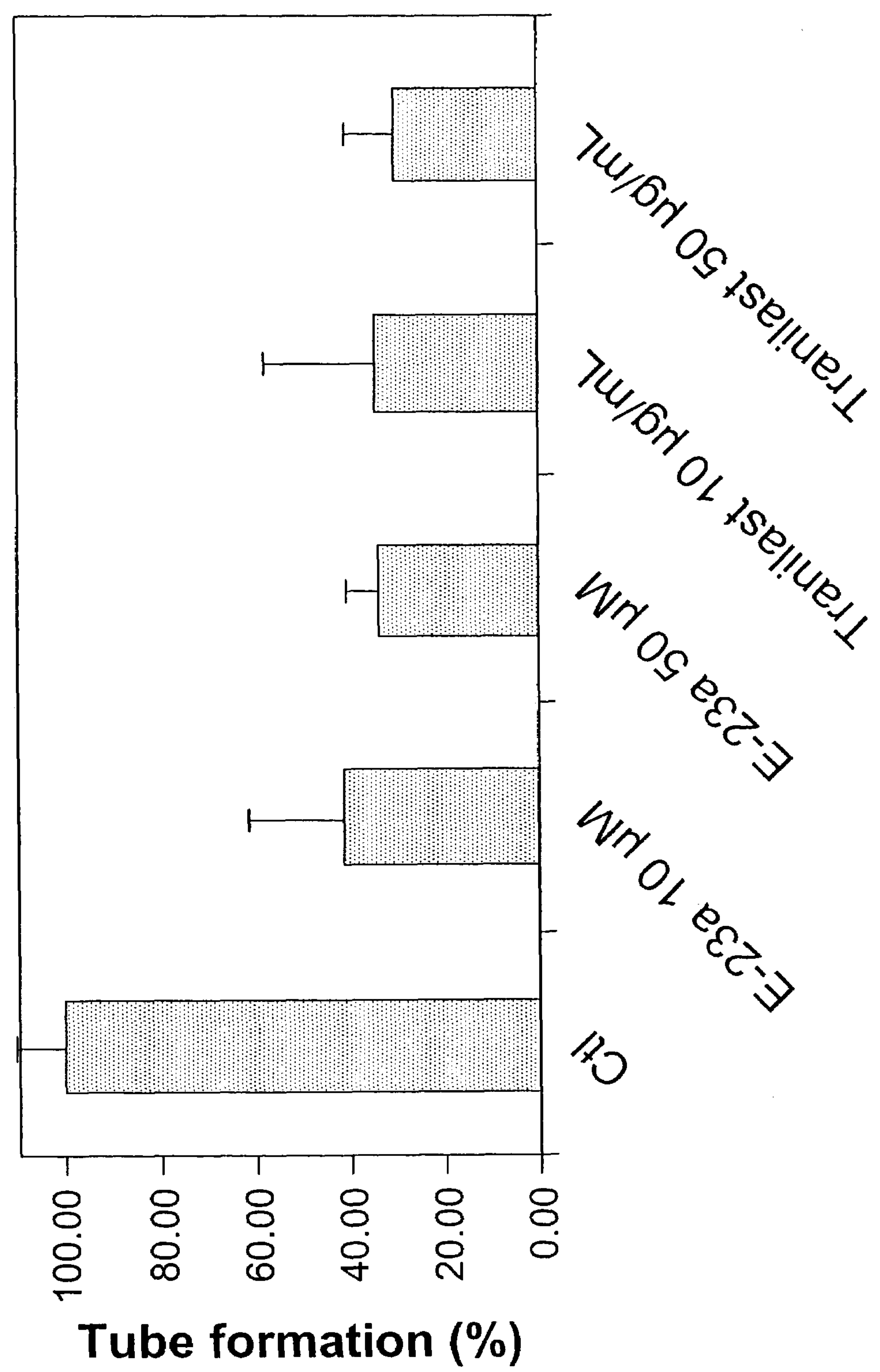
FIG. 11 shows a histogram with quantification of tube formation of HUVEC cells in the presence of increasing concentrations of E-23a and of Tranilast used as a positive control.
Figure 13:
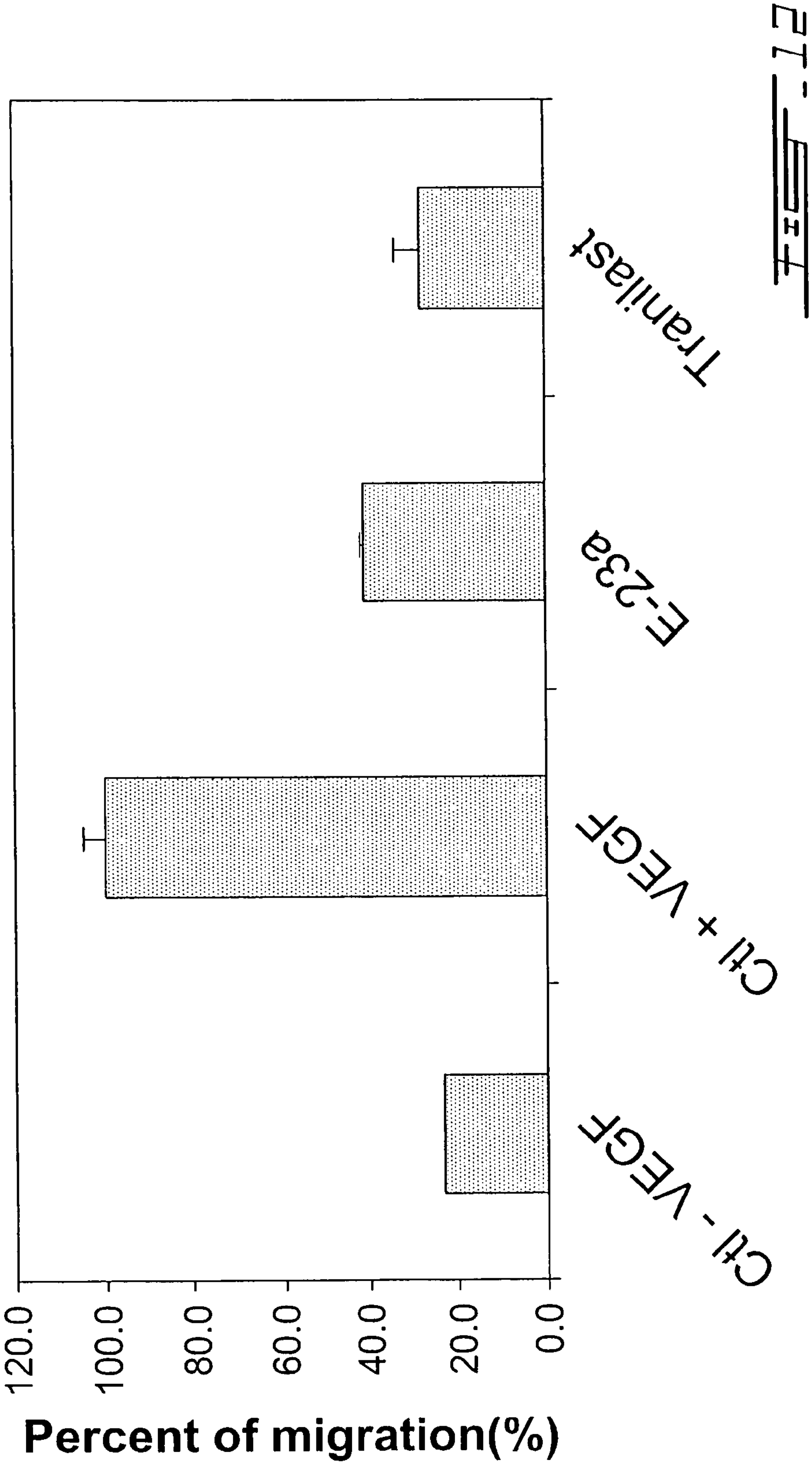

FIG. 11 shows a histogram with quantification of tube formation of HUVEC cells in the absence of a test compound (Ctl) defined as 100% relative amount of tube formation; relative amount of tube formation in the presence of 10 µM of E-23a (approximately 40% relative to control); relative amount of tube formation in the presence of 50 µM of E-23a (approximately 35% relative to control); relative amount of tube formation in the presence of 10 µg/mL of Tranilast (approximately 35% relative to control); and relative amount of tube formation in the presence of 50 µg/mL of Tranilast (approximately 30% relative to control). Tranilast is used as a positive control. For this experiment, 15,000 HUVEC cells were plated on ECMatrix™ and incubated for 6-8 h alone before quantification. Results are presented as mean± SEM for one experiment analyzed in duplicate. Tranilast (N-(3',4'-Dimethoxycinnamoyl)anthranilic Acid) (Calbiochem) acts as a potent inhibitor of VEGF- and vascular permeability factor-induced angiogenesis and collagen synthesis. Tranilast inhibits VEGF- and PMA-stimulated PKC activity in capillary endothelial cells without affecting the VEGF binding or VEGF receptor phosphorylation. It is used as a positive control.

The effect of compounds of this invention on cell migration can be tested in a cell migration assay. A common assay uses Boyden or Transwell chambers, a compartmentalized cell cultures system. Cells are plated in the upper compartment of the Transwell chamber, and the ability of a compound under evaluation to block cell migration through, for example the pores of a Fluoroblok membrane, to the bottom compartment is measured. Cell migration chambers are commercially available, e.g., from BD BioScience, Mississauga, Ontario, Canada. Typically, a chemoattractant is added to the bottom well or compartment. In the case of endothelial cells, a useful chemoattractant is vascular endothelial growth factor (VEGF). VEGF can be purchased (Cedarlane Laboratories Ltd., Hornby, Ontario, Canada). Experiments can be performed in 24-well plates (individual insert or multiwell insert) or in 96-multiwell insert plates with appropriate correction for volume and cell density. For a 24-well plate, the commercially available chamber package is stored at −20° C. The package is allowed to equilibrate to room temperature before opening. Cell suspensions are prepared by first trypsinizing the cell monolayers of low passage (P<6) endothelial cells (EC) and then resuspending the cells in culture medium without serum or with 0.1% FBS at 100,000 cells or at a cell density required for assay. For initial seeding density, it is recommended to use cell density in the same range used for non-porous surface. Endothelial cells are usually seeded at around $10^5$ cells/$cm^2$. Cell density can be optimized by evaluating densities in the range between $0.5\times10^5$ to $5\times10^5$ cells/$cm^2$. A cell suspension is added to the top chamber in 250 µl to give ≈$1.5\times10^5$ cells/$cm^2$, with and without the test article (i.e., a drug to be evaluated). Another 750 μl of culture medium containing endothelial cell normal growth medium or appropriate growth factor (VEGF) in basal medium with or without a compound of this invention is added to each of the bottom wells using the respective sample ports available for access to the bottom chambers. The plate is incubated for 20±1 hour at 37° C., 5% $CO_2$ atmosphere. Cell migration measurement is facilitated by labeling of the cells with a suitable dye such as Calcein AM dye (i.e., Calcein-O,O'-diacetate tetrakis(acetoxymethyl) ester, a non-fluorescent cell permeable derivative of calcein which becomes fluorescent on hydrolysis, e.g., $\lambda_{ex}$~496 nm, $\lambda_{emm}$~516 nm). Following incubation with the cell dye, fluorescence from invaded cells is read in a fluorescence plate reader with bottom reading capabilities at excitation/emission wavelengths of 485/530 nm without further manipulation. Only those labeled cells that have migrated through the pores of the Fluoroblok membrane will be detected.

The data may be expressed as either fluorescent units (FU) or as "fold migration", i.e., the FU value of the cells migrating through the fibronectin coated insert membrane in response to a chemoattractant with inhibitor relative to the FU value of a control, i.e., without inhibitor. Expressing data, as "percent migration" is useful in normalizing date variability from different experiments due to differences in cell seed, variability, etc.

FIG. 12 is a histogram showing the effect of E-23a on endothelial cell migration in the presence of VEGF in the bottom chamber of a Boyden chamber. HUVEC cells were cultured for 20 h with 0.1% FBS in basal growth media supplemented with 10 ng/mL VEGF into fibronectin-coated transwells. 50 μM of E-23a or Tranilast, a known inhibitor of endothelial cells migration, was added. Results are reported as mean±SD for one experiment analyzed at least in duplicate. Relative to Ctl (control)+VEGF defined as 100% of migration, Ctl−VEGF provides migration of approximately 25% of the amount observed with Ctl+VEGF. The presence of E-23a provides migration of approximately 40% of the amount observed with Ctl+VEGF. Positive control Tranilast provides migration of approximately 30% of the amount observed with Ctl+VEGF.

Example 60

Determination of Cell Permeability of Compounds of the Invention

The Caco-2 cell line, derived from a human colorectal carcinoma (human Caucasian colon adenocarcinoma), has become an established in vitro model for the prediction of drug absorption across the human intestine. When cultured on semipermeable membranes, Caco-2 cells differentiate into a highly functionalized epithelial barrier with remarkable morphological and biochemical similarity to the small intestinal columnar epithelium. The membrane transport properties of novel compounds can thereby be assessed using these differentiated cell monolayers. The apparent permeability coefficients (Papp) obtained from Caco-2 cell transport studies have been shown to correlate to human intestinal absorption. Thus, a method useful to evaluate permeability of compounds of this invention consists of seeding the cells in a semipermeable membrane, culturing them for a predetermined time, and then adding the test compound to the apical or basolateral compartment. After incubation, samples are taken from the apical and basolateral compartment and the concentration of the test compound is determined by LCMS (liquid chromatography/mass spectroscopy).

Stock cultures of Caco-2 (ATCC Number: CRL-2002, clone of HTB-37) cells are maintained in MEM Earles medium containing 10% fetal bovine serum (FBS), 0.1 mM non-essential amino acids and 1 mM sodium pyruvate at 37° C. in a humidified, 5% $CO_2$ atmosphere. Stock cultures are sub-cultured every 7 days when cells have reached 80-90% confluency. Studies are conducted with Caco-2 cells, used between passage 21 to 40. Cells are plated on Transwell™ inserts at a density of $1\times10^4$ cells/well in 24-well culture plates. Cells are incubated at 37° C. under 5% $CO_2$ atmosphere, and media (MEM Earles medium containing 10% FBS, 0.1 mM non-essential amino acids and 1 mM sodium pyruvate) are changed 3 times per week. Cells are used for permeability studies between 20 to 22 days after seeding. On the day of the assay, cell monolayers are washed 3 times. Each wash consists of aspirating liquid from the apical (A) and basolateral (B) sides, and adding 0.5 and 1 mL, respectively, of fresh Dulbecco's phosphate-buffered saline with $Mg^{2+}$ and $Ca^{2+}$, pH 7.4 (PBS). After the final wash, a volt-ohm-meter is used to determine the trans-epithelial electrical resistance (TEER), a measure of the integrity of the monolayer. Cells are not be used if the TEER values are less than 200 ohms/$cm^2$. Working solutions of the test compounds are prepared in PBS. [$^3$H]Mannitol and [$^3$H]propranolol are prepared at a concentration of 1 μCi/mL, in PBS. The [$^3$H]propranolol solution is supplemented with unlabelled propranolol for a final propranolol concentration of 100 μM. For each test compound and standard, apical to basolateral (A to B) and basolateral to apical (B to A) transport is measured. The final volume on the basolateral side is 1 mL; the final volume on the apical side is 0.3 mL. The test compound working solution or radiolabeled standard solution is added to the 'donor' side. Blank buffer is added to the 'acceptor' side. Assays are carried out in duplicate on 24-well plates. Plates are incubated at 37° C. on a rotary shaker set at 150 rpm. The permeability of each compound and control is measured by sampling 200μL of medium from the acceptor compartment at time zero and following 60 minutes of incubation. A 100 μL sample is also be taken from the donor compartment at the beginning of the study (immediately following addition to the donor compartment) and a 200 μL sample is taken at the end of the incubation (60 min), for determination of mass balance. All samples are placed in labeled 1.5 mL polypropylene tubes and stored frozen at −70° C. until bioanalysis. Prior to bioanalysis of the test compounds, an appropriate aliquot of an internal standard (IS) solution in mobile phase is added to an aliquot of each sample. In the case of E-23a, the standard is a sample of E-23a. Samples are then centrifuged for 2 minutes at 10,000×g prior to injection of an aliquot of the supernatant into the LC-MS/MS instrument. 100 μL aliquots of the samples containing the radiolabeled standards are added to 6.5 mL scintillation vials. A 3 mL aliquot of liquid scintillant is added to the vials, and disintegrations per minute (dpm) are determined in a liquid scintillation counter. In order to determine if the barrier function of the monolayers containing the test compounds remained intact during incubation with the test compounds, solutions of the test compounds remaining in the apical and basolateral compartments are removed. A 100 μM solution of Lucifer Yellow in assay buffer is added to the apical compartment (0.3 mL) of the Transwell inserts and 1.0 mL of blank assay buffer is added to the basolateral compartment. The plate is incubated at 37° C. on the rotary shaker set at 150 rpm. The permeability of Lucifer Yellow is measured by sampling 100 μL of medium from the basolateral compartment following 60 minutes of incubation. Two 100 μL samples are taken from the donor compartment at the beginning of the study. The samples containing Lucifer Yellow are added to a 96-well polypropylene plate and fluorescence measured in a plate reader with excitation and emission wavelengths set at 485 and 530 nm, respectively. The permeability coefficient ($P_{app}$) of each compound and radiolabeled standard is determined using the following equation:

$$P_{app}=dQ/dT\times 1/C_i\times 1/A$$

wherein dQ/dT represents the permeability rate, $C_i$ denotes the initial concentration in the donor compartment, and A represents the surface area of the filter. $C_i$ is determined from the mean concentration of duplicate samples taken immediately following the addition to the donor compartment. Permeability rates are calculated by plotting the cumulative amount of compound measured in the acceptor compartment over time and determining the slope of the line by linear regression analysis.

The % recovery (mass balance) of each compound and radiolabeled standard can be determined using the following equation:

$$\%\ \text{Recovery} = \frac{C_D V_D + C_A V_A}{C_i V_D} \times 100\%$$

wherein $C_D$ and $C_A$ represent the concentration of the compound or radiolabeled standard in the donor and acceptor compartments at the last sampling time-point (60 min), respectively, and $V_D$ and $V_A$ denote the volumes of the donor and acceptor compartments, respectively.

Lucifer Yellow (LY) permeability can be expressed as the % Retained in the apical compartment, and can be calculated as: 1−(the amount of LY in the basolateral (acceptor) compartment at 60 min divided by the average amount of LY added to the donor compartment at t=0), multiplied by 100%.

Table 4 shows a summary Of $P_{app}$ values determined for test compound E-23a in the Caco-2 permeability assay. [$^3$H] mannitol and [$^3$H]propranolol were used as controls.

The results indicate that E-23a has good permeability.

TABLE 4

Apparent cell permeability coefficients for E-23a in a Caco-2 permeability assay

| Compound | Initial Concentration measured (ng/mL) | $P_{app}$ A to B (n/ms) | $P_{app}$ B to A (n/ms) | B − A/ A − B $P_{app}$ ratio |
|---|---|---|---|---|
| [$^3$H]-Mannitol | 0.0000241[a] | 10.1 ± 1.46 | 8.21 ± 3.62 | 0.81 |
| [$^3$H]-Propranolol | 100[a] | 360 ± 16.5 | 278 ± 36.8 | 0.77 |
| E-23a | 11030 | 107 | 141 | 1.31 |

[a]Concentrations reported as μM.
$P_{app}$ is the apparent permeability coefficient.
A refers to the apical side and B refers to the basolateral side.

Example 61

Determination of Plasma Protein Binding of Compounds of the Invention

The pharmacokinetic and pharmacodynamic properties of drugs are largely a function of the reversible binding of drugs to plasma or serum proteins. Such proteins include albumin, $\alpha_1$-acid glycoprotein, lipoproteins and α, β and γ globulins. Generally, only unbound drug is available for diffusion or transport across cell membranes, and for interaction with a pharmacological target (e.g. receptor, ion channel, transporter, enzyme). As a result, the extent of plasma protein binding of a drug influences the drug's action as well as its distribution and elimination. Highly plasma protein bound drugs are confined to the vascular space, thereby having a relatively low volume of distribution. In contrast, drugs that remain largely unbound in plasma are generally available for distribution to other organs and tissues, resulting in large volumes of distribution. The binding of drugs to proteins both in the vascular space and/or the extravascular space results in a decrease in drug clearance and a prolonged drug half-life. Only unbound drug is available for glomerular filtration and, in some cases, hepatic clearance. However, for high extraction ratio drugs, clearance is relatively independent of protein binding. Plasma or serum protein binding assays using the equilibrium dialysis method are used to determine drug availability. Equilibrium dialysis studies using a 96-well microplate format or using conventional 2-chambered Teflon dialysis cells can be used to determine plasma or serum binding, and LC/MS/MS analysis is used for test compound quantification. The Teflon dialysis cell system is commonly used to determine the time to reach equilibrium, the fraction of a compound bound and unbound to plasma proteins and the effect of concentration on the extent of binding. Test compound quantification is performed by HPLC or LC/MS/MS analysis.

To perform equilibrium dialysis the following procedures can be used. To 0.990 mL of thawed plasma (37° C.), a 10 μL aliquot of the stock solutions is added for test compound concentrations of 35 μM. An appropriate volume of buffer (Dulbecco's phosphate buffered saline, pH 7.4) is spiked with each test compound at a concentration of 35 μM. Duplicate aliquots (130 μL) of each spiked plasma and buffer solution are collected prior to dialysis into labeled 1.5 mL polypropylene tubes and stored frozen at −40° C. Useful standards, [$^3$H]-propranolol and [$^3$H]-warfarin, are prepared in plasma from each species to be tested at a concentration of 1 μCi/mL. Equilibrium dialysis is performed in a 96-well Teflon dialysis unit. Each well of the unit consists of two chambers separated by a vertically aligned dialysis membrane (regenerated cellulose) with a molecular weight cut-off of 12-14 KDa. The equilibrium dialysis membranes are first pre-soaked in deionized water for 30 min, then soaked in 20% ethanol for 20 min, followed by rinsing twice with deionized water. The equilibrium dialysis apparatus is assembled according to the manufacturer's directions. One chamber of each well is filled with 150 μL of blank buffer (to prevent membrane dehydration). Aliquots (150 μL) of spiked plasma or spiked buffer are added to the opposing chamber in each well. The top of the plate is sealed with an adhesive sealing film to prevent evaporation and to maintain constant pH during incubation. All dialysis experiments with the test compounds and standards are assessed using duplicate samples. The dialysis apparatus is incubated at 37° C. in an orbital shaker/incubator (Lab-Line Enviro) samples are collected following 24 hours of incubation. Samples containing the test compounds are stored frozen at −70° C. until analysis. Samples (100 μL) containing the radiolabels are added and mixed by vortex. The disintegrations per minute (dpm) in each vial are measured with a liquid scintillation counter. The fraction of each test compound and standard unbound ($f_u$) to human serum proteins is calculated according to the following equation:

$$f_u = \frac{C_{buffer}}{C_{plasma}}$$

wherein $C_{buffer}$ and $C_{plasma}$ represent the concentration of the compound measured in the buffer and plasma chambers, respectively, following dialysis. The fraction bound ($f_b$) to the plasma proteins is determined as: $1-f_u$. The recovery (mass balance) of the compounds and standards from the dialysis apparatus can be calculated as:

$$\text{Recovery (\%)} = \frac{C_{plasma}V_{plasma} + C_{buffer}V_{buffer}}{C_{plasma(t=0)}V_{plasma}} \times 100\%$$

wherein $C_{plasma(t=0)}$ represents the concentration of the compound measured in plasma prior to dialysis, and $V_{plasma}$ and $V_{buffer}$ represent the volumes of plasma and buffer, respectively, that are added to the opposing sides of the dialysis chambers.

Table 5 shows a binding of E-23a to human plasma proteins as determined by the equilibrium dialysis method. (S)-Propranolol and (R,S)-Warfarin were used as standards. The results indicate that E-23a is relatively available in the unbound form in plasma.

TABLE 5

Binding of E-23a to human plasma proteins

| Compound | Plasma Concentration (ng/mL)[a] | Unbound (%) | Bound (%) |
|---|---|---|---|
| (S)-Propranolol | 72.8[b] | 8.67 | 91.3 |
| (R,S)-Warfarin | 160[b] | 0.895 | 99.1 |
| E-23a | 5575 | 92.7 | 7.26 |

[a]Plasma concentrations measured following 24 h of dialysis.
[b]Concentrations reported as pM.

We claim:

1. A substituted piperidine compound having the structure represented by formula I:

I

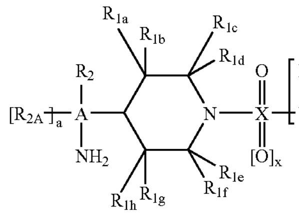

wherein

A is carbon;

a is one;

x is 0 or 1;

X is carbon or sulfur provided that X is carbon only when x is 0, and X is sulfur only when x is 1;

n is 0;

each of $R_{1a}$, $R_{1b}$, $R_{1c}$, $R_{1d}$, $R_{1e}$, $R_{1f}$, $R_{1g}$, and $R_{1h}$ are hydrogen;

$R_2$ and $R_{2A}$ are independently selected from the group consisting of: hydrogen, a C1 to C10 alkyl group, and $R_3$ is isoquinolinyl quinolinyl and a pharmaceutically acceptable salt thereof.

2. The substituted piperidine compound of claim 1, wherein x is zero, X is carbon, a is one, A is carbon, and n is zero.

3. The substituted piperidine compound of claim 1, wherein x is zero, X is carbon, a is one, A is carbon, each of $R_{1a}$, $R_{1b}$, $R_{1c}$, $R_{1d}$, $R_{1e}$, $R_{1f}$, $R_{1g}$, and $R_{1h}$ is hydrogen, and n is zero.

4. The substituted piperidine compound of claim 1, wherein x is zero, X is carbon, a is one, A is carbon, each of $R_{1a}$, $R_{1b}$, $R_{1c}$, $R_{1d}$, $R_{1e}$, $R_{1f}$, $R_{1g}$, and $R_{1h}$ is hydrogen, one of $R_2$ and $R_{2A}$ is hydrogen and the other is alkyl, and n is zero.

5. The substituted piperidine compound of claim 1, wherein x is one, X is sulfur, a is one, A is carbon, and n is zero.

6. The substituted piperidine compound of claim 1, wherein x is one, X is sulfur, a is one, A is carbon, each $R_{1a}$, $R_{1b}$, $R_{1c}$, $R_{1d}$, $R_{1e}$, $R_{1f}$, $R_{1g}$, and $R_{1h}$ is hydrogen, and n is zero.

7. The substituted piperidine compound of claim 1, wherein x is one, x is sulfur, a is one, A is carbon, each of $R_{1a}$, $R_{1b}$, $R_{1c}$, $R_{1d}$, $R_{1e}$, $R_{1f}$, $R_{1g}$, and $R_{1h}$ is hydrogen, one of $R_2$ and $R_{2A}$ is hydrogen and the other is alkyl, and n is zero.

8. A pharmaceutical composition comprising a compound of claim 1 and a pharmaceutically acceptable carrier therefor.

9. The pharmaceutical composition of claim 8, wherein the carrier comprises a sterile isotonic aqueous solution suitable for injection.

10. The pharmaceutical composition of claim 9, wherein the solution comprises a buffer salt.

11. The pharmaceutical composition of claim 9, wherein the solution comprises phosphate buffered saline.

12. The substituted piperidine compound of claim 1, wherein:

a) A is carbon;

b) a is one;

c) $R_2$ is selected from the group consisting of hydrogen, and a C1 to C10 alkyl group;

d) each of $R_{1a}$, $R_{1b}$, $R_{1c}$, $R_{1d}$, $R_{1e}$, $R_{1f}$, $R_{1g}$, $R_{1h}$ and $R_{2a}$ is hydrogen;

e) X is S;

f) x is one;

g) n is 0; and h) $R_3$ is 5-isoquinolinyl.

13. The substituted piperidine compound of claim 12, wherein:

a) A is carbon;

b) a is one;

c) $R_2$ is selected from the group consisting of H and a C1 to C5 alkyl group;

d) each of $R_{1a}$, $R_{1b}$, $R_{1c}$, $R_{1d}$, $R_{1e}$, $R_{1f}$, $R_{1g}$, $R_{1h}$ and $R_{2a}$ is hydrogen;

e) X is S;

f) x is one;

g) n is 0; and h) $R_3$ is 5-isoquinolinyl.

14. The substituted piperidine compound of claim 13, wherein:

a) A is carbon;

b) a is one;

c) $R_2$ is a methyl group;

d) each Of $R_{1a}$, $R_{1b}$, $R_{1c}$, $R_{1d}$, $R_{1e}$, $R_{1f}$, $R_{1g}$, $R_{1h}$ and $R_{2a}$ is hydrogen;

e) X is S;

f) x is one;

g) n is 0; and h) $R_3$ is 5-isoquinolinyl.

15. The substituted piperidine compound of claim 13, wherein:

a) A is carbon;

b) a is one;

c) $R_2$ is a propyl group;

d) each Of $R_{1a}$, $R_{1b}$, $R_{1c}$, $R_{1d}$, $R_{1e}$, $R_{1f}$, $R_{1g}$, $R_{1h}$ and $R_{2a}$ is hydrogen;

e) X is S;

f) x is one;

g) n is 0; and h) $R_3$ is 5-isoquinolinyl.

16. A pharmaceutical composition comprising a substituted piperidine compound as defined in claim 12 and a pharmaceutically acceptable carrier therefor.

17. A pharmaceutical composition comprising a substituted piperidine compound as defined in claim 13 and a pharmaceutically acceptable carrier therefor.

18. A pharmaceutical composition comprising a substituted piperidine compound as defined in claim 14 and a pharmaceutically acceptable carrier therefor.

19. A pharmaceutical composition comprising a substituted piperidine compound as defined in claim 15 and a pharmaceutically acceptable carrier therefor.

* * * * *

UNITED STATES PATENT AND TRADEMARK OFFICE

CERTIFICATE OF CORRECTION

PATENT NO. : 7,572,913 B2
APPLICATION NO. : 11/065696
DATED : August 11, 2009
INVENTOR(S) : McKerracher et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 928 days.

Signed and Sealed this

Seventh Day of September, 2010

David J. Kappos

*Director of the United States Patent and Trademark Office*